US007396914B2

(12) United States Patent
Ambrosino et al.

(10) Patent No.: US 7,396,914 B2
(45) Date of Patent: Jul. 8, 2008

(54) SARS NUCLEIC ACIDS, PROTEINS, ANTIBODIES, AND USES THEREOF

(75) Inventors: Donna Ambrosino, Avon, MA (US); Hector Hernandez, Canton, MA (US); Thomas Greenough, Shrewsbury, MA (US); Katherine Luzuriaga, Harvard, MA (US); Mohan Somasundaran, Shrewsbury, MA (US); Gregory J. Babcock, Marlborough, MA (US); William D. Thomas, Jr., Somerville, MA (US); John Sullivan, West Boylston, MA (US)

(73) Assignee: University of Massachusetts, Boston, MA (US)

( * ) Notice: Subject to any disclaimer, the term of this patent is extended or adjusted under 35 U.S.C. 154(b) by 517 days.

(21) Appl. No.: 10/911,838

(22) Filed: Aug. 4, 2004

(65) Prior Publication Data

US 2005/0069869 A1 Mar. 31, 2005

Related U.S. Application Data

(60) Provisional application No. 60/565,595, filed on Apr. 26, 2004, provisional application No. 60/545,670, filed on Feb. 18, 2004, provisional application No. 60/510,251, filed on Oct. 9, 2003, provisional application No. 60/492,529, filed on Aug. 4, 2003.

(51) Int. Cl.
*C12P 21/08* (2006.01)
*C07K 16/00* (2006.01)

(52) U.S. Cl. .............. 530/387.3; 530/388.1; 530/388.8; 530/388.3

(58) Field of Classification Search ....................... None
See application file for complete search history.

(56) References Cited

U.S. PATENT DOCUMENTS

| | | | | |
|---|---|---|---|---|
| 5,545,806 | A | 8/1996 | Lonberg et al. | |
| 5,569,825 | A | 10/1996 | Lonberg et al. | |
| 5,625,126 | A | 4/1997 | Lonberg et al. | |
| 5,633,425 | A | 5/1997 | Lonberg et al. | |
| 5,661,016 | A | 8/1997 | Lonberg et al. | |
| 5,770,429 | A | 6/1998 | Lonberg et al. | |
| 5,789,650 | A | 8/1998 | Lonberg et al. | |
| 5,814,318 | A | 9/1998 | Lonberg et al. | |
| 2006/0240515 | A1* | 10/2006 | Dimitrov et al. | 435/69.1 |

FOREIGN PATENT DOCUMENTS

| | | | |
|---|---|---|---|
| WO | WO 92/03918 | A1 | 3/1992 |
| WO | WO 94/25585 | A1 | 11/1994 |
| WO | WO 98/24884 | A1 | 6/1998 |

OTHER PUBLICATIONS

Kashmiri S. et al. "SDR grafting—a new approach to antibody humanization". Methods. May 2005;36(1):25-34.*

Tamura M. et al "Structural correlates of an anticarcinoma antibody: identification of specificity-determining residues (SDRs) and development of a minimally immunogenic antibody variant by retention of SDRs only". J Immunol. Feb. 1, 2000;164(3)1432-41.*

Altman, L. "More SARS cases are reported; virus found to persist in patients." Retrieved from the Internet: www.nytimes.com/2003/05/02/science/sciencespecial/02INFE.thml?th . . . Retrieved on May 2, 2003. 3 pages.

Altman, L. "Study in Hong Kong suggests a higher rate of SARS death." Retrieved from the Internet: www.nytimes.com/2003/05/07/science/sciencespecial/07INFE.html?th. Retrieved on May 7, 2003. 3 pages.

American Association of Blood Banks. "FDA recommends deferrals for SARS exposure." Retrieved from the Internet: www.aabb.org/Pressroom/In_the_News/wnsars041803.thm. Retrieved on Apr. 23, 2003. 2 pages.

Ang, A. "WHO raises SARS death rate as death toll tops 500; New study suggests SARS may have been in humans longer than previously thought." *AP Worldstream* 2003 3 pages.

Ang, A. "China's tests of SARS vaccine shift to humans." Retrieved from the Internet: www.philly.com/mld/inquirer/news/nation/7342856.thm?template=contentModules/printstory. Retrieved on Nov. 25, 2003.

Associated Press, et al. "New SARS travel warning issued." Retrieved from the Internet: www.msnbc.com/news/885653.asp?vts=-42320030855. Retrieved on Apr. 23, 2003. 7 pages.

Associated Press. "China to begin testing SARS vaccine." Retrieved from the Internet: www.msnbc.com/m/pt/printthis_main?storyID=997544. Retrieved on Nov. 25, 2003. 2 pages.

Associated Press. "Bone ailment found in some SARS survivors." Retrieved from the Internet:www.miami.com/mld/miamiherald/7221736.htm?template=contentModules/prinstory.jsp. Retrieved on Nov. 10, 2003. 1 page.

Babcock, G., et al. "Amino acids 270 to 510 of the severe acute respiratory syndrome coronavirus spike protein are required for interaction with receptor." *J Virol*. May 2004;78(9):4552-60.

Boeckh, M., et al. "Phase 1 evaluation of the respiratory syncytial virus-specific monoclonal antibody palivizumab in recipients of hematopoietic stem cell transplants." *J Infect Dis*. Aug. 1, 2001;184(3):350-4.

Booth, C., et al. "Clinical features and short-term outcomes of 144 patients with SARS in the greater Toronto area." *JAMA*. Jun. 4, 2003;289(21):2801-9.

Bonavia, A., et al. "Identification of a receptor-binding domain of the spike glycoprotein of human coronavirus HCoV-229E." *J Virol*. Feb. 2003;77(4):2530-8.

Breslin, J., et al. "Human coronavirus 229E: receptor binding domain and neutralization by soluble receptor at 37 degrees C." *J Virol*. Apr. 2003;77(7):4435-8.

(Continued)

*Primary Examiner*—Zachariah Lucas
*Assistant Examiner*—Bo Peng
(74) *Attorney, Agent, or Firm*—Lahive & Cockfield, LLP; Jane E. Remillard

(57) ABSTRACT

Codon-optimized nucleic acids, polypeptides, and antibodies are described herein.

12 Claims, 72 Drawing Sheets

OTHER PUBLICATIONS

Broder, J. "Aggressive steps help U.S. avoid SARS brunt." Retrieved from the internet: www.nytimes.com/2003/05/05/national/05SARS.html?th. Retrieved on May 5, 2003. 3 pages.

Brown, E., et al. "Comparative analysis of the SARS coronavirus genome: a good start to a long journey." Published online May 9, 2003. image.thelancet.com/extras/03cmt124web.pdf.

Bukreyev, A., et al. "Mucosal immunisation of African green monkeys (Cercopithecus aethiops) with an attenuated parainfluenza virus expressing the SARS coronavirus spike protein for the prevention of SARS." Lancet. Jun. 26, 2004;363(9427):2122-7.

Burns, R. "WHO raises SARS death rate as death toll tops 500: China says situation grim." AP Worldstream 2003, 5 pages.

Callow, K., et al. "The time course of the immune response to experimental coronavirus infection of man." Epidemiol Infect. Oct. 1990;105(2):435-46.

Callow, K. "Effect of specific humoral immunity and some non-specific factors on resistance of volunteers to respiratory coronavirus infection." J Hyg (Lond). Aug. 1985;95(1):173-89.

Cavallaro, J., et al. "Community-wide outbreak of infection with a 229E-like coronavirus in Tecumseh, Michigan." J Infect Dis. Oct. 1970;122(4):272-9.

Centers for Disease Control and Prevention (CDC). "Efficiency of quarantine during an epidemic of severe acute respiratory syndrome—Beijing, China, 2003." MMWR Morb Mortal Wkly Rep. Oct. 31, 2003; 52(43):1037-40.

Centers for Disease Control and Prevention (CDC). "Prevalence of IgG antibody to SARS-associated coronavirus in animal traders—Guangdong Province, China, 2003." MMWR Morb Mortal Wkly Rep. Oct. 17, 2003;52(41):986-7.

Centers for Disease Control and Prevention (CDC). "Severe acute respiratory syndrome—Singapore, 2003." MMWR Morb Mortal Wkly Rep. May 9, 2003;52(18):405-11.

Centers for Disease Control and Prevention (CDC) Press Release. "CDC lab sequences genome of new coronavirus." Retrieved from the Internet: www.cdc.gov/od/oc/media/pressrel/r030414.htm. Retrieved on Apr. 23, 2003. 2 pages.

Centers for Disease Control and Prevention (CDC). "Update: Severe acute respiratory syndrome—United States, 2003." MMWR Morb Mortal Wkly Rep. May 2003;52(17):388-91.

Centers for Disease Control and Prevention. "Severe Acute Respiratory Syndrome (SARS) and coronavirus testing—United States, 2003." JAMA. May 7, 2003;289(17):2203-6.

Centers for Disease Control and Prevention (CDC). "Update: outbreak of severe acute respiratory syndrome—worldwide, 2003." MMWR Morb Mortal Wkly Rep. Apr. 4, 2003;52(13):269-72.

Champlin, R., et al. "Community respiratory virus infections in bone marrow transplant recipients: the M.D. Anderson Cancer Center experience." Biol Blood Marrow Transplant. 2001;7 Suppl:8S-10S.

The Chinese SARS Molecular Epidemiology Consortium. "Molecular Evolution of the SARS coronavirus during the course of the SARS epidemic in China." Published online Jan. 30, 2004. www.sciencemag.org/10/1126/science.1092002. 28 pages.

Collins, A., et al. "Monoclonal antibodies to murine hepatitis virus-4 (strain JHM) define the viral glycoprotein responsible for attachment and cell—cell fusion." Virology. Jun. 1982;119(2):358-71.

Collins, A. "Interferon gamma potentiates human coronavirus OC43 infection of neuronal cells by modulation of HLA class I expression." Immunol Invest. Nov. 1995;24(6):977-86.

Collins, A. "Human coronavirus OC43 interacts with major histocompatibility complex class I molecules at the cell surface to establish infection." Immunol Invest. Aug. 1994;23(4-5):313-21.

Connor, A., et al. "Comparison of human respiratory syncytial virus A2 and 8/60 fusion glycoprotein gene sequences and mapping of sub-group specific antibody epitopes." J Med Virol. Feb. 2001;63(2):168-77.

Connor, S. Secrets of SARS virus's lethal mutation unlocked by scientists. Retrieved from the Internet: www.independent.co.uk/news. Retrieved on Jan. 30, 2004. 2 pages.

Consensus document on the epidemiology of severe acute respiratory syndrome (SARS). Meeting held May 16-17, 2003. WHO/CDS/CSR/GAR. [Abstract].

Corapi, W., et al. "Localization of antigenic sites of the S glycoprotein of feline infectious peritonitis virus involved in neutralization and antibody-dependent enhancement." J Virol. May 1995;69(5):2858-62.

Corr, P. "SARS and drug makers." Retrieved from the Internet: www.nytimes.com/2003/04/23/opinion/L23SARS.html. Retrieved on Apr. 23, 2003. 1 page.

Cortez, K., et al. "Immune-globulin prophylaxis of respiratory syncytial virus infection in patients undergoing stem-cell transplantation." J Infect Dis. Sep. 15, 2002;186(6):834-8.

Cui, W., et al. "Expression of lymphocytes and lymphocyte subsets in patients with severe acute respiratory syndrome." Clin Infect Dis. Sep. 15, 2003;37(6):857-9.

de Groot, R., et al. "Evidence for a coiled-coil structure in the spike proteins of coronaviruses." J Mol Biol. Aug. 20, 1987;196(4):963-6.

Delmas, B., et al. "Aminopeptidase N is a major receptor for the entero-pathogenic coronavirus TGEV." Nature. Jun. 4, 1992;357(6377):417-19.

Delmas, B., et al. "Assembly of coronavirus spike protein into trimers and its role in epitope expression." J Virol. Nov. 1990;64(11):5367-75.

DeVincenzo, J., et al. "Respiratory syncytial virus immune globulin treatment of lower respiratory tract infection in pediatric patients undergoing bone marrow transplantation—a compassionate use experience." Bone Marrow Transplant. Jan. 2000;25(2):161-5.

Dick, E. et al. "Coronaviruses." Textbook of Pediatric Infectious Diseases, 4th Edition, vol. 2. W.B. Saunders Company, 1998, Subsection Ten, Chapter 188, pp. 2132-2141.

Donnelly, C., et al. "Epidemiological determinants of spread of causal agent of severe acute respiratory syndrome in Hong Kong." Published online May 7, 2003. //image.thelancet.com/extras/03art4453web.pdf. 6 pages.

Drazen, J. "Case clusters of the severe acute respiratory syndrome." N Engl J Med. May 15, 2003;348(20):Drazen 1-2.

Drosten, C., et al. "Identification of a novel coronavirus in patients with severe acute respiratory syndrome." N Engl H Med. May 15, 2003;348(20):Drosten 1-10.

Dveksler, G., et al. "Expression of the recombinant anchorless N-terminal domain of mouse hepatitis virus (MHV) receptor makes hamster of human cells susceptible to MHV infection." J Virol. Jun. 1996;70(6):4142-5.

Dveksler, G., et al. "Mouse hepatitis virus receptor activities of an MHVR/mph chimera and MHVR mutants lacking N-linked glycosylation of the N-terminal domain." J Virol. Jan. 1995;69(1):543-6.

Dye, C., et al. "Epidemiology. Modeling the SARS epidemic." Science. Jun. 20, 2003;300(5627):1884-5.

Eckholm, E. "Beijing closes schools and posts another sharp rise in SARS." Retrieved from the Internet: www.nytimes.com/2003/04/23/science/sciencespecial/23CND-CHIN.html. Retrieved on Apr. 23, 2003. 3 pages.

Endy, T., et al. "Relationship of preexisting dengue virus (DV) neutralizing antibody levels to viremia and severity of disease in a prospective cohort study of DV infection in Thailand." J Infect Dis. Mar. 15, 2004;189(6):990-1000.

Fazakerley, J., et al. "The V5A13.1 envelope glycoprotein deletion mutant of mouse hepatitis virus type-4 is neuroattenuated by its reduced rate of spread in the central nervous system." Virology. Mar. 1992;187(1):178-88.

Fehr, D., et al. "Placebo-controlled evaluation of a modified life virus vaccine against feline infectious peritonitis: safety and efficacy under field conditions." Vaccine. Jul. 1997;15(10):1101-9.

Fleming, J., et al. "Antigenic relationships of murine coronaviruses: analysis using monoclonal antibodies to JHM (MHV-4) virus." Virology. Dec. 1983;131(2):296-307.

Foreman, W. "WHO raises SARS death rate as death toll tops 500; China says situation grim; Russia closes some border checkpoints with China." AP Worldstream 2003 4 pages.

Fouchier, R., et al. "Aetiology: Koch's postulates fulfilled for SARS virus." Nature. May 15, 2003;423(6937):240.

Foxwell, A., et al. "Mucosal immunisation and immunoprophylaxis as potential strategies for prevention of SARS." Lancet. Jun. 26, 2004;363(9427):2102-3.

Gagneten, S., et al. "Interaction of mouse hepatitis virus (MHV) spike glycoprotein with receptor glycoprotein MHVR is required for infection with an MHV strain that expresses the hemagglutinin-esterase glycoprotein." *J Virol.* Feb. 1995;69(2):889-95.

Gerberding, J. "Faster . . . but fast enough? Responding to the epidemic of severe acute respiratory syndrome." *N Engl J Med.* May 15, 2003;348(20):Gerberding 1-2.

Godet, M., et al. "Major receptor-binding and neutralization determinants are located within the same domain of the transmissible gastroenteritis virus (coronavirus) spike protein." *J Virol.* Dec. 1994;68(12):8008-16.

Haagmans, B., et al. "Pegylated interferon-alpha protects type 1 pneumocytes against SARS coronavirus infection in macaques." *Nat Med.* Mar. 2004;10(3):290-3.

Haller, A., et al. "Bovine parainfluenza virus type 3 (PIV3) expressing the respiratory syncytial virus (RSV) attachment and fusion proteins protects hamsters from challenge with human PIV3 and RSV." *J Gen Virol.* Aug. 2003;84(Pt 8):2153-62.

Hamre, D., et al. "Virologic studies of acute respiratory disease in young adults. V. Coronavirus 229E infections during six years of surveillance." *Am J Epidemiol.* Aug. 1972;96(2):94-106.

Hasony, H., et al. "Prevalence of human coronavirus antibody in the population of southern Iraq." *J Med Virol.* 1982;9(3):209-16.

Haynes, L., et al. "Neutralizing anti-F glycoprotein and anti-substance P antibody treatment effectively reduces infection and inflammation associated with respiratory syncytial virus infection." *J Virol.* Jul. 2002;76(14):6873-81.

Hingley, S., et al. "MHV-A59 fusion mutants are attenuated and display altered hepatotropism." *Virology.* Apr. 1994;200(1):1-10.

Hohdatsu, T., et al. "Antibody-dependent enhancement of feline infectious peritonitis virus infection in feline alveolar macrophages and human monocyte cell line U937 by serum of cats experimentally or naturally infected with feline coronavirus." *J Vet Med Sci.* Jan. 1998;60(1):49-55.

Holmes, K, et al. "SARS coronavirus: a new challenge for prevention and therapy." *J Clin Invest.* Jun. 2003;111(11):1605-9.

Holmes, K., et al. "Virology, The SARS coronavirus: a postgenomic era." *Science.* May 30, 2003;300(5624):1377-8.

"Household Contact" (more like community contacts) CDC. Use of quarantine to prevent transmission of severe acute respiratory syndrome. *MMWR*, Jul. 25, 2003:680-683. [Abstract].

Hull, J., et al. "Variants of the chemokine receptor CCR5 are associated with severe bronchiolitis caused by respiratory syncytial virus." *J Infect Dis.* Sep. 15, 2003;188(6):904-7.

Hviid, A., et al. "Association between thimerosal-containing vaccine and autism." *JAMA.* Oct. 1, 2003;290(13):1763-6.

IDSA Symposium. "SARS: Global epidemiology and control." Oct. 11, 2003. [Abstract].

Komatsu, T., et al. "Molecular cloning, mRNA expression and chromosomal localization of mouse angiotensin-converting enzyme-related carboxypeptidase (mACE2)." *DNA Seq.* Aug. 2002;13(4):217-20.

Kontoyiannis, D., et al. "Aminopeptidase N inhibitors and SARS." *Lancet.* May 3, 2003;361(9368):1558.

Krueger, D., et al. "Variations in disparate regions of the murine coronavirus spike protein impact the initiation of membrane fusion." *J Virol.* Mar. 2001;75(6):2792-802.

Ksiazek, T., et al. "ELISA for the detection of antibodies to Ebola viruses." *J Infect Dis.* Feb. 1999;179 Supl 1:S192-8.

Ksiazek, T., et al. "A novel coronavirus associated with severe acute respiratory syndrome." *N Engl J Med.* May 15, 2003;348(20):Anderson 1-12.

Kubo, H, et al. "Localization of neutralizing epitopes and the receptor-binding site within the amino-terminal 330 amino acids of the murine coronavirus spike protein." *J Virol.* Sep. 1994;68(9):5403-10.

La Montagne, J., et al. "Severe acute respiratory syndrome: developing a research response." *J Infect Dis.* Feb. 15, 2004;189(4):634-41.

Langedijk, J., et al. "Identification of a conserved neutralization site in the first heptad repeat of the fusion protein of respiratory syncytial virus." *Arch Virol.* 1998;143(2):313-20.

Lee, N., et al. "A major outbreak of severe acute respiratory syndrome in Hong Kong." *N Engl J Med.* May 15, 2003;348(20):1986-94.

Leung, D., et al. "Antibody response of patients with severe acute respiratory syndrome (SARS) targets the viral nucleocapsid." *J Infect Dis.* Jul. 15, 2004;190(2):379-86.

Li, G., et al. "Profile of specific antibodies to the SARS-associated coronavirus." *N Engl J Med.* Jul. 31, 2003;349(5):508-9.

Li, W., et al. "Angiotensin-converting enzyme 2 is a functional receptor for the SARS coronavirus." 19 pages, *Unpublished Manuscript.*

Lipsitch, M., et al. "Transmission dynamics and control of severe acute respiratory syndrome." *Science.* Jun. 20, 2003;300(5627):1966-70.

Liu, I., et al. "Disease-specific B Cell epitopes for serum antibodies from patients with severe acute respiratory syndrome (SARS) and serologic detection of SARS antibodies by epitope-based peptide antigens." *J Infect Dis.* Aug. 15, 2004;190(4):797-809.

Luo, Z., et al. "Roles in cell-to-cell fusion of two conserved hydrophobic regions in the murine coronavirus spike protein." *Virology.* May 10, 1998;244(2):483-94.

MacNaughton, M. "Occurrence and frequency of coronavirus infections in humans as determined by enzyme-linked immunosorbent assay." *Infect Immun.* Nov. 1982;38(2):419-23.

MacNaughton, M., et al. "Antibody to virus components in volunteers experimentally infected with human coronavirus 229E group viruses." *Infect Immun.* Mar. 1981;31(3):845-9.

Mara, M., et al. "The genome sequence of the SARS-associated coronavirus." *Science.* May 30, 2003;300(5624):1399-404.

Marzi, A., et al. "DC-SIGN and DC-SIGNR interact with the glycoprotein of Marburg virus and the S protein of severe acute respiratory syndrome coronavirus." *J Virol.* Nov. 2004;78(21):12090-5.

McNeill, D., et al. "Health agency took swift action against SARS." Retrieved from the Internet: www.nytimes.com/2003/05/04/health/04WHO.html?th. Retrieved on May 5, 2003. 3 pages.

MSNBC News Services. "WHO raises SARS death rate." Retrieved from the Internet: www.msnbc.com/m/pt/printthis_main.asp?storyID=88563. Retrieved on May 8, 2003. 3 pages.

Mydans, S. "Halt of SARS in Vietnam could hold lessons for other nations." Retrieved from the Internet: www.nytimes.com/2003/05/07/international/asia/07viet.html?th. Retrieved on May 7, 2003. 3 pages.

Nature. "Gene-based SARS vaccine." Retrieved from the Internet: www.nature.com/nature/links/040401/040401.9.html. Retrieved on Apr. 1, 2004. 1 page.

Ng, M., et al. "Proliferative growth of SARS coronavirus in Vero E6 cells." *J Gen Virol.* Dec. 2003;84(Pt 12):3291-303.

Nichols, W.G., et al. "Community-acquired respiratory syncytial virus and parainfluenza virus infections after hematopoietic stem cell transplantation: the Fred Hutchinson Cancer Research Center experience." *Biol Blood Marrow Transplant.* 2001;7 Suppl:11S-15S.

Nicolaou, S., et al. "SARS: imaging of severe acute respiratory syndrome." *AJR Am J Roentgenol.* May 2003;180(5):1247-9.

Opstelten, DJ., et al. "Disulfide bonds in folding and transport of mouse hepatitis coronavirus glycoproteins." *J Virol.* Dec. 1993;67(12):7394-401.

OsBorne, R. "GenVec moves fast on SARS; News of contract boosts stock." *BioWorld Today* 2003 14(81)1-6.

Pang, X., et al. "Evaluation of control measures implemented in the severe acute respiratory syndrome outbreak in Beijing," 2003. *JAMA.* Dec. 24, 2003;290(24):3215-21.

Peiris, J., et al. "Severe acute respiratory syndrome." *Nat Med.* Dec. 2004;10(12 Suppl):S88-97.

Peiris, J., et al. "Clinical progression and viral load in a community outbreak of coronavirus-associated SARS pneumonia: a prospective study." Published online May 9, 2003. image.thelancet.com/extras/03art4432web.pdf. 6 pages.

Pene, F., et al. "Coronavirus 229E-related pneumonia in immunocompromised patients." *Clin Infect Dis.* Oct. 1, 2003;37(7):929-32.

Pohl-Koppe, A., et al. "Detection of human coronavirus 229E-specific antibodies using recombinant fusion proteins." *J Virol Methods.* Oct. 1995;55(2):175-83.

Pollack, A. "Persuading big business to help look for a SARS vaccine." Retrieved from the Internet: www.nytimes.com/2003/04/16/science/sciencespecial/16INDU.html?fta=y. Retrieved on Apr. 23, 2003. 3 pages.

Pollack, A. "A respiratory illness: Treatments; Intense hunt is on to find existing drug that works." Retrieved from the Internet: www.nytimes.com. Abstract. Apr. 15, 2003, 1 page.

Popova, R., et al. "The spike but not the hemagglutinin/esterase protein of bovine coronavirus is necessary and sufficient for viral infection." *Virology*. Mar. 1, 2002;294(1):222-36.

Poutanen, S., et al. "Identification of severe acute respiratory syndrome in Canada." *N Engl J Med*. May 15, 2003;348(20): Low 1-11.

Prabakaran, P., et al. "A model of the ACE2 structure and function as a SARS-CoV receptor." *Biochem Biophys Res Commun*. Jan. 30, 2004;314(1):235-41.

ProMed-Mail. "SARS—Worldwide (102): Cases." Retrieved from the Internet: www.promedmail.org/pls/askus/f?p=2400;1001:156994504080350436::NO::F2400_P1001. Retrieved on May 12, 2003, 6 pages.

Pulendran, B., et al. "Sensing pathogens and tuning-immune responses." *Science*. Jul. 13, 2001;293(5528):253-6.

Qinfen, Z., et al. "The life cycle of SARS coronavirus in Vero E6 cells." *J Med Virol*. Jul. 2004;73(3):332-7.

Qureshi, S., et al. "Toll-like receptors and their role in experimental models of microbial infection." *Genes Immun*. Mar. 2003;4(2):87-94.

Reaney, P. "All Koch's postulates now demonstrated in experiments with macaques." Retrieved from the Internet: www.nature.com/nature/links/030515/030515-2.html. 3 pages.

Reed, S. "The behaviour of recent isolates of human respiratory coronavirus in vitro and in volunteers: evidence of heterogeneity among 229E-related strains." *J Med Virol*. 1984;13(2):179-92.

Reuters. "Blood banks take SARS precautions: FDA urges new guidelines to ensure safety of blood supply." Retrieved from the Internet: www.msnbc.com/news/902214.asp. Retrieved on Apr. 23, 2003. 4 pages.

Riley, S., et al. "Transmission dynamics of the etiological agent of SARS in Hong Kong: impact of public health interventions." *Science*. Jun. 20, 2003;300(5627):1961-6.

Risco, C., et al. "Membrane protein molecules of transmissible gastroenteritis coronavirus also expose the carboxy-terminal region on the external surface to the virion." *J Virol*. Sep. 1995;69(6):5269-77.

Risco, C., et al: "The transmissible gastroenteritis coronavirus contains a spherical core shell consisting of M and N proteins." *J Virol*. Jul. 1996;70(7):4773-7.

Rota, P., et al "Characterization of a novel coronavirus associated with severe acute respiratory syndrome." *Science*. May 30, 2003;300(5624):1394-9.

Rowe, T., et al. "Macaque model for severe actue respiratory syndrome." *J Virol*. Oct. 2004;78(20):11401-4.

Rowe, T., et al. "Generation of coronavirus spike deletion variants by high-frequency recombination at regions of predicted RNA secondary structure." *J Virol*. Aug. 1997;71(8):6183-90.

Rowe, T., et al. "Evolution of mouse hepatitis virus: detection and characterization of spike deletion variants during persistent infection." *J Virol*. Apr. 1997;71(4):2959-69.

Ruan, Y., et al. "Comparative full-length genome sequence analysis of 14 SARS coronavirus isolates and common mutations associated with putative origins of infection." Published online May 9, 2003. http://image.thelancet.com/extras/03art4454web.pdf.

Sanchez, C., et al. "Targeted recombination demonstrates that the spike gene of transmissible gastroenteritis coronavirus is a determinant of its enteric tropism and virulence." *J Virol*. Sep. 1999;73(9):7607-18.

Sawyer, L. "Antibodies for the prevention and treatment of viral diseases." *Antiviral Res*. Aug. 2000;47(2):57-77.

Scales, D., et al. "Illness in Intensive care staff after brief exposure to severe acute respiratory syndrome." *Emerg Infect Dis*. Oct. 2003;9(10):1205-10.[Abstract] 1 page.

Sciencexpress Report. "Molecular evolution of the SARS coronavirus during the course of the SARSepidemic in china." Retrieved from the Internet: www.sciencexpress.org/29january2004/page1/10.1126/science.1092002.

Seto, W., et al. "Effectiveness of precautions against droplets and contact in prevention of nosocomial transmission of severe acute respiratory syndrome (SARS)." *Lancet*. May 3, 2003;361(9368):1519-20.

Shortridge. K. "SARS exposed, pandemic influenza lurks." *Lancet*. May 10, 2003;361(9369):1649.

So, L., et al. "Development of a standard treatment protocol for severe acute respiratory syndrome." *Lancet*. May 10, 2003;361(9369):1615-7.

Sola, I., et al. "Interference of coronavirus infection by expression of IgG or IgA virus neutralizing antibodies." *Coronaviruses and Arteriviruses*. Plenum Press, New York, 1998, pp. 665-674.

Stephenson, J. "Studies explore impact of new pathogens: investigators report on metapneumovirus, SARS." *JAMA*. Oct. 22, 2003;290(16):2112-5.

Subbarao, K., et al. "Prior infection and passive transfer of neutralizing antibody prevent replication of severe acute respiratory syndrome coronavirus in the respiratory tract of mice." *J Virol*. Apr. 2004;78(7):3572-7.

Sui, J., et al. "Potent neutralization of severe actue respiratory syndrome (SARS) coronavirus by a human mAb to S1 protein that blocks receptor association." *Proc Natl Acad Sci U S A*. Feb. 24, 2004;101(8):2536-41.

Suzuki, H., et al. "Analysis of the receptor-binding site of murine coronavirus spike protein." *J Virol*. Apr. 1996;70(4):2632-6.

Tan, K., et al. "Crystal structure of murine sCEACAM1a[1,4]: a coronavirus receptor in the CEA family." *EMBO J*. May 1, 2002;21(9):2076-86.

Tsai, J., et al. "The N-terminal domain of the murine coronavirus spike glycoprotein determines the CEACAM1 receptor specificity of the virus strain." *J Virol*. Jan. 2003;77(2):841-50.

Tsang, K., et al. "A cluster of cases of severe acute respiratory syndrome in Hong Kong." *N Engl J Med*. May 15, 2003;348(20):1977-85.

Tso, E., et al. "Natural course of severe acute respiratory syndrome-associated coronavirus immunoglobulin after infection." *J Infect Dis*. Nov. 1, 2004;190(9):1706-7; author reply 1707.

Varia, M., et al. "Investigation of a nosocomial outbreak of severe acute respiratory syndrome (SARS) in Toronto, Canada." *CMAJ*. Aug. 19, 2003;169(4):285-92.[Abstract].

Vennema, H., et al. "Intracellular transport of recombinant coronavirus spike proteins: implications for virus assembly." *J Virol*. Jan. 1990;64(1):339-46.

Weingartl, H., et al. "Immunization with modified vaccinia virus Ankara-based recombinant vaccine against severe acute respiratory syndrome is associated with enhanced hepatitis in ferrets." *J Virol*. Nov. 2004;78(22):12672-6.

Whimbey, E.; et al. "Community respiratory virus infections among hospitalized adult bone marrow transplant recipients." *Clin Infect Dis*. May 1996;22(5):778-82.

Wong, K., et al. "Thin-section CT of severe acute respiratory syndrome: evaluation of 73 patients exposed to or with the disease." *Radiology*. Aug. 2003;228(2):395-400.

World Health Organization. "WHO SARS scientific research advisory committee concludes its first meeting." Retrieved from the Internet: www.who.int/csr/sars/archive/research/en/print.html. Retrieved on Apr. 5, 2005. 4 pages.

World Health Organization. "Consensus document on the edpidemiology of severe acute respiratory syndrome (SARS)." Department of Communicable Disease Surveillance and Response, May 16-17, 2003, 44 pages.

World Health Organization. "WHO global scientific meeting on severe acute respiratory syndrome (SARS) WHO Geneva, Jun. 17-18, 2003." Retrieved from the Internet: www.who.int/csr/sars/meeting2003_15_04/en/print.html. 1 page.

World Health Organization. "Areas with recent local transmission of severe acute respiratory syndrome (SARS)." Retrieved from the Internet: www.who.int/csr/sarsareas/2003_05_06/en/. Retrieved on May 7, 2003. 5 pages.

Xiao, X., et al. "The SARS-CoV S glycoprotein: expression and functional characterization." *Biochem Biophys Res Commun*. Dec. 26, 2003;312(4):1159-64.

Yan, H., et al. "SARS coronavirus induces apoptosis in Vero E6 cells." *J Med Virol.* Jul. 2004;73(3):323-31.

Yang, Z., et al. "Evasion of antibody neutralization in emerging severe acute respiratory syndrome coronaviruses." *Proc Natl Acad Sci U S A.* Jan. 18, 2005;102(3):797-801.

Yang, Z., et al. "A DNA vaccine induces SARS coronavirus neutralization and protective immunity in mice." *Nature.* Apr. 1, 2004;428(6982):561-4.

Yang, Z., et al. "pH-dependent entry of severe acute respiratory syndrome coronavirus is mediated by the spike glycoprotein and enhanced by dendritic cell transfer through DC-SIGN." *J Virol.* Jun. 2004;78(11):5642-50.

Yao, Y., et al. "Cleavage and serum reactivity of the severe acute respiratory syndrome coronavirus spike protein." *J Infect Dis.* Jul. 1, 2004;190(1):91-8.

Yeager, C., et al. "Human aminopeptidase N is a receptor for human coronavirus 229E." *Nature.* Jun. 4, 1992;357(6377):420-2.

Yoo, D., et al. "A single amino acid change within antigenic domain II of the spike protein of bovine coronavirus confers resistance to virus neutralization." *Clin Diagn Lab Immunol.* Mar. 2001;8(2):297-302.

Zelus, B., et al. "Conformational changes in the spike glycoprotein of murine coronavirus are induced at 37 degrees C either by soluble murine CEACAM1 receptors or by pH 8." *J Virol.* Jan. 2003;77(2):830-40.

Zhong, M., et al. "Epidemiology and cause of severe acute respiratory syndrome (SARS) in Guangdong, People's Republic of China, in Feb. 2003." *Lancet.* Oct. 25, 2003;362(9393):1353-8.

Zinkernagel, R., et al. "Regulation of the immune response by antigen." *Science.* Jul. 13, 2001;293(5528):251-3.

Bradel-Tretheway, B.G. et al, "Effects of condon-optimization on protein expression by the human herpesvirus 6 and 7 U51 open reading frame," *J. Virol. Method.* vol. 111(2):145-156 (2003).

Haas, Jürgen et al, "Codon usage limitation in the expression of HIV-1 envelope glycoprotein," *Current Biology.* vol. 6(3):315-324 (1996).

Kieny, Marie-Paule, "SARS Vaccine Development," WHO Global Conference of Severe Acute Respiratory Syndrome (SARS), Jun. 17, 2003, retrieved online at www.who.int/csr/sars/conference/june_2003/materials/presentations/vaccinedevelopment.pdf.

International Search Report for Application No. PCT/US04/25321, dated Feb. 7, 2006.

* cited by examiner

FIG. 1A

Nucleotides 1-3570 correspond to SEQ ID NO:1
Amino acids 1-1190 correspond to SEQ ID NO:2
Nucleotides 1-1050 correspond to SEQ ID NO:3
Amino acids 1-350 correspond to SEQ ID NO:4

```
DNA: ATGTTCATCTTCCTGCTGTTCCTGACCCTGACCTCCGGCTCCGACCTGGAC
 +1: M  F  I  F  L  L  F  L  T  L  T  S  G  S  D  L  D

DNA: CGCTGCACCACCTTCGACGACGTGCAGGCTCCTAACTACACCCAGCACACC
 +1: R  C  T  T  F  D  D  V  Q  A  P  N  Y  T  Q  H  T

DNA: TCCTCCATGCGCGGCGTGTACTACCCTGACGAGATCTTCCGCTCCGACACC
 +1: S  S  M  R  G  V  Y  Y  P  D  E  I  F  R  S  D  T

DNA: CTGTACCTGACCCAGGACCTGTTCCTGCCCTTCTACTCCAACGTGACCGGC
 +1: L  Y  L  T  Q  D  L  F  L  P  F  Y  S  N  V  T  G

DNA: TTCCACACCATCAACCACACCTTCGGCAATCCCGTGATTCCCTTCAAGGAC
 +1: F  H  T  I  N  H  T  F  G  N  P  V  I  P  F  K  D

DNA: GGCATCTACTTCGCCGCCACCGAGAAGTCCAACGTGGTGCGCGGCTGGGTG
 +1: G  I  Y  F  A  A  T  E  K  S  N  V  V  R  G  W  V

DNA: TTCGGCTCCACCATGAACAACAAGTCCCAGTCCGTGATCATCATCAACAAC
 +1: F  G  S  T  M  N  N  K  S  Q  S  V  I  I  I  N  N

DNA: TCCACCAACGTGGTGATCCGCGCCTGCAACTTCGAGCTGTGCGACAATCCC
 +1: S  T  N  V  V  I  R  A  C  N  F  E  L  C  D  N  P

DNA: TTCTTCGCCGTGTCCAAGCCCATGGGCACCCAGACCCACACCATGATCTTC
 +1: F  F  A  V  S  K  P  M  G  T  Q  T  H  T  M  I  F

DNA: GACAACGCCTTCAACTGCACCTTCGAGTACATCTCCGACGCCTTCTCCCTG
 +1: D  N  A  F  N  C  T  F  E  Y  I  S  D  A  F  S  L

DNA: GACGTGTCCGAGAAGTCCGGCAACTTCAAGCACCTGCGCGAGTTCGTGTTC
 +1: D  V  S  E  K  S  G  N  F  K  H  L  R  E  F  V  F

DNA: AAGAACAAGGACGGCTTCCTGTACGTGTACAAGGGCTACCAGCCCATCGAC
 +1: K  N  K  D  G  F  L  Y  V  Y  K  G  Y  Q  P  I  D

DNA: GTGGTGCGCGACCTGCCCTCCGGCTTCAACACCCTGAAGCCCATCTTCAAG
 +1: V  V  R  D  L  P  S  G  F  N  T  L  K  P  I  F  K

DNA: CTGCCTCTGGGCATCAACATTACCAACTTCCGCGCCATTCTGACCGCCTTC
 +1: L  P  L  G  I  N  I  T  N  F  R  A  I  L  T  A  F

DNA: TCTCCCGCCCAGGACATCTGGGGCACCTCCGCCGCCGCCTACTTCGTGGGC
 +1: S  P  A  Q  D  I  W  G  T  S  A  A  A  Y  F  V  G

DNA: TACCTGAAGCCCACCACCTTCATGCTGAAGTACGACGAGAACGGCACCATT
 +1: Y  L  K  P  T  T  F  M  L  K  Y  D  E  N  G  T  I
```

FIG. 1B

```
DNA: ACCGACGCCGTGGACTGCTCCCAGAACCCTCTGGCCGAGCTGAAGTGCTCC
 +1:  T  D  A  V  D  C  S  Q  N  P  L  A  E  L  K  C  S

DNA: GTGAAGTCCTTCGAGATTGACAAGGGCATTTACCAGACCTCCAACTTCCGC
 +1:  V  K  S  F  E  I  D  K  G  I  Y  Q  T  S  N  F  R

DNA: GTGGTGCCCTCCGGCGACGTGGTGCGCTTTCCCAACATTACCAACCTGTGT
 +1:  V  V  P  S  G  D  V  V  R  F  P  N  I  T  N  L  C

DNA: CCCTTCGGCGAGGTGTTCAACGCCACCAAGTTTCCCTCCGTGTACGCCTGG
 +1:  P  F  G  E  V  F  N  A  T  K  F  P  S  V  Y  A  W

DNA: GAGCGCAAGAAGATTTCCAACTGCGTGGCCGACTACTCCGTGCTGTACAAC
 +1:  E  R  K  K  I  S  N  C  V  A  D  Y  S  V  L  Y  N

DNA: TCCACCTTCTTCTCCACCTTCAAGTGCTACGGCGTGTCCGCCACCAAGCTG
 +1:  S  T  F  F  S  T  F  K  C  Y  G  V  S  A  T  K  L

DNA: AACGATCTGTGCTTCTCCAACGTGTACGCCGACTCCTTCGTGGTGAAGGGC
 +1:  N  D  L  C  F  S  N  V  Y  A  D  S  F  V  V  K  G

DNA: GATGATGTGCGCCAGATTGCTCCCGGCCAGACCGGCGTGATTGCCGATTAC
 +1:  D  D  V  R  Q  I  A  P  G  Q  T  G  V  I  A  D  Y

DNA: AACTACAAGCTGCCCGATGATTTCATGGGCTGCGTGCTGGCCTGGAACACC
 +1:  N  Y  K  L  P  D  D  F  M  G  C  V  L  A  W  N  T

DNA: CGCAACATTGATGCCACCTCCACCGGCAACTACAACTACAAGTACCGCTAC
 +1:  R  N  I  D  A  T  S  T  G  N  Y  N  Y  K  Y  R  Y

DNA: CTGCGCCACGGCAAGCTGCGTCCCTTCGAGCGCGATATTTCCAACGTGCCC
 +1:  L  R  H  G  K  L  R  P  F  E  R  D  I  S  N  V  P

DNA: TTCTCtCCCGATGGCAAGCCCTGCACTCCTCCCGCCCTGAACTGCTACTGG
 +1:  F  S  P  D  G  K  P  C  T  P  P  A  L  N  C  Y  W

DNA: CCTCTGAACGATTACGGCTTCTACACCACCACCGGCATTGGCTACCAGCCC
 +1:  P  L  N  D  Y  G  F  Y  T  T  T  G  I  G  Y  Q  P

DNA: TACCGCGTGGTGGTGCTGTCCTTCGAGCTGCTGAACGCTCCCGCCACCGTG
 +1:  Y  R  V  V  V  L  S  F  E  L  L  N  A  P  A  T  V

DNA: TGCGGTCCCAAGCTGTCCACCGATCTGATTAAGAACCAGTGCGTGAACTTC
 +1:  C  G  P  K  L  S  T  D  L  I  K  N  Q  C  V  N  F

DNA: AACTTCAACGGCCTGACCGGCACCGGCGTGCTGACTCCCTCCTCCAAGCGC
 +1:  N  F  N  G  L  T  G  T  G  V  L  T  P  S  S  K  R

DNA: TTCCAGCCCTTCCAGCAGTTCGGCCGCGATGTGTCCGATTTCACCGATTCC
 +1:  F  Q  P  F  Q  Q  F  G  R  D  V  S  D  F  T  D  S
```

FIG. 1C

```
DNA: GTGCGCGATCCCAAGACCTCCGAGATTCTGGATATTTCTCCCTGCGCCTTC
 +1:  V  R  D  P  K  T  S  E  I  L  D  I  S  P  C  A  F

DNA: GGCGGCGTGTCCGTGATTACTCCCGGCACCAACGCCTCCTCCGAGGTGGCC
 +1:  G  G  V  S  V  I  T  P  G  T  N  A  S  S  E  V  A

DNA: GTGCTGTACCAGGATGTGAACTGCACCGATGTGTCCACCGCCATTCACGCC
 +1:  V  L  Y  Q  D  V  N  C  T  D  V  S  T  A  I  H  A

DNA: GATCAGCTGACTCCCGCCTGGCGCATTTACTCCACCGGCAACAACGTGTTC
 +1:  D  Q  L  T  P  A  W  R  I  Y  S  T  G  N  N  V  F

DNA: CAGACCCAGGCCGGCTGCCTGATTGGCGCCGAGCACGTGGATACCTCCTAC
 +1:  Q  T  Q  A  G  C  L  I  G  A  E  H  V  D  T  S  Y

DNA: GAGTGCGATATTCCCATTGGCGCCGGCATTTGCGCCTCCTACCACACCGTG
 +1:  E  C  D  I  P  I  G  A  G  I  C  A  S  Y  H  T  V

DNA: TCCCTGCTGCGCTCCACCTCCCAGAAGTCCATTGTGGCCTACACCATGTCC
 +1:  S  L  L  R  S  T  S  Q  K  S  I  V  A  Y  T  M  S

DNA: CTGGGCGCCGATTCCTCCATTGCCTACTCCAACAACACCATTGCCATTCCC
 +1:  L  G  A  D  S  S  I  A  Y  S  N  N  T  I  A  I  P

DNA: ACCAACTTCTCCATTTCCATTACCACCGAGGTGATGCCCGTGTCCATGGCC
 +1:  T  N  F  S  I  S  I  T  T  E  V  M  P  V  S  M  A

DNA: AAGACCTCCGTGGATTGCAACATGTACATTTGCGGCGATTCCACCGAGTGC
 +1:  K  T  S  V  D  C  N  M  Y  I  C  G  D  S  T  E  C

DNA: GCCAACCTGCTGCTGCAGTACGGCTCCTTCTGCACCCAGCTGAACCGCGCC
 +1:  A  N  L  L  L  Q  Y  G  S  F  C  T  Q  L  N  R  A

DNA: CTGTCCGGCATTGCCGCCGAGCAGGATCGCAACACCCGCGAGGTGTTCGCC
 +1:  L  S  G  I  A  A  E  Q  D  R  N  T  R  E  V  F  A

DNA: CAGGTGAAGCAGATGTACAAGACTCCCACCCTGAAGTACTTCGGCGGCTTC
 +1:  Q  V  K  Q  M  Y  K  T  P  T  L  K  Y  F  G  G  F

DNA: AACTTCTCCCAGATTCTGCCCGATCCTCTGAAGCCCACCAAGCGCTCCTTC
 +1:  N  F  S  Q  I  L  P  D  P  L  K  P  T  K  R  S  F

DNA: ATTGAGGATCTGCTGTTCAACAAGGTGACCCTGGCCGATGCCGGCTTCATG
 +1:  I  E  D  L  L  F  N  K  V  T  L  A  D  A  G  F  M

DNA: AAGCAGTACGGCGAGTGCCTGGGCGATATTAACGCCCGCGATCTGATTTGC
 +1:  K  Q  Y  G  E  C  L  G  D  I  N  A  R  D  L  I  C

DNA: GCGCAGAAGTTCAACGGCCTGACCGTGCTGCCTCCTCTGCTGACCGATGAT
 +1:  A  Q  K  F  N  G  L  T  V  L  P  P  L  L  T  D  D
```

FIG. 1D

```
DNA: ATGATTGCGGCGTACACCGCGGCGCTGGTGTCCGGCACCGCCACCGCGGGC
 +1: M   I   A   A   Y   T   A   A   L   V   S   G   T   A   T   A   G

DNA: TGGACCTTCGGCGCGGGCGCGGCGCTGCAGATTCCCTTCGCGATGCAGATG
 +1: W   T   F   G   A   G   A   A   L   Q   I   P   F   A   M   Q   M

DNA: GCGTACCGCTTCAACGGCATTGGCGTGACCCAGAACGTGCTGTACGAGAAC
 +1: A   Y   R   F   N   G   I   G   V   T   Q   N   V   L   Y   E   N

DNA: CAGAAGCAGATTGCGAACCAGTTCAACAAGGCGATTTCCCAGATTCAGGAG
 +1: Q   K   Q   I   A   N   Q   F   N   K   A   I   S   Q   I   Q   E

DNA: TCCCTGACCACCACCTCCACCGCGCTGGGCAAGCTGCAGGATGTGGTGAAC
 +1: S   L   T   T   T   S   T   A   L   G   K   L   Q   D   V   V   N

DNA: CAGAACGCGCAGGCGCTGAACACCCTGGTGAAGCAGCTGTCCTCCAACTTC
 +1: Q   N   A   Q   A   L   N   T   L   V   K   Q   L   S   S   N   F

DNA: GGCGCGATTTCCTCCGTGCTGAACGATATTCTGTCCCGCCTGGATAAGGTG
 +1: G   A   I   S   S   V   L   N   D   I   L   S   R   L   D   K   V

DNA: GAGGCGGAGGTGCAGATTGATCGCCTGATTACCGGCCGCCTGCAGTCCCTG
 +1: E   A   E   V   Q   I   D   R   L   I   T   G   R   L   Q   S   L

DNA: CAGACCTACGTGACCCAGCAGCTGATTCGCGCGGCGGAGATTCGCGCGTCC
 +1: Q   T   Y   V   T   Q   Q   L   I   R   A   A   E   I   R   A   S

DNA: GCGAACCTGGCGGCGACCAAGATGTCCGAGTGCGTGCTGGGCCAGTCCAAG
 +1: A   N   L   A   A   T   K   M   S   E   C   V   L   G   Q   S   K

DNA: CGCGTGGATTTCTGCGGCAAGGGCTACCACCTGATGTCCTTCCCTCAGGCG
 +1: R   V   D   F   C   G   K   G   Y   H   L   M   S   F   P   Q   A

DNA: GCGCCtCATGGCGTGGTGTTCCTGCACGTGACCTACGTGCCCTCCCAGGAG
 +1: A   P   H   G   V   V   F   L   H   V   T   Y   V   P   S   Q   E

DNA: CGCAACTTCACCACCGCGCCCGCGATTTGCCACGAGGGCAAGGCGTACTTC
 +1: R   N   F   T   T   A   P   A   I   C   H   E   G   K   A   Y   F

DNA: CCTCGCGAGGGCGTGTTCGTGTTCAACGGCACCTCCTGGTTCATTACCCAG
 +1: P   R   E   G   V   F   V   F   N   G   T   S   W   F   I   T   Q

DNA: CGCAACTTCTTCTCTCCTCAGATTATTACCACCGATAACACCTTCGTGTCC
 +1: R   N   F   F   S   P   Q   I   I   T   T   D   N   T   F   V   S

DNA: GGCAACTGCGATGTGGTGATTGGCATTATTAACAACACCGTGTACGATCCt
 +1: G   N   C   D   V   V   I   G   I   I   N   N   T   V   Y   D   P
```

FIG. 1E

```
DNA: CTGCAGCCCGAGCTGGATTCCTTCAAGGAGGAGCTGGATAAGTACTTCAAG
 +1: L  Q  P  E  L  D  S  F  K  E  E  L  D  K  Y  F  K

DNA: AACCACACCTCTCCCGATGTGGATCTGGGCGATATTTCCGGCATTAACGCC
 +1: N  H  T  S  P  D  V  D  L  G  D  I  S  G  I  N  A

DNA: TCCGTGGTGAACATTCAGAAGGAGATTGATCGCCTGAACGAGGTGGCCAAG
 +1: S  V  V  N  I  Q  K  E  I  D  R  L  N  E  V  A  K

DNA: AACCTGAACGAGTCCCTGATTGATCTGCAGGAGCTGGGCAAGTACGAGCAG
 +1: N  L  N  E  S  L  I  D  L  Q  E  L  G  K  Y  E  Q

DNA: TACATTAAGTGGCCCTGGTACGTGTGGCTGGGCTTCATTGCCGGCCTGATT
 +1: Y  I  K  W  P  W  Y  V  W  L  G  F  I  A  G  L  I

DNA: GCCATTGTGATGGTGACCATTCTGCTGTGCTGCATGACCTCCTGCTGCTCC
 +1: A  I  V  M  V  T  I  L  L  C  C  M  T  S  C  C  S

DNA: TGCCTGAAGGGCGCCTGCTCCTGCGGCTCCTGCTGCAAGTTCGATGAGGAT
 +1: C  L  K  G  A  C  S  C  G  S  C  C  K  F  D  E  D

DNA: GATTCCGAGCCCGTGCTGAAGGGCGTGAAGCTGCACTACACCTAA    (SEQ ID NO:22)
 +1: D  S  E  P  V  L  K  G  V  K  L  H  Y  T  *     (SEQ ID NO:23)
```

FIG. 2A

Query = Codon Optimized version
Sbjct = Native sequence
74% identical

```
Query:   1   atgttcatcttcctgctgttcctgaccctgacctccggctcc    42
             ||| || || |||  |  ||| | || || ||      ||
Sbjct:   1   atgtttattttcttattatttcttactctcactagtggtagt    42

Query:  43   gacctggaccgctgcaccaccttcgacgacgtgcaggctcctaactacacccagcacacc   102
             |||||  |||||  |||||||||| || || || || || ||||||||| ||||| || ||
Sbjct:  43   gaccttgaccggtgcaccactttt gatgatgttcaagctcctaattacactcaacatact   102

Query: 103   tcctccatgcgcggcgtgtactaccctgacgagatcttccgctccgacaccctgtacctg   162
             || || ||| | || || ||||| |||||  ||  || | || ||||| || || |
Sbjct: 103   tcatctatgagggggggtttactatcctgatgaaattttt agatcagacactctttattta   162

Query: 163   acccaggacctgttcctgcccttctactccaacgtgaccggcttccacaccatcaaccac   222
             || |||||  | || || || || || || || || || || || || || || || ||
Sbjct: 163   actcaggatttatttcttccatttt attctaatgttacagggtttcatactattaatcat   222

Query: 223   accttcggcaatcccgtgattcccttcaaggacggcatctacttcgccgccaccgagaag   282
             || || |||||| || || || || || ||||| || || || || || || ||||| |||||
Sbjct: 223   acgtttggcaaccctgtcatacctttt aaggatggtatttatttt gctgccacagagaaa   282

Query: 283   tccaacgtggtgcgcggctgggtgttcggctccaccatgaacaacaagtcccagtccgtg   342
             ||  | || || || || |||||  || || || |||||||||||||||||  || || |||
Sbjct: 283   tcaaatgttgtccgtggttgggttttt ggttctaccatgaacaacaagtcacagtcggtg   342

Query: 343   atcatcatcaacaactccaccaacgtggtgatccgcgcctgcaacttcgagctgtgcgac   402
             || || ||  |||| || || || |||| || || || || ||||| ||  |||| ||
Sbjct: 343   attattattaacaattctactaatgttgttatacgagcatgtaactttgaattgtgtgac   402

Query: 403   aatcccttcttcgccgtgtccaagcccatgggcacccagacccacaccatgatcttcgac   462
             || || |||||| || || || || |||||||| || ||||| || || || ||||| |||||
Sbjct: 403   aacccttt ctttgctgtttctaaacccatgggtacacagacacatactatgatattcgat   462

Query: 463   aacgccttcaactgcaccttcgagtacatctccgacgccttctccctggacgtgtccgag   522
             || || || || || || |||||  |||||||||| || || || || || || || ||
Sbjct: 463   aatgcatttaattgcactttcgagtacatatctgatgccttttcgcttgatgtttcagaa   522
```

FIG. 2B

```
Query: 523   aagtccggcaacttcaagcacctgcgcgagttcgtgttcaagaacaaggacggcttcctg 582
             ||||| || || || || ||| | || ||||| ||||| || || || || || || ||
Sbjct: 523   aagtcaggtaattttaaacacttacgagagtttgtgtttaaaaataaagatgggtttctc 582

Query: 583   tacgtgtacaagggctaccagcccatcgacgtggtgcgcgacctgccctccggcttcaac 642
             || || || ||||||||| || || || || || || || ||| || || || || |||
Sbjct: 583   tatgtttataagggctatcaacctatagatgtagttcgtgatctaccttctggttttaac 642

Query: 643   accctgaagcccatcttcaagctgcctctgggcatcaacattaccaacttccgcgccatt 702
             || |||| || || || ||| ||||||| || || |||||||| || | ||||||
Sbjct: 643   actttgaaacctattttaagttgcctcttggtattaacattacaaattttagagccatt 702

Query: 703   ctgaccgccttctctcccgcccaggacatctgggcacctccgccgccgcctacttcgtg 762
             || || |||||| || || || ||||| ||||||||| || || || ||||| || ||
Sbjct: 703   cttacagccttttcacctgctcaagacatttggggcacgtcagctgcagcctattttgtt 762

Query: 763   ggctacctgaagcccaccaccttcatgctgaagtacgacgagaacggcaccattaccgac 822
             |||||   | ||||| || || || ||||| ||||| || || || || || || || ||
Sbjct: 763   ggctatttaaagccaactacatttatgctcaagtatgatgaaaatggtacaatcacagat 822

Query: 823   gccgtggactgctcccagaaccctctggccgagctgaagtgctccgtgaagtccttcgag 882
             || || || || || || || || || || || ||||| || ||| ||| ||| |||
Sbjct: 823   gctgttgattgttctcaaaatccacttgctgaactcaaatgctctgttaagagctttgag 882

Query: 883   attgacaagggcatttaccagacctccaacttccgcgtggtgccctccggcgacgtggtg 942
             |||||||| || |||||||||||||| || ||| | || || ||||| || || || |||
Sbjct: 883   attgacaaaggaatttaccagacctctaatttcagggttgttccctcaggagatgttgtg 942

Query: 943   cgctttcccaacattaccaacctgtgtcccttcggcgaggtgttcaacgccaccaagttt 1002
             | || || || |||||  ||| |||||| || |||||  || || || || || || ||
Sbjct: 943   agattccctaatattacaaacttgtgtccttttggagaggttttaatgctactaaattc 1002

Query: 1003  ccctccgtgtacgcctgggagcgcaagaagatttccaactgcgtggccgactactccgtg 1062
             || || || || || |||||| | || || || || |||| || || || ||||| |||
Sbjct: 1003  ccttctgtctatgcatgggagagaaaaaaaatttctaattgtgttgctgattactctgtg 1062

Query: 1063  ctgtacaactccaccttcttctccaccttcaagtgctatggcgtatctgccaccaagctg 1122
             || ||||||||| || |||||| ||||| ||||||||||||||| |||||||| || ||
Sbjct: 1063  ctctacaactcaacattttttcaaccttttaagtgctatggcgtttctgccactaagttg 1122
```

FIG. 2C

```
Query: 1123 aacgatctttgcttctccaacgtgtacgctgactccttcgtggtgaaaggtgatgatgtt 1182
             || |||||||||||||||| || || || || || || || || || || ||||||||
Sbjct: 1123 aatgatctttgcttctccaatgtctatgcagattcttttgtagtcaagggagatgatgta 1182

Query: 1183 cgtcagattgctcctggtcagactggtgtgattgctgattacaactacaagctgcctgat 1242
             | || || || || || || |||||||| |||||||||| || || ||   |||| |||
Sbjct: 1183 agacaaatagcgccaggacaaactggtgttattgctgattataattataaattgccagat 1242

Query: 1243 gatttcatggggttgcgtgctggcttggaacactcgtaacattgatgctacctccactggt 1302
             |||||||||||||| || || |||||||||  ||| | ||||||||||||| || ||||||
Sbjct: 1243 gatttcatggggttgtgtccttgcttggaatactaggaacattgatgctacttcaactggt 1302

Query: 1303 aactacaactacaagtatcgttacctgcgtcatggtaagctgcgtcctttcgagcgtgat 1362
             || || || || || ||| ||| | ||| ||||| ||||| || || || ||| | ||
Sbjct: 1303 aattataattataaatataggtatcttagacatggcaagcttaggccctttgagagagac 1362

Query: 1363 atttccaacgtgcctttctctcctgatggcaagccttgcactcctccagctctgaactgc 1422
             || || || |||||||||||  |||||||||| ||||||||| ||  || || ||  ||
Sbjct: 1363 atatctaatgtgcctttctccctgatggcaaaccttgcaccccacctgctcttaattgt 1422

Query: 1423 tactggcctctgaacgattacggtttctacaccactaccggcattggctaccagccttat 1482
             |  |||||  | || |||||| |||||||||||||||| ||||||||||||| ||||| 
Sbjct: 1423 tattggccattaaatgattatggttttacaccactactggcattggctaccaaccttac 1482

Query: 1483 cgtgtggttgtgctgtctttcgagctgctgaacgctcctgctaccgtgtgcggtcctaag 1542
             |  || || || |||| || || || |  ||| ||   |  || || || || ||  ||
Sbjct: 1483 agagttgtagtactttcttttgaacttttaaatgcaccggccacggtttgtggaccaaaa 1542

Query: 1543 ctgtctaccgatctgattaagaaccagtgcgtgaacttcaacttcaacggcctgaccggc 1602
             | ||  | || || || ||||||||||||| || |||  || ||  || |||| ||||
Sbjct: 1543 ttatccactgaccttattaagaaccagtgtgtcaattttaattttaatggactcactggt 1602

Query: 1603 accggcgtgctgactccctcctccaagcgcttccagcccttccagcagttcggccgcgat 1662
             || || ||| | || || || ||  || || || || || || || || |||| |||
Sbjct: 1603 actggtgtgttaactccttcttcaaagagatttcaaccatttcaacaatttggccgtgat 1662

Query:  1663 gtgtccgatttcaccgattccgtgcgcgatcccaagacctccgagattctggatatttct 1722
              || || |||||||| |||||||| || || || |||| || || || || | || |||||
Sbjct: 1663 gtttctgatttcactgattccgttcgagatcctaaaacatctgaaatattagacatttca 1722

Query: 1723 ccctgcgccttcggcggcgtgtccgtgattactcccggcaccaacgcctcctccgaggtg 1782
             || |||||| || || || ||    || |||||| || || || || || || || ||
Sbjct: 1723 ccttgcgcttttgggggtgtaagtgtaattacacctggaacaaatgcttcatctgaagtt 1782
```

FIG. 2D

```
Query: 1783 gccgtgctgtaccaggatgtgaactgcaccgatgtgtccaccgccattcacgccgatcag 1842
              ||  ||  ||  ||  || |||||  ||||||||  |||||  || || ||  ||||| || |||||
Sbjct: 1783 gctgttctatatcaagatgttaactgcactgatgtttctacagcaattcatgcagatcaa 1842

Query: 1843 ctgactcccgcctggcgcatttactccaccggcaacaacgtgttccagacccaggccggc 1902
              || ||  ||  ||  |||||||| ||  || || || |||||  || |||||||||  ||  || |||
Sbjct: 1843 ctcacaccagcttggcgcatatattctactggaaacaatgtattccagactcaagcaggc 1902

Query: 1903 tgcctgattggcgccgagcacgtggatacctcctacgagtgcgatattcccattggcgcc 1962
              || || || ||  ||  || |||||  || || || || ||  || ||||||||  ||||| ||||| ||
Sbjct: 1903 tgtcttataggagctgagcatgtcgacacttcttatgagtgcgacattcctattggagct 1962

Query: 1963 ggcatttgcgcctcctaccacaccgtgtccctgctgcgctccacctcccagaagtccatt 2022
              ||||||||  ||       |||||  ||  || ||   | ||    ||       ||| || || |||
Sbjct: 1963 ggcatttgtgctagttaccatacagtttctttattacgtagtactagccaaaaatctatt 2022

Query: 2023 gtggcctacaccatgtccctgggcgccgattcctccattgcctactccaacaacaccatt 2082
              |||||  || || || |||||  |  || || ||      || |||| ||||| || |||||||||
Sbjct: 2023 gtggcttatactatgtctttaggtgctgatagttcaattgcttactctaataacaccatt 2082

Query: 2083 gccattcccaccaacttctccatttccattaccaccgaggtgatgcccgtgtccatggcc 2142
              ||  ||  ||  ||  ||||| ||  |||  ||||||| ||  ||  ||  |||||  ||  || |||||
Sbjct: 2083 gctatacctactaacttttcaattagcattactacagaagtaatgcctgtttctatggct 2142

Query: 2143 aagacctccgtggattgcaacatgtacatttgcggcgattccaccgagtgcgccaacctg 2202
              ||  ||||||||| ||||| ||  || ||||||||| ||||| ||||| ||||| ||  || ||  ||
Sbjct: 2143 aaaacctccgtagattgtaatatgtacatctgcggagattctactgaatgtgctaatttg 2202

Query: 2203 ctgctgcagtacggctccttctgcacccagctgaaccgcgccctgtccggcattgccgcc 2262
              ||  || || || ||      ||| |||||  || || ?| || || || || ||  ||||| ||
Sbjct: 2203 cttctccaatatggtagcttttgcacacaactaaatcgtgcactctcaggtattgctgct 2262

Query: 2263 gagcaggatcgcaacacccgcgaggtgttcgcccaggtgaagcagatgtacaagactccc 2322
              ||  |||||||||||||| ||  || |||||||| ||  || || || || ||||||||  ||  ||
Sbjct: 2263 gaacaggatcgcaacacacgtgaagtgttcgctcaagtcaaacaaatgtacaaacccca 2322

Query: 2323 accctgaagtacttcggcggcttcaacttctcccagattctgcccgatcctctgaagccc 2382
              ||  ||||  || || || ||  || || || || || || || ||  ||  || ||||| ||||
Sbjct: 2323 actttgaaatattttggtggttttaattttcacaaatattacctgaccctctaaagcca 2382

Query: 2383 accaagcgctccttcattgaggatctgctgttcaacaaggtgaccctggccgatgccggc 2442
              || ||| |  ||  || |||||||||  ||| || || ||||||||  || || ||||| |||
Sbjct: 2383 actaagaggtcttttattgaggacttgctcttaataaggtgacactcgctgatgctggc 2442

Query: 2443 ttcatgaagcagtacggcgagtgcctgggcgatattaacgcccgcgatctgatttgcgcg 2502
              |||||||||||  || |||||  ||||| || |||||||||  || |  |||| ||||| |||
Sbjct: 2443 ttcatgaagcaatatggcgaatgcctaggtgatattaatgctagagatctcatttgtgcg 2502
```

FIG. 2E

```
Query:  2503  cagaagttcaacggcctgaccgtgctgcctcctctgctgaccgatgatatgattgcggcg  2562
              ||||||||||  ||  ||  ||  |||  ||||  ||||||||||  ||  ||||||||||||||||  ||
Sbjct:  2503  cagaagttcaatggacttacagtgttgccacctctgctcactgatgatatgattgctgcc  2562

Query:  2563  tacaccgcggcgctggtgtccggcaccgccaccgcgggctggaccttcggcgcgggcgcg  2622
              |||||  ||  ||  ||  ||        ||  ||  |||||  ||  ||  |||||  ||  ||  ||  |||||
Sbjct:  2563  tacactgctgctctagttagtggtactgccactgctggatggacatttggtgctggcgct  2622

Query:  2623  gcgctgcagattcccttcgcgatgcagatggcgtaccgcttcaacggcattggcgtgacc  2682
              ||  ||  ||  ||  ||  ||  ||  |||||  |||||  ||   |  |||||  ||||||||||  ||  |||
Sbjct:  2623  gctcttcaaataccttttgctatgcaaatggcatataggttcaatggcattggagttacc  2682

Query:  2683  cagaacgtgctgtacgagaaccagaagcagattgcgaaccagttcaacaaggcgatttcc  2742
              ||  ||  ||  ||  ||  ||  |||||||||  ||  ||  ||  ||  |||||  ||  ||||||||||||
Sbjct:  2683  caaaatgttctctatgagaaccaaaaacaaatcgccaaccaatttaacaaggcgattagt  2742

Query:  2743  cagattcaggagtccctgaccaccacctccaccgcgctgggcaagctgcaggatgtggtg  2802
              ||  |||||  ||  ||  ||  ||  ||  ||  ||  ||   ||||||||||||  ||  ||
Sbjct:  2743  caaattcaagaatcacttacaacaacatcaactgcattgggcaagctgcaagacgttgtt  2802

Query:  2803  aaccagaacgcgcaggcgctgaacaccctggtgaagcagctgtcctccaacttcggcgcg  2862
              ||||||||  ||  ||  ||   |  |||||  ||  ||  ||  ||  ||     |||  ||  ||  ||  ||
Sbjct:  2803  aaccagaatgctcaagcattaaacacacttgttaaacaacttagctctaattttggtgca  2862

Query:  2863  atttcctccgtgctgaacgatattctgtcccgcctggataaggtggaggcggaggtgcag  2922
              |||||     |||||  ||  ||||||  ||  ||  ||  ||  |||||  ||  ||||||||||||  ||
Sbjct:  2863  atttcaagtgtgctaaatgatatccttt cgcgacttgataaagtcgaggcggaggtacaa  2922

Query:  2923  attgatcgcctgattaccggccgcctgcagtccctgcagacctacgtgacccagcagctg  2982
              |||||  |  |  ||||||  |||  |  ||  ||     |||  ||  |||||  ||  ||  ||  ||  ||
Sbjct:  2923  attgacaggttaattacaggcagacttcaaagccttcaaacctatgtaacacaacaacta  2982

Query:  2983  attcgcgcggcggagattcgcgcgtccgcgaacctggcggcgaccaagatgtccgagtgc  3042
              ||  |  ||  ||  ||  ||   |  ||  ||  ||  ||  ||  ||  ||  ||  |||||  |||||
Sbjct:  2983  atcagggctgctgaaatcagggcttctgctaatcttgctgctactaaaatgtctgagtgt  3042

Query:  3043  gtgctgggccagtccaagcgcgtggatttctgcggcaagggctaccacctgatgtccttc  3102
              ||  ||  ||  ||  ||  ||   |  ||  ||  ||  ||  ||||||||||||||||  |||||||||
Sbjct:  3043  gttcttggacaatcaaaaagagttgacttttgtggaaagggctaccaccttatgtccttc  3102

Query:  3103  cctcaggcggcgctcatggcgtggtgttcctgcacgtgacctacgtgccctcccaggag  3162
              ||  ||  ||  ||  ||  |||||  ||  ||  ||||||  ||  ||  ||  |||||  ||||||||
Sbjct:  3103  ccacaagcagccccgcatggtgttgtcttcctacatgtcacgtatgtgccatcccaggag  3162
```

FIG. 2F

```
Query: 3163 cgcaacttcaccaccgcgcccgcgatttgccacgagggcaaggcgtacttccctcgcgag 3222
             | ||||||||||| ||||| || ||||| || || ||||| || |||||||||||| ||
Sbjct: 3163 aggaacttcaccacagcgccagcaatttgtcatgaaggcaaagcatacttccctcgtgaa 3222

Query: 3223 ggcgtgttcgtgttcaacggcacctcctggttcattacccagcgcaacttcttctctcct 3282
             || || || |||||| || ||||| || ||||| ||||| ||| | |||||||| |||||
Sbjct: 3223 ggtgttttgtgtttaatggcacttcttggtttattacacagaggaacttcttttctcca 3282

Query: 3283 cagattattaccaccgataacaccttcgtgtccggcaactgcgatgtggtgattggcatt 3342
             || || ||||| || || || || || || || ||| ||||| || |||||| |||||||
Sbjct: 3283 caaataattactacagacaatacatttgtctcaggaaattgtgatgtcgttattggcatc 3342

Query: 3343 attaacaacaccgtgtacgatcctctgcagcccgagctggattccttcaaggaggagctg 3402
            ||||||||||| || || .|||||||| || || ||||| || || ||||| || ||||||
Sbjct: 3343 attaacaacacagtttatgatcctctgcaacctgagcttgactcattcaaagaagagctg 3402

Query: 3403 gataagtacttcaagaaccacacctctcccgatgtggatctgggcgatatttccggcatt 3462
             || ||||||||||| || || || || || ||||| ||||| ||||| ||||| ||||||
Sbjct: 3403 gacaagtacttcaaaaatcatacatcaccagatgttgatcttggcgacatttcaggcatt 3462

Query: 3463 aacgcctccgtggtgaacattcagaaggagattgatcgcctgaacgaggtggccaagaac 3522
             ||||| || || || || |||||| || || ||||| ||||| || ||||| || || ||
Sbjct: 3463 aacgcttctgtcgtcaacattcaaaaagaaattgaccgcctcaatgaggtcgctaaaaat 3522

Query: 3523 ctgaacgagtccctgattgatctgcaggagctgggcaagtacgagcac 3570 (SEQ ID NO:1)
             | || || || || |||||| || || || |||| || || |||||
Sbjct: 3523 ttaaatgaatcactcattgaccttcaagaattgggaaaatatgagcaa 3570 (SEQ ID NO:5)
```

FIG. 3A

F1  GCGCTGCAAGCTTGCCGCCACCATGTTCATCTTCC (SEQ ID NO:24)

F2
TGCTGTTCCTGACCCTGACCTCCGGCTCCGACCTGGACCGCTGCACCACCTTCGACGACGTGCAGGCtCC
(SEQ ID NO:25)

F3
tAACTACACCCAGCACACCTCCTCCATGCGCGGCGTGTACTACCCtGACGAGATCTTCCGCTCCGACACC
(SEQ ID NO:26)

F4
CTGTACCTGACCCAGGACCTGTTCCTGCCCTTCTACTCCAACGTGACCGGCTTCCACACCATCAACCACA
(SEQ ID NO:27)

F5
CCTTCGGCAAtCCCGTGATtCCCTTCAAGGACGGCATCTACTTCGCCGCCACCGAGAAGTCCAACGTGGT
(SEQ ID NO:28)

F6
GCGCGGCTGGGTGTTCGGCTCCACCATGAACAACAAGTCCCAGTCCGTGATCATCATCAACAACTCCACC
(SEQ ID NO:29)

F7
AACGTGGTGATCCGCGCCTGCAACTTCGAGCTGTGCGACAAtCCCTTCTTCGCCGTGTCCAAGCCCATGG
(SEQ ID NO:30)

F8
GCACCCAGACCCACACCATGATCTTCGACAACGCCTTCAACTGCACCTTCGAGTACATCTCCGACGCCTT
(SEQ ID NO:31)

F9
CTCCCTGGACGTGTCCGAGAAGTCCGGCAACTTCAAGCACCTGCGCGAGTTCGTGTTCAAGAACAAGGAC
(SEQ ID NO:32)

F10
GGCTTCCTGTACGTGTACAAGGGCTACCAGCCCATCGACGTGGTGCGCGACCTGCCCTCCGGCTTCAACA
(SEQ ID NO:33)

F11
CCCTGAAGCCCATCTTCAAGCTGCCtCTGGGCATCAACATTACCAACTTCCGCGCCATTCTGACCGCCTT
(SEQ ID NO:34)

F12
CTCtCCCGCCCAGGACATCTGGGGCACCTCCGCCGCCGCCTACTTCGTGGGCTACCTGAAGCCCACCACC
(SEQ ID NO:35)

F13
TTCATGCTGAAGTACGACGAGAACGGCACCATTACCGACGCCGTGGACTGCTCCCAGAACCCtCTGGCCG
(SEQ ID NO:36)

F14
AGCTGAAGTGCTCCGTGAAGTCCTTCGAGATTGACAAGGGCATTTACCAGACCTCCAACTTCCGCGTGGT
(SEQ ID NO:37)

FIG. 3B

F15
GCCCTCCGGCGACGTGGTGCGCTTtCCCAACATTACCAACCTGTGtCCCTTCGGCGAGGTGTTCAACGCC
(SEQ ID NO:38)

F16
ACCAAGTTtCCCTCCGTGTACGCCTGGGAGCGCAAGAAGATTTCCAACTGCGTGGCCGACTACTCCGTGC
(SEQ ID NO:39)

F17
TGTACAACTCCACCTTCTTCTCCACCTTCAAGTGCTAtGGCGTaTCtGCCACCAAGCTGAACGATCTtTG
(SEQ ID NO:40)

F18
CTTCTCCAACGTGTACGCtGACTCCTTCGTGGTGAAaGGtGATGATGTtCGtCAGATTGCTCCtGGtCAG
(SEQ ID NO:41)

F19
ACtGGtGTGATTGCtGATTACAACTACAAGCTGCCtGATGATTTCATGGGtTGCGTGCTGGCtTGGAACA
(SEQ ID NO:42)

F20
CtCGtAACATTGATGCtACCTCCACtGGtAACTACAACTACAAGTAtCGtTACCTGCGtCAtGGtAAGCT
(SEQ ID NO:43)

F21
GCGTCCtTTCGAGCGtGATATTTCCAACGTGCCtTTCTCtCCtGATGGCAAGCCtTGCACTCCTCCaGCt
(SEQ ID NO:44)

F22
CTGAACTGCTACTGGCCTCTGAACGATTACGGtTTCTACACCACtACCGGCATTGGCTACCAGCCtTAtC
(SEQ ID NO:45)

F23
GtGTGGTtGTGCTGTCtTTCGAGCTGCTGAACGCTCCtGCtACCGTGTGCGGTCCtAAGCTGTCtACCGA
(SEQ ID NO:46)

F24
TCTGATTAAGAACCAGTGCGTGAACTTCAACTTCAACGGCCTGACCGGCACCGGCGTGCTGACtCCCTCC
(SEQ ID NO:47)

F25
TCCAAGCGCTTCCAGCCCTTCCAGCAGTTCGGCCGCGATGTGTCCGATTTCACCGATTCCGTGCGCGATC
(SEQ ID NO:48)

F26
CCAAGACCTCCGAGATTCTGGATATTTCtCCCTGCGCCTTCGGCGGCGTGTCCGTGATTACtCCCGGCAC
(SEQ ID NO:49)

F27
CAACGCCTCCTCCGAGGTGGCCGTGCTGTACCAGGATGTGAACTGCACCGATGTGTCCACCGCCATTCAC
(SEQ ID NO:50)

F28
GCCGATCAGCTGACtCCCGCCTGGCGCATTTACTCCACCGGCAACAACGTGTTCCAGACCCAGGCCGGCT
(SEQ ID NO:51)

FIG. 3C

F29
GCCTGATTGGCGCCGAGCACGTGGATACCTCCTACGAGTGCGATATTCCCATTGGCGCCGGCATTTGCGC
(SEQ ID NO:52)

F30
CTCCTACCACACCGTGTCCCTGCTGCGCTCCACCTCCCAGAAGTCCATTGTGGCCTACACCATGTCCCTG
(SEQ ID NO:53)

F31
GGCGCCGATTCCTCCATTGCCTACTCCAACAACACCATTGCCATTCCCACCAACTTCTCCATTTCCATTA
(SEQ ID NO:54)

F32
CCACCGAGGTGATGCCCGTGTCCATGGCCAAGACCTCCGTGGATTGCAACATGTACATTTGCGGCGATTC
(SEQ ID NO:55)

F33
CACCGAGTGCGCCAACCTGCTGCTGCAGTACGGCTCCTTCTGCACCCAGCTGAACCGCGCCCTGTCCGGC
(SEQ ID NO:56)

F34
ATTGCCGCCGAGCAGGATCGCAACACCCGCGAGGTGTTCGCCCAGGTGAAGCAGATGTACAAGACtCCCA
(SEQ ID NO:57)

F35
CCCTGAAGTACTTCGGCGGCTTCAACTTCTCCCAGATTCTGCCCGATCCtCTGAAGCCCACCAAGCGCTC
(SEQ ID NO:58)

F36
CTTCATTGAGGATCTGCTGTTCAACAAGGTGACCCTGGCCGATGCCGGCTTCATGAAGCAGTACGGCGAG
(SEQ ID NO:59)

F37
TGCCTGGGCGATATTAACGCCCGCGATCTGATTTGCGCGCAGAAGTTCAACGGCCTGACCGTGCTGCCtC
(SEQ ID NO:60)

F38
CtCTGCTGACCGATGATATGATTGCGGCGTACACCGCGGCGCTGGTGTCCGGCACCGCCACCGCGGGCTG
(SEQ ID NO:61)

F39
GACCTTCGGCGCGGGCGCGGCGCTGCAGATTCCCTTCGCGATGCAGATGGCGTACCGCTTCAACGGCATT
(SEQ ID NO:62)

F40
GGCGTGACCCAGAACGTGCTGTACGAGAACCAGAAGCAGATTGCGAACCAGTTCAACAAGGCGATTTCCC
(SEQ ID NO:63)

F41
AGATTCAGGAGTCCCTGACCACCACCTCCACCGCGCTGGGCAAGCTGCAGGATGTGGTGAACCAGAACGC
(SEQ ID NO:64)

F42
GCAGGCGCTGAACACCCTGGTGAAGCAGCTGTCCTCCAACTTCGGCGCGATTTCCTCCGTGCTGAACGAT
(SEQ ID NO:65)

FIG. 3D

F43
ATTCTGTCCCGCCTGGATAAGGTGGAGGCGGAGGTGCAGATTGATCGCCTGATTACCGGCCGCCTGCAGT
(SEQ ID NO:66)

F44
CCCTGCAGACCTACGTGACCCAGCAGCTGATTCGCGCGGCGGAGATTCGCGCGTCCGCGAACCTGGCGGC
(SEQ ID NO:67)

F45
GACCAAGATGTCCGAGTGCGTGCTGGGCCAGTCCAAGCGCGTGGATTTCTGCGGCAAGGGCTACCACCTG
(SEQ ID NO:68)

F46
ATGTCCTTCCCtCAGGCGGCGCCtCATGGCGTGGTGTTCCTGCACGTGACCTACGTGCCCTCCCAGGAGC
(SEQ ID NO:69)

F47
GCAACTTCACCACCGCGCCCGCGATTTGCCACGAGGGCAAGGCGTACTTCCCtCGCGAGGGCGTGTTCGT
(SEQ ID NO:70)

F48
GTTCAACGGCACCTCCTGGTTCATTACCCAGCGCAACTTCTTCTCtCCtCAGATTATTACCACCGATAAC
(SEQ ID NO:71)

F49
ACCTTCGTGTCCGGCAACTGCGATGTGGTGATTGGCATTATTAACAACACCGTGTACGATCCtCTGCAGC
(SEQ ID NO:72)

F50
CCGAGCTGGATTCCTTCAAGGAGGAGCTGGATAAGTACTTCAAGAACCACACCTCtCCCGATGTGGATCT
(SEQ ID NO:73)

F51
GGGCGATATTTCCGGCATTAACGCCTCCGTGGTGAACATTCAGAAGGAGATTGATCGCCTGAACGAGGTG
(SEQ ID NO:74)

F52
GCCAAGAACCTGAACGAGTCCCTGATTGATCTGCAGGAGCTGGGCAAGTACGAGCAGTCTAGAGGTTGCG
(SEQ ID NO:75)

R1
CGCAACC*TCTAGA*CTGCTCGTACTTGCCCAGCTCC(SEQ ID NO:76)

R2
TGCAGATCAATCAGGGACTCGTTCAGGTTCTTGGCCACCTCGTTCAGGCGATCAATCTCCTTCTGAATGT
(SEQ ID NO:77)

R3
TCACCACGGAGGCGTTAATGCCGGAAATATCGCCCAGATCCACATCGGGAGAGGTGTGGTTCTTGAAGTA
(SEQ ID NO:78)

R4
CTTATCCAGCTCCTCCTTGAAGGAATCCAGCTCGGGCTGCAGAGGATCGTACACGGTGTTGTTAATAATG
(SEQ ID NO:79)

FIG. 3E

R5
CCAATCACCACATCGCAGTTGCCGGACACGAAGGTGTTATCGGTGGTAATAATCTGAGGAGAGAAGAAGT
(SEQ ID NO:80)

R6
TGCGCTGGGTAATGAACCAGGAGGTGCCGTTGAACACGAACACGCCCTCGCGAGGGAAGTACGCCTTGCC
(SEQ ID NO:81)

R7
CTCGTGGCAAATCGCGGGCGCGGTGGTGAAGTTGCGCTCCTGGGAGGGCACGTAGGTCACGTGCAGGAAC
(SEQ ID NO:82)

R8
ACCACGCCATGAGGCGCCGCCTGAGGGAAGGACATCAGGTGGTAGCCCTTGCCGCAGAAATCCACGCGCT
(SEQ ID NO:83)

R9
TGGACTGGCCCAGCACGCACTCGGACATCTTGGTCGCCGCCAGGTTCGCGGACGCGCGAATCTCCGCCGC
(SEQ ID NO:84)

R10
GCGAATCAGCTGCTGGGTCACGTAGGTCTGCAGGGACTGCAGGCGGCCGGTAATCAGGCGATCAATCTGC
(SEQ ID NO:85)

R11
ACCTCCGCCTCCACCTTATCCAGGCGGGACAGAATATCGTTCAGCACGGAGGAAATCGCGCCGAAGTTGG
(SEQ ID NO:86)

R12
AGGACAGCTGCTTCACCAGGGTGTTCAGCGCCTGCGCGTTCTGGTTCACCACATCCTGCAGCTTGCCCAG
(SEQ ID NO:87)

R13
CGCGGTGGAGGTGGTGGTCAGGGACTCCTGAATCTGGGAAATCGCCTTGTTGAACTGGTTCGCAATCTGC
(SEQ ID NO:88)

R14
TTCTGGTTCTCGTACAGCACGTTCTGGGTCACGCCAATGCCGTTGAAGCGGTACGCCATCTGCATCGCGA
(SEQ ID NO:89)

R15
AGGGAATCTGCAGCGCCGCGCCCGCGCCGAAGGTCCAGCCCGCGGTGGCGGTGCCGGACACCAGCGCCGC
(SEQ ID NO:90)

R16
GGTGTACGCCGCAATCATATCATCGGTCAGCAGAGGAGGCAGCACGGTCAGGCCGTTGAACTTCTGCGCG
(SEQ ID NO:91)

R17
CAAATCAGATCGCGGGCGTTAATATCGCCCAGGCACTCGCCGTACTGCTTCATGAAGCCGGCATCGGCCA
(SEQ ID NO:92)

R18
GGGTCACCTTGTTGAACAGCAGATCCTCAATGAAGGAGCGCTTGGTGGGCTTCAGAGGATCGGGCAGAAT
(SEQ ID NO:93)

FIG. 3F

R19
CTGGGAGAAGTTGAAGCCGCCGAAGTACTTCAGGGTGGGAGTCTTGTACATCTGCTTCACCTGGGCGAAC
(SEQ ID NO:94)

R20
ACCTCGCGGGTGTTGCGATCCTGCTCGGCGGCAATGCCGGACAGGGCGCGGTTCAGCTGGGTGCAGAAGG
(SEQ ID NO:95)

R21
AGCCGTACTGCAGCAGCAGGTTGGCGCACTCGGTGGAATCGCCGCAAATGTACATGTTGCAATCCACGGA
(SEQ ID NO:96)

R22
GGTCTTGGCCATGGACACGGGCATCACCTCGGTGGTAATGGAAATGGAGAAGTTGGTGGGAATGGCAATG
(SEQ ID NO:97)

R23
GTGTTGTTGGAGTAGGCAATGGAGGAATCGGCGCCCAGGGACATGGTGTAGGCCACAATGGACTTCTGGG
(SEQ ID NO:98)

R24
AGGTGGAGCGCAGCAGGGACACGGTGTGGTAGGAGGCGCAAATGCCGGCGCCAATGGGAATATCGCACTC
(SEQ ID NO:99)

R25
GTAGGAGGTATCCACGTGCTCGGCGCCAATCAGGCAGCCGGCCTGGGTCTGGAACACGTTGTTGCCGGTG
(SEQ ID NO:100)

R26
GAGTAAATGCGCCAGGCGGGAGTCAGCTGATCGGCGTGAATGGCGGTGGACACATCGGTGCAGTTCACAT
(SEQ ID NO:101)

R27
CCTGGTACAGCACGGCCACCTCGGAGGAGGCGTTGGTGCCGGGAGTAATCACGGACACGCCGCCGAAGGC
(SEQ ID NO:102)

R28
GCAGGGAGAAATATCCAGAATCTCGGAGGTCTTGGGATCGCGCACGGAATCGGTGAAATCGGACACATCG
(SEQ ID NO:103)

R29
CGGCCGAACTGCTGGAAGGGCTGGAAGCGCTTGGAGGAGGGAGTCAGCACGCCGGTGCCGGTCAGGCCGT
(SEQ ID NO:104)

R30
TGAAGTTGAAGTTCACGCACTGGTTCTTAATCAGATCGGTAGACAGCTTAGGACCGCACACGGTAGCAGG
(SEQ ID NO:105)

R31
AGCGTTCAGCAGCTCGAAAGACAGCACAACCACACGATAAGGCTGGTAGCCAATGCCGGTAGTGGTGTAG
(SEQ ID NO:106)

R32
AAACCGTAATCGTTCAGAGGCCAGTAGCAGTTCAGAGCTGGAGGAGTGCAAGGCTTGCCATCAGGAGAGA
(SEQ ID NO:107)

FIG. 3G

R33
AAGGCACGTTGGAAATATCACGCTCGAAAGGACGCAGCTTACCATGACGCAGGTAACGATACTTGTAGTT
(SEQ ID NO:108)

R34
GTAGTTACCAGTGGAGGTAGCATCAATGTTACGAGTGTTCCAAGCCAGCACGCAACCCATGAAATCATCA
(SEQ ID NO:109)

R35
GGCAGCTTGTAGTTGTAATCAGCAATCACACCAGTCTGACCAGGAGCAATCTGACGAACATCATCACCTT
(SEQ ID NO:110)

R36
TCACCACGAAGGAGTCAGCGTACACGTTGGAGAAGCAAAGATCGTTCAGCTTGGTGGCAGATACGCCATA
(SEQ ID NO:111)

R37
GCACTTGAAGGTGGAGAAGAAGGTGGAGTTGTACAGCACGGAGTAGTCGGCCACGCAGTTGGAAATCTTC
(SEQ ID NO:112)

R38
TTGCGCTCCCAGGCGTACACGGAGGGAAACTTGGTGGCGTTGAACACCTCGCCGAAGGGACACAGGTTGG
(SEQ ID NO:113)

R39
TAATGTTGGGAAAGCGCACCACGTCGCCGGAGGGCACCACGCGGAAGTTGGAGGTCTGGTAAATGCCCTT
(SEQ ID NO:114)

R40
GTCAATCTCGAAGGACTTCACGGAGCACTTCAGCTCGGCCAGAGGGTTCTGGGAGCAGTCCACGGCGTCG
(SEQ ID NO:115)

R41
GTAATGGTGCCGTTCTCGTCGTACTTCAGCATGAAGGTGGTGGGCTTCAGGTAGCCCACGAAGTAGGCGG
(SEQ ID NO:116)

R42
CGGCGGAGGTGCCCCAGATGTCCTGGGCGGGAGAGAAGGCGGTCAGAATGGCGCGGAAGTTGGTAATGTT
(SEQ ID NO:117)

R43
GATGCCCAGAGGCAGCTTGAAGATGGGCTTCAGGGTGTTGAAGCCGGAGGGCAGGTCGCGCACCACGTCG
(SEQ ID NO:118)

R44
ATGGGCTGGTAGCCCTTGTACACGTACAGGAAGCCGTCCTTGTTCTTGAACACGAACTCGCGCAGGTGCT
(SEQ ID NO:119)

R45
TGAAGTTGCCGGACTTCTCGGACACGTCCAGGGAGAAGGCGTCGGAGATGTACTCGAAGGTGCAGTTGAA
(SEQ ID NO:120)

R46
GGCGTTGTCGAAGATCATGGTGTGGGTCTGGGTGCCCATGGGCTTGGACACGGCGAAGAAGGGATTGTCG
(SEQ ID NO:121)

FIG. 3H

R47
CACAGCTCGAAGTTGCAGGCGCGGATCACCACGTTGGTGGAGTTGTTGATGATGATCACGGACTGGGACT
(SEQ ID NO:122)

R48
TGTTGTTCATGGTGGAGCCGAACACCCAGCCGCGCACCACGTTGGACTTCTCGGTGGCGGCGAAGTAGAT
(SEQ ID NO:123)

R49
GCCGTCCTTGAAGGGAATCACGGGATTGCCGAAGGTGTGGTTGATGGTGTGGAAGCCGGTCACGTTGGAG
(SEQ ID NO:124)

R50
TAGAAGGGCAGGAACAGGTCCTGGGTCAGGTACAGGGTGTCGGAGCGGAAGATCTCGTCAGGGTAGTACA
(SEQ ID NO:125)

R51
CGCCGCGCATGGAGGAGGTGTGCTGGGTGTAGTTAGGAGCCTGCACGTCGTCGAAGGTGGTGCAGCGGTC
(SEQ ID NO:126)

R52
CAGGTCGGAGCCGGAGGTCAGGGTCAGGAACAGCAGGAAGATGAACATGGTGGCGGC*AAGCTT*GCAGCGC
(SEQ ID NO:127)

ENV F1
ACCAAGTTtCCCTCCGTGTACGCCTGGGAGCGCAAGAAGATTTCCAACTGCGTGGCCTCTAGAGGTTGCG
(SEQ ID NO:128)

ENV R1
CGCAACCTCTAGAGGCCACGCAGTTGGAAATCTTC(SEQ ID NO:129)

4-S1R
GCACTTGAAGGTGGAGAAGAAGGTGGAGTTGTACAGCACGGAGTAGTCGGCCACGCAGTTGGAAATCTTCT
TGCGCTCCCAGGCGTACACGG(SEQ ID NO:130)

AinsR
GAGTGCCTCTAGAGCACTTGAAGGTGGAGAAGAAGGTGGAGTTGTACA(SEQ ID NO:131)

BinsF
GACTGCCAAGCTTTGTACAACTCCACCTTCTTCTCCACCTTCAAGTGC(SEQ ID NO:132)

BinsR
GATTGCCTCTAGAGTAGGAGGTATCCACGTGCTCGGCGCCAATCAGGC(SEQ ID NO:133)

CinsF
GACCGCAAAGCTTGCCTGATTGGCGCCGAGCACGTGGATACCTCCTAC(SEQ ID NO:134)

CinsR
GGACTGCTCTAGACGCGGTGGAGGTGGTGGTCAGGGACTCCTGAATCT(SEQ ID NO:135)

DinsF
CGAGTACAAGCTTAGATTCAGGAGTCCCTGACCACCACCTCCACCGCG(SEQ ID NO:136)

AexF
GCGCTGC*AAGCTT*GCCGCCACCATGTTCATCTTCCTGCTGTTCCTGACCC(SEQ ID NO:137)

FIG. 3I

AexR2 -
CAAAGATCGTTCAGCTTGGTGGCAGATACGCCATAGCACTTGAAGGTGGAGAAGAAGGTGGAGTTGTACA
(SEQ ID NO:138)

BexF -
GAAGATTTCCAACTGCGTGGCCGACTACTCCGTGCTGTACAACTCCACCTTCTTCTCCACCTTCAAGTGC
(SEQ ID NO:139)

BexR -
GCGCAAATGCCGGCGCCAATGGGAATATCGCACTCGTAGGAGGTATCCACGTGCTCGGCGCCAATCAGGC
(SEQ ID NO:140)

CexF -
CACCGGCAACAACGTGTTCCAGACCCAGGCCGGCTGCCTGATTGGCGCCGAGCACGTGGATACCTCCTAC
(SEQ ID NO:141)

CexR -
GCGTTCTGGTTCACCACATCCTGCAGCTTGCCCAGCGCGGTGGAGGTGGTGGTCAGGGACTCCTGAATCT
(SEQ ID NO:142)

DexF -
GCAGATTGCGAACCAGTTCAACAAGGCGATTTCCCAGATTCAGGAGTCCCTGACCACCACCTCCACCGCG
(SEQ ID NO:143)

DexR -
CGCAACC*TCTAGA*CTGCTCGTACTTGCCCAGCTCCTGCAGATCAATCAGG(SEQ ID NO:144)

NoLBacF -
GCGTAGTGGATCCGGCTCCGACCTGGACCGCTGCACCACCTTCGACGAC(SEQ ID NO:145)

BacR -
CGCAACC**AAGCTT*CTA***GGCCACGCAGTTGGAAATCTTCTTGCGCTCCCAGG(SEQ ID NO:146)

NoLBacF -
GCGTAGTGGATCCGGCTCCGACCTGGACCGCTGCACCACCTTCGACGAC (SEQ ID NO:147)

NBS1R -
CCATGCTGAGCTCGCGGCCACGCAGTTGGAAATCTTCTTGCGCTCCCAGG(SEQ ID NO:148)

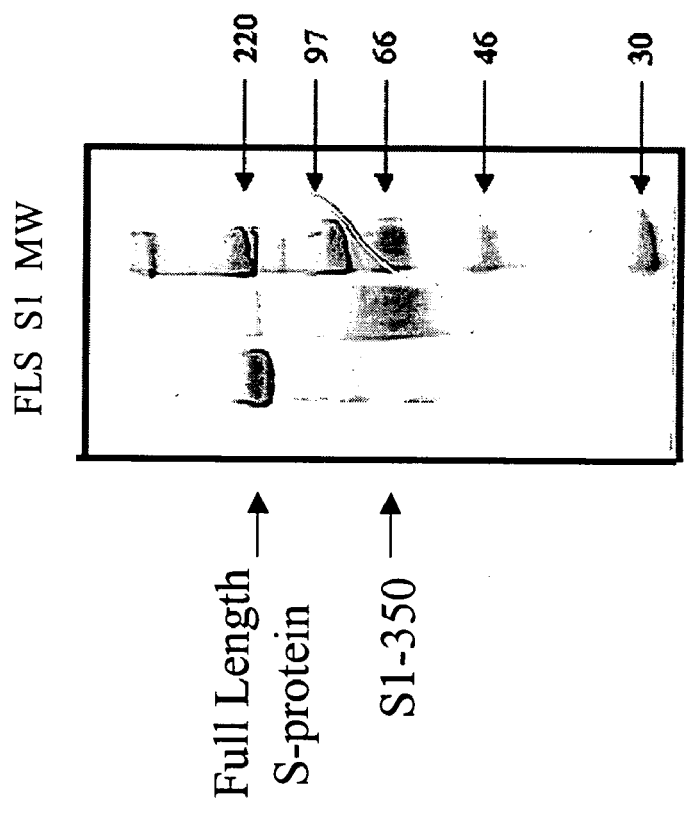
FIG. 4 Coomassie Stained SDS-page Gels of S1-350 and Full-Length S protein

FIG. 12

Serum Results

| Immunogen | $S_{1190}$ ELISA | Viral Neutralization | Species Tested |
|---|---|---|---|
| SARS CoV | + | + | HUMAN |
| $S_{350}$ | + | − | Ms, HuMab |
| $S_{590}$ | + | + | Ms |
| $S_{1190}$ | + | + | Rb, Ms, HuMab |

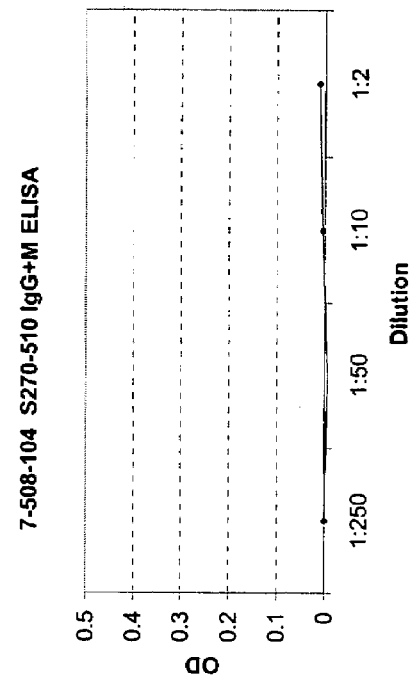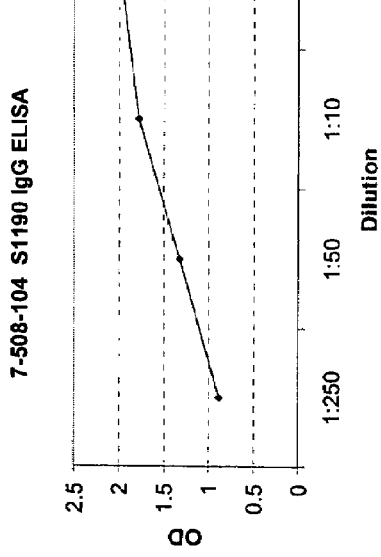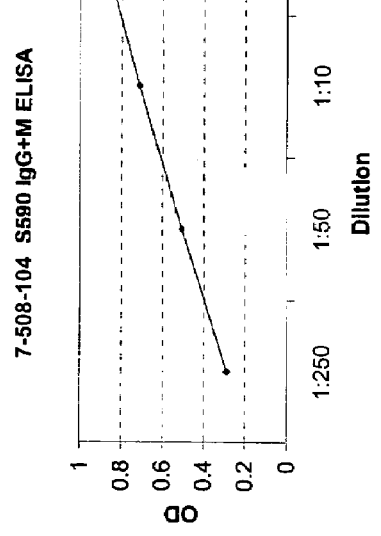

Anti-SARS 201.2 VH

V segment:       DP-44
    D segment:       undetermined
    J segment:       JH4b

```
        E   V   Q   L   V   Q   S   G   G   G   L   V   H   P   G   G   S   L
  1    GAG GTT CAG CTG GTG CAG TCT GGG GGA GGC TTG GTA CAT CCT GGG GGG TCC CTG

CDR1
                                                            ~~~~~~~~~~~~~~~~~~
        R   L   S   C   A   G   S   G   F   T   F   S   S   Y   D   M   H   W
 55    AGA CTC TCC TGT GCA GGC TCT GGA TTC ACC TTC AGT AGC TAT GAT ATG CAC TGG

CDR2
                                                            ~~~~~~~~~~~~~~~~~~
        V   R   Q   A   P   G   K   G   L   E   W   V   S   V   V   G   T   G
109    GTT CGC CAG GCT CCA GGA AAA GGT CTG GAG TGG GTA TCA GTT GTT GGT ACT GGT

CDR2
       ~~~~~~~~~~~~~~~~~~~~~~~~~~~~~~~~~~~~~~~~~~~~
        D   G   T   Y   Y   A   D   S   V   K   G   R   F   T   I   S   R   D
163    GAT GGC ACA TAC TAT GCA GAC TCC GTG AAG GGC CGA TTC ACC ATC TCC AGA GAC

N   A   K   N   S   L   Y   L   Q   M   N   S   L   R   A   E   D   M
217    AAT GCC AAG AAC TCC TTG TAT CTT CAA ATG AAC AGC CTG AGA GCC GAG GAC ATG

CDR3
                                ~~~~~~~~~~~~~~~~~~~~~~~~~~~~~~~~~~~~~
        A   V   Y   Y   C   A   R   D   Q   W   W   G   S   D   Y   W   G   Q
271    GCT GTG TAT TAC TGT GCA AGA GAT CAA TGG TGG GGA TCC GAC TAC TGG GGC CAG

G   T   L   V   T   V   S   S   (SEQ ID NO:13)
325    GGA ACC CTG GTC ACC GTC TCC TCA  (SEQ ID NO:15)
```

CDR 1 amino acid sequence= SEQ ID NO:7
CDR 2 amino acid sequence= SEQ ID NO:8
CDR 3 amino acid sequence= SEQ ID NO:9

FIG. 35

Anti-SARS 201.2 VK

```
V segment:     L6
J segment:     JK4
```

```
       E   I   V   L   T   Q   S   P   A   T   L   S   L   S   P   G   E   R
  1   GAA ATT GTG TTG ACA CAG TCT CCA GCC ACC CTG TCT TTG TCT CCA GGG GAA AGA

CDR1
                          ~~~~~~~~~~~~~~~~~~~~~~~~~~~~~~~~~~~~~~~~~~~~~~
       A   T   L   S   C   R   A   S   Q   S   V   S   S   Y   L   A   W   Y
 55   GCC ACC CTC TCC TGC AGG GCC AGT CAG AGT GTT AGC AGC TAC TTA GCC TGG TAC

CDR2
                                                          ~~~~~~~~~~~~~~~~~~~
       Q   Q   K   P   G   Q   A   P   R   L   L   I   Y   D   A   S   N   R
109   CAA CAG AAA CCT GGC CAG GCT CCC AGG CTC CTC ATC TAT GAT GCA TCC AAC AGG

CDR2
      ~~~~~~~
       A   T   G   I   P   A   R   F   S   G   S   G   S   G   T   D   F   T
163   GCC ACT GGC ATC CCA GCC AGG TTC AGT GGC AGT GGG TCT GGG ACA GAC TTC ACT

CDR3
                                                                    ~~~~~~~
       L   T   I   S   S   L   E   P   E   D   F   A   V   Y   Y   C   Q   Q
217   CTC ACC ATC AGC AGC CTA GAG CCT GAA GAT TTT GCA GTT TAT TAC TGT CAG CAG

CDR3
      ~~~~~~~~~~~~~~~~~~~~~~~~~~~
       R   S   N   W   P   L   T   F   G   G   G   T   K   V   E   I   K (SEQ
      ID NO:14)
271   CGT AGC AAC TGG CCT CTC ACT TTC GGC GGA GGG ACC AAG GTG GAG ATC AAA(SEQ
      ID NO:16)
```

```
CDR 1 amino acid sequence= SEQ ID NO:10
CDR 2 amino acid sequence= SEQ ID NO:11
CDR 3 amino acid sequence= SEQ ID NO:12
```

FIG. 36

```
                                                                        CDR1
DP44 Germline:     E V Q L V Q S G G G L V H P G G S L R L S C A G S G F T F S S Y A M H
3-7 Germline:      - - - - - - E - - - - - - Q - - - - - - - - A - - - - - - - W - S
3-23 Germline:     - - - L E - - - - - - - - Q - - - - - - - - A - - - - - - - - - -
201.2 VH:          - - - - - - - - - - - - - - X - - - - - - - - - - - - - - D - -
201.2(mut) VH:     - - - - - - - - - - - - - - X - - - - - - - - - - - - - - D - -

CDR2
DP44 Germline:     W V R Q A P G K G L E W V S A I G T G G G T Y Y A D S V K G R F T I
3-7 Germline:      - - - - - - - - - - - - - - A N - K Q D - S E K - V - - - - - - -
3-23 Germline:     - - - - - - - - - - - - - - - - - S G S - - S - - - - - - - - - -
201.2 VH:          - - - - - - - - - - - - - - - V V - - - D - - - - - - - - - - - -
201.2(mut) VH:     - - - - - - - - - - - - - - - V V - - - D - - - - - - - - - - - -

CDR3
DP44 Germline:     S R D N A K N S L Y L Q M N S L R A E D M A V Y Y C A R                       (SEQ ID NO:18)
3-7 Germline:      - - - - - - - - - - - - - - - - - - - - - T - -                               (SEQ ID NO:19)
3-23 Germline:     - - - - - S - - - T - - - - - - - - - - - - - -
201.2 VH:          - - - - - - - - - - - - - - - - - - - - - T - - - - D Q W W G S D Y          (SEQ ID NO:20)
201.2(mut) VH:     - - - - - - - - - - - - - - - - - - - - - T - K - - D Q W W G S D Y          (SEQ ID NO:17)
                                                                                                 (SEQ ID NO:13)
```

FIG. 37 wherein X = K or Q

Anti-SARS 201.2 VK Region

```
                              CDR1
L6 germline:   E I V L T Q S P A

FIG. 39

SARS Virus Titer in Lungs of Hamsters 3 or 5 days after Challenge

* Animal 3443 had no serum antibodies so data was not included

FIG. 40

Mean SARS Virus Titer in Hamster Lung after Challenge

FIG. 41

| | | | | | | | trachea | | | | lung | | |
|---|---|---|---|---|---|---|---|---|---|---|---|---|---|
| SARS lung titer | id # | sac'd | SARS-ELISA (μg/ml)* | IgG-ELISA (μg/ml)* | SARS-neut | inflammation | debris | piled cells | SARS Virus IHC | interst inflam | conso-lidation | other | SARS Virus IHC |
| Neg Control Ab | 3429 | d3 | ND | 477 | 5.7 | | | | | | | | |
| Neg Control Ab | 3430 | d3 | ND | 490 | 5.7 | | | | | | | | |
| Neg Control Ab | 3431 | d3 | ND | 436 | 5.7 | | | | | | | | |
| Neg Control Ab | 3435 | d5 | ND | 514 | 5.7 | | | | | | | | |
| Neg Control Ab | 3436 | d5 | ND | 332 | 5.7 | | | | | | | | |
| Neg Control Ab | 3437 | d5 | ND | 464 | 5.7 | | | | | | | | |
| Neg Control Ab | 3426 | d3 | ND | 470 | 5.7 | yes | yes | yes | yes | 0 | 0 | | 0 |
| Neg Control Ab | 3427 | d3 | ND | 610 | 5.7 | yes | yes | yes | yes | 0 | 0 | | rare |
| Neg Control Ab | 3428 | d3 | ND | 493 | 5.7 | yes | yes | 0 | yes | yes | 0 | | yes |
| Neg Control Ab | 3432 | d5 | ND | 339 | 5.7 | yes | yes | yes | yes | yes | yes | hemorrhage | yes |
| Neg Control Ab | 3433 | d5 | ND | 444 | 5.7 | yes | yes | yes | yes | yes | yes | | yes |
| Neg Control Ab | 3434 | d5 | ND | 495 | 5.7 | yes | 0 | yes | yes | yes | yes | | yes |
| MAb 201 40 mg/kg | 3441 | d3 | 228 | 299 | 40.3 | | | | | | | | |
| MAb 201 40 mg/kg | 3442 | d3 | 178 | 232 | 32.0 | | | | | | | | |
| MAb 201 40 mg/kg | 3443 | d3 | ND | ND | 5.7 | (MAb was not detected in this animal) | | | | | | | |
| MAb 201 40 mg/kg | 3447 | d5 | 167 | 317 | 40.3 | | | | | | | | |
| MAb 201 40 mg/kg | 3448 | d5 | 114 | 182 | 32.0 | | | | | | | | |
| MAb 201 40 mg/kg | 3449 | d5 | 95 | 160 | 32.0 | | | | | | | | |
| MAb 201 40 mg/kg | 3438 | d3 | 179 | 222 | 80.6 | minimal | 0 | 0 | non-sp | 0 | 0 | | 0 |
| MAb 201 40 mg/kg | 3439 | d3 | 143 | 221 | 40.3 | minimal | 0 | 0 | 0 | 0 | 0 | | 0 |
| MAb 201 40 mg/kg | 3440 | d3 | 207 | 277 | 32.0 | minimal | 0 | 0 | 0 | 0 | 0 | | 0 |
| MAb 201 40 mg/kg | 3444 | d5 | 67 | 221 | 40.3 | yes | 0 | yes | 0 | 0 | 0 | | 0 |
| MAb 201 40 mg/kg | 3445 | d5 | 173 | 140 | 25.4 | yes | 0 | yes | 0 | 0 | 0 | | 0 |
| MAb 201 40 mg/kg | 3446 | d5 | 250 | 352 | 40.3 | yes | 0 | yes | non-sp | minimal | 0 | | 0 |
| MAb 201 4 mg/kg | 3453 | d3 | 16 | 39 | 5.7 | | | | | | | | |
| MAb 201 4 mg/kg | 3454 | d3 | 18 | 37 | 6.3 | | | | | | | | |
| MAb 201 4 mg/kg | 3455 | d3 | 8 | 31 | 10.1 | | | | | | | | |
| MAb 201 4 mg/kg | 3459 | d5 | 19 | 41 | 5.7 | | | | | | | | |
| MAb 201 4 mg/kg | 3460 | d5 | 13 | 25 | 10.1 | | | | | | | | |
| MAb 201 4 mg/kg | 3461 | d5 | 8 | 37 | 5.7 | | | | | | | | |
| MAb 201 4 mg/kg | 3450 | d3 | 20 | 48 | 5.7 | yes | yes | 0 | 0 | yes | 0 | | yes |
| MAb 201 4 mg/kg | 3451 | d3 | 23 | 37 | 5.7 | yes | yes | yes | yes | yes | 0 | | yes |
| MAb 201 4 mg/kg | 3452 | d3 | 34 | 48 | 5.7 | 0 | 0 | 0 | rare | yes | 0 | | yes |
| MAb 201 4 mg/kg | 3456 | d5 | 14 | 39 | 8.0 | yes | 0 | yes | 0 | yes | 0 | | 0 |
| MAb 201 4 mg/kg | 3457 | d5 | 14 | 36 | 10.1 | 0 | 0 | 0 | 0 | 0 | 0 | | 0 |
| MAb 201 4 mg/kg | 3458 | d5 | 8 | 32 | 10.1 | yes | 0 | 0 | 0 | yes | 0 | | 0 |
| | | d3 | | Naive | | 0 | 0 | 0 | 0 | 0 | 0 | 0 | 0 |
| | | d5 | | Naive | | 0 | 0 | 0 | 0 | 0 | 0 | 0 | 0 |

*ND not detected

… # SARS NUCLEIC ACIDS, PROTEINS, ANTIBODIES, AND USES THEREOF

CROSS-REFERENCE TO RELATED APPLICATIONS

This application claims the benefit of priority of U.S. Provisional Patent Application Ser. Nos. 60/492,529, filed on Aug. 4, 2003, 60/510,251, filed on Oct. 9, 2003, 60/545,670, filed on Feb. 18, 2004, and 60/565,595, filed on Apr. 26, 2004. The entire contents of the aforementioned applications are incorporated herein by reference.

STATEMENT AS TO FEDERALLY SPONSORED RESEARCH

The work described herein was funded, in part, through a grant from the National Institutes of Health (NIH Contract NO1-AI-65315). The United States government, therefore has certain rights in the invention.

TECHNICAL FIELD

This invention relates to viral nucleic acids sequences, proteins, and antibodies that recognize the viral proteins, and more particularly to viral nucleic acids sequences that have been optimized for expression in mammalian host cells.

BACKGROUND

Severe Acute Respiratory Syndrome (SARS) is an emerging infectious illness with a tendency for rapid spread from person to person (*MMWR Morb Mortal Wkly Rep*, 52 (12): 255-6, 2003; *MMWR Morb Mortal Wkly Rep*, 52 (12): 241-6, 248, 2003; Lee N et al., *N Engl J Med*, 348(20):1986-94, 2003; Poutanen S M et al., *N Engl J Med*, 348(20):1995-2005, 2003). A newly identified coronavirus is now established as the etiologic agent (Drosten C et al., *N Engl J Med*, 348(20): 1967-76, 2003; Ksiazek T G et al., *N Engl J Med, N Engl J Med*, 348(20):1953-66, 2003). Coronaviruses have characteristic surface peplomer spikes formed by oligomers of the surface S-glycoprotein. The S-glycoproteins are believed to bind receptors on target cells. The S-proteins are the principal targets for neutralizing antibodies (Saif L J, *Vet Microbiol*, 37 (3-4): 285-97, 1993). The protective efficacy of humoral immunity has been demonstrated in several animal models of coronavirus disease (e.g., avian infectious bronchitis virus disease and respiratory bovine coronavirus disease) (Lin X et al., *Clin Diagn Lab Immunol*, 8 (2): 357-62, 2001; Mondal S P, and Naqi S A, *Vet Immunol Immunopathol*, 79 (1-2): 31-40, 2001; Wang X et al., *Avian Dis*, 46 (4): 831-8, 2002.18).

The recently published sequence of the human SARS corona virus (human SARS-CoV) reveals that it represents a new strain (Drosten C et al., *N Engl J Med*, 348(20):1967-76, 2003; Ksiazek T G et al., *N Engl J Med*, 348(20):1953-66, 2003). While it is seroreactive with some antisera and monoclonal antibodies to group 1 coronaviruses, it appears to be best classified as a fourth serogroup given its sequence divergence from other strains. Neutralization with available antibodies has not been reported. With the rapid spread of the SARS epidemic and a mortality rate of 5%, it is crucial to develop therapeutic and prophylactic agents. The most severe clinical outcomes of this infection have been associated with prolonged viremia (Drosten C et al., *N Engl J Med*, 348(20): 1967-76, 2003).

Laboratory analyses of convalescent serum samples from individuals with SARS have shown high levels of specific reactivity with infected cells and conversion from negative to positive reactivity or diagnostic rises in the indirect fluorescence antibody test (Ksiazek T G et al., *N Engl J Med*, 348 (20):1953-66, 2003). In contrast, sera from United States blood donors and persons with known HCV 229E or OC43 infection were negative for antibodies to this novel coronavirus. These results indicate that this virus has not been widely circulated in human populations (Ksiazek T G et al., *N Engl J Med*, 348(20):1953-66, 2003).

SUMMARY

The present invention is based, in part, on the observation that codon-optimized variant forms of nucleic acids encoding the SARS-CoV spike glycoprotein (S protein) can be used to achieve high expression of the S protein in appropriate host cells. Enhanced expression provides large quantities of the S protein and fragments for diagnostic and therapeutic applications, as well as the generation of antibodies (e.g., monoclonal antibodies) for diagnostic and therapeutic applications.

In one aspect, the invention features isolated nucleic acids including sequences encoding a SARS-CoV spike glycoprotein polypeptide (an S polypeptide), or fragment thereof, wherein the sequences have been optimized for expression in a human host (e.g., wherein the sequence is synthetic or artificial). In one embodiment, the sequences encoding an S polypeptide, or fragment thereof, have at least 80% identity with the sequence set forth in SEQ ID NO:1, e.g., 80%, 85%, 90%, 95%, 96%, 97%, 98%, 99%, or 100% identity with SEQ ID NO:1. In various embodiments, the sequences are operably linked to a promoter. Also featured are kits that include the nucleic acids. The kits can include instructions for expressing the nucleic acids in a host cell.

In another aspect, the invention features nucleic acid expression vectors including a sequence encoding a SARS-CoV S polypeptide, or fragment thereof, wherein the sequences have at least 80% identity with the sequence set forth in SEQ ID NO:1.

In another aspect, the invention features isolated cells including the expression vectors described herein.

In another aspect, the invention features isolated polypeptides including an extracellular portion of the SARS-CoV S polypeptide, or fragment thereof.

In another aspect, the invention features isolated antibodies or antigen binding fragments thereof that specifically bind to an S polypeptide, e.g., the antibodies bind to an epitope within the extracellular portion of the S polypeptide. In one embodiment, the antibodies bind to an epitope between amino acids 1-269 (e.g., between amino acids 130-150 or 90-190) or amino acids 490-1190 (e.g., between amino acids 490-510 or amino acids 511-1190) of the S protein. In certain embodiments, the antibodies or antigen binding fragments thereof inhibit binding of the S protein to a receptor on a cell (e.g., a Vero E6 cell). In certain embodiments, the antibodies neutralize SARS-CoV-mediated cellular toxicity in vitro, and/or inhibit replication of SARS-CoV in mammals, such as mice or hamsters, exposed to the virus intranasally. For example, the antibodies can inhibit replication in the lungs and/or nasal passages. In certain embodiments, the antibodies are useful for treatment post-infection (e.g., the antibodies reduce viral load in animals when administered after animals are infected with SARS-CoV as compared to animals that are not treated with the antibody). The antibodies can be monoclonal antibodies, or an antigen-binding portions thereof, human antibodies, chimeric or humanized antibodies, a full-length antibodies of an IgG1 or IgG4 isotype, antibody fragments or single-chain antibodies. The invention also features the human monoclonal antibody 201.2 (also referred to herein as "508-201" and "7-508-201" and "the antibody produced by clone 508-201") and antigen binding portions thereof. The $V_H$ amino acid sequence of 201.2 is shown in SEQ ID NO:13. The $V_L$ amino acid sequence of 201.2 is shown in SEQ ID NO:14.

Also provided herein are isolated monoclonal antibodies, or antigen binding portions thereof, that include: (a) a heavy chain variable region of 201.2, including the amino acid sequence shown in SEQ ID NO:13; and/or (b) a light chain variable region of 201.2, including the amino acid sequence shown in SEQ ID NO:14; wherein the antibodies specifically bind to the S protein (e.g., an epitope within amino acids 490-510 of the S protein).

Also provided are antibodies and antigen binding portions thereof, that include the heavy chain and light chain CDR1s, CDR2s, and CDR3s of 201.2 (e.g., antibodies that include CDRs of SEQ ID NOs:7 to 12).

Also provided are isolated monoclonal antibodies, or antigen binding portions thereof, that include: (a) a heavy chain variable region CDR1 including SEQ ID NO:7; (b) a heavy chain variable region CDR2 including SEQ ID NO:8; (c) a heavy chain variable region CDR3 including SEQ ID NO:9; (d) a light chain variable region CDR1 including SEQ ID NO:10; (e) a light chain variable region CDR2 including SEQ ID NO:11; and (f) a light chain variable region CDR3 including SEQ ID NO:12; wherein the antibodies specifically bind to the S protein.

In certain embodiments, anti-S protein antibodies include a heavy chain variable region from a particular germline heavy chain immunoglobulin gene (e.g., a human $V_H$ DP44 gene, a human $V_H$ 3-23 gene, or a human $V_H$ 3-7 gene) and/or a light chain variable region from a particular germline light chain immunoglobulin gene (e.g., a human $V_K$ L6 gene), wherein the antibodies specifically bind to the S protein (e.g., to an epitope within amino acids 130-150 or amino acids 490-510 of the S protein).

The invention also provides isolated monoclonal antibodies, or antigen-binding portions thereof, that include: (a) a heavy chain variable region that is the product of or derived from a human $V_H$ DP44, $V_H$ 3-23, or $V_H$ 3-7 gene (which encode the amino acid sequences set forth in SEQ ID NO:18, 19 and 20, respectively); (b) a light chain variable region that is the product of or derived from a human $V_k$ L6 gene (which encodes the amino acid sequences set forth in SEQ ID NO:21); and (c) specifically bind to the S protein.

In yet another embodiment, an antibody of the invention can include heavy and light chain variable regions with amino acid sequences that are homologous to the amino acid sequences of antibody 201.2, and that also specifically bind to the S protein. In certain embodiments, the antibody neutralizes SARS-CoV in vitro and/or in vivo.

For example, the invention provides isolated monoclonal antibodies, or antigen binding portions thereof, including a heavy chain variable region and a light chain variable region, wherein: (a) the heavy chain variable region includes an amino acid sequence that is at least 80% homologous to the amino acid sequence shown in SEQ ID NO:13; (b) the light chain variable region includes an amino acid sequence that is at least 80% homologous to the amino acid sequence shown in SEQ ID NO:14; and (c) the antibody specifically binds to the S protein. In various embodiments, the antibody can be, for example, a human antibody, a humanized antibody or a chimeric antibody.

The $V_H$ and/or $V_L$ amino acid sequences may be 85%, 90%, 95%, 96%, 97%, 98% or 99% homologous or identical to the sequences of 201.2. An antibody having $V_H$ and $V_L$ regions having high (i.e., 80% or greater) homology to the $V_H$ and $V_L$ regions of 201.2, can be obtained by mutagenesis (e.g., site-directed or PCR-mediated mutagenesis) of nucleic acid molecules encoding SEQ ID NOs:13 and/or 14 (e.g., nucleic acid molecules of SEQ ID NOs:15 and/or 16), followed by testing of the encoded altered antibody for binding to the S protein, and/or neutralizing SARS-CoV in vitro and/or in vivo.

In certain embodiments, an antibody of the invention includes a heavy chain variable region including CDR1, CDR2 and CDR3 sequences and a light chain variable region including CDR1, CDR2 and CDR3 sequences, wherein one or more of these CDR sequences have specified amino acid sequences based on 201.2, or conservative modifications thereof, and wherein the antibodies retain the desired functional properties of the antibodies of the invention. Accordingly, the invention provides isolated monoclonal antibodies, or antigen binding portions thereof, including a heavy chain variable region comprising CDR1, CDR2, and CDR3 sequences and a light chain variable region including CDR1, CDR2, and CDR3 sequences, wherein: (a) the heavy chain variable region CDR3 sequence includes the amino acid sequence shown in SEQ ID NO:9, and conservative modifications thereof; (b) the light chain variable region CDR3 sequence comprises the amino acid sequence shown in SEQ ID NO:12, and conservative modifications thereof; (c) the antibody specifically binds to the S protein.

The heavy chain variable region CDR2 sequence of the antibody can include the amino acid sequence shown in SEQ ID NO:8, and conservative modifications thereof; and the light chain variable region CDR2 sequence can comprise the amino acid sequence shown in SEQ ID NO:11, and conservative modifications thereof. In another embodiment, the heavy chain variable region CDR1 sequence includes the amino acid sequence shown in SEQ ID NO:7, and conservative modifications thereof; and the light chain variable region CDR1 sequence comprises the amino acid sequence shown in SEQ ID NO:10, and conservative modifications thereof. In various embodiments, the antibody can be, for example, human, humanized, or chimeric.

In another embodiment, the invention provides antibodies that bind to the same epitope on the S protein as any of the monoclonal antibodies described herein (i.e., antibodies that have the ability to cross-compete for binding to the S protein with the antibody produced by clone 508-68 or with 201.2). In one embodiment, the reference antibody for cross-competition studies is the monoclonal antibody 201.2 (having $V_H$ and $V_L$ sequences as shown in SEQ ID NOs:13 and 14, respectively.

Also provided are isolated monoclonal antibodies, or antigen binding portions thereof, including the $V_H$ and $V_L$ CDR sequences of monoclonal antibody 201.2, yet such antibodies may contain different framework sequences from this antibody.

In another embodiment, the invention provides methods for preparing an anti-S protein antibody by (a) providing: (i) a heavy chain variable region antibody sequence including a CDR1 sequence shown in SEQ ID NO:7, a CDR2 sequence shown in SEQ ID NO:8 and/or a CDR3 sequence shown in SEQ ID NO:9; and/or (ii) a light chain variable region antibody sequence including a CDR1 sequence shown in SEQ ID NO:10, a CDR2 sequence shown in SEQ ID NO:11 and/or a CDR3 sequence shown in SEQ ID NO:12; (b) altering at least one amino acid residue within the heavy chain variable region antibody sequence and/or the light chain variable region antibody sequence to create at least one altered antibody sequence; and (c) expressing the altered antibody sequence as a protein. The antibody encoded by the altered antibody sequence(s) can be one that retains one, some or all of the functional properties of the anti-S protein from which the sequences are derived, e.g., one or more functional properties of 201.2.

The invention also features kits that include an antibody described herein. The kits can further include instructions for using the antibody (e.g., for a diagnostic or therapeutic application).

In another aspect, the invention features pharmaceutical compositions including an antibody that specifically binds to an S polypeptide, and a pharmaceutically acceptable carrier.

In another aspect, the invention features pharmaceutical compositions including an S polypeptide and a pharmaceutically acceptable carrier.

In another aspect, the invention features methods for making an S polypeptide of SARS-CoV by constructing a nucleic acid, wherein the nucleic acid includes a sequence encoding an S polypeptide of SARS-CoV, and wherein the codons encoding the S polypeptide are optimized for expression in a host cell, expressing the nucleic acid in the host cell under conditions that allow the S polypeptide to be produced, and isolating the S polypeptide.

In another aspect, the invention features methods for making an antibody or antigen binding fragment thereof that specifically binds to an S polypeptide of SARS-CoV by providing a nucleic acid, wherein the nucleic acid comprises a sequence encoding a SARS-CoV S polypeptide, or fragment thereof, and wherein the sequence has at least 80% identity with the sequence set forth in SEQ ID NO:1; expressing the nucleic acid in a host cell under conditions that allow the S polypeptide to be produced, isolating the S polypeptide, immunizing an animal with the S polypeptide, and isolating an antibody from the animal.

In another aspect, the invention features methods for evaluating a biological sample for the presence of SARS-CoV by providing a biological sample; contacting the sample with an antibody or antigen binding fragment thereof that specifically binds to an S polypeptide of SARS-CoV, and evaluating binding of the antibody to an antigen in the sample, wherein binding indicates the presence of SARS-CoV.

In another aspect, the invention features methods for evaluating an antibody for inhibition of infection by SARS-CoV by providing a cell which is permissive for infection by SARS-CoV; contacting the cell with an S polypeptide of SARS-CoV, or fragment thereof, in the presence and the absence of an antibody, wherein inhibition of binding of the S polypeptide to the cell in the presence of the antibody indicates that the antibody inhibits infection by SARS-CoV.

In another aspect, the invention features methods for treating a subject at risk for, or exposed to SARS-CoV by administering to the subject a composition including an antibody or antigen binding fragment thereof that specifically binds to an S polypeptide of SARS-CoV (e.g., a human monoclonal antibody, e.g., monoclonal antibody 201.2 or an antigen-binding fragment thereof, e.g., a monoclonal antibody described herein). In some embodiments, the antibody or antigen binding fragment thereof is administered to a subject at risk for exposure to SARS-CoV. In some embodiments, the antibody or antigen-binding fragment thereof is administered to a subject that has been exposed to SARS-CoV (e.g., the subject exhibits symptoms of SARS-CoV and/or has been diagnosed with a SARS-CoV infection).

In another aspect, the invention features a method for treating a subject at risk for, or exposed to SARS-CoV by administering to the subject a composition including an extracellular portion of the SARS-CoV S polypeptide, or fragment thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A-1E are a representation of a codon-optimized sequence of the S protein gene and the corresponding amino acid sequence. The underlined region represents the last amino acids of the 350 amino acid fragment that was constructed. The bold area at the end of the sequence represents the predicted transmembrane and cytoplasmic domains.

FIGS. 2A-2F are a representation of the alignment of a codon-optimized DNA sequence of the S protein gene and a native DNA sequence of the S protein gene.

FIGS. 3A-3I are a representation of the oligonucleotides (F1 to F52 and R1 to R52 as well as others) used to construct a codon-optimized sequence of the S protein gene. The underlined sequences represent restriction sites incorporated for cloning purposes.

FIG. 4 is a representation of SDS-PAGE and Coomassie analysis of expressed S(1190) and S1 (350) proteins.

FIG. 12 is a table depicting binding and neutralization properties of serum from human, mouse (Ms), rabbit (Rb), and HuMAb™ mice with SARS-CoV, S(350), S(590), and S(1190) as immunogens.

FIG. 13A is a graph depicting the results of binding to S(1190) by ELISA. FIG. 13B is a graph depicting the results of binding to S(590) by ELISA. FIG. 13C is a graph depicting the results of binding to S(270-510) by ELISA. FIG. 13D is a bar graph depicting the results of neutralization of SARS-CoV as determined by metabolic viability assays. "Dilution" on the x-axis indicates the dilution of the antibody that was tested. The number on the y-axis corresponds to the ratio of absorbance of antibody-treated virus-infected cells to uninfected cells. FIG. 13E is a graph depicting the results of FACS assays to determine antibody inhibition of S(590) binding to Vero E6 cells at dilutions of 1:4, 1:20, and 1:100. FIG. 13F is a graph depicting the results of assays to determine antibody binding to a cell-surface expressed form of the S protein, S(1255). Antibody was tested at dilutions of 1:4, 1:20, and 1:100.

FIG. 14D is a bar graph depicting the results of neutralization of SARS-CoV as determined by metabolic viability assays. Cells were exposed to low, high, and higher levels of virus (x-axis). The number on the y-axis corresponds to the ratio of absorbance of antibody-treated virus-infected cells to uninfected cells.

FIGS. 18A-F are graphs depicting the results of analyses of binding and neutralization properties of the human monoclonal antibody produced by clone 7-508-104. The figure legends for FIGS. 18A-18F are identical to those for the corresponding panels in FIG. 13.

FIG. 19D is a bar graph depicting the results of neutralization of SARS-CoV as determined by metabolic viability assays. Cells were exposed to low and high levels of virus (x-axis). The number on the y-axis corresponds to the ratio of absorbance of antibody-treated virus-infected cells to uninfected cells.

FIG. 21D is a bar graph depicting the results of neutralization of SARS-CoV as determined by metabolic viability assays. Cells were exposed to low and high levels of virus (x-axis). The number on the y-axis corresponds to the ratio of absorbance of antibody-treated virus-infected cells to uninfected cells.

FIG. 22D is a bar graph depicting the results of neutralization of SARS-CoV as determined by metabolic viability assays. Cells were exposed to low and high levels of virus (x-axis). The number on the y-axis corresponds to the ratio of absorbance of antibody-treated virus-infected cells to uninfected cells.

FIG. 35 is a representation of the nucleotide sequence (SEQ ID NO:15) and amino acid sequence (SEQ ID NO:13) of the heavy chain variable region of the 201.2 human monoclonal antibody. The CDR1 (SEQ ID NO:7), CDR2 (SEQ ID NO:8) and CDR3 (SEQ ID NO:9) regions are delineated and the V, D and J germline derivations are indicated.

FIG. 36 is a representation of the nucleotide sequence (SEQ ID NO:16) and amino acid sequence (SEQ ID: 14) of the light chain variable region of the 201.2 human monoclonal antibody. The CDR1 (SEQ ID NO:10), CDR2 (SEQ ID NO:11) and CDR3 (SEQ ID NO:12) regions are delineated and the V and J germline derivations are indicated.

FIG. 37 is a representation of an alignment of the amino acid sequence of the heavy chain variable region of 201.2 (SEQ ID NO:13) and a mutated form of the heavy chain variable region of 201.2 referred to as 201.2(mut) (SEQ ID NO: 17) with the human germline $V_H$ DP44, $V_H$ 3-23 and $V_H$ 3-7 amino acid sequences (SEQ ID NOs: 18, 19 and 20, respectively).

FIG. 38 is a representation of an alignment of the amino acid sequence of the light chain variable region of 201.2 (SEQ ID NO:13) with the human germline $V_k$ L6 amino acid sequence (SEQ ID NO:21).

FIG. 39 is a a bar graph depicting the results of assays to determine SARS-CoV titers isolated from lung tissue of hamsters treated with 40 mg/kg of an irrelevant antibody (negative control, Neg), 40 mg/kg of 508-201, or 4 mg/kg of 508-201, following challenge with SARS-CoV. Results for individual mice are depicted.

FIG. 40 is a bar graph depicting the results of assays to determine SARS-CoV titers isolated from lung tissue of hamsters treated with 40 mg/kg of an irrelevant antibody (negative control, Neg), 40 mg/kg of 508-201, or 4 mg/kg of 508-201, following challenge with SARS-CoV. The mean virus titer for groups of mice receiving the same treatment are depicted.

FIG. 41 is a table depicting the results of assays to determine the pathological effects of SARS-CoV infection on hamsters receiving 40 mg/kg of an irrelevant antibody (negative control, Neg), 40 mg/kg of 508-201, or 4 mg/kg of 508-201, following challenge with the virus.

Like reference symbols in the various drawings indicate like elements.

DETAILED DESCRIPTION

Figure 5:
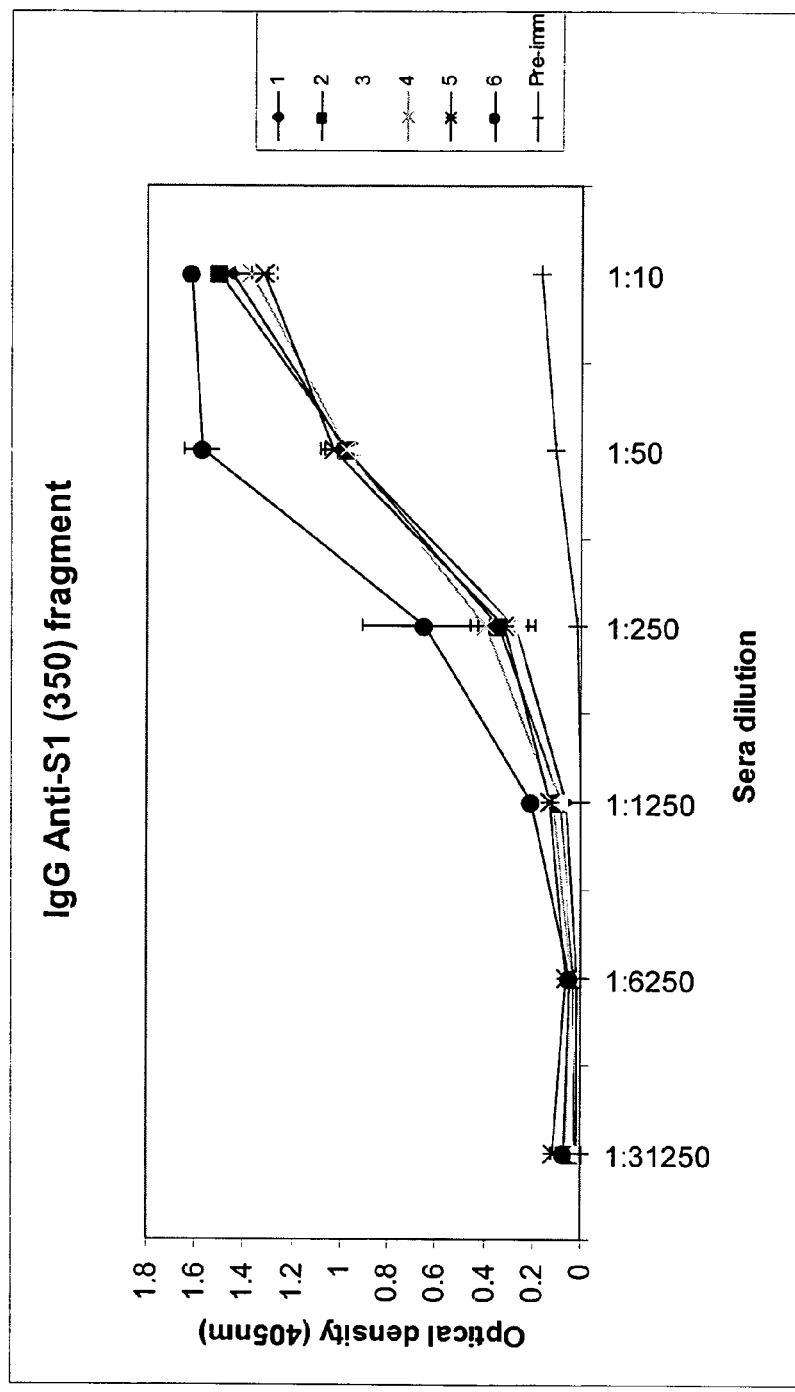
FIG. 5 is a graph depicting ELISA results of binding of mouse anti-S1 antiserum to S1 protein. Sera from six mice (1-6) were tested individually.

Coronaviruses display peplomer spikes formed by oligomers of the surface S-glycoprotein. These proteins can mediate interaction of the viruses with receptors on host cells to allow entry and fusion, and also are major targets for neutralizing antibodies. Efficient expression of S proteins is useful for the preparation of therapeutic and diagnostic proteins and antibodies for, e.g., diagnosing, treating, preventing, and analyzing coronaviruses.

Provided herein are codon-optimized nucleic acid sequences of the SARS-CoV S protein and methods for the construction of such sequences. Also described are proteins that can be expressed by these sequences, and methods of expressing the proteins, as well as antibodies that recognize the S protein and fragments of the S protein, and can be used in the diagnosis, prevention, and treatment of SARS.

In order that the present invention may be more readily understood, certain terms are first defined. Additional definitions are set forth throughout the detailed description.

The term "S protein" refers to the spike glycoprotein encoded by SARS-CoV. "Protein" is used interchangeably with "polypeptide." The full length amino acid sequence of the SARS-CoV S protein is shown in FIG. 1 (also, SEQ ID NO:2). The predicted leader sequence corresponds to amino acids 1-14 of SEQ ID NO:2. The predicted extracellular portion of the mature S protein corresponds to amino acids 15-1190 of SEQ ID NO:2. The predicted transmembrane domain corresponds to amino acids 1191-1226 of SEQ ID NO:2. The predicted cytoplasmic domain corresponds to amino acids 1227-1255 of SEQ ID NO:2. As described herein, the extracellular portion of the S protein is soluble and is secreted by cells.

An "anti-S protein antibody" or "anti-S antibody" is an antibody that interacts with (e.g., binds to) the S protein. Preferably, the anti-S protein antibody interacts with the extracellular domain of the S protein, e.g., a portion of the protein encoded by amino acids 1-1190. An anti-S protein antibody may bind to an epitope, e.g., a conformational or a linear epitope, or to a fragment of the full-length S protein. In one embodiment, the interaction occurs with high affinity (e.g., with an affinity constant of $10^{-8}$ M or less, $10^{-9}$ M or less or $10^{-10}$ M or less for the S protein or fragment thereof).

As used herein, the term "treat" or "treatment" is defined as the application or administration of an S protein or fragment thereof, or an anti-S protein antibody or antigen binding fragment thereof, to a subject, e.g., a patient, or application or administration to an isolated tissue or cell from a subject, e.g., a cell from a patient, which can be returned to the patient. The S protein, anti-S protein antibody, or antigen binding fragment thereof, can be administered alone or in combination with, a second agent. The subject can be a patient having a disorder (e.g., a viral disorder, e.g., SARS), a symptom of a disorder, or a predisposition toward a disorder. The treatment can be to cure, heal, alleviate, relieve, alter, remedy, ameliorate, palliate, improve, or affect the disorder, the symptoms of the disorder, or the predisposition toward the disorder.

The terms "agonize," "induce," "inhibit," "potentiate," "elevate," "increase," "decrease," or the like, e.g., terms that denote quantitative differences between two states, refer to a difference, e.g., a statistically or clinically significant difference, between the two states.

As used herein, "specific binding" or "specifically binds to" refer to the ability of an antibody to: (1) bind to an S protein with an affinity of at least $1 \times 10^7$ $M^{-1}$, or (2) bind to an S protein with an affinity that is at least >2 standard deviations over a control antibody.

As used herein, the term "antibody" refers to a protein including at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework regions and CDRs has been precisely defined (see, Kabat E. A. et al., (1991) *Sequences of Proteins of Immunological Interest, Fifth Edition*, U.S. Department of Health and Human Services, NIH Publication No. 91-3242, and Chothia, C. et al., (1987) *J. Mol. Biol.*, 196:901-917, which are incorporated herein by reference). Preferably, each VH and VL is composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, the term "immunoglobulin" refers to a protein including one or more polypeptides encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a non-human source, e.g., from a non-human antibody, e.g., from a mouse immunoglobulin or another non-human immunoglobulin, or from a consensus sequence, or any other method of generating diversity; and having a framework that is less antigenic in a human than a non-human framework, e.g., in the case of CDRs from a non-human immunoglobulin, less antigenic than the non-human framework from which the non-human CDRs were taken. The framework of the immunoglobulin can be human, humanized non-human, e.g., from a mouse, or synthetic, e.g., a consensus sequence, or can be modified to decrease antigenicity in humans.

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to a portion of an antibody that specifically binds to an antigen (e.g., a SARS-CoV S protein), e.g., a molecule in which one or more immunoglobulin chains is not full length, but which specifically binds to an S protein. Examples of binding fragments encompassed within the term "antigen-binding fragment" of an antibody include (i) a Fab fragment, which is a monovalent fragment consisting of the VL, VH, CL and CH1 domains; (ii) a F(ab')$_2$ fragment, which is a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature,* 341:544-546), which consists of a VH domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al., (1988) *Science,* 242:423-426; and Huston et al., (1988) *Proc. Natl. Acad. Sci. USA,* 85:5879-5883). Such single-chain antibodies are also intended to be encompassed within the term "antigen-binding fragment" of an antibody. These antibody fragments are obtained using conventional techniques known to those skilled in the art, and the fragments are screened for utility in the same manner as are intact antibodies.

The term "monospecific antibody" refers to an antibody that displays a single binding specificity and affinity for a particular target, e.g., an epitope. This term includes a "monoclonal antibody" or "monoclonal antibody composition," which as used herein refer to a preparation of antibodies or fragments thereof with a single molecular composition and a single binding specificity and affinity for a particular epitope.

An "isolated antibody" is an antibody that is substantially free (e.g., contains less than 50% w/v) of other antibodies having different antigenic specificities (e.g., an isolated antibody that specifically binds to an S protein of SARS-CoV is substantially free of antibodies that specifically bind to antigens other than the S protein). Moreover, an isolated antibody may be substantially free of other cellular material and/or chemicals.

A "human antibody" is an antibody having variable regions in which both the framework and CDR regions are derived from human germline immunoglobulin sequences. If the antibody contains a constant region, the constant region also is derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). Human antibodies do not include antibodies in which CDR sequences derived from the germline of another mammalian species, such as a mouse, have been grafted onto human framework sequences.

As used herein, a human antibody includes heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation.

In certain cases, a human antibody may be at least 95%, or even at least 96%, 97%, 98%, 99%, or 100% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference(s) from the amino acid sequence encoded by the germline immunoglobulin gene.

A "human monoclonal antibody" is an antibody that displays a single binding specificity that has variable regions in which both the framework and CDR regions are derived from human germline immunoglobulin sequences. In one embodiment, the human monoclonal antibodies are produced by a hybridoma that includes a B cell obtained from a transgenic nonhuman animal, e.g., a transgenic mouse, having a genome including a human heavy chain transgene and a light chain transgene fused to an immortalized cell.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences.

A "recombinant human antibody" is a recombinant antibody that is, e.g., (a) an antibody isolated from an animal (e.g., a mouse) that is transgenic or transchromosomal for human immunoglobulin genes or a hybridoma prepared therefrom, (b) an antibody isolated from a host cell transformed to express the human antibody, e.g., from a transfectoma, (c) an antibody isolated from a recombinant, combinatorial human antibody library, and (d) an antibody prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A humanized antibody is an antibody that has CDRs derived from a non-human antibody and the remaining portions of the antibody molecule are human.

The terms "$K_{assoc}$" or "$K_a$", refer to the association rate of a particular antibody-antigen interaction, whereas the term "$K_{dis}$" or "$K_d$," refer to the dissociation rate of a particular antibody-antigen interaction. The term "$K_D$", refers to the dissociation constant, which is obtained from the ratio of $K_d$ to $K_a$ (i.e, $K_d/K_a$) and is expressed as a molar concentration (M). $K_D$ values for antibodies can be determined using methods well established in the art. The $K_D$ of an antibody is determined by measuring surface plasmon resonance using a Biacore® system.

As used herein, the term "high affinity" for an IgG antibody refers to an antibody having a $K_D$ of $10^{-8}$ M or less, e.g., $10^{-9}$ M or less, or $10^{-10}$ M or less for a target antigen. However, "high affinity" binding can vary for other antibody isotypes. "High affinity" binding for an IgM isotype refers to an antibody having a $K_D$ of $10^{-7}$ M or less, e.g., $10^{-8}$ M or less.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity for the same target as the first antibody.

Calculations of "homology" or "identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). For substantial identity, the length of a reference sequence aligned for comparison purposes is at least 80%, but can be higher, e.g., at least 85%, 90%, 85%, 96%, 97%, 98%, 99% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences are accomplished using a mathematical algorithm. In particular, percent homology between two amino acid sequences is determined using the Needleman and Wunsch (1970), *J. Mol. Biol.*, 48:444-453, algorithm which has been incorporated into the GAP program in the GCG software package, using a Blossum 62 scoring matrix with a gap penalty of 12, a gap extend penalty of 4, and a frameshift gap penalty of 5.

As used herein, the phrase "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated herein by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

It is understood that the new antibodies and antigen binding fragment thereof may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie, J U et al., (1990) *Science,* 247:1306-1310. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

Construction of Optimized Sequences

Viral proteins and proteins that are naturally expressed at low levels can provide challenges for efficient expression by recombinant means. Viral proteins often display a codon usage that is inefficiently translated in a host cell. Alteration of the codons native to the viral sequence can facilitate more robust expression of these proteins. Codon preferences for abundantly-expressed proteins have been determined in a number of species, and can provide guidelines for codon substitution. Examples of human proteins for which codon preferences have been determined include rhodopsin. Substitution of viral codons can be done by routine methods, such as site-directed mutagenesis, or construction of oligonucleotides corresponding to the optimized sequence and synthesis of sequences by PCR. See, e.g., the construction method described in the Examples, below. See also Mirzabekov T. et al., *J. Biol. Chem.,* 274(40):28745-50, 1999. The optimization should also include consideration of other factors that can affect synthesis of oligos and/or expression. For example, long runs of G and/or C residues can interfere with synthesis, and should be avoided in the resulting optimized sequence.

The optimized S protein sequences described herein contained a native leader sequence. The optimized sequence was designed by replacing a subset of viral codons with codons used in an abundantly-expressed human protein, rhodopsin. Oligos corresponding to fragments of this optimized sequence were synthesized for both the positive and negative DNA strands to reduce PCR errors. Convenient restriction sites for cloning were also included in the sequence. The oligos were used in PCR to generate DNA encoding the S protein and S-protein fragments.

Nucleic Acids, Vectors, and Host Cells

New isolated nucleic acid, vector, and host cell compositions are described herein that can be used for recombinant expression of the optimized nucleic acid sequences to form S proteins, and of antibodies and antigen-binding fragments that specifically bind to S proteins.

Host cells and vectors (e.g., recombinant expression vectors) containing the nucleic acids, e.g., the optimized sequences encoding an S protein, or a sequence encoding an anti-S protein antibody, or an antigen binding fragment thereof, are also described.

Prokaryotic or eukaryotic host cells can be used. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic, e.g., bacterial cells such as *E. coli*, or eukaryotic, e.g., insect cells, yeast, or mammalian cells (e.g., cultured cell or a cell line, e.g., a primate cell such as a Vero cell, or a human cell). Other suitable host cells are known to those skilled in the art.

Preferred mammalian host cells for expressing the anti-S protein antibodies, or antigen-binding fragments thereof, include Chinese Hamster Ovary (CHO cells), lymphocytic cell lines, human 293T cells and COS cells.

New vectors, e.g., recombinant expression vectors, are described. The recombinant expression vectors can be designed for expression of the S proteins, anti-S protein antibodies, or an antigen-binding fragments thereof, in prokaryotic or eukaryotic cells. For example, the new polypeptides can be expressed in *E. coli*, insect cells (e.g., using baculovirus expression vectors), yeast cells, or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is often carried out in *E. coli* with vectors containing constitutive or inducible promoters directing the expression of either fusion or non-fusion proteins. Fusion vectors add a number of amino acids to protein or antibody encoded thereby, usually to the constant region of a recombinant antibody.

A codon-optimized nucleic acid can be expressed in mammalian cells using a mammalian expression vector. Examples of mammalian expression vectors include pCDM8 (Seed B., *Nature,* 329:840, 1987) and pMT2PC (Kaufman et al., *EMBO J.,* 6:187-195, 1987). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989.

In one embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., *Genes Dev.* 1:268-277, 1987), lymphoid-specific promoters (Calame and Eaton, *Adv. Immunol.,* 43:235-275, 1988), in particular promoters of T cell receptors (Winoto and Baltimore, *EMBO J.,* 8:729-733, 1989) and immunoglobulins (Banerji et al., *Cell,* 33:729-740, 1983; Queen and Baltimore, *Cell,* 33:741-748, 1983), neuron-specific promoters (e.g., the neurofilament promoter; Byrne and Ruddle, *Proc. Natl. Acad.*

Sci. USA, 86:5473-5477, 1989), pancreas-specific promoters (Edlund et al., Science, 230:912-916, 1985), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, Science, 249:374-379, 1990 and the α-fetoprotein promoter (Campes and Tilghman, Genes Dev., 3:537-546, 1989).

In addition to the coding sequences, the new recombinant expression vectors carry regulatory sequences that are operatively linked and control the expression of the proteins/antibody genes in a host cell and provide affinity domains for easy purification.

Antibodies

New antibodies, or antigen-binding fragments thereof, that specifically bind to the S protein and/or specific fragments of the S protein, e.g., of the extracellular portion of the S protein, are also described herein.

Many types of anti-S protein antibodies, or antigen-binding fragments thereof, are useful in the new methods described herein. The antibodies can be of the various isotypes, including: IgG (e.g., IgG1, IgG2, IgG3, IgG4), IgM, IgA1, IgA2, IgD, or IgE. For example, the antibody can be an IgG isotype, e.g., IgG1. The antibody molecules can be full-length (e.g., an IgG1 or IgG4 antibody) or can include only an antigen-binding fragment (e.g., a Fab, $F(ab')_2$, Fv or a single chain Fv fragment). These include monoclonal antibodies, recombinant antibodies, chimeric antibodies, human antibodies, and humanized antibodies, as well as antigen-binding fragments of the foregoing.

Monoclonal anti-S protein antibodies can be used in the new methods. Preferably, the monoclonal antibodies bind to the extracellular domain of an S protein (i.e., an epitope of an S protein located outside of a SARS virion or a SARS-infected cell).

Additional monoclonal antibodies to an S protein can be generated using techniques known in the art. Monoclonal antibodies can be produced by a variety of techniques, including conventional monoclonal antibody methodology, e.g., the standard somatic cell hybridization technique of Kohler and Milstein, *Nature* 256: 495 (1975). See generally, Harlow, E. and Lane, D. (1988) *Antibodies: A Laboratory Manual*, Cold Spring Harbor Laboratory Press, Cold Spring Harbor, N.Y.

Useful immunogens include the S proteins described herein, e.g., S protein expressed from optimized nucleic acid sequences, e.g., S proteins expressed in human cells, or soluble fragments of S proteins. Fragments useful for immunization include the extracellular domain (1-1190); the receptor binding domain (S1); membrane fusion domain (S2); any neutralizing epitopes or any fragments that express well (1-590).

Anti-S protein antibodies or fragments thereof useful herein may also be recombinant antibodies produced by host cells transformed with DNA encoding immunoglobulin light and heavy chains of a desired antibody. Recombinant antibodies can be produced by known genetic engineering techniques. For example, recombinant antibodies can be produced by cloning a nucleotide sequence, e.g., a cDNA or genomic DNA, encoding the immunoglobulin light and heavy chains of the desired antibody. The nucleotide sequence encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding may be renatured according to well known methods (Kim and Baldwin, "Specific Intermediates in the Folding Reactions of Small Proteins and the Mechanism of Protein Folding," *Ann. Rev. Biochem.,* 51, pp. 459-89 (1982)). It is possible that the host cells will produce portions of intact antibodies, such as light chain dimers or heavy chain dimers, which also are antibody homologs according to the present invention.

It will be understood that variations on the above procedure are useful herein. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods of this invention. In addition, bifunctional antibodies may be produced in which one heavy and one light chain are anti-S protein antibody and the other heavy and light chain are specific for an antigen other than an S protein, or another epitope of an S protein.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al., U.S. Pat. No. 4,816,567; Cabilly et al., European Patent Application 125,023; Better et al. (1988 *Science,* 240:1041-1043); Liu et al. (1987) *PNAS,* 84:3439-3443; Liu et al., 1987, *J. Immunol.,* 139:3521-3526; Sun et al. (1987) *PNAS,* 84:214-218; Nishimura et al., 1987, *Canc. Res.,* 47:999-1005; Wood et al. (1985) *Nature,* 314: 446-449; and Shaw et al., 1988, *J. Natl Cancer Inst.,* 80:1553-1559).

An antibody or an immunoglobulin chain can be humanized by methods known in the art. For example, once murine antibodies are obtained, variable regions can be sequenced. The location of the CDRs and framework residues can be determined (see, Kabat, E. A. et al. (1991) *Sequences of Proteins of Immunological Interest, Fifth Edition*, U.S. Department of Health and Human Services, NIH Publication No. 91-3242, and Chothia, C. et al. (1987) J. Mol. Biol., 196:901-917, which are incorporated herein by reference). The light and heavy chain variable regions can, optionally, be ligated to corresponding constant regions.

Murine anti-S protein antibodies can be sequenced using art-recognized techniques. Humanized or CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al., 1986, *Nature,* 321:552-525; Verhoeyan et al., 1988, *Science,* 239:1534; Beidler et al., 1988, *J. Immunol.*, 141:4053-4060; and Winter, U.S. Pat. No. 5,225,539, the contents of all of which are hereby expressly incorporated by reference.

Winter describes a CDR-grafting method that may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science*, 229:1202-1207, by Oi et al., 1986, *BioTechniques*, 4:214, and by Queen et al., U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

Also described herein are humanized antibodies in which specific amino acids have been substituted, deleted, or added. In particular, certain humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089 (e.g., columns 12-16), the contents of which are hereby incorporated by reference. The acceptor framework can be a mature human antibody framework sequence or a consensus sequence.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence. Other techniques for humanizing antibodies are described in Padlan et al., EP 519596 A1, published on Dec. 23, 1992.

Human monoclonal antibodies can be generated using transgenic mice expressing human immunoglobulin genes rather than mouse immunoglobulin genes. These transgenic mice, also referred to as "HuMAb-Mouse™," contain human immunoglobulin gene miniloci that encode unrearranged human heavy (μ and γ) and κ light chain immunoglobulin sequences, together with targeted mutations that inactivate the endogenous μ and κ chain loci (see e.g., Lonberg, N. et al. (1994) *Nature*, 368(6474): 856-859 and U.S. Pat. No. 5,770, 429). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology*, 113:49-101; Lonberg, N. and Huszar, D. (1995) *Intern. Rev. Immunol.*, 13: 65-93, and Harding, F. and Lonberg, N. (1995) *Ann. N.Y. Acad. Sci*, 764:536-546). The preparation of such transgenic mice is described in further detail in Taylor, L. et al. (1992) *Nucleic Acids Research*, 20:6287-6295; Chen, J. et al. (1993) *International Immunology*, 5: 647-656; Tuaillon et al. (1993) *Proc. Natl. Acad. Sci. USA*, 90:3720-3724; Choi et al. (1993) *Nature Genetics*, 4:117-123; Chen, J. et al. (1993) *EMBO J.*, 12: 821-830; Tuaillon et al. (1994) *J. Immunol.*, 152:2912-2920; Taylor, L. et al. (1994) *International Immunology*, 6: 579-591; and Fishwild, D. et al. (1996) *Nature Biotechnology*, 14: 845-851. See further, U.S. Pat. Nos. 5,545,806; 5,569,825; 5,625,126; 5,633,425; 5,661,016; 5,770,429; 5,789,650; 5,814,318; 5,874,299 and 5,877,397, all by Lonberg and Kay, and PCT Publication Nos. WO 01/14424, WO 98/24884, WO 94/25585, WO 93/1227, and WO 92/03918.

An S protein, anti-S protein antibody, or antigen-binding fragment thereof, can be derivatized or linked to another functional molecule (e.g., another peptide or protein). For example, a protein or antibody can be functionally linked (by chemical coupling, genetic fusion, noncovalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag).

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a protein can be derivatized (or labeled) to include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, β-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; (ii) to detect a predetermined antigen (e.g., an S protein, or a SARS virion, e.g., in a cellular lysate or a serum sample) in order to evaluate the abundance and pattern of expression of the protein; and (iii) to monitor protein levels in tissue as part of a clinical testing procedure, e.g., to determine the efficacy of a given treatment regimen.

An S protein or an anti-S protein antibody or antigen-binding fragment thereof may be conjugated to another molecular entity, typically a label or a therapeutic (e.g., a cytotoxic or cytostatic) agent or moiety.

Radioactive isotopes can be used in diagnostic or therapeutic applications. Radioactive isotopes that can be coupled to proteins and antibodies include, but are not limited to α-, β-, or γ-emitters, or β- and γ-emitters.

Antibody 201.2 and Variants Thereof

One exemplary antibody provided herein is the human monoclonal antibody 201.2 (also referred to herein as "508-201" and "7-508-201" and "the antibody produced by clone 508-201"), structurally characterized as described in Example 17. The $V_H$ amino acid sequence of 201.2 is shown in SEQ ID NO:13 and FIG. 35. The $V_L$ amino acid sequence of 201.2 is shown in SEQ ID NO:14 and FIG. 36. Antibodies that include portions of 201.2 (e.g., a heavy chain, a light chain, CDRs), and which specifically bind to the S protein, are also provided. The CDR regions are delineated using the Kabat system (Kabat, E. A. et al. (1991) Sequences of Proteins of Immunological Interest, Fifth Edition, U.S. Department of Health and Human Services, NIH Publication No. 91-3242).

Antibodies with Particular Germline Sequences. In certain embodiments, the new antibodies include a heavy chain variable region from a particular germline heavy chain immunoglobulin gene and/or a light chain variable region from a particular germline light chain immunoglobulin gene. For example, an isolated monoclonal antibody or an antigen-binding portion thereof, that includes a heavy chain variable region that is the product of or derived from a human $V_H$ DP44 gene, a human $V_H$ 3-23 gene, or a human $V_H$ 3-7 gene, is provided, wherein the antibody specifically binds to the S protein. In yet another embodiment, an isolated monoclonal antibody or an antigen-binding portion thereof that includes a light chain variable region that is the product of or derived from a human $V_K$ L6 gene is provided, wherein the antibody specifically binds to the S protein. As discussed in Example 17, given the structural relatedness of $V_H$ DP44 to $V_H$ 3-23 and $V_H$ 3-7, it is expected that other anti-S protein antibodies can be selected that utilize a $V_H$ region derived from either of these additional germline sequences.

Homologous Antibodies. Also provided herein are antibodies that include amino acid sequences that are homologous (i.e., identical or substantially identical) to the amino acid sequences of 201.2, wherein the antibodies specifically bind to the S protein, and wherein the antibodies retain one or more additional properties of 201.2 (e.g., neutralization of SARS-CoV in vitro or neutralization of SARS-CoV in vivo). For example, isolated monoclonal antibodies, or antigen binding portions thereof, with a heavy chain variable region amino acid sequence that is at least 80% (e.g., 85%, 90%, 95%, 96%, 97%, 98% or 99%) identical to the amino acid sequence shown in SEQ ID NO:13 and a light chain variable region amino acid sequence that is at least 80% (e.g., 85%, 90%, 95%, 96%, 97%, 98% or 99%) identical to the amino acid sequence shown in SEQ ID NO:14, wherein the antibody specifically binds to the S protein are provided herein. In various embodiments, the antibodies can be, for example, human antibodies, humanized antibodies or chimeric antibodies. An antibody having $V_H$ and $V_L$ regions having high (i.e., 80% or greater) identity to the $V_H$ and $V_L$ regions of the sequences set forth above, can be obtained by mutagenesis (e.g., site-directed or PCR-mediated mutagenesis) of nucleic acid molecules encoding SEQ ID NOs:13 and/or 14 (e.g., nucleic acid molecules of SEQ ID NOs:15 and/or 16), followed by testing of the encoded altered antibody for retained function (i.e., S protein binding, viral neutralization in vitro and/or in vivo) using the functional assays described herein.

Antibodies with Conservative Modifications. Also provide are antibodies that include a heavy chain variable region CDR1, CDR2, and CDR3 sequences and a light chain variable region comprising CDR1, CDR2, and CDR3 sequences, wherein one or more of these CDR sequences includes specified amino acid sequences based on 201.2, or conservative modifications thereof, and wherein the antibodies retain one or more functional properties of 201.2 (e.g., binding to the S protein, neutralization of SARS-CoV in vitro and/or in vivo).

Antibodies that Bind to the Same Epitope as Antibodies Described Herein. Also provided are antibodies that bind to the same epitope on the S protein as any of the monoclonal antibodies described herein (i.e., antibodies that have the ability to cross-compete for binding to the S protein with 201.2, or an antibody produced by clone 508-16, 508-39, 508-68, 508-104, 508-415, 508-395, or 73-121, described elsewhere herein). In various embodiments, the reference antibody for cross-competition studies is the monoclonal antibody 201.2 (having $V_H$ and $V_L$ sequences as shown in SEQ ID NOs:13 and 14, respectively).

Cross-competing antibodies can be identified based on their ability to cross-compete with an anti-S protein antibody (e.g., 201.2) in standard binding assays. For example, BIAcore analysis, ELISA assays, or flow cytometry may be used to demonstrate cross-competition with the antibodies of the current invention. The ability of a test antibody to inhibit the binding of, for example, 201.2, to the S protein demonstrates that the test antibody can compete with 201.2 for binding to the S protein and thus binds to the same epitope on as 201.2. In some embodiments, the antibody that binds to the same epitope as 201.2 is a human monoclonal antibody or a humanized monoclonal antibody or a chimeric antibody. Such monoclonal antibodies can be prepared and isolated as described herein.

Engineered and Modified Antibodies. An anti-S protein antibody can be prepared using an antibody having one or more of the $V_H$ and/or $V_L$ sequences disclosed herein as starting material to engineer a modified antibody, which modified antibody can have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al.

(1998) *Nature,* 332:323-327; Jones, P. et al. (1986) *Nature,* 321:522-525; Queen, C. et al. (1989) *Proc. Natl. Acad. Sci. U.S.A.,* 86:10029-10033; U.S. Pat. No. 5,225,539 to Winter, and U.S. Pat. Nos. 5,530,101; 5,585,089; 5,693,762 and 6,180,370 to Queen et al.)

Accordingly, an isolated monoclonal antibody, or antigen binding portion thereof, including the $V_H$ and $V_L$ CDR sequences of monoclonal antibody 201.2 is provided. Such antibody may contain different framework sequences from 201.2. Such framework sequences can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk/vbase), as well as in Kabat, E. A. et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops," *J. Mol. Biol.,* 227:776-798; and Cox, J. P. L. et al. (1994) "A Directory of Human Germ-line $V_H$ Segments Reveals a Strong Bias in their Usage," *Eur. J. Immunol.,* 24:827-836.

Framework sequences for use in the new antibodies can be those that are structurally similar to the framework sequences used by selected antibodies described herein, e.g., similar to the $V_H$ DP44 sequences (SEQ ID NO:18) and/or the $V_H$ 3-23 sequences (SEQ ID NO:19) and/or the $V_H$ 3-7 sequences (SEQ ID NO:20) and/or the $V_k$ L6 framework sequence (SEQ ID NO:21) used by 201.2. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. For example, conservative modifications (as discussed herein) can be introduced. The mutations may be amino acid substitutions, additions, or deletions, but are usually substitutions. Moreover, typically no more than one, two, three, four or five residues within a CDR region are altered.

Accordingly, in another embodiment, isolated anti-S protein monoclonal antibodies, or antigen binding portions thereof, include one of the following regions: (a) a $V_H$ CDR1 region including the amino acid sequence shown in SEQ ID NO:7, or an amino acid sequence having one, two, three, four, or five amino acid substitutions, deletions, or additions as compared to SEQ ID NO:7; (b) a $V_H$ CDR2 region including the amino acid sequence shown in SEQ ID NO:8, or an amino acid sequence having one, two, three, four, or five amino acid substitutions, deletions, or additions as compared to SEQ ID NO:8; (c) a $V_H$ CDR3 region including the amino acid sequence shown in SEQ ID NO:9, or an amino acid sequence having one, two, three, four, or five amino acid substitutions, deletions, or additions as compared to SEQ ID NO:9; (d) a $V_K$ CDR1 region including the amino acid sequence shown in SEQ ID NO:10, or an amino acid sequence having one, two, three, four, or five amino acid substitutions, deletions, or additions as compared to SEQ ID NO:10; (e) a $V_K$ CDR2 region including the amino acid sequence shown in SEQ ID NO:11, or an amino acid sequence having one, two, three, four, or five amino acid substitutions, deletions, or additions as compared to SEQ ID NO:11; and (f) a $V_K$ CDR3 region including the amino acid sequence shown in SEQ ID NO:12, or an amino acid sequence having one, two, three, four, or five amino acid substitutions, deletions, or additions as compared to SEQ ID NO:12.

Engineered antibodies include those in which modifications have been made to framework residues within $V_H$ and/or $V_K$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis.

In other embodiments, certain residues within $V_H$ of 201.2 are mutated to residues identical to or similar to residues in other human germline sequences (discussed further in Example 17). In one example, a heavy chain variable region of 201.2 is mutated by replacing the histidine at position 13 with lysine and the methionine at position 90 is replaced with threonine (SEQ ID NO:149). In another example, a heavy chain variable region of 201.2 is mutated by replacing the histidine at position 13 with glutamine and the methionine at position 90 is replaced with threonine. The amino acid sequence of the $V_H$ of 201.2(mut) is shown in SEQ ID NO:17. In another embodiment, the antibody includes a heavy chain variable region including the amino acid sequence of SEQ ID NO:17 and a light chain variable region including the amino acid sequence of SEQ ID NO:14.

As another approach, antibodies can be mutated to framework residues of similarly related germline sequences. For example, the germline sequence $V_H$ DP44 is highly similar to the $V_H$ 3-23 and $V_H$ 3-7 (SEQ ID NOs:19 and 20) germline sequences. To obtain an antibody with these germline configurations, the somatic sequences can be mutated to the similar germline sequences by, for example, site-directed mutagenesis or PCR-mediated mutagenesis (e.g., residues 6, 13, and 24 of the $V_H$ of 201.2 can be mutated from glutamine to glutamic acid, histidine to glutamine, and glutamine to alanine, respectively. In this way, a new antibody can be created that includes, for example, the $V_H$ 3-23 and $V_H$ 3-7 germline sequences.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition to, or as an alternative to, modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or otherwise modified to alter its glycosylation, again to alter one or more functional properties of the antibody. The numbering of residues in the Fc region is that of the EU index of Kabat.

In one embodiment, the hinge region of CH1 can be modified by increasing or decreasing the number of cysteine residues in the hinge region. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody can be mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, and 322 can be replaced with a different amino acid residue such that the antibody has an altered affinity for an effector ligand, but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.*, 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (Gn-TIII)) such that antibodies expressed in the engineered cell lines exhibit increased bisecting GlcNac structures, which results in increased ADCC activity of the antibodies (see also Umana et al. (1999) *Nat. Biotech.* 17:176-180).

Another modification of the antibodies described herein is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

The anti-S protein antibodies having $V_H$ and $V_K$ sequences disclosed herein can be used to create new anti-S protein antibodies by modifying the VH and/or $V_K$ sequences, or the constant region(s) attached thereto. Thus, in another aspect, the structural features of an anti-S protein antibody, e.g., 201.2, are used to create structurally related anti-S protein antibodies that retain at least one functional property of the antibodies, such as binding to the S protein, or neutralizing SARS-CoV in vitro and/or in vivo. For example, one or more CDR regions of 201.2, or mutations thereof, can be combined recombinantly with known framework regions and/or other CDRs to create additional, recombinantly-engineered, anti-S protein antibodies, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) can be used as the starting material to create a "second generation" sequence(s) derived from the original sequence(s) and then the "second generation" sequence(s) is prepared and expressed as a protein.

The functional properties of the altered antibodies can be assessed using standard assays available in the art and/or described herein, such as those set forth in the Examples (e.g., flow cytometry and binding assays).

In certain embodiments of the methods of engineering the new antibodies described herein, mutations can be introduced randomly or selectively along all or part of an anti-S protein antibody coding sequence and the resulting modified anti-S protein antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Generation of Hybridomas Producing Monoclonal Antibodies

To generate hybridomas producing monoclonal antibodies, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin, and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies also can be produced in a host cell transfectoma using, for example, a combination of recombinant DNA techniques and gene transfection methods as is well known in the art (e.g., Morrison, S. (1985) Science, 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present).

The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the new recombinant expression vectors carry regulatory sequences that control the expression of the antibody chain genes in a host cell. The term "regulatory sequence" includes promoters, enhancers, and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). It will be appreciated by those skilled in the art that the design of the expression vector, including the selection of regulatory sequences, depends on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.,* 8:466-472).

In addition to the antibody chain genes and regulatory sequences, the now recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in dhfr—host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, and DEAE-dextran transfection.

Useful mammalian host cells for expressing the recombinant antibodies described herein include Chinese Hamster Ovary (CHO cells) (including dhfr—CHO cells, described in Urlaub and Chasin, (1980) *Proc. Natl. Acad. Sci. USA,* 77:4216-4220, used with a DHFR selectable marker, e.g., as described in R. J. Kaufman and P. A. Sharp (1982) *Mol. Biol.,* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Viral Assays

The proteins and antibodies described herein can be tested using tranfected cells and/or SARS-infected cells. Protocols have been developed to grow SARS-CoV in culture. These methods use growth of Vero E6 cells. Supernatants from these cultures can contain up to $10^7$ copies of viral RNA per mL (Drosten C et al., *N Engl J Med,* 348(20):1967-76, 2003; Ksiazek T G et al., *N Engl J Med,* 348(20):1953-66, 2003). A cytopathic effect (CPE) assay can be used to measure infectious titers of viral stocks, using established techniques (Bonavia A. et al., *J. Virol.,* 77 (4):2530-8, 2003).

Western blotting can be used to test reactivity of protein products with anti-Histidine tag, anti-Myc tag, or antiserum to SARS-CoV as a screening step to measure protein expression and reactivity with antibodies produced in natural human infection. Protein fragments that are well expressed and reactive with antiserum can be chosen for large-scale expression and purification.

Antibodies to the S-protein of certain coronaviruses have been shown to induce antibody dependent enhancement (ADE) of infection and increased pathology (notably Feline Infectious Peritonitis Virus). We can test for ADE using protocols adapted from those used to study ADE in FIPV infection (Hohdatsu T. et al., *J. Vet. Med. Sci.,* 60 (1):49-55, 1998). This protocol measures enhanced infection of U-937 cells (a human monocytoid cell line) when virus is preincubated with immunoglobulin. Readouts include titration of virus in culture supernatant and quantitation of infected cells by indirect immunofluorescence assay.

Vero Cell Binding Assay:

This assay can be used, e.g., to monitor the quality of the response in any mammal including transgenic mice and, humans (e.g., for diagnosis of infection, monitoring response to vaccine, or determining suitability of a unit of plasma for processing). This assay also has the advantage of being safe compared to virus neutralization.

Epitope-tagged S protein (or any fragment of S protein) can be added to target cells (e.g., Vero cells) for detection of binding by FACS analysis. Cells and S proteins are mixed and incubated, e.g., at 4-37° C. About 0.1 nM to 3 µM of spike protein with $10^6$ Vero cells at 4° C., RT, or 37° C. can be used.

Bound spike protein can be detected with antibodies to the epitope tag or mouse antibodies raised against the S1 350 spike protein at appropriate dilution followed by fluorescent anti-mouse antibodies, e.g., a range of 1:10-1:$10^6$ for mouse sera against S1 350 can be tested. Cells can be analyzed by FACS and relative binding determined. Antibodies (polyclonal, monoclonal, human or murine) can be added with the S protein to interfere with binding. Antibodies that interfere with binding could be neutralizing and would be good candidates for monoclonal antibody (Mab) development or vaccine or plasma potency assessment.

SARS Virus Neutralization:

This assay can be used to monitor the quality of the response in any mammal including transgenic mice, humans (e.g., for diagnosis of infection, for monitoring response to vaccine or suitability of a unit of plasma for processing).

Vero cells are grown and infected with SARS virus in the presence and absence of antibodies (e.g., antibodies from mice, humanized mice, humans or hybridoma cultures). The effect of the antibodies on viral replication (e.g., by PCR-based detection of viral RNA) or cytopathic effect on cells is determined by comparison of samples containing antibody with control samples.

Pharmaceutical Compositions

In another aspect, the present invention includes compositions, e.g., pharmaceutical compositions, which include a protein or an antibody molecule described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal, or epidermal administration (e.g., by injection or infusion).

The new pharmaceutical compositions can be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Useful compositions are in the form of injectable or infusible solutions. A useful mode of administration is parenteral (e.g., intravenous, subcutaneous, intraperitoneal, intramuscular). For example, the protein or antibody can be administered by intravenous infusion or injection. In another embodiment, the protein or antibody is administered by intramuscular or subcutaneous injection.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The proteins, antibodies, and antibody-fragments of the present invention can be administered by a variety of methods known in the art, although for many therapeutic applications. As will be appreciated by the skilled artisan, the route and/or mode of administration will vary depending upon the desired results.

In certain embodiments, a protein, an antibody, or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion described herein is 0.1-500 mg/kg, e.g., 1-100 mg/kg, 5-25 mg/kg. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The new pharmaceutical compositions can include a "therapeutically effective amount" or a "prophylactically effective amount" of a protein, antibody, or antibody portion of the invention. A "therapeutically effective amount" refers to an amount effective, at dosages and for periods of time necessary, to achieve the desired therapeutic result (e.g., reduction in SARS-CoV viral load or reduction in symptoms caused by SARS-CoV infection). A therapeutically effective amount of the antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody fragment is outweighed by the therapeutically beneficial effects. The ability of a compound to inhibit a measurable parameter can be evaluated in an animal model system predictive of efficacy in humans.

Alternatively, this property of a composition can be evaluated by examining the ability of the compound to modulate, such modulation in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount can be less than the therapeutically effective amount.

Also within the scope of the invention are kits including an S protein, and/or an anti-S protein antibody or antigen-binding fragment thereof. The kits can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the S protein or antibody for administration; pharmaceutically acceptable carriers; and devices or other materials for administration to a subject.

Instructions for use can include instructions for diagnostic applications of the proteins, antibodies (or antigen-binding fragment thereof) to detect SARS, in vitro, e.g., in a sample, e.g., a biopsy or cells from a patient, or in vivo. The instructions can include details for therapeutic application including suggested dosages and/or modes of administration, e.g., in a patient with a respiratory disorder. Other instructions can include details on coupling of the antibody to a chelator, a label or a therapeutic agent, or for purification of a conjugated antibody, e.g., from unreacted conjugation components.

As discussed above, the kit can include a label, e.g., any of the labels described herein. As discussed above, the kit can include a therapeutic agent, e.g., a therapeutic agent described herein. The kit can include a reagent useful for chelating or otherwise coupling a label or therapeutic agent to the antibody, e.g., a reagent discussed herein. Additional coupling agents, e.g., an agent such as N-hydroxysuccinimide (NHS), can be supplied for coupling the chelator, to the antibody. In some applications the antibody will be reacted with other components, e.g., a chelator or a label or therapeutic agent, e.g., a radioisotope. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-S protein antibodies (or fragments thereof), formulated as appropriate, in one or more separate pharmaceutical preparations.

Other kits can include optimized nucleic acids encoding S proteins or anti-S protein antibodies, and instructions for expression of the nucleic acids.

Therapeutic Uses of Proteins and Antibodies

The new proteins and antibodies have in vitro and in vivo diagnostic, therapeutic, and prophylactic utilities. For example, these antibodies can be administered to cells in culture, e.g. in vitro or ex vivo, or in a subject, e.g., in vivo, to treat, prevent, and/or diagnose SARS.

As used herein, the term "subject" includes human and non-human animals. The term "non-human animals" includes all vertebrates, e.g., mammals and non-mammals, such as non-human primates, sheep, chickens, mice, dogs, cats, pigs, cows, and horses, amphibians, and reptiles.

The proteins and antibodies can be used on cells in culture, e.g., in vitro or ex vivo. For example, cells can be cultured in vitro in culture medium and the contacting step can be effected by adding the S protein or the anti-S protein antibody or fragment thereof, to the culture medium. The methods can be performed on virions or cells present in a subject, as part of an in vivo (e.g., therapeutic or prophylactic) protocol. For in vivo embodiments, the contacting step is effected in a subject and includes administering an S protein or the anti-S protein or fragment thereof to the subject under conditions effective to permit binding of the protein, antibody, or fragment to the virus or infected cell.

Methods of administering antibody molecules are described above. Suitable dosages of the molecules used will depend on the age and weight of the subject and the particular drug used. The antibody molecules can be used as competitive agents for ligand binding to inhibit or reduce an undesirable interaction, e.g., to inhibit binding of a SARS virion to a cell.

Immunogenic compositions and vaccines that contain an immunogenically effective amount of an S protein, or fragments thereof, are provided. Immunogenic epitopes in an S protein sequence can be identified according to methods known in the art, and proteins, or fragments containing those epitopes can be delivered by various means, in a vaccine composition. Suitable compositions can include, for example, lipopeptides (e.g., Vitiello et al., *J. Clin. Invest.*, 95:341 (1995)), peptide compositions encapsulated in poly (DL-lactide-co-glycolide) ("PLG") microspheres (see, e.g., Eldridge et al., *Molec. Immunol.*, 28:287-94 (1991); Alonso et al., *Vaccine,* 12:299-306 (1994); Jones et al., *Vaccine,* 13:675-81 (1995)), peptide compositions contained in immune stimulating complexes (ISCOMS) (see, e.g., Takahashi et al., *Nature,* 344:873-75 (1990); Hu et al., *Clin. Exp. Immunol.,* 113:235-43 (1998)), and multiple antigen peptide systems (MAPs) (see, e.g., Tam, *Proc. Natl. Acad. Sci. U.S.A.,* 85:5409-13 (1988); Tam, *J. Immunol. Methods,* 196:17-32 (1996)). Toxin-targeted delivery technologies, also known as receptor-mediated targeting, such as those of Avant Immunotherapeutics, Inc. (Needham, Mass.) can also be used.

Useful carriers that can be used with immunogenic compositions and vaccines described herein are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating S proteins (or fragments, derivative or analogs thereof) to lipids, such as tripalmitoyl-S-glycerylcysteinyl-seryl-serine ($P_3CSS$).

Immunization with a composition or vaccine containing an S protein composition, e.g., via injection, aerosol, oral, transdermal, transmucosal, intrapleural, intrathecal, or other suitable routes, induces the immune system of the host to respond to the composition or vaccine by producing large amounts of CTL's, and/or antibodies specific for the desired antigen. Consequently, the host typically becomes at least partially immune to later infection (e.g., with SARS-CoV), or at least partially resistant to developing an ongoing chronic infection, or derives at least some therapeutic benefit. In other words, the subject is protected against subsequent viral infection by the SARS virus.

Diagnostic Uses of Proteins and Antibodies

An anti-S protein antibody (e.g., monoclonal antibody) can be used to isolate S protein or SARS virions by standard techniques, such as affinity chromatography or immunoprecipitation. Moreover, an anti-S protein antibody can be used to detect S protein (e.g., in a cellular lysate or cell supernatant or blood sample), e.g., screen samples for the presence of SARS, or to evaluate the abundance and pattern of expression of SARS. Anti-S protein antibodies can be used diagnostically to monitor S protein or SARS levels in tissue as part of a clinical testing procedure, e.g., to, for example, determine the efficacy of a given treatment regimen.

S proteins, and fragments thereof can be used to detect expression of a SARS receptor, e.g., to identify cells and tissues susceptible to SARS infection, or to isolate a SARS receptor on a host cell.

EXAMPLES

The invention is further described in the following examples, which do not limit the scope of the invention described in the claims.

Example 1

Construction of Codon-Optimized S Protein Coding Sequences

A nucleic acid encoding a codon-optimized S protein was constructed as follows. Various codons of a native nucleic acid sequence encoding the S protein were replaced with codons that encode rhodopsin in human cells. The following codons were used: alanine (GCC), arginine (CGC), asparagine (AAC), aspartic acid (GAC), cysteine (TGC), glutamic acid (GAG), glutamine (CAG), glycine (GGC), histidine (CAC), isoleucine (ATC), leucine (CTG), lysine (AAG), methionine (ATG), phenylalanine (TTC), proline (CCC), serine (TCC), threonine (ACC), tryptophan (TGG), tyrosine (TAC), and valine (GTG).

The least used codons for primates, presented in Table 1, were avoided in the construction of the optimized sequences.

TABLE 1

Least used codons in *E. coli*, yeast, *Drosophila*, and primates (Zhang SP et al., Gene. 105(1):61-72, 1991).

| *E. coli* | yeast | *Drosophila* | primates | amino acid |
|---|---|---|---|---|
| AGG | AGG | | | arginine |
| AGA | | AGA | | arginine |
| AUA | | AUA | | isoleucine |
| CUA | | | | leucine |
| CGA | CGA | CGA | CGA | arginine |
| CGG | CGG | CGG | CGG | arginine |
| CCC | | | | proline |
| UCG | | | UCG | serine |
| | CGC | | CGC | arginine |
| | CCG | | CCG | proline |
| | CUC | | | leucine |
| | GCG | | GCG | alanine |
| | ACG | | ACG | threonine |
| | | UUA | | leucine |
| | | GGG | | glycine |
| | | AGU | | serine |
| | | UGU | | cysteine |
| | | | CGU | arginine |

Two codon-optimized sequences were constructed: a sequence encoding amino acids 1-1190 (S(1190)), and a sequence encoding amino acids 1-350 (S1) as follows.

Oligonucleotides corresponding to the entire plus and minus strands of the optimized sequences were designed and synthesized. The oligos each contained 70 nucleotides, 35 of which overlapped an adjacent oligo. The F1 and R52 oligos, which were used to construct the extreme 5' end of the S protein coding sequences, contained a Hind III site and a Kozak sequence. The 5' Hind III site and the 3' Xba I site were chosen to allow cloning into pcDNA3.1$^-$Myc/His. (Invitrogen)

The F52 and R1 oligos, which were used to construct the extreme 3' end of the coding sequence for the long form of the S protein (i.e., encoding amino acids 1-1190, S1190), contained an Xba I site. The F1 35 mer and the F2-F52 70 mers correspond to the positive strand. The R1 35 mer and the R2-R52 70 mers correspond to the negative strand.

The S1 fragment was constructed with same oligos, except that the envR1 and envF1 oligos replaced the F16 and R37 oligos during synthesis, and the oligos encoding the C-terminal portion were not used (i.e., F1-F15 and envF were used for the positive strand, R38-R52 and envR were used for the negative strand). The oligos used to construct the codon-optimized sequences are shown in FIG. 3.

Oligos F17 to F23 and R30 to R36 were not the original oligos designed for synthesis. Fragments 5 and 6 (described below) could not be efficiently synthesized so new oligos were designed where some of the G and C runs were broken up by some T's. All lowercase letters in the oligos represent changes in which the optimum codon was not used so that runs of G's and C's were avoided.

These oligos were synthesized and used in PCR to create fragments of the full length and S1 (350) protein. Thirteen fragments were required initially for the full length (fragments 1-13) and four were required to create the S1(350) protein (fragments 1, 2, 3 and 4S). These fragments were synthesized with the following sets of oligos:

Fragment 1—F1-4, R52-49 (280 bp)
Fragment 2—F5-8, R48-45 (315 bp)
Fragment 3—F9-12, R41-44 (315 bp)
Fragment 4—F13-16, R37-40 (315 bp)
Fragment 4S—F13-15, env F1, R38-40, env R1 (280 bp)
Fragment 5—F17-20, R33-36 (315 bp)
Fragment 6—F21-24, R29-32 (315 bp)
Fragment 7—F25-28, R25-28 (315 bp)
Fragment 8—F29-32, R21-24 (315 bp)
Fragment 9—F33-36, R17-20 (315 bp)
Fragment 10—F37-40, R13-16 (315 bp)
Fragment 11—F41-44, R9-12 (315 bp)
Fragment 12—F45-48, R5-8 (315 bp)
Fragment 13—F49-52, R1-4 (280 bp)

These PCR reactions were performed for 35 cycles using a 62° C. annealing temperature. All products were obtained as anticipated. Fragments 5 and 6 did not work at first as previously noted. However, the second set of oligos discussed above did work correctly. All 13 fragments were purified and stored at −20° C.

Once all 13 pieces were obtained, larger fragments were constructed. The last 35 nucleotides of fragment 1 were identical to the first 35 nucleotides of fragment 2, and the last 35 nucleotides of fragment 2 were identical to the first 35 nucleotides of fragment 3, etc., up to fragment 13. PCR was performed by mixing fragments and amplifying with the end oligos. This was performed to create fragments A, B, C, and D as well as S1(350) in the following manner:

Fragment A—Fragment 1+2+3+4—Amplified with F1 and R37 (1120 bp)
S1(350)—Fragment 1+2+3+4STOP —Amplified with F1 and envR1 (1085 bp)
Fragment B—Fragment 5+6+7—Amplified with F17 and R25 (875 bp)
Fragment C—Fragment 8+9+10—Amplified with F29 and R13 (875 bp)
Fragment D—Fragment 11+12+13—Amplified with F41 and R1 (840 bp)

Fragments B, C, D and S1(350) were easily synthesized after optimization of the PCR reaction. The reaction for fragment A was inefficient.

The S1(350) was cloned into pcDNA 3.1⁻Myc/His (Invitrogen) using Hind III and Xba I. Isolates were sequenced. Four out of nine isolates that were sequenced had the correct nucleotide sequence. The incorrect sequences contained PCR-generated errors. pcDNA 3.1⁻Myc/His S1(350) #6 was used for all subsequent experiments.

After the sequence of S1(350) was verified, fragment A was synthesized from the S1(350) fragment by PCR. This was possible since fragment A is S1 with about 48 more nucleotides on the 3' end. Primer 4-S1R was designed to synthesize fragment A from S1. 4-SIR contains the matching 22 bp contained within both fragment A and S1(350) and the sequence required to extend the end of S1 to generate full length fragment A. This PCR was performed at 50° C. to ensure that annealing and amplification would occur.

All four intermediate fragments (A, B, C, and D) were cloned into pcDNA 3.1⁻Myc/His. In this way we can select PCR products that are of the correct sequence rather than using a mixture of PCR products that contains many variants. Once we have plasmids containing appropriate fragments we can then PCR out the fragments and link them together to get the full length sequence.

Figure 7:
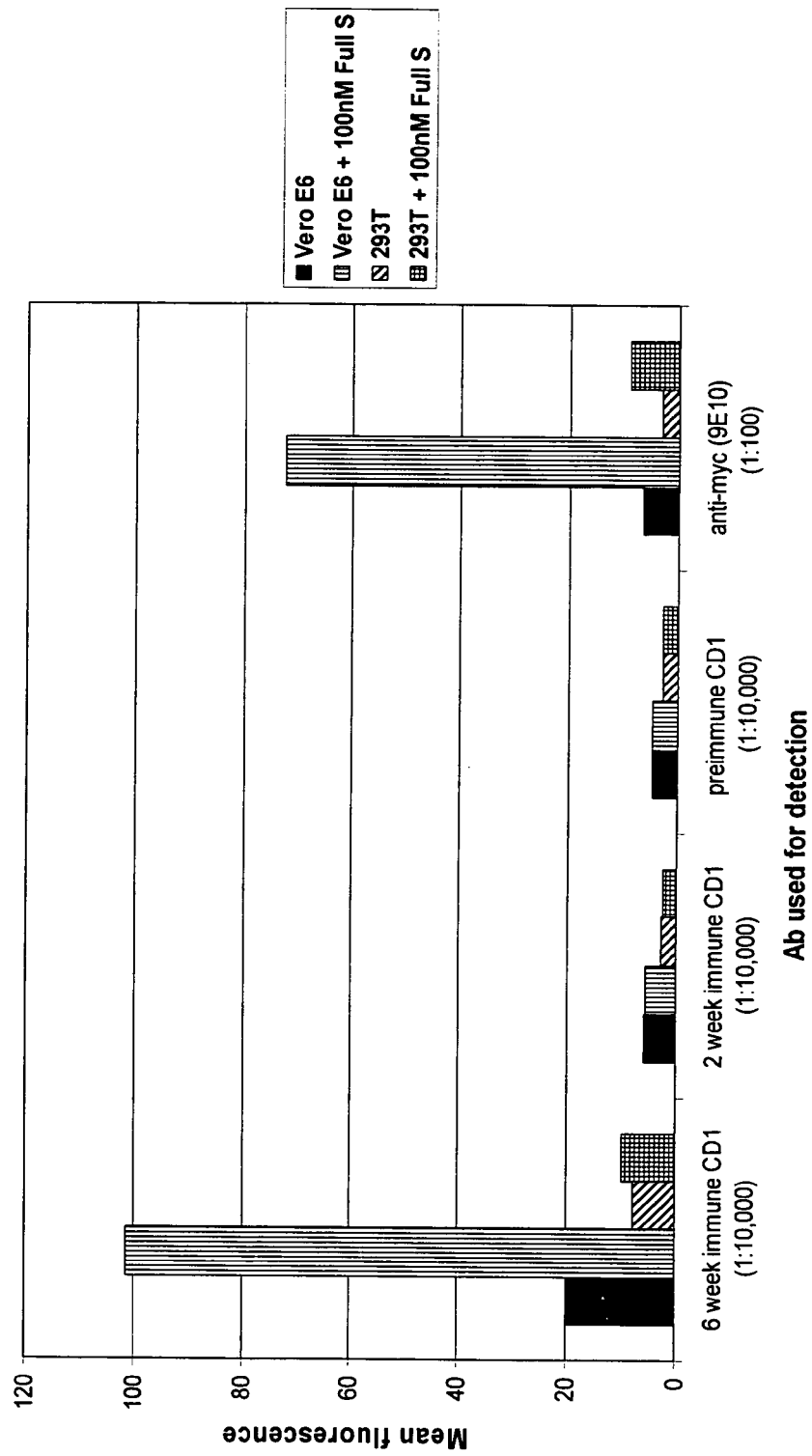
FIG. 7 is a graph depicting binding of recombinant S1 proteins to Vero cells and HEK293T cells.

PCR was performed on the PCR products for A, B, C, and D to add Hind III and Xba I ends to each so they could be cloned. Fragment A already had a Hind III site at its 5' end and fragment D already had a Xba I site at its 3' end so these sites did not need to be added. The oligos for creation of these new PCR products were F1, AinsR, BinsF, BinsR, CinsF, CinsR, DinsF, and R1. These PCRs were performed and all products were cloned into pcDNA 3.1⁻ Myc/His and sequenced. Nearly all of the clones were correct. One clone had a deletion. One plasmid was selected for further experiments (FIG. 4 and FIG. 7).

Example 2

Expression of S1(350) and S(1190)

Human embryonic kidney fibroblasts (HEK293T) cells were transfected with S1(350) or S(1190) using Lipofectamine™ 2000 as follows. HEK293T cells were grown to 90% confluence in 150 mm tissue culture dishes. Cells were transfected using 30 μg of pcDNA 3.1⁻Myc/His (Invitrogen) containing the optimized DNA encoding the S1(350) or S(1190) proteins. Transfections used lipofectamine 2000 (Invitrogen) as described by the manufacturer.

After three days, supernatants were immunoprecipitated using the His tag in conjunction with Nickel-NTA (Ni-NTA) resin and Western blot was performed using an anti-myc antibody. S1(350) was expressed in the 293T transfectants.

Next, five T175 flasks were transfected with S1(350) using lipofectamine. After 48 hours, cultures were treated with Na-butyrate to increase protein expression. S1(350) was purified affinity from supernatants using a NiNTA resin. Fractions were taken and analyzed by Coomassie staining to determine the purity of the preparation. The first purification was unsuccessful. The second purification yielded 2 mg of protein. S(1190) was expressed and purified in a similar manner. It was determined that S(1190) was expressed at a level of approximately 5 mg/L after purification. SDS-PAGE analysis of Coomassie stained S1 and S(1190) purified proteins are shown in FIG. 4.

To express and purify cells using a nickel resin, cells were incubated for 24 hours and the medium replaced with fresh DMEM/10% FCS/1×penicillin-streptomycin. After an additional 24 hours, sodium butyrate was added to each plate to a final concentration of 3 mM and the cells were incubated for 24 more hours. Medium was then harvested and filtered. Filtered supernatant was aliquoted to 50 ml conical tubes (40 ml/conical) and 1 ml of NiNTA agarose beads (Invitrogen) was added to each. Conical tubes were rocked on a nutator for 2 hours at room temperature. Supernatants were then poured through an empty column in order to collect the agarose resin. The resin was then washed 3×20 ml in PBS and eluted with PBS/250 mM imidazole. Eluted material was concentrated using a centriprep concentration device and stored at 4° C.

The S1(350) DNA fragment was cloned into a bacterial expression vector. The sequence to be cloned excluded the mammalian leader sequence.

Oligos NoLBacF and NBSIR were designed to clone S1(350) into pET32+(Novagen), which contains many useful epitope tags. The oligos introduce BamHI and SacI restriction sites at the end of S1(350). The GC sequence following the underlined site in NBS1R (FIG. 3) represents nucleotides needed to introduce S1(350) in frame with the C-terminal tags. Expression of S1 (350) was confirmed and reactivity demonstrated by Western Blot.

Example 3

Generation and Characterization of Anti-S1 Antiserum

Figure 6:
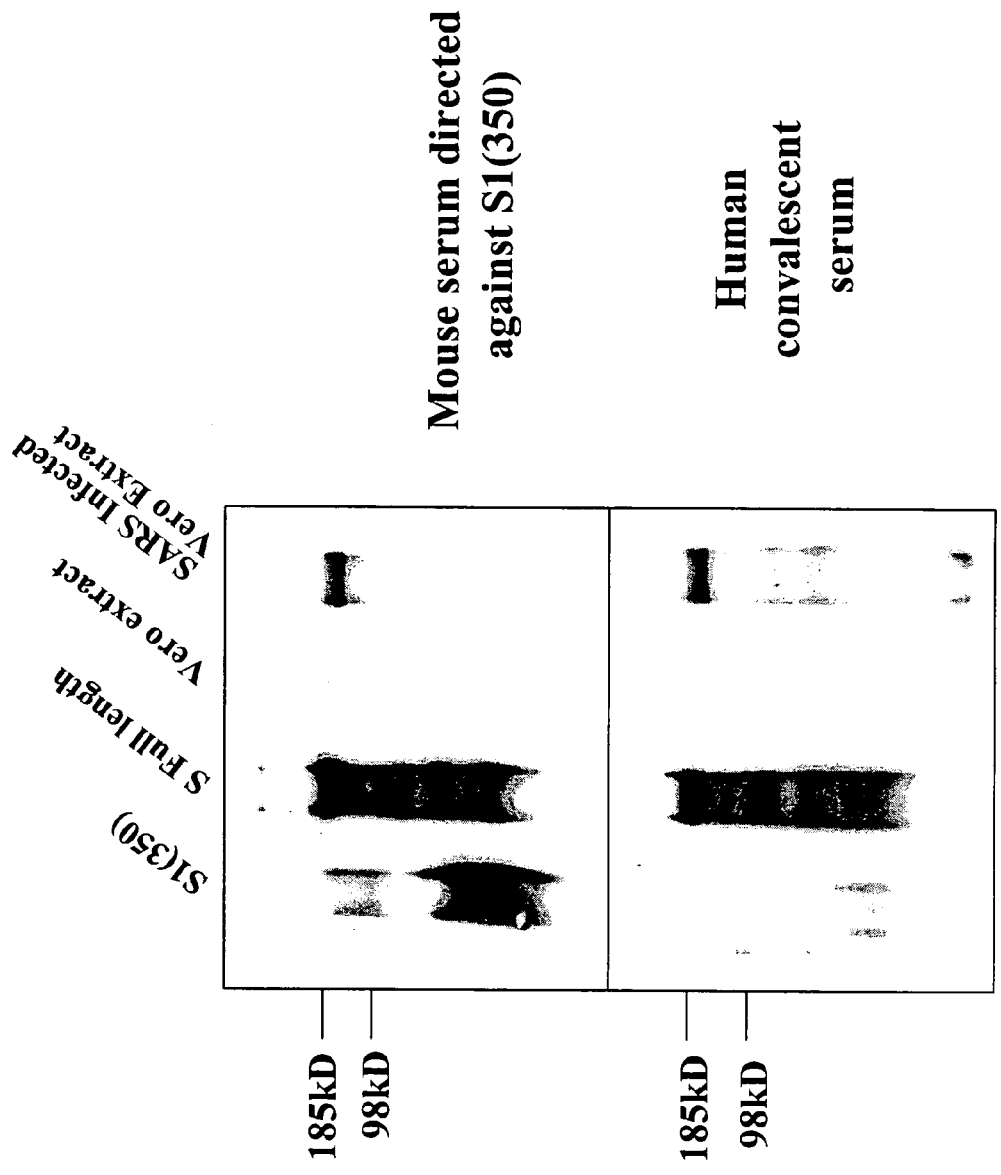
FIG. 6 is a representation of a Western blot depicting recognition of recombinant S proteins, uninfected Vero cells, and SARS infected Vero cell extracts by anti-S1 antiserum and human SARS convalescent serum.

Serum was collected from three pre-immune CD1 mice and pooled. Six CD1 mice were immunized (IP) three times each with 10 μg of purified S1(350) protein in RIBI adjuvant. Sera was collected from each mouse and tested individually. To test the sera, two ELISA plates were coated with 60 μl/well of a 1 μg/ml dilution of S1 (350) Batch 2 (0.67 mg/ml) and incubated overnight at 4° C. Plates were washed and blocked with 200 μl/well 1% BSA in PBS/Tween for 2 h. AP conjugated goat anti-mouse Fc gamma was used to detect binding of antibodies in the sera to S1 protein. The results for binding of each antiserum to the S1 protein are depicted in FIG. 5, which shows that an each mouse immunized with the S1 protein generated antibodies reactive to the S1 protein. The S1 (350) antibodies also bind full length S protein.

Next, anti-S1 antiserum was tested for recognition of SARS proteins in infected cells. Extracts from SARS-CoV-infected Vero cells were separated by SDS-PAGE and transferred onto a membrane for Western blotting. S1 protein, S(1190) protein, and uninfected Vero extracts were also separated and blotted in parallel as controls. Binding of anti-S1 antiserum was compared to binding by human convalescent serum. As shown in FIG. 6, mouse anti-S1 serum recognized full-length SARS protein in infected Vero extracts, as well as the S1 and S(1190) proteins. The most immunoreactive band in the virus lysate was the S protein. The recombinant S1 (350) protein stimulated production of antibodies that bound SARS virus. The S protein may be immunodominant in convalescent sera and, therefore, a good diagnostic antigen. It also appeared that most of the S protein is not cleaved into S1 and S2 fragments as seen in other coronaviruses.

Example 4

Characterization of S Protein Binding to Cells

Mouse serum raised against S1(350) or the anti-myc antibody (9E10) were used to detect binding of the full length S protein to the surfaces of either Vero E6 or 293T cells. The antibody dilution used is listed on the x-axis. Cells were incubated with 100 nM S protein at room temperature for 1 hour. Cells were washed and incubated with the listed antibodies at 4° C. for 45 minutes. After another wash, cells were incubated at 4° C. with anti-mouse IgG-PE and FACS analysis was performed. Both the anti-myc antibody (directed against the epitope tag) and the 6 week immune CD1 serum readily detected S protein bound to the surface of Vero E6 cells. This experiment demonstrates the specific binding of full length S protein to the surface of Vero E6 cells, a cell known to be permissive to SARS CoV infection.

Example 5

Generation of Human Monoclonal Antibodies

A protocol for the production of human monoclonal antibodies is as follows
1) Immunize transgenic mice carrying human antibody genes. This immunization method could be applied to any mammal including humans as vaccine or donor stimulation for immune plasma production. To immunize, inject 1-100 µg SARS spike protein (e.g., 10 µg) which is expressed in human cells intraperitoneally, intramuscularly, mucosally, intradermally, intravenously, or subcutaneously. The protein may be injected with or without adjuvant such as Freunds complete; RIBI or aluminum hydroxide (alum) to augment the response. Boost multiple times with a schedule of weekly doses. A minimum of about 3 doses can be given, with up to a maximum of about 12 doses.
2) Monitor the immune response in the immunized animals
Blood is obtained after immunization by retro-orbital bleeding. Serum is screened by ELISA for human IgG antibodies to the S protein. Serum can also be screened for interference of S protein binding to target cells (e.g., Vero cells). Serum can also be screened for interference of S protein mediated membrane fusion (e.g., inhibition of syncytia formation).

Serum can also be screened for neutralizing antibody levels which prevent viral infection of target cells (e.g., Vero cells).
3) Obtain hybridomas. Choose the animal for fusion based on serum antibody levels. Inject 1-100 µg SARS spike protein expressed in human cells intravenously. Remove spleen 3-4 days later and extract splenic B-cells. Fuse B-cells to myeloma cells (P3X) using polyethylene glycol. Plate out fusion in 96 well microtiter dishes containing culture medium with 5-20% serum supplemented with Origen at a cell density of 1000-5000 cells per well. Wells that are positive for growth are screened for human IgG antibodies to the S proteins.
4) Screen Hybridoma
Hybridomas will be screened for IgG ELISA against the spike proteins. Positive IgG hybridomas will be cloned and scaled up to produce Mabs. Hybridoma cultures can also be screened for interference of Spike protein binding to target cells (e.g., Vero cells). Hybridoma cultures can also be screened for interference of S protein mediated membrane fusion (inhibition of syncytia formation). Hybridoma cultures can also be screened for neutralizing antibody levels which prevent viral infection of target cells (e.g., Vero cells). Neutralizing hybridomas will be expanded to produce material for neutralization testing in animal models of SARS infection. Rodents will be attempted followed by primates.

Example 6

ELISA Assay

This method can be used, e.g., to monitor the response in any mammal including transgenic mice, e.g., identification of hybridomas, for diagnosis of infection in humans, or to monitor response to vaccine or suitability of a unit of plasma for processing.

Coat plates with spike protein at a protein concentration of 0.1-50 µg/ml in PBS or Carbonate buffer at 4° C. (full length or any truncated part). We used S1 350 coated at 1 µg/ml in PBS. Wash then block plates with NFDSM or other protein. Wash then add test sample mammalian antibody at appropriate dilution (e.g., mouse antibody). Wash then add developing antibody at appropriate dilution (e.g., goat anti-mouse Fc gamma alkaline phosphatase (AP) conjugate at 1:5000). Wash then add AP substrate at appropriate dilution and monitor color development.

Example 7

Human Convalescent Serum Blocks Binding of S(1190) to Vero E6 Cells

Figure 8:
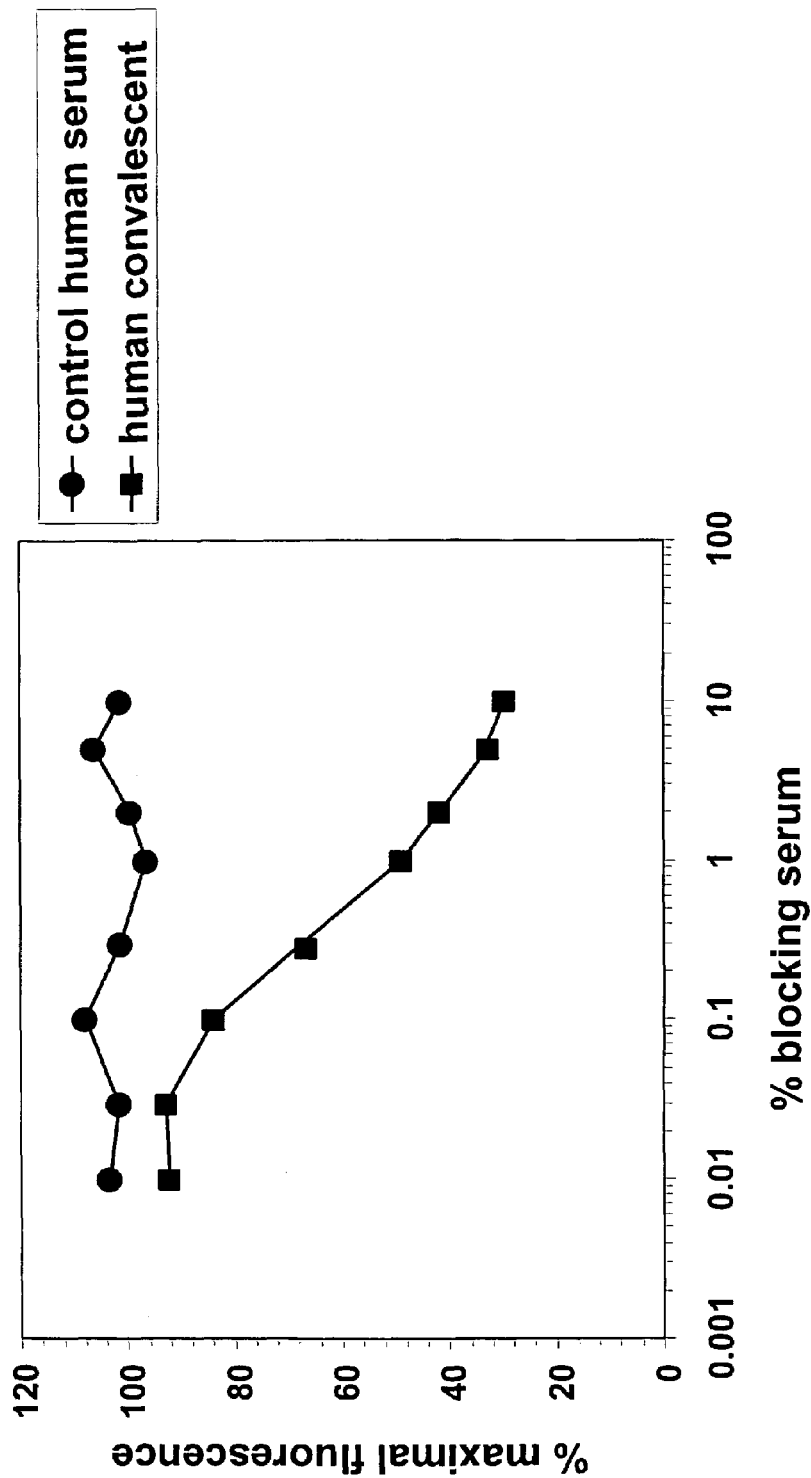
FIG. 8 is graph depicting binding of S(1190) to Vero E6 cells in the presence of human convalescent serum or control human serum.

Binding of S(1190) to Vero E6 cells in the presence of either human convalescent serum or control human serum was assayed as described in Example 4. Briefly, cells were incubated with S(1190) protein in the presence of varying percentages of human convalescent serum or control human serum. Cells were washed and incubated with antibodies that detect bound S(1190 protein). Cells were washed, incubated with a labeled secondary antibody, and analyzed by FACS. Human convalescent serum inhibited binding of S(1190) to Vero E6 cells in a dose-dependent manner (FIG. 8). Control human serum did not inhibit binding of S(1190) to Vero E6 cells (FIG. 8).

Example 8

Mapping the Ligand Binding Domain of the S Protein

Figure 9:
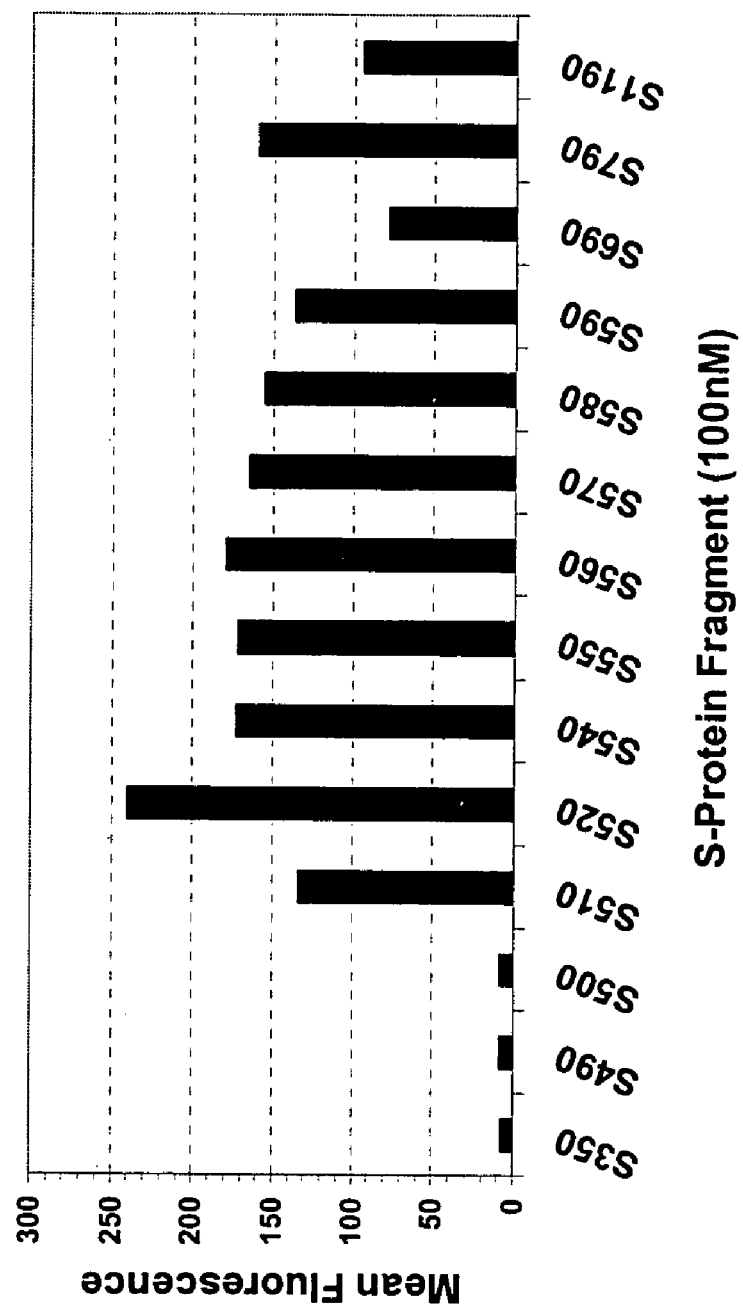
FIG. 9 is a graph depicting binding of thirteen different N-terminal fragments of S(1190) and S(1190) to Vero E6 cells.

The following N-terminal fragments of the S(1190) protein were generated: S(350) (corresponding to the 350 N-terminal amino acids of S(1190)), S(490), S(500), S(510), S(520), S(540), S(550), S(560), S(570), S(580), S(590), S(690), S(790). Each fragment was expressed with a C-terminal myc tag. All of these proteins were expressed at levels greater than 5 μg/mL from transfected HEK-293 cells. These S protein fragments and S(1190) were assayed for binding to Vero E6 cells as described in Example 4. All proteins containing at least the first 510 amino acids of the S protein specifically bound to the surface of Vero E6 cells. Amino terminal fragments smaller than S(510) exhibited binding signals equivalent to that observed with secondary antibody alone. Interaction of S glycoprotein fragments with Vero E6 cells was blocked by incubation with human convalescent serum, indicating that the interaction was specific. S(350), S(490), and S(500) did not bind to Vero E6 cells (FIG. 9). Binding of S(350) and S(450) to Vero cells was not detected at concentrations as high as 1 μM. All other fragments bound to Vero E6 cells (FIG. 9). Thus, amino acids 1-510 are required for binding of S(1190) to a ligand on Vero E6 cells.

To verify that the amino-terminal 510 amino acid domain represents the entire receptor-binding domain, the binding kinetics of both S (1190) and S(510) for Vero E6 cells were determined at concentrations ranging from 0.01 nM to 1 mM. As a negative control, S(350) was included in the experiment. S protein binding was detected via flow cytometry as described herein. FACS was used to compare relative affinity of two differing proteins. S(1190) and S(510) exhibited very similar profiles for binding to the Vero E6 cell surface. These data suggest that S(510) binds to Vero E6 cells at least as well as S(1190) binding. S(350) did not bind specifically to the surface of Vero E6 cells at any concentration tested. All other soluble S proteins containing at least the first 510 amino acids were also tested in this way and all showed similar binding profiles to the cellular surface (data not shown). These data demonstrate that S(510) contains the ligand-binding domain of the S protein.

To map the ligand-binding domain in further detail, amino-terminal truncations of the S(510) glycoprotein were synthesized to map the minimal receptor-binding region within the S1 domain of the spike glycoprotein. Specifically, sequences corresponding to the leader peptide were fused to sequences downstream in the S(510) coding region resulting in genes encoding S(90-510) (amino acids 90-510), S(150-510) (amino acids 150-510), S(210-510) (amino acids 210-510), S(270-510) (amino acids 270-510), S(330-510) (amino acids 330-510) and S(390-510) (amino acids 390-510). All constructs were transfected into HEK-293T/17 cells and the protein purified by metal affinity chromatography. Interestingly, only expression of S(270-510) was observed, and expression levels were similar to the other S protein fragments.

Purified S(270-510) was incubated with Vero E6 cells at varying concentrations, and analyzed by FACS. S(270-510) binding to Vero E6 cells was nearly identical to that observed for S(590). S(350) showed no specific binding to Vero E6 cells. Neither S(270-510), nor S(590) exhibited specific binding to the surface of HEK-293 cells. These data demonstrate that the minimal receptor-binding region of the SARS-CoV S glycoprotein is contained within amino acids 270-510.

Example 9

S(1190) is Immunogenic in HuMAbT Mice

Figure 10:
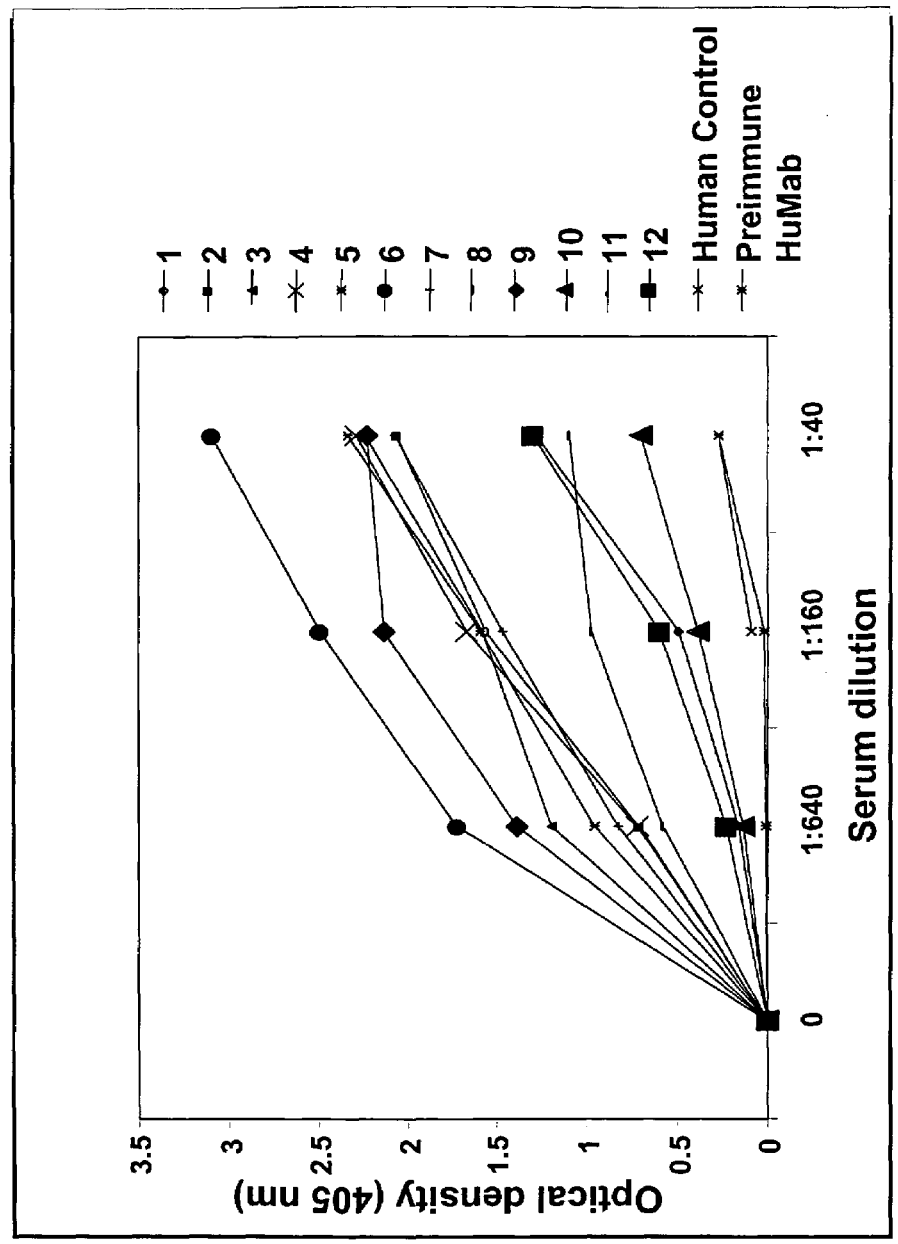
FIG. 10 is a graph depicting ELISA results of S(1190) binding activity of serum from twelve HuMAb™ mice immunized with S(1190), preimmune serum, and control human serum.

HuMAb™ mice are transgenic mice that contain human antibody genes rather than mouse antibody genes (see "Antibodies" section in the Detailed Description, above). Twelve HuMAb™ mice were injected IP four times each with 5 μg of purified S(1190) and S(350) protein in RIBI adjuvant. Sera were tested for binding to S(1190) by ELISA as described in Example 3. The results for binding of antiserum raised against S(1190) to S(1190) are depicted in FIG. 10, which shows that each mouse immunized with the S(1190) protein generated antibodies reactive to S(1190). The relative amount of S(1190) binding activity varied amongst the sera samples from the different mice, indicating that the mice did not mount a uniform response to the antigen.

Example 10

Serum from HuMAb™ Mice Immunized with S(1190) Neutralizes SARS-CoV

Figure 11:
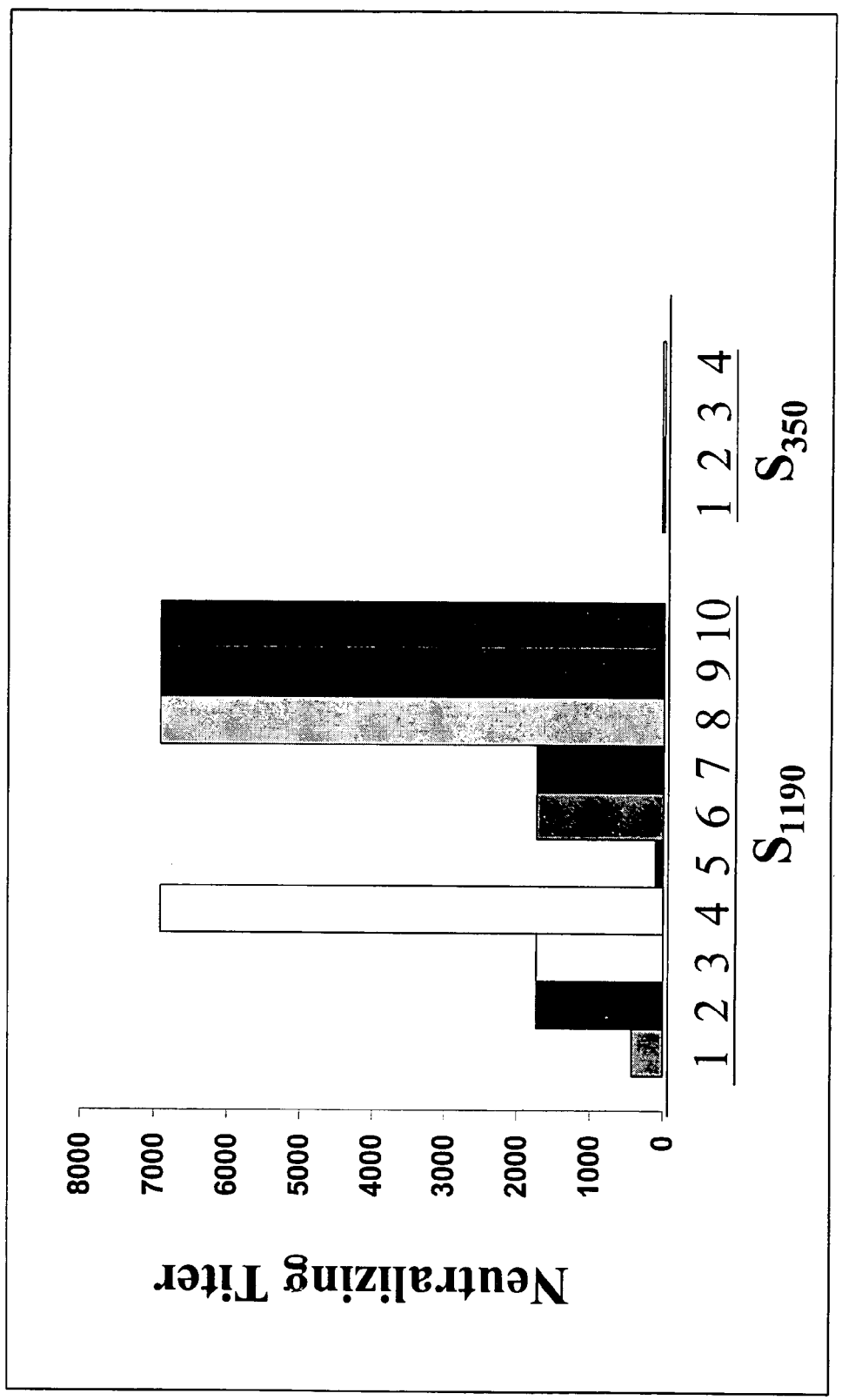
FIG. 11 is a graph depicting the neutralizing titer of serum samples from HuMAb™ mice immunized with either S(1190) or S(350). Serum samples 1-10 from mice immunized with S(1190) correspond to serum samples 1-10 in FIG. 10.
Figure 13C:
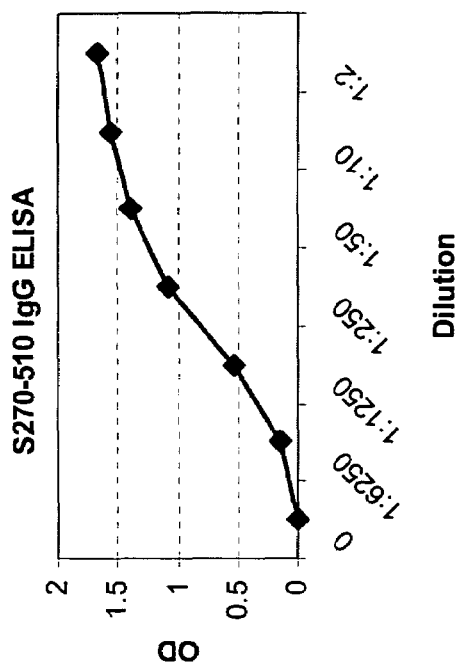
FIGS. 13A-F are graphs depicting the results of analyses of binding and neutralization properties of the human monoclonal antibody produced by clone 12-28-1.
Figure 13A:
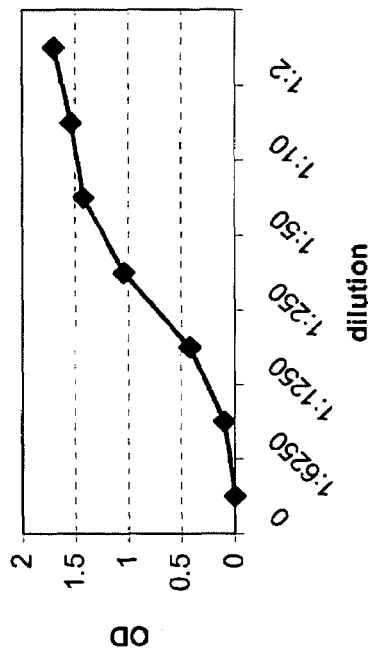
Figure 13B:
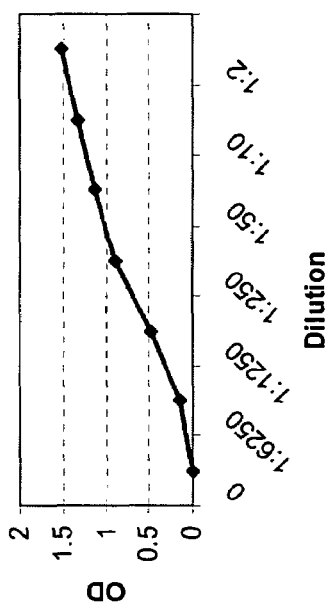
Figure 13F:
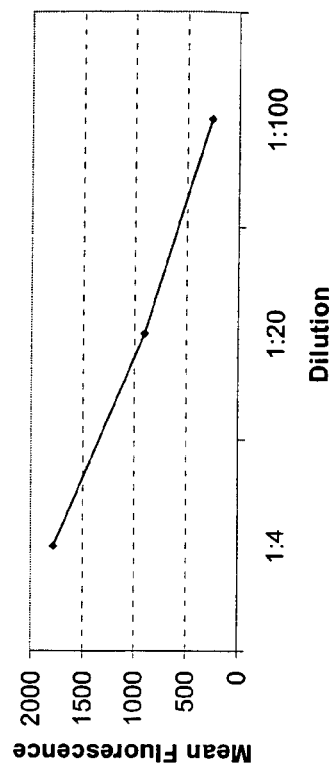
Figure 13D:
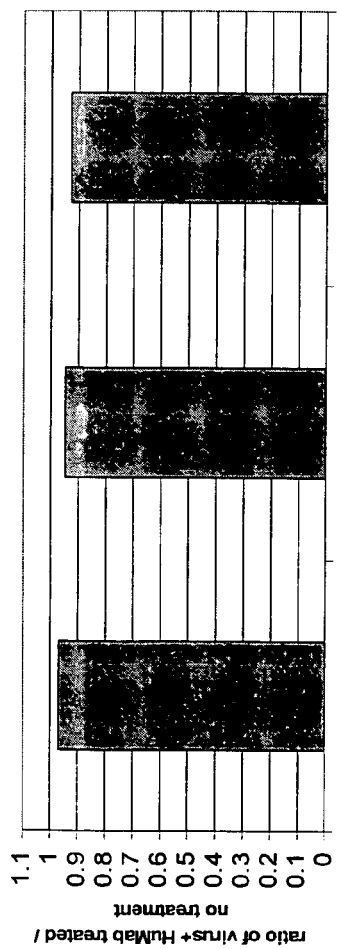
Figure 13E:
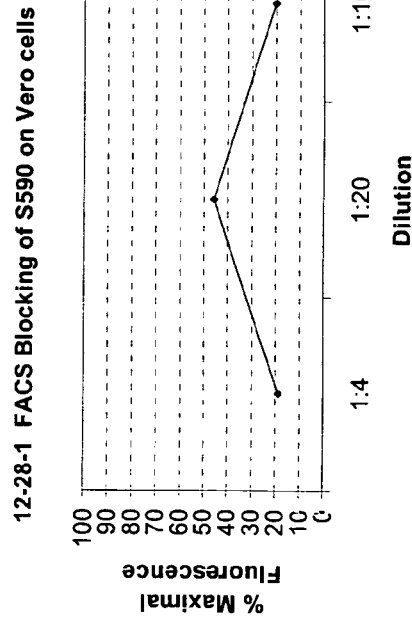
Figure 14C:
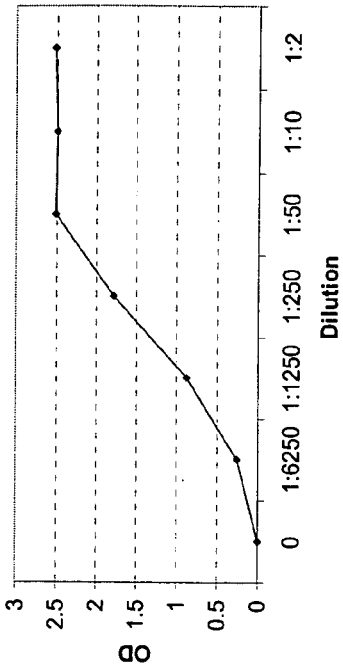
FIGS. 14A-F are graphs depicting the results of analyses of binding and neutralization properties of the human monoclonal antibody produced by clone 7-73-121. The figure legends for FIGS. 14A, 14B, 14C, 14E, and 14F are identical to those for the corresponding panels in FIG. 13.
Figure 14A:
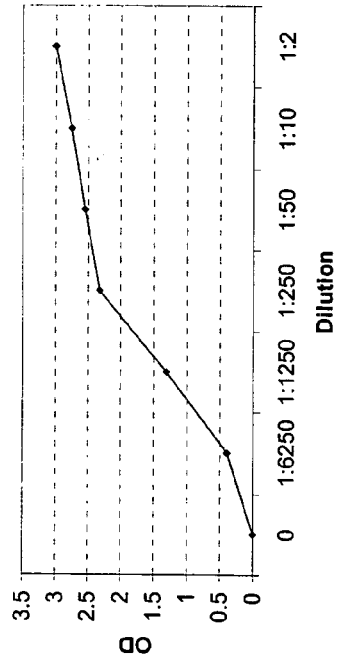
Figure 14B:
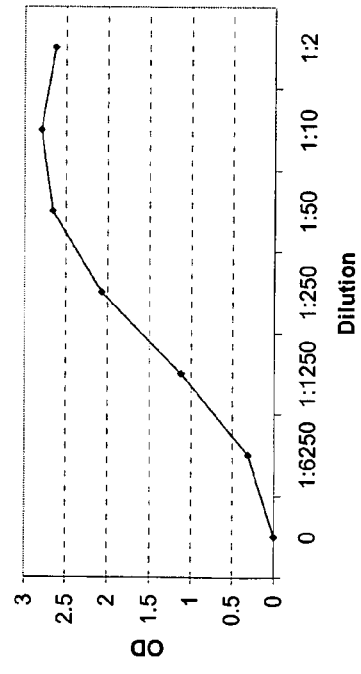
Figure 14F:
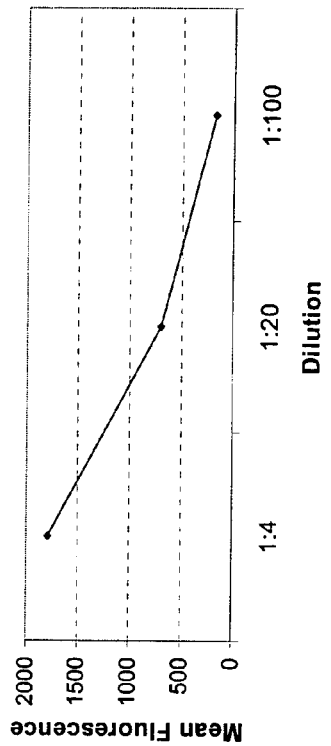
Figure 14D:
Figure 14E:
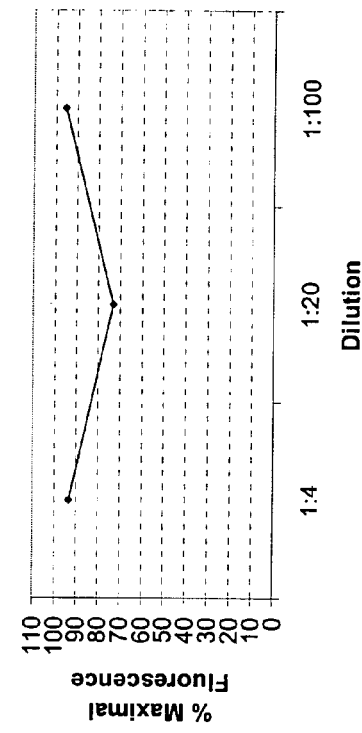
Figure 15C:
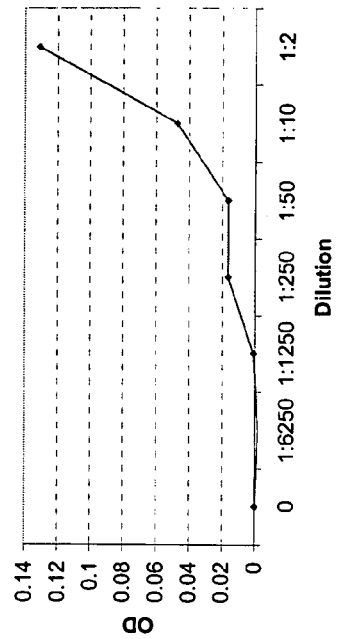
FIGS. 15A-F are graphs depicting the results of analyses of binding and neutralization properties of the human monoclonal antibody produced by clone 7-508-16. The figure legends for FIGS. 15A-15F are identical to those for the corresponding panels in FIG. 13.
Figure 15A:
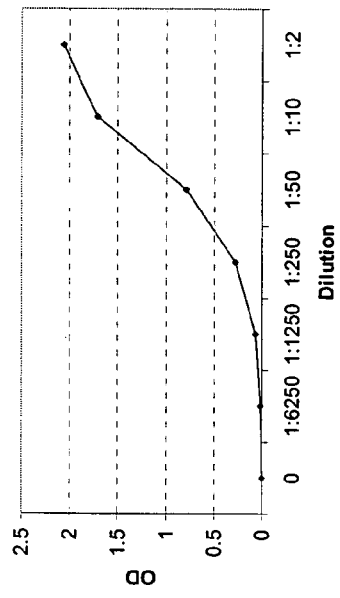
Figure 15B:
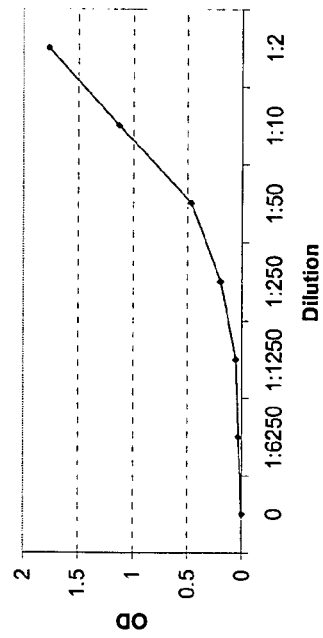
Figure 15F:
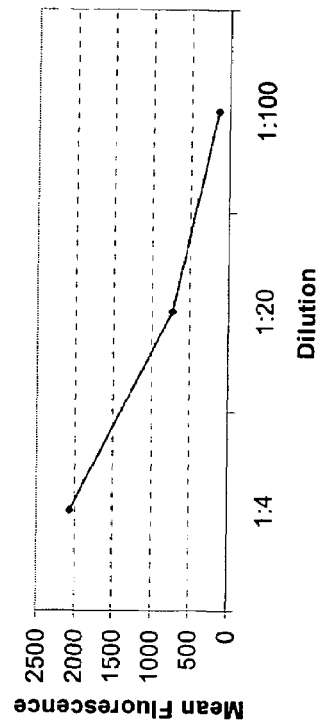
Figure 15D:
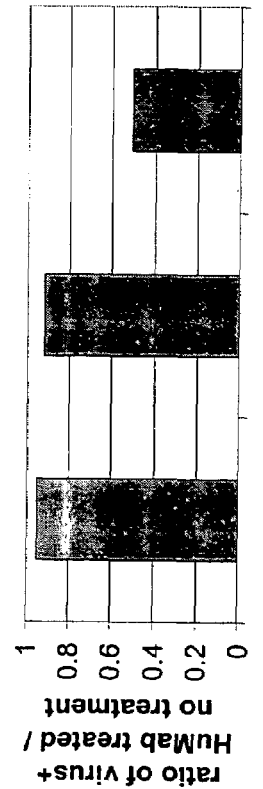
Figure 15E:
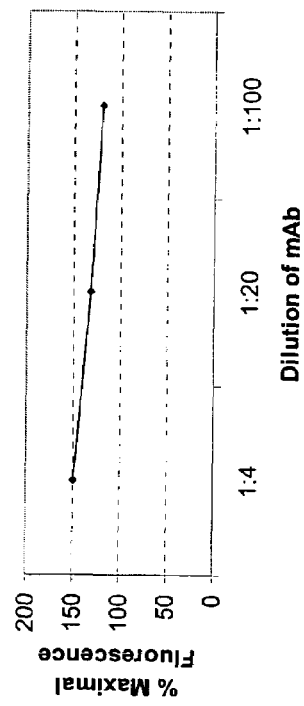
Figure 16C:
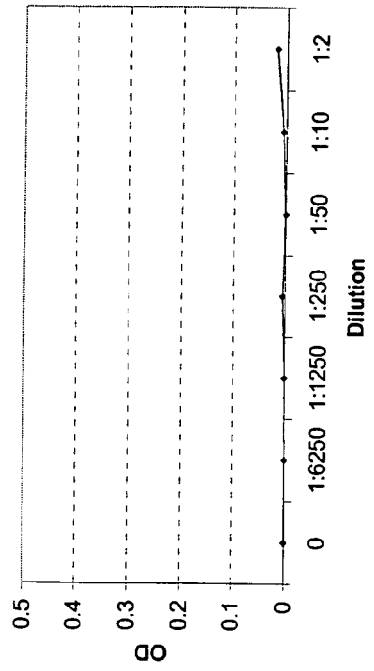
FIGS. 16A-F are graphs depicting the results of analyses of binding and neutralization properties of the human monoclonal antibody produced by clone 7-508-39. The figure legends for FIGS. 16A-16F are identical to those for the corresponding panels in FIG. 13.
Figure 16A:
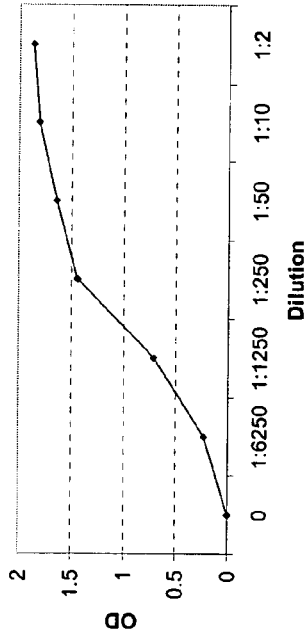
Figure 16B:
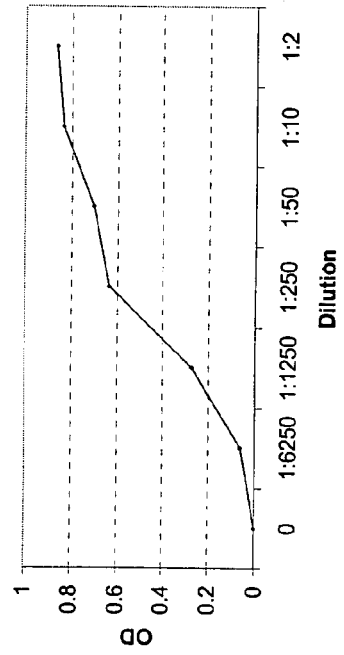
Figure 16D:
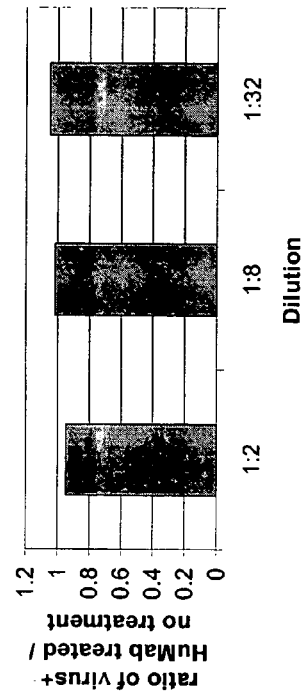
Figure 16F:
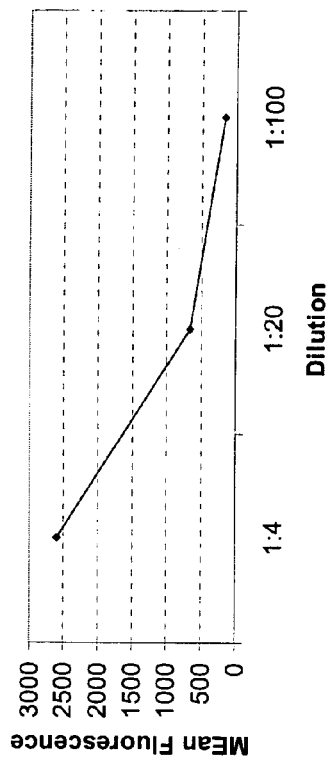
Figure 16E:
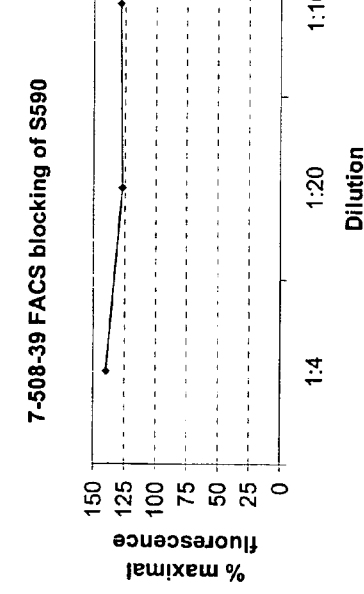
Figure 17A:
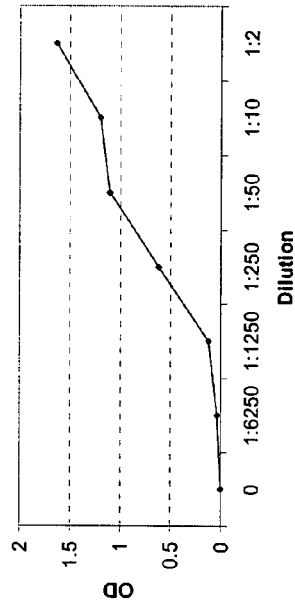
FIGS. 17A-F are graphs depicting the results of analyses of binding and neutralization properties of the human monoclonal antibody produced by clone 7-508-68. The figure legends for FIGS. 17A-17F are identical to those for the corresponding panels in FIG. 13.
Figure 17B:
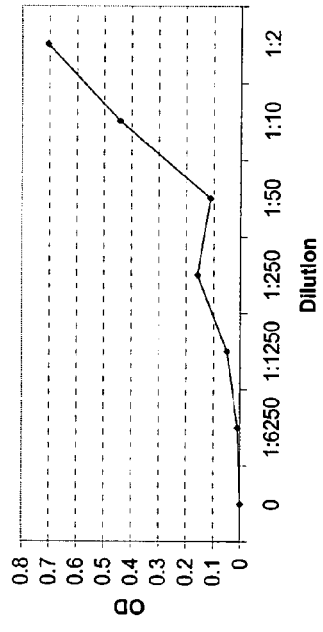
Figure 17C:
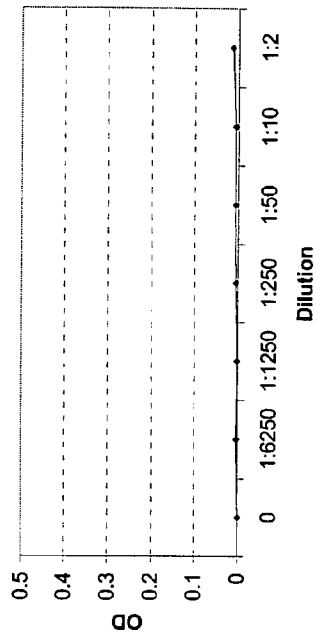
Figure 17F:
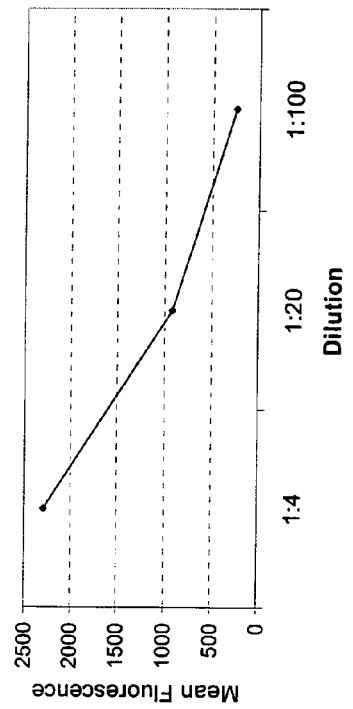
Figure 17D:
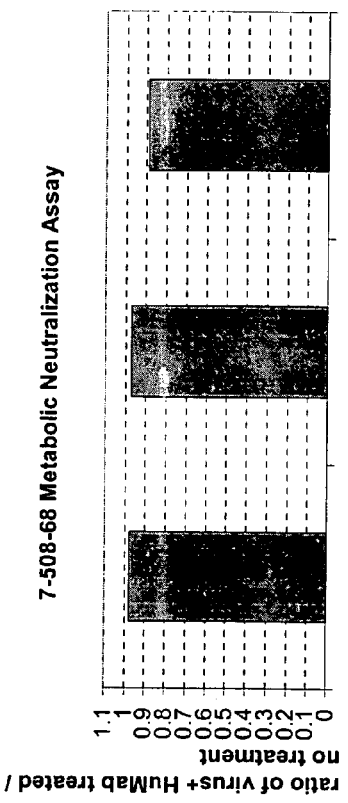
Figure 17E:
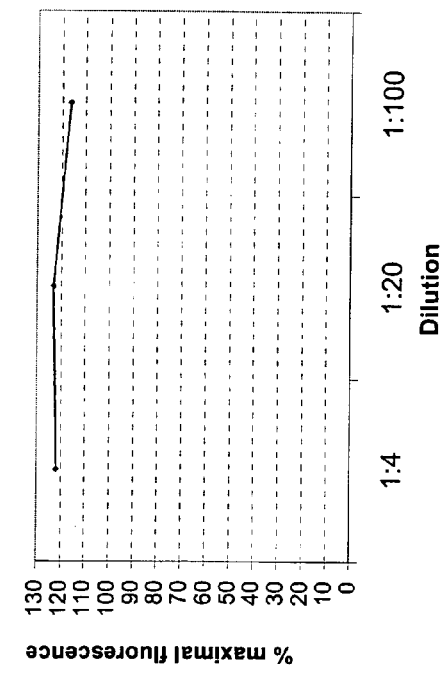
Figure 18F:
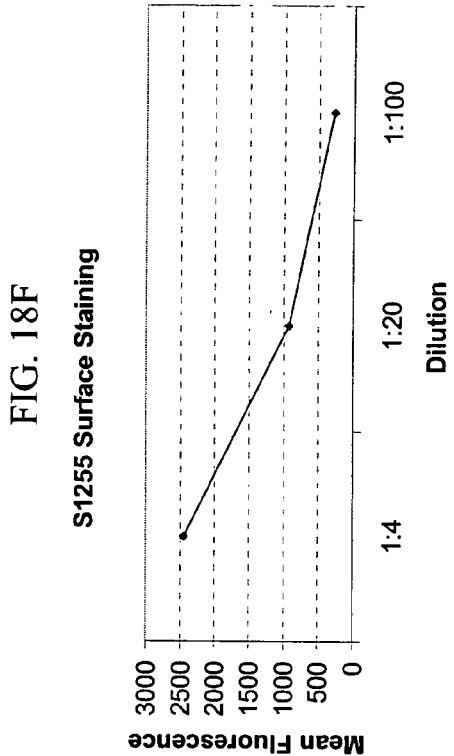
Figure 18D:
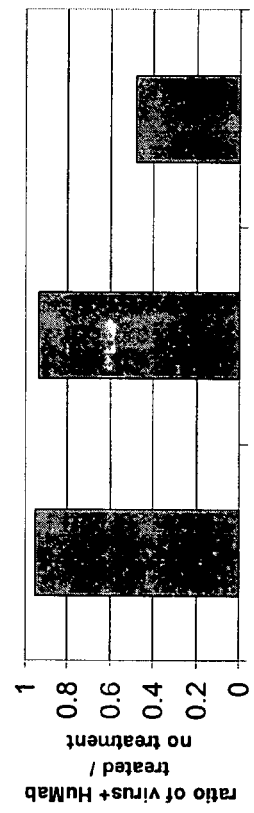
Figure 18E:
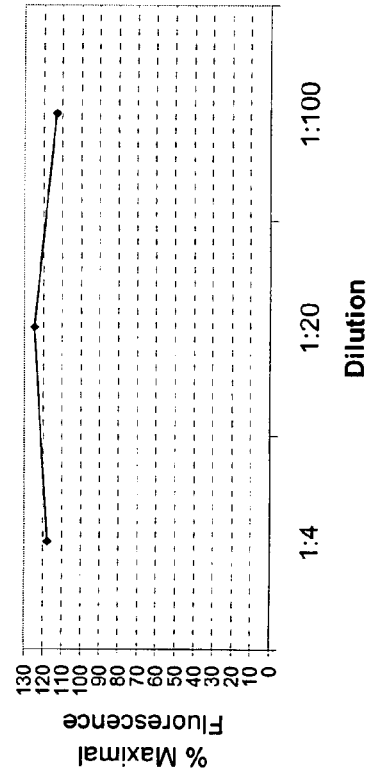
Figure 19C:
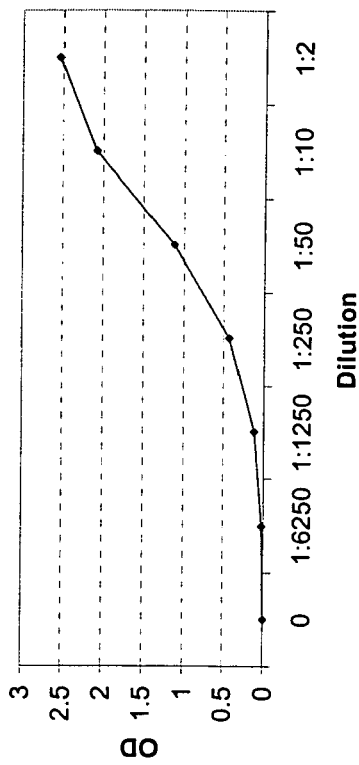
FIGS. 19A-F are graphs depicting the results of analyses of binding and neutralization properties of the human monoclonal antibody produced by clone 7-508-201. The figure legends for FIGS. 19A, 19B, 19C, 19E, and 19F are identical to those for the corresponding panels in FIG. 13.
Figure 19A:
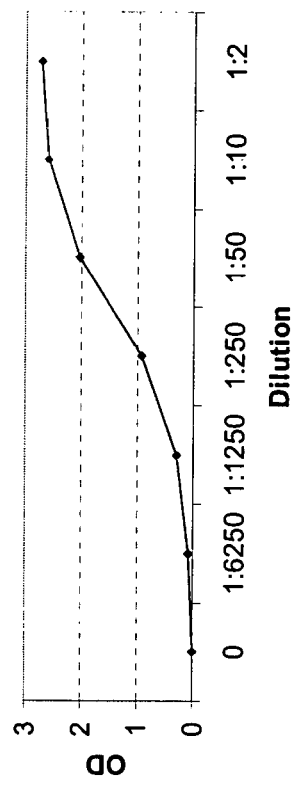
Figure 19B:
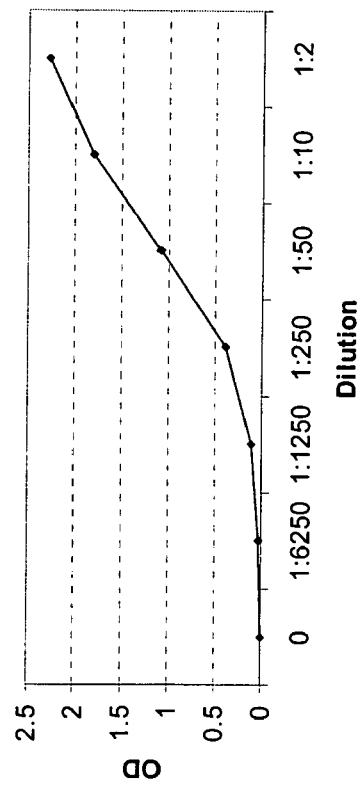
Figure 19F:
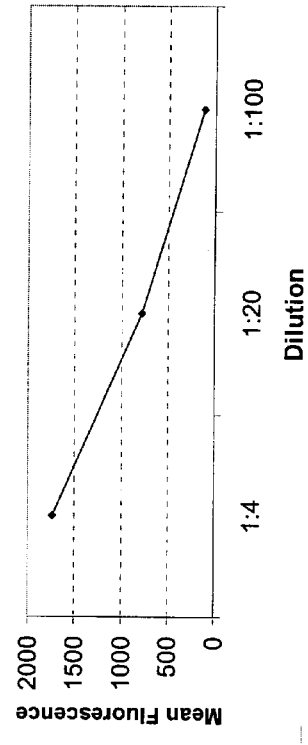
Figure 19D:
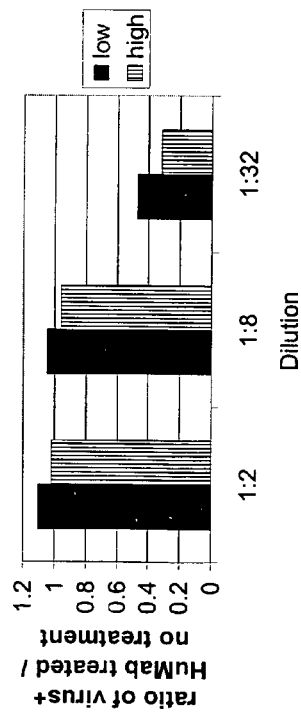
Figure 19E:
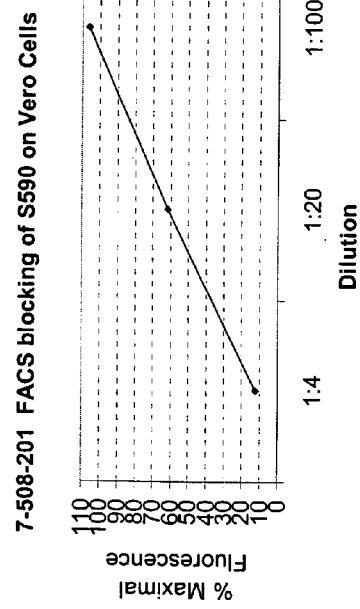
Figure 20C:
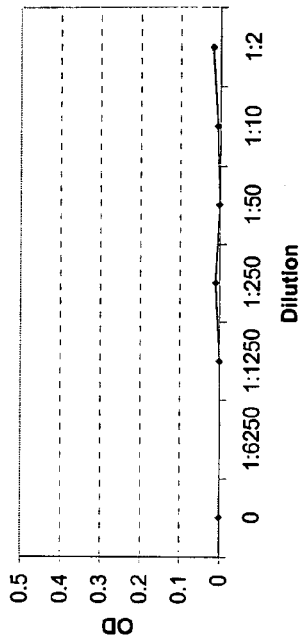
FIGS. 20A-F are graphs depicting the results of analyses of binding and neutralization properties of the human monoclonal antibody produced by clone 7-508-395. The figure legends for FIGS. 18A-18F are identical to those for the corresponding panels in FIG. 13.
Figure 20A:
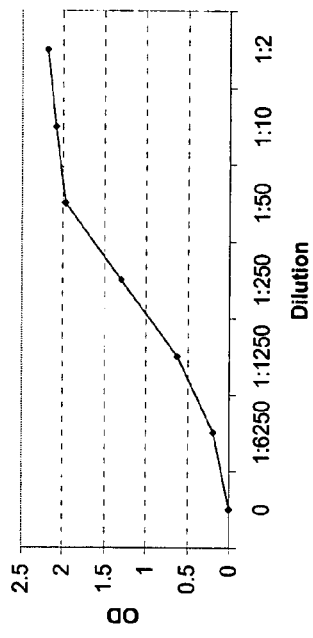
Figure 20B:
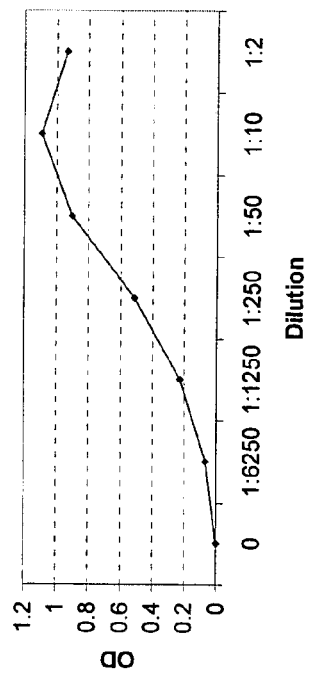
Figure 20D:
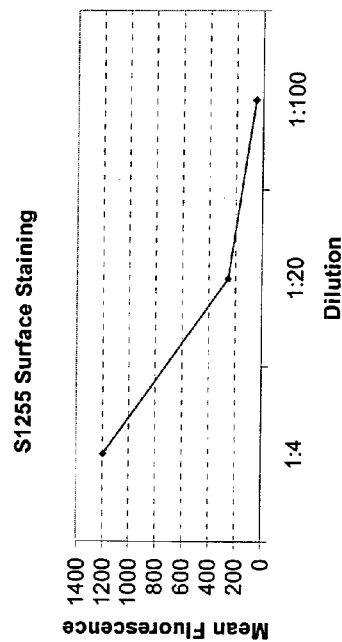
Figure 20E:
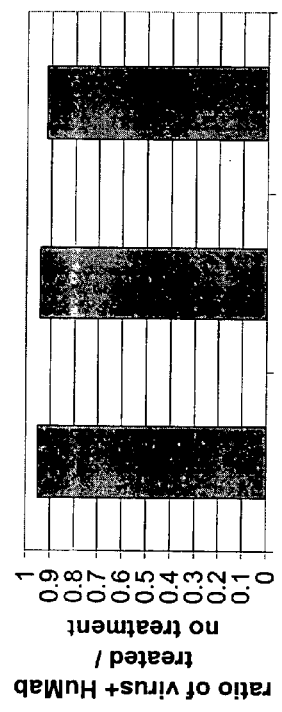
Figure 20F:
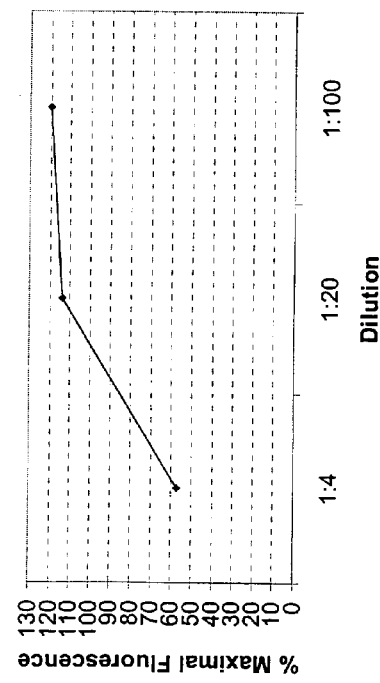
Figure 21C:
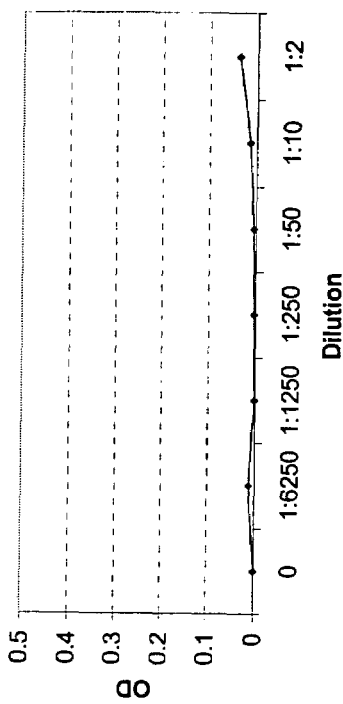
FIGS. 21A-F are graphs depicting the results of analyses of binding and neutralization properties of the human monoclonal antibody produced by clone 7-508-415. The figure legends for FIGS. 21A-21C, 21E and 21F are identical to those for the corresponding panels in FIG. 13.
Figure 21A:
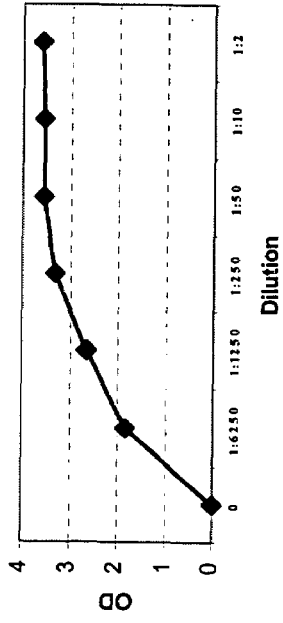
Figure 21B:
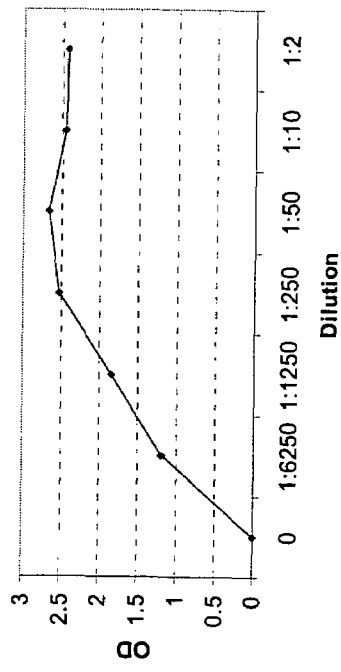
Figure 21F:
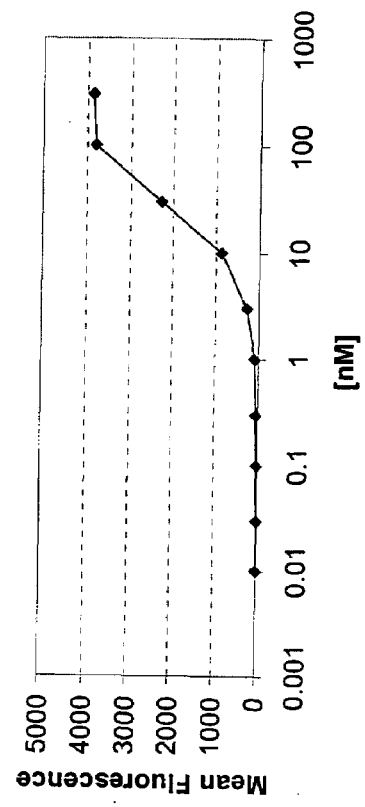
Figure 21D:
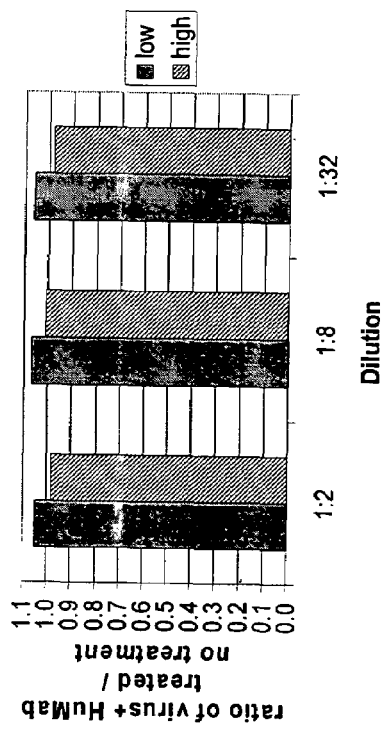
Figure 21E:
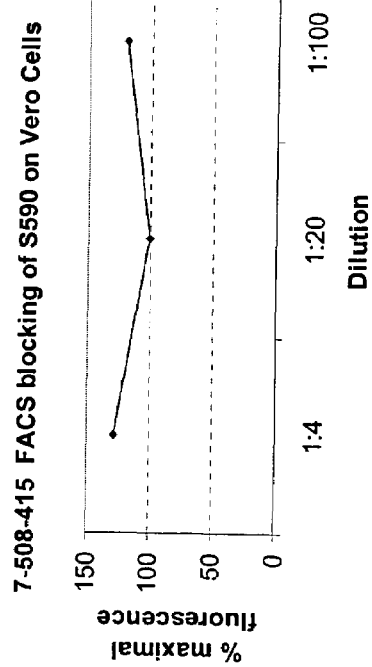
Figure 22C:
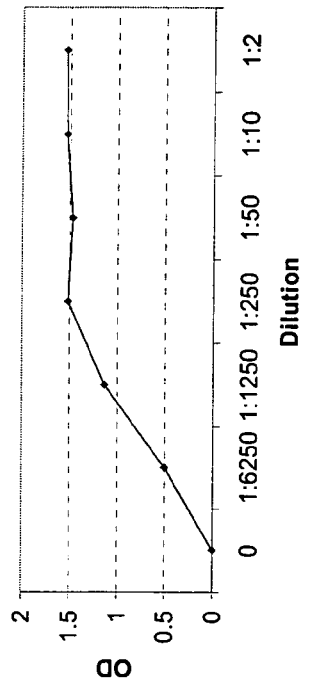
FIGS. 22A-F are graphs depicting the results of analyses of binding and neutralization properties of the human monoclonal antibody produced by clone 7-508-478. The figure legends for FIGS. 22A-22C, 22E and 22F are identical to those for the corresponding panels in FIG. 13.
Figure 22A:
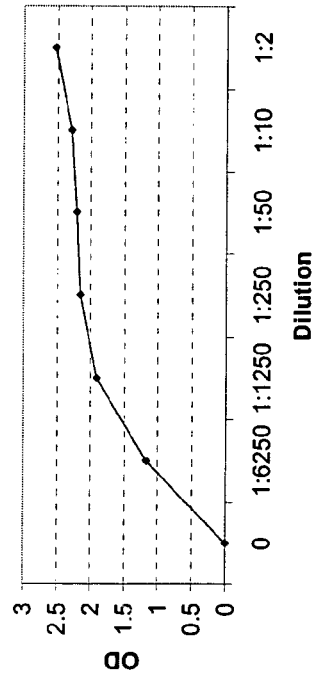
Figure 22B:
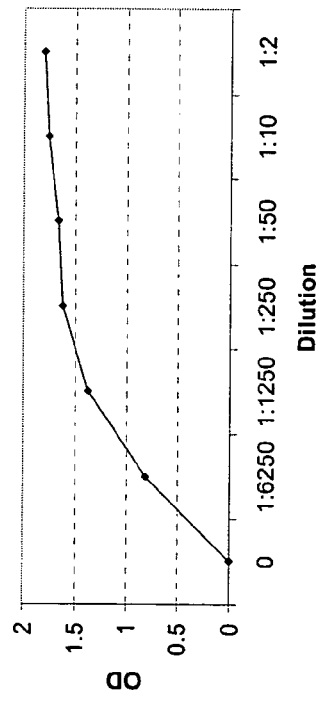
Figure 22D:
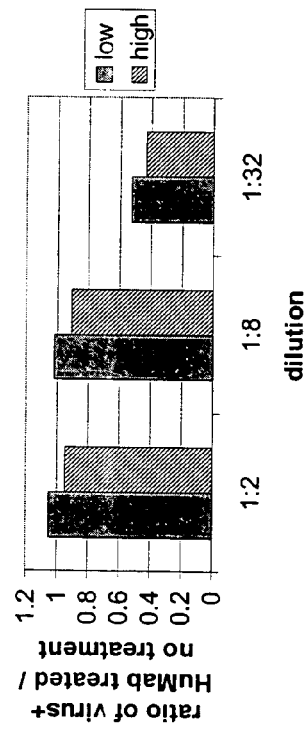
Figure 22F:
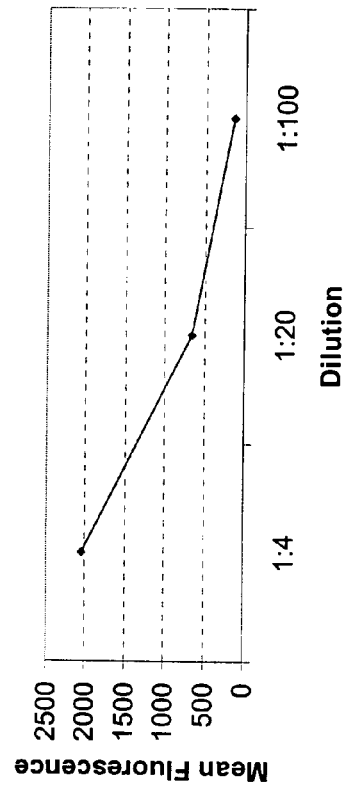
Figure 22E:
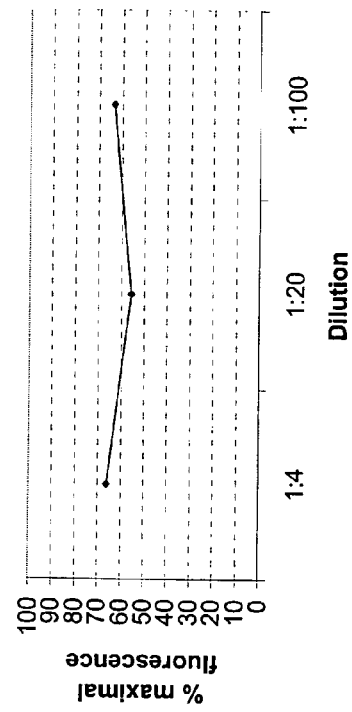
Figure 23C:
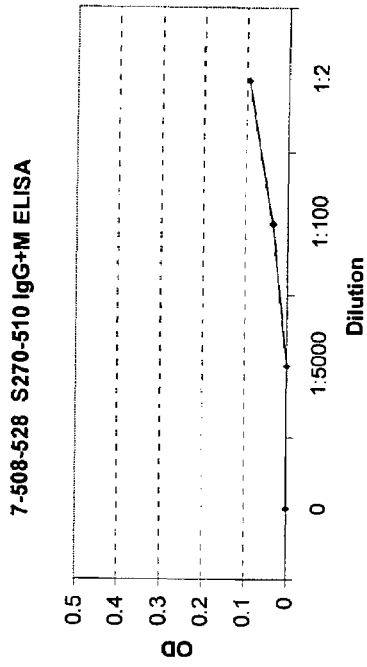
FIGS. 23A-F are graphs depicting the results of analyses of binding and neutralization properties of the human monoclonal antibody produced by clone 7-508-528. The figure legends for FIGS. 23A-23F are identical to those for the corresponding panels in FIG. 13.
Figure 23A:
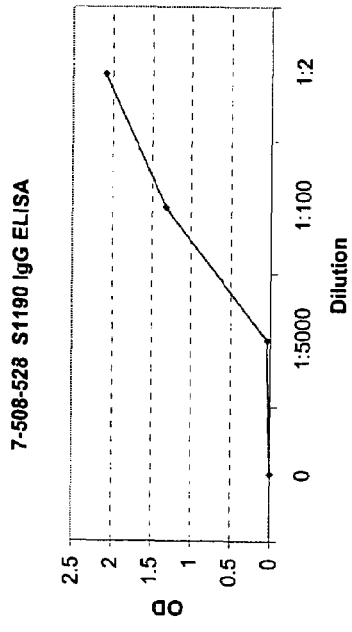
Figure 23B:
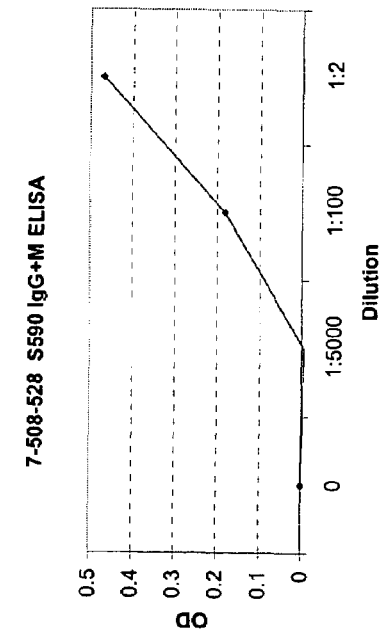
Figure 23F:
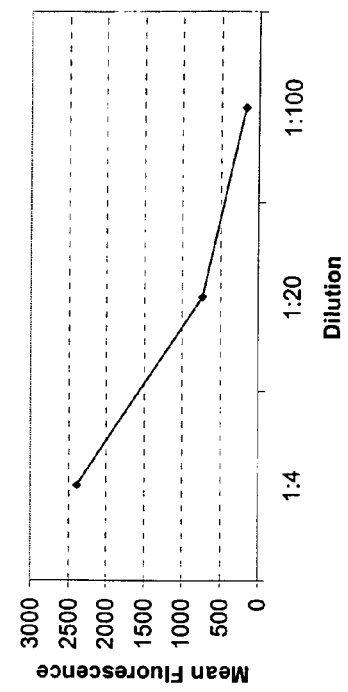
Figure 23D:
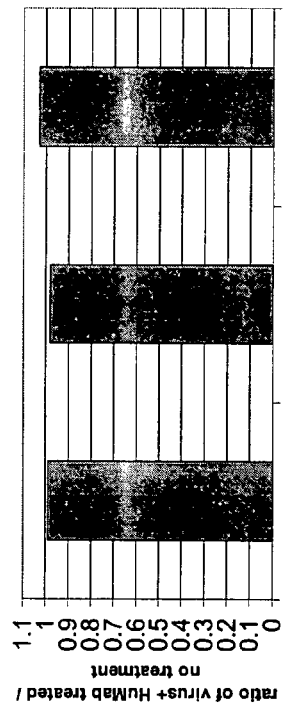
Figure 23E:
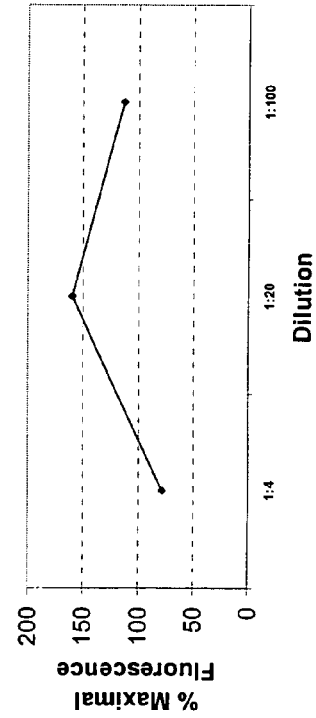
Figure 24A:
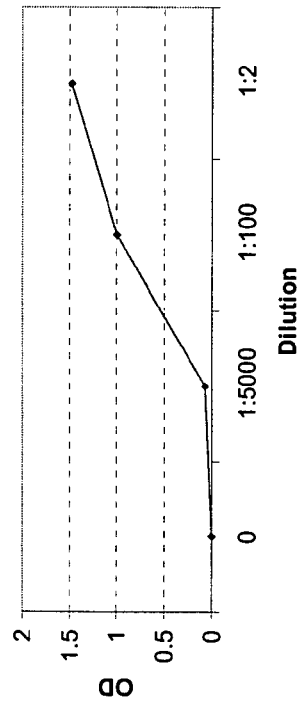
FIGS. 24A-F are graphs depicting the results of analyses of binding and neutralization properties of the human monoclonal antibody produced by clone 7-508-573. The figure legends for FIGS. 24A-24F are identical to those for the corresponding panels in FIG. 13.
Figure 24B:
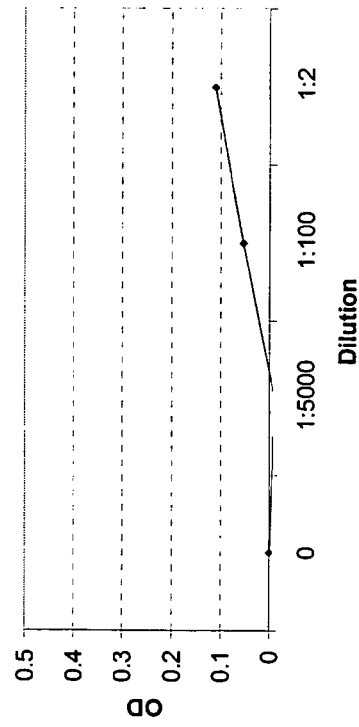
Figure 24C:
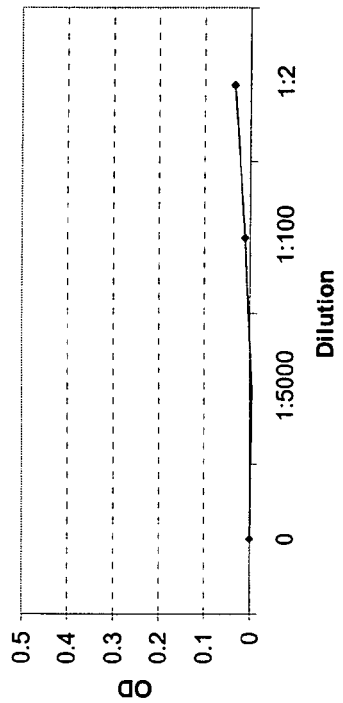
Figure 24F:
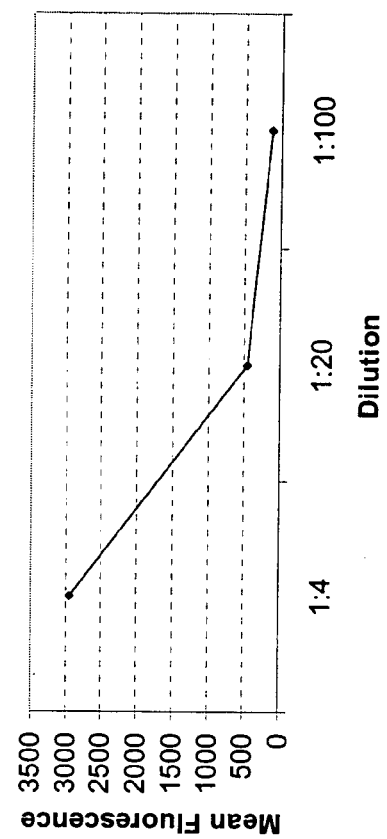
Figure 24D:
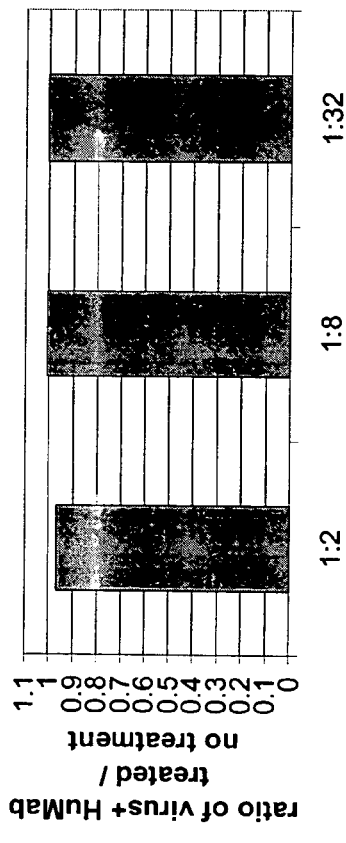
Figure 24E:
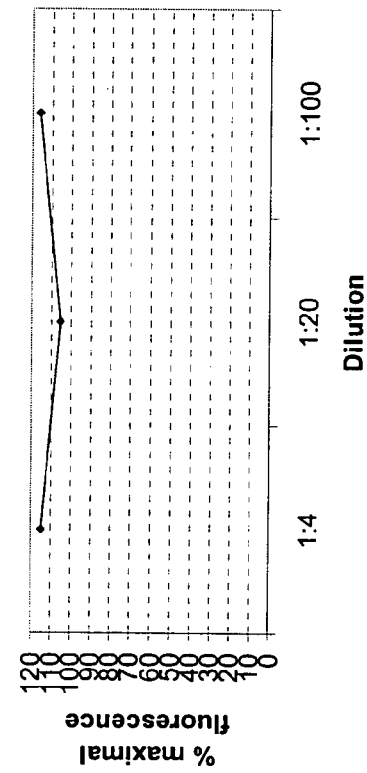
Figure 25A:
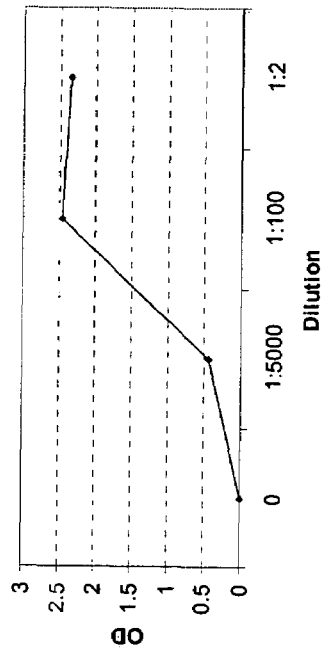
FIGS. 25A-F are graphs depicting the results of analyses of binding and neutralization properties of the human monoclonal antibody produced by clone 7-508-699. The figure legends for FIGS. 25A-25F are identical to those for the corresponding panels in FIG. 13.
Figure 25B:
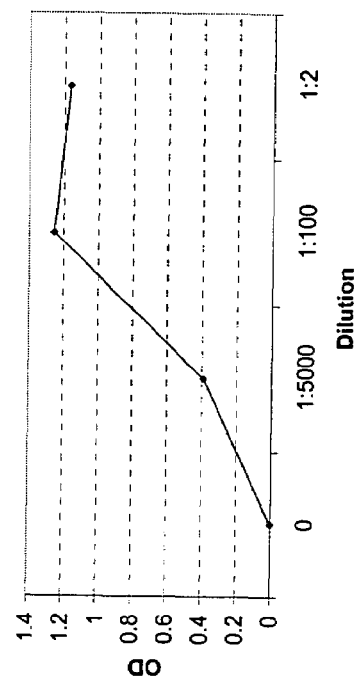
Figure 25C:
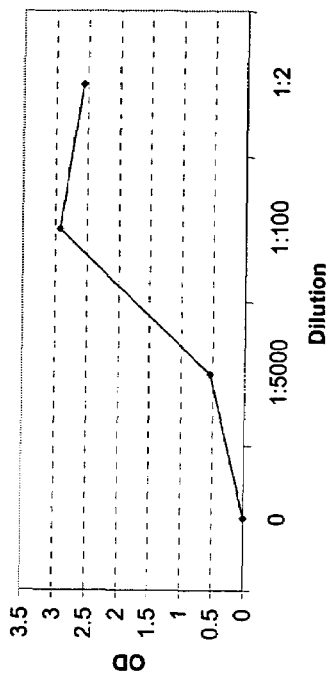
Figure 25F:
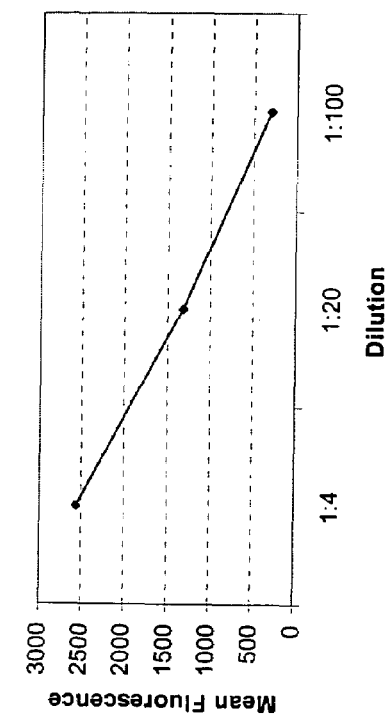
Figure 25D:
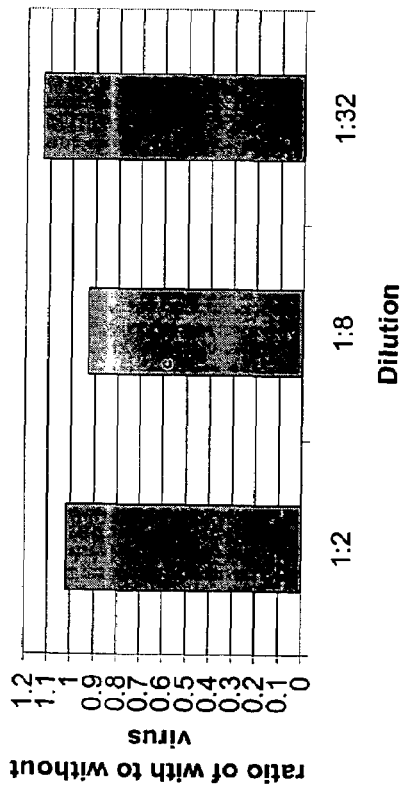
Figure 25E:
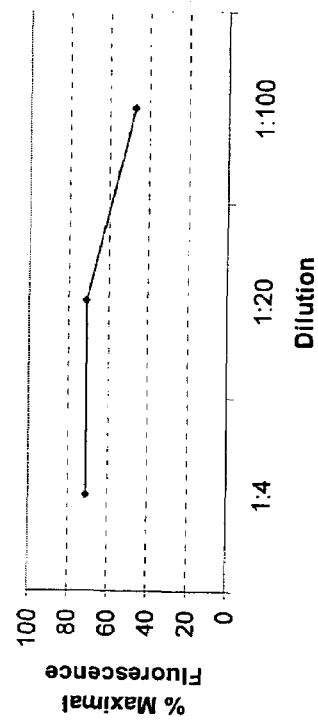
Figure 26C:
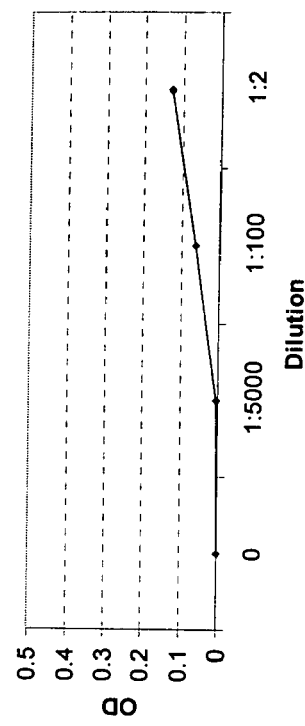
FIGS. 26A-F are graphs depicting the results of analyses of binding and neutralization properties of the human monoclonal antibody produced by clone 7-512-9. The figure legends for FIGS. 26A-26F are identical to those for the corresponding panels in FIG. 13.
Figure 26A:
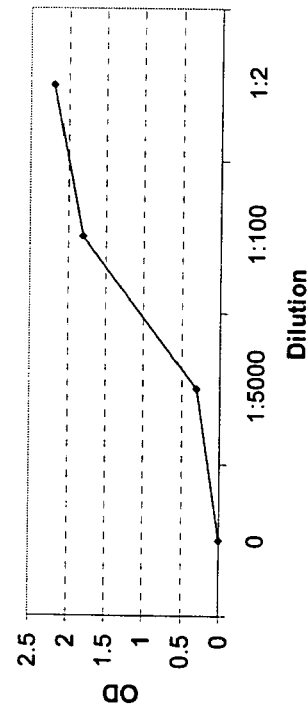
Figure 26B:
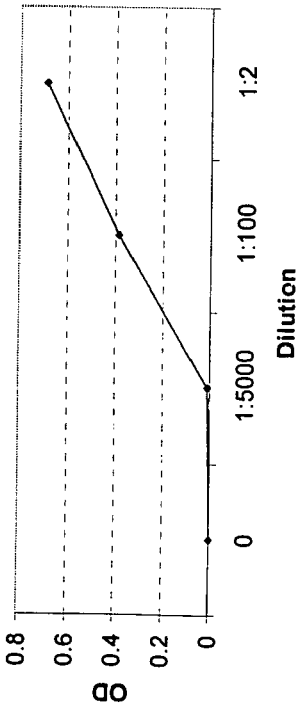
Figure 26F:
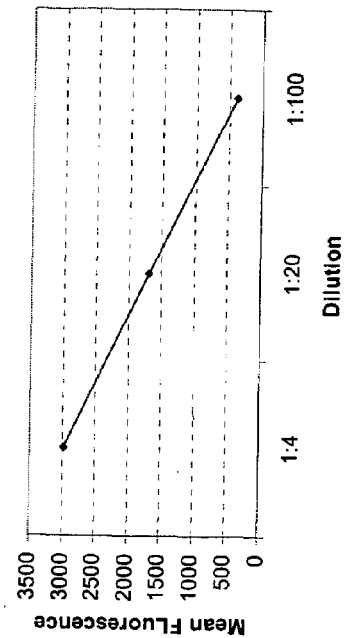
Figure 26D:
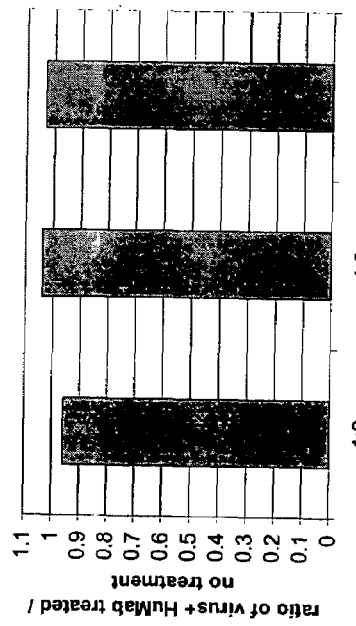
Figure 26E:
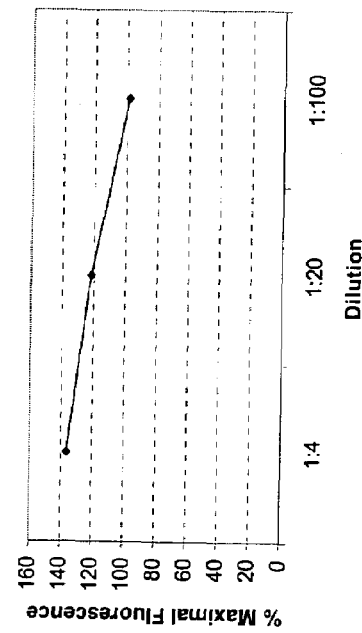
Figure 27:
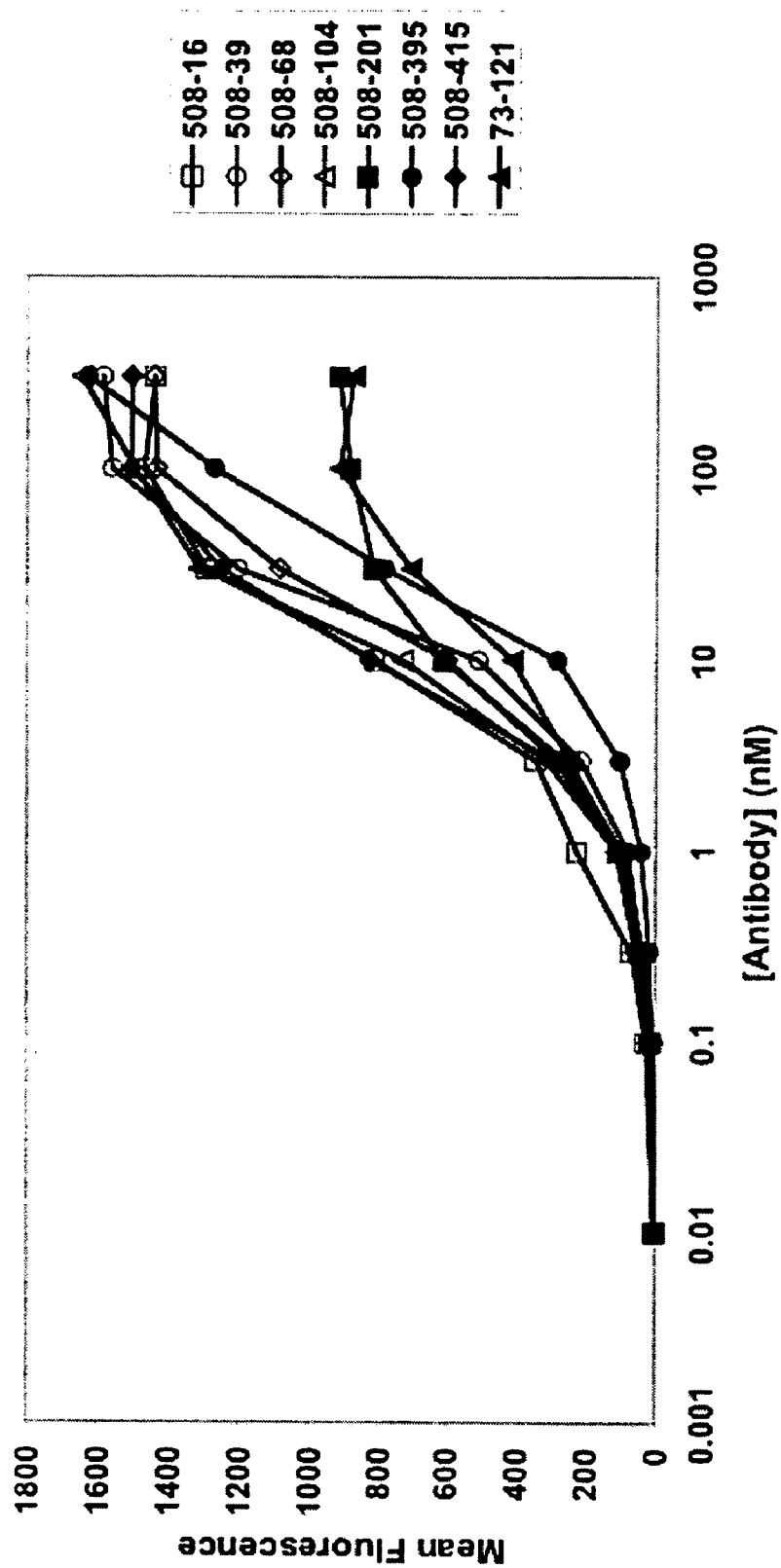
FIG. 27 is a graph depicting the results of FACS experiments in which monoclonal antibodies were incubated with HEK 293T cells transfected with S(1255). Antibody concentration vs. mean fluorescence is depicted for each monoclonal antibody.

Sera from HuMAb™ mice immunized with S(1190) or S(350) were tested in an assay to measure neutralization of SARS-CoV. Neutralization assays were performed by plating Vero E6 cells, adding a dose of SARS-CoV, Urbani strain that is ~100 times the 50% infective dose in tissue culture, in the presence of immune serum from HuMAb™ mice, and determining cytopathic effect of the virus after 72 hours. Cytopathic effect (CPE) of infection is apparent by visual inspection of cells. The neutralizing titer represents the endpoint dilution at which the antiserum neutralized virus. For example, antiserum from mouse number 8, which was immunized with S(1190), neutralized virus when diluted up to 1:7000. The results of neutralization assays with immune serum from HuMAb™ mice injected with S(1190) or S(350) are depicted in FIG. 11. Antiserum from mice 1, 2, 3, 4, 6, 7, 8, 9, and 10 which had been injected with S(1190) neutralized SARS-CoV infection. Antiserum from mice injected with S(350) and mouse 5 injected with S(1190) did not neutralize SARS-CoV infection. Sera 1-10 from mice immunized with S(1190) correspond to sera 1-10 assayed in FIG. 10. As shown in FIG. 10, the neutralizing titer varied between the antisera from mice injected with S(1190), with mice 4, 8, 9, and 10 containing the highest neutralizing titers. Thus, the immune response against neutralizing epitopes varies between mice.

FIG. 12 is a table depicting binding and neutralization properties of serum from human, mouse (Ms), rabbit (Rb), and HuMAb™ mice with SARS-CoV, S(350), S(590), and S(1190) as immunogens. SARS-CoV, S(590), and S(1190) stimulated production of antibodies reactive to S(1190) by ELISA, and antibodies that neutralized the virus. S(350) stimulated production of antibodies reactive to S(1190) by ELISA, but did not stimulate production of neutralizing antibodies.

Example 11

Serum from Mice Immunized with Minimum Ligand-Binding Domain of the S Protein Neutralizes SARS-CoV To test whether the fragment bearing the minimal Vero E6 cell-binding domain could also induce neutralizing activity, antisera against S(270-510) (which contains the minimal ligand binding domain) were raised in CD1 mice. S(270-510) produced neutralization titers of up to 1:2048, similar to titers obtained with S(1190).

Example 12

Characterization of Human Monoclonal Antibodies

Human anti-S protein monoclonal hybridomas were generated from splenocytes of HuMab™ mice immunized with S(1190) in adjuvant. Clones 12-28-1 and 7-73-121 were generated from HuMab™ mice immunized with S(1190) in RIBI. The remaining clones were generated from HuMab™ mice immunized with S(1190) in Freund's adjuvant. Monoclonal antibodies produced by the hybridomas were characterized by ELISA. Fourteen IgG-expressing clones were selected for further characterization. 96-well plates were coated with S(1190), S(590) or S(270-510) in a volume of 60 μl at a concentration of 1 or 2 μg/ml. Plates were blocked with 3% BSA solution in PBS pH 7.0. Antibody dilutions were prepared in blocking solution. Plates were washed between steps using PBS Tween (1%). Human IgG antibodies were detected using an alkaline phosphatase conjugated goat anti-human IgG Fc antibody from Southern Biotech. The absorbance at 405 nm was measured and plotted against dilution. The results of binding of the antibodies of each clone to forms of the S protein are summarized in Table 3, columns 2, 3, and 4 (below) and depicted graphically in FIGS. 13-26, parts A-C. As shown in these figures and the table, all of the clones bound S(1190) and S(590). A subset of clones bound S(270-510).

Human IgG monoclonal antibodies were assayed for binding to S protein fragments by Western blotting. S proteins of various lengths were precipitated from culture supernatants of transiently transfected HEK 293 cells using $Ni^{++}$ beads. Protein samples were separated by SDS-PAGE and transferred to polyvinylidene fluoride (PVDF) membranes. PVDF membranes were probed with each monoclonal human IgG to determine which S protein fragments were bound. Bound human IgGs were detected with horseradish peroxidase conjugated polyclonal goat anti-human IgG reagent. The results of these assays are presented as the minimum amino acid range bound by the individual monoclonal in column 8 of Table 3. Clones 7-73-121, 7-508-201, and 7-508-669 bound amino acids 490-510 of the S protein. Clones 7-508-16, 7-508-68, 7-508-104, 7-508-395, and 7-508-415 bound amino acids 90-190.

Antibodies were assayed for the ability to interfere with S protein binding to Vero E6 cells. S(590) with a Myc epitope tag was incubated with Vero E6 cells. A PE-labeled murine MAb was added to detect the Myc antibody. Cells labeled with fluorescence were detected by FACS analysis. Antibodies were added to the S(590) preparations to determine their ability to interfere with S protein binding. The results of these assays are depicted graphically in FIGS. 13-26, part E. Antibody inhibition of binding is also tabulated in column 6 of Table 3 as blocking binding (+), does not block binding (−), or enhances fluorescence (−). Antibodies that blocked binding bound to S(270-510). Numbers provided in columns 5, 6, and 7 are estimates of the purified antibody concentration in nM that reduce binding by 50%.

Binding of each antibody to a full length form of S protein, S(1255), which includes the transmembrane and cytoplasmic domains, was determined. Binding to S(1255) on the surface of transfected HEK 293 cells was assessed. S protein expressed and presented in this manner, rather than solubly, may have different epitopes exposed. HEK 293 cells were transfected with lipofectamine and cells expressing S(1255) were harvested after 48 hours. Antibodies were added at several dilutions and detected using a PE labeled anti-human reagent. Fluorescent cells were detected by FACS analysis. The results of these assays are depicted graphically in FIGS. 13-26, part F. Antibodies did not bind to cells that were not transfected with S(1255), demonstrating specificity of the antibodies for the antigen.

Figure 28:
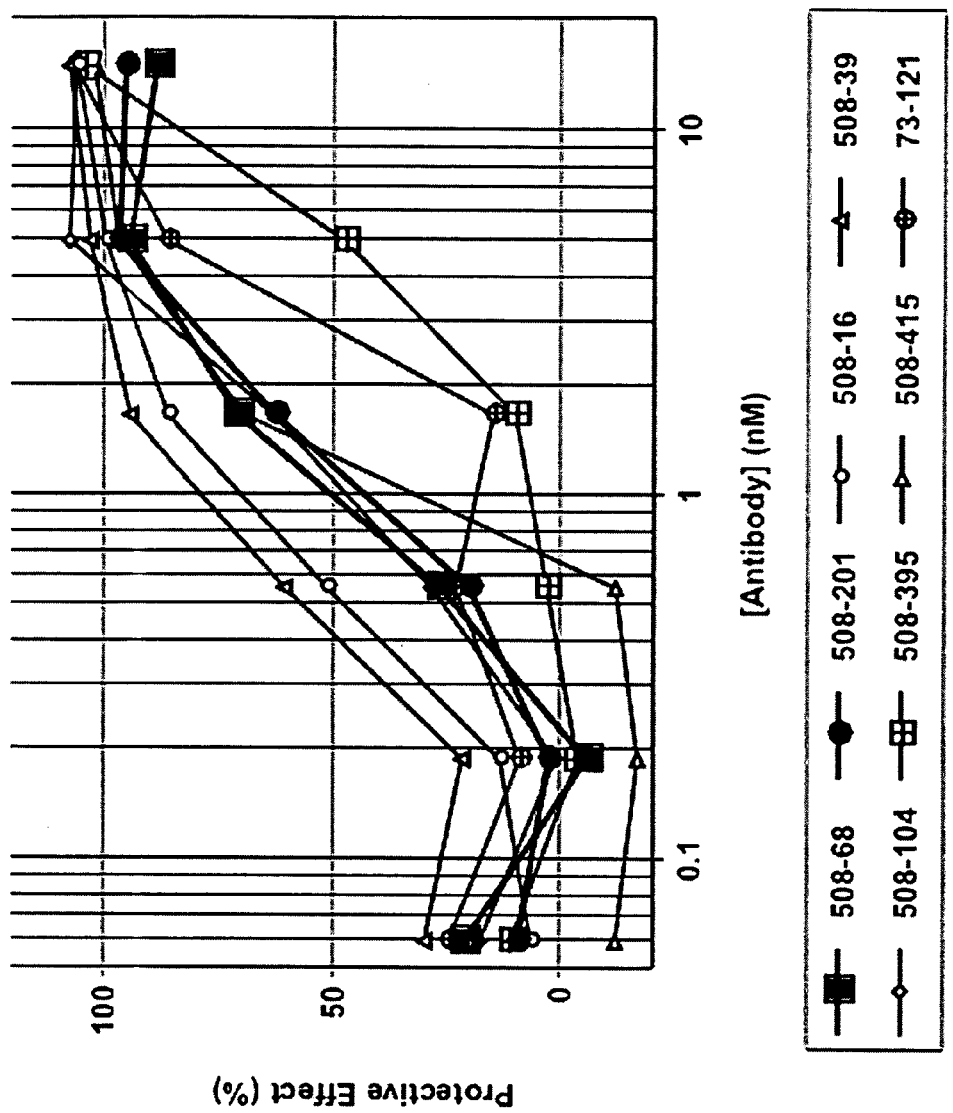
FIG. 28 is a graph depicting the results of assays to determine the concentrations at which eight different monoclonal antibodies protected cells from SARS-CoV cytotoxicity in vitro.

The dose-dependent binding curves of 508-16, 508-39, 508-68, 508-104 and 508-415 were quite similar (FIG. 28). Antibodies of clone 508-395 reached a similar maximal fluorescence as these five antibodies, but 50% maximal binding occurred at a higher concentration. The antibodies of clone 73-121 reached a 50% maximal level of binding at a higher concentration than the antibody of clone 508-201. Thus, all antibodies tested bound to S(1255) in this analysis, indicating that they could recognize S protein in its membrane bound form, as would be associated with virus.

Viral neutralization assays were performed to determine if the human monoclonals could inhibit SARS virus infection. Monolayers of Vero E6 cells were seeded at 5,000 cell/well in 96-well microtiter plates on assay day −1 in a volume of 100 μl. Cells were infected with ~100 $TCID_{50}$ of SARS-CoV (Urbani strain) on day 0. The virus was mixed with 4 fold dilutions of antibodies ranging from 1:2-1:32 before addition to the cell monolayers. One additional set of antibody dilutions without virus was included as a control to detect toxicity. Positive and negative controls (rabbit anti-S(1190) serum and pre-immune serum, respectively) were included in each assay. Virus stock was back-titrated in each assay to ensure that the inoculum was between 30 and 300 $TCID_{50}$/well. Rabbit antiserum controls included in all assays gave consistent neutralizing titers. The plates were inspected visually under a microscope for cytopathic effect 72 hours after infection and scored 0+ to 4+ with 0+ corresponding to a normal monolayer and 4+ corresponding to cytopathogenicity effects visible on most cells. The results of these assays are depicted in Table 2.

TABLE 2

Neutralization of SARS-CoV-induced CPE by Monoclonal Antibodies

| Antibody Clone | 1:2 dilution | 1:8 dilution | 1:32 dilution |
|---|---|---|---|
| 12-28-1 | 1+ | 1+ | 2+ |
| 7-73-121 |  | 1+ | 3+ |
| 7-508-16 |  |  | 3+ |
| 7-508-39 | 1+ | 1+ | 0+ |
| 7-508-68 |  | 1+ | 1+ |
| 7-508-104 |  |  | 3+ |
| 7-508-201 |  | 1+ |  |
| 7-508-395 | 1+ | 1+ | 0+ |
| 7-508-415 |  |  | 1+ |
| 7-508-478 |  | 1+ |  |
| 7-508-528 |  | 1+ | 2+ |
| 7-508-573 |  | 1+ | 0+ |
| 7-508-669 |  |  | 1+ |
| 7-512-9 |  |  | 1+ |

Next, cell viability was determined using a reagent containing a metabolic dye. After CPE was assessed, medium was removed from each well and 100 μl PBS was added. Twenty microliters of CellTiter 96® reagent (Promega) was added to each well, and plates were incubated for 2-4 hours until gradations of color between infected an uninfected controls could be easily distinguished visually. The CellTiter 96® reagent contains a dye that live cells metabolize to a product that is detectable at a wavelength of 490 nM. Thirty microliters of 10% SDS solution was added to each well to inactivate virus, and the absorbance was read using a plate reader.

The metabolic viability results for each clone are represented as the ratio of the absorbance from antibody treated infected cells compared to untreated cells in part D of FIGS. 13-26. More than one concentration of virus challenge was tested in the metabolic assay for several antibodies (7-508-201, 7-73-121, 7-508-415 and 7-508-478), with "low," "high," and "tox" referring to low or high concentrations of virus or media alone to assess toxicity of in the presence of hybridoma supernatants. The visual results are reported in column 5 of Table 3 as negative, positive (+, ++ or +++), or as a number indicating the dilution of antibody which tested positive for neutralization.

Various titrations of antibodies were tested in triplicate in the MST cell protection assay. Numbers in column 5 of Table 3 are estimates of purified antibody concentration in nM that protect 50% (2+) of cells. Antibodies of six clones, 508-16, 508-39, 508-68, 508-104, 508-201, 508-415, showed similar levels of protection against cell killing with concentrations that provided 50% cell protection ranging from 0.5 to 1.3 nM (Table 3, column 5, and FIG. 28). Antibodies of clones 73-121 and 508-395 were less effective, with concentrations that provided 50% cell protection pf 2.8 nM and 3.8 nM, respectively (Table 3, column 5, and FIG. 28). Thus, all antibodies tested neutralized SARS virus in this assay. The neutralization data indicate that antibodies that bind outside of the ligand-binding domain of the S protein also effectively neutralize virus. This was unexpected.

Figure 29:
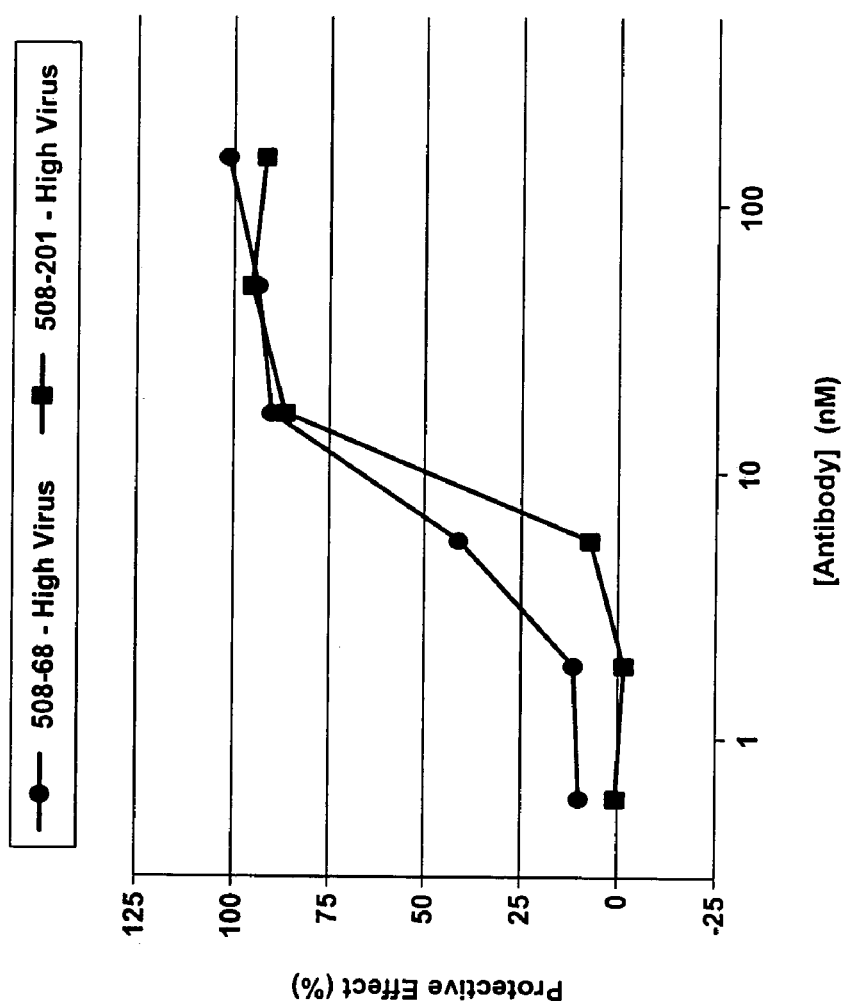
FIG. 29 is a graph depicting the results of assays to determine the concentrations at which two different monoclonal antibodies protected cells from SARS-CoV cytotoxicity in vitro.
Figure 30:
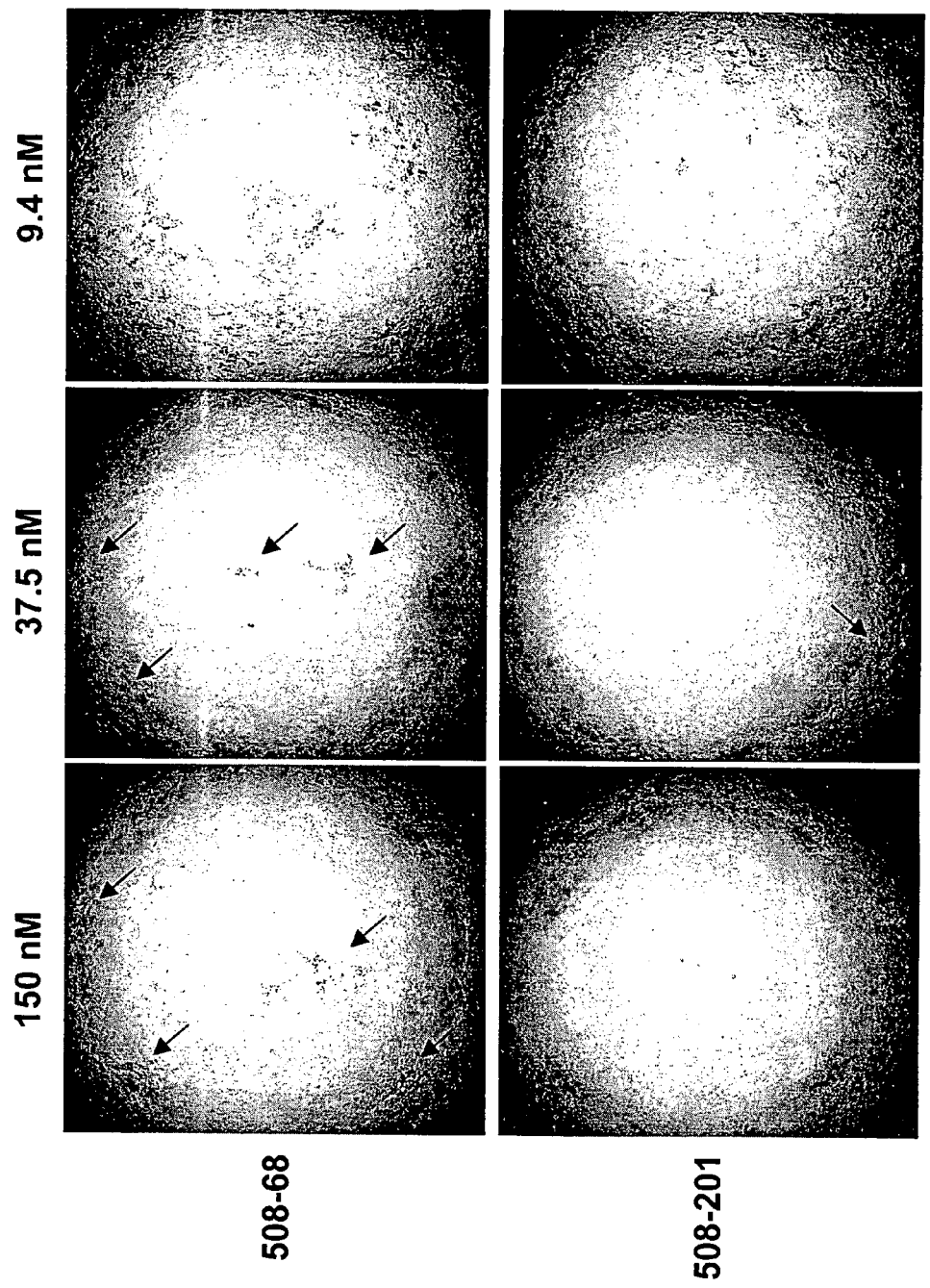
FIG. 30 is a representation of cytopathic effects of SARS-CoV on monolayers of Vero cells in the presence of three different concentrations (150 nM, 37.5 nM, and 9.4 nM) of two antibodies (508-68 and 508-21).

Despite the results with the cell protection assays, microscopic inspection of cell monolayers revealed subtle differences between samples that suggested infection of cells at even the highest concentrations of some antibodies, but not others. Specifically, tiny foci of CPE were observed in nearly all wells of antibodies from clones 508-16, 508-39, 508-68, 508-104, 508-395 and 508-415, even where cell protection assays showed results indistinguishable from uninfected controls. In contrast, antibodies of clones 121 and 201 showed no CPE whatsoever at these higher concentrations (Table 4). To determine whether the protection by the antibodies could be overcome by higher virus concentrations, the microneutralization assays were repeated with two candidate antibodies (508-68 and 508-201) using 3,000 $TCID_{50}$/well instead of the standard 100 $TCID_{50}$/well inocula. It was hypothesized that the antibodies that failed to completely block CPE would be unable to neutralize SARS-CoV at higher virus concentrations. The cytoprotective effects of the two antibodies were again indistinguishable, although curves were shifted slightly toward higher concentrations (FIG. 29). The small foci of CPE seen in the presence of 508-68 were more numerous than with the standard viral inocula, while 508-201 again demonstrated near complete protection from CPE (FIG. 30).

TABLE 4

| [Antibody] (nM) | 508-68 | | | 508-201 | | |
|---|---|---|---|---|---|---|
| 150.00 | + | + | + | 0 | 0 | 0 |
| 37.50 | + | + | + | 0 | 0 | 0 |
| 9.38 | + | + | + | + | 0 | 0 |
| 2.34 | 0 | + | + | + | ++ | 0 |
| 0.59 | +++ | ++ | ++ | ++ | +++ | +++ |
| 0.15 | ++++ | ++++ | ++++ | ++++ | ++++ | ++++ |

Example 13

Figure 31:
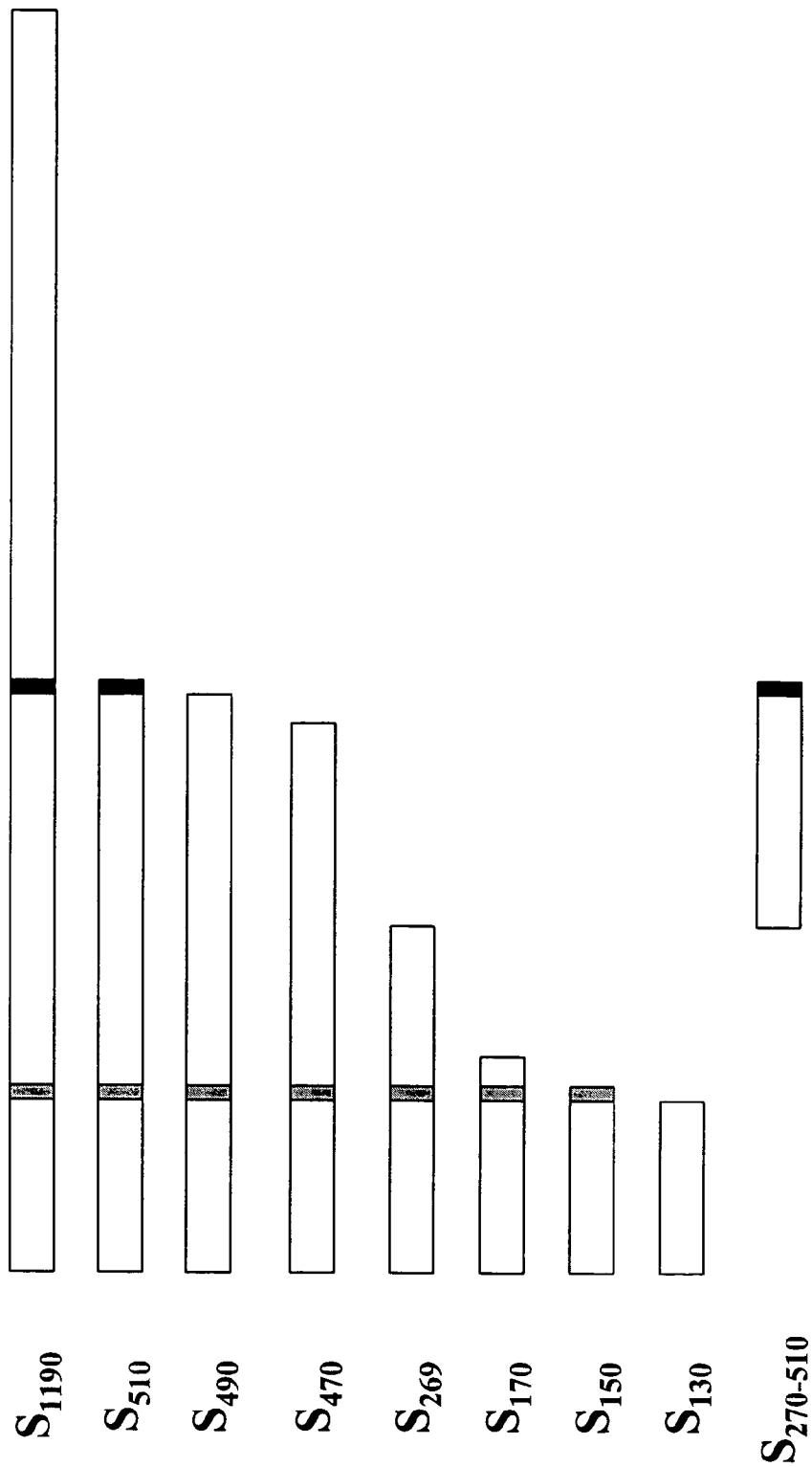
FIG. 31 is a schematic diagram of ten different truncated forms of the S protein used to map epitopes bound by monoclonal anti-S protein antibodies.
Figure 32:
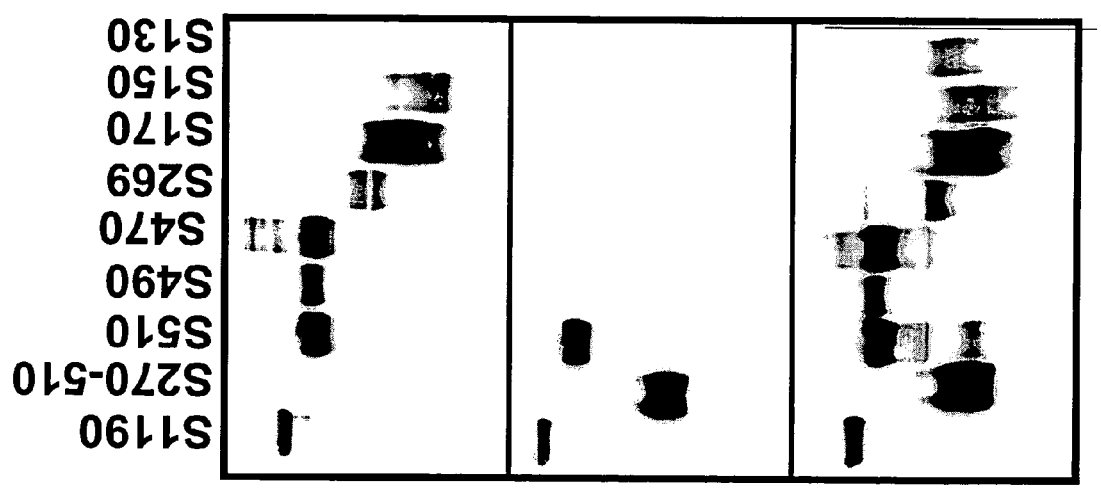
FIGS. 32A, B, and C are depictions of Western blots in which two anti-S protein antibodies, 508-68 and 508-201, were tested for binding to various truncated forms of the S protein. An antibody against a histidine tag (anti-His6) was used as a control.

Human Monoclonal Antibodies Recognize Two Distinct Epitopes Within the SARS CoV S Glycoprotein To map the epitopes within the $S_{1190}$ glycoprotein that were recognized by the eight human monoclonal antibodies were tested for binding to various carboxy- and amino-terminally truncated S glycoproteins encoded by PCR-synthesized. Specifically, antibodies were tested against soluble forms of S proteins containing amino acids 1-130 (S(130)), 1-150 (S(150)), 1-170 (S(170)), 1-269 (S(269)), 1-470 (S(470)), 1-490 (S(490)), 1-510 (S(510)) and 270-510 (S(270-510)). Representations of each form are depicted in FIG. 31. The constructs encoding these forms were transfected into HEK-293T cells and culture supernatants were harvested 48 hours following transfection. Each of eight human monoclonal antibodies were used to immunoprecipitate various S-glycoproteins from culture supernatant. Immunoprecipitated proteins were resolved by SDS-PAGE and Western blotting performed using an anti-$His_6$ antibody for protein detection. As shown in FIG. 32, two distinct binding patterns were observed by blotting. The antibody of clone 508-68 (FIG. 32A), 508-16, 508-39, 508-104, 508-395 and 508-415 precipitated S(150), S(170), S(269), S(470), S(490), S(510) and S(1190) but not S(130) or S(270-510). This demonstrates that this group of human monoclonal antibodies recognizes an epitope from amino acids 130 to 150 within the SARS CoV S glycoprotein. In contrast, 508-201 (FIG. 32B), and 73-121 recognized S(510), S(270-510), and S(1190), and

TABLE 3

Binding and Neutralization Properties of Human Monoclonal Antibodies

| Clone | Binds S1190 IgG | Binds S270-510 IgG + M | Binds S590 IgG + M | Viral Neut. in vitro ($IC_{50}$, nM) | FACS Blocking of S(590) to Vero cells ($IC_{50}$) | S1255 Binding ($ED_{50}$, nM) | S protein fragment reactivity by Western (AA) |
|---|---|---|---|---|---|---|---|
| 12-28-1 | + | + | + | +++ | | +++ | |
| 7-73-121 | + | + | + | 2.8 | – | 10 | 490-510 |
| 7-508-201 | + | + | + | 0.7 | 2 nM | 6 | 490-510 |
| 7-508-669 | + | + | + | +++ | | +++ | 490-510 |
| 7-508-478 | + | + | + | 5 | | +++ | |
| 7-508-16 | + | – | + | 0.5 | – | 8 | 130-150 |
| 7-508-39 | + | – | + | 0.4 | – | 14 | |
| 7-508-68 | + | – | + | 0.6 | – | 12 | 130-150 |
| 7-508-104 | + | – | + | 1.2 | – | 13 | 130-150 |
| 7-508-395 | + | – | + | 3.8 | – | 34 | 130-150 |
| 7-508-415 | + | – | + | 1.3 | – | 9 | 130-150 |
| 7-508-528 | + | – | + | +++ | | +++ | |
| 7-512-9 | + | – | + | +++ | | +++ | |
| 7-508-573 | + | – | – | +++ | | +++ | | did not recognized the other fragments tested. These data suggest that this set of antibodies recognizes amino acids 490 to 510 of the SARS CoV S glycoprotein.

To determine if these epitopes were linear or conformational, 2 μg of each truncated form of the S protein was resolved by SDS-PAGE, transferred to solid support and a Western blot performed using eight of the purified human monoclonal antibodies for detection. All eight antibodies reacted with the identical fragments by Western blot as seen with the immunoprecipitation studies (data not shown). These data, taken together, demonstrate that the antibodies of this panel of eight recognize two distinct linear epitopes, amino acids 490 to 510, and amino acids 130 to 150, of the SARS CoV S glycoprotein.

Example 14

Figure 33:
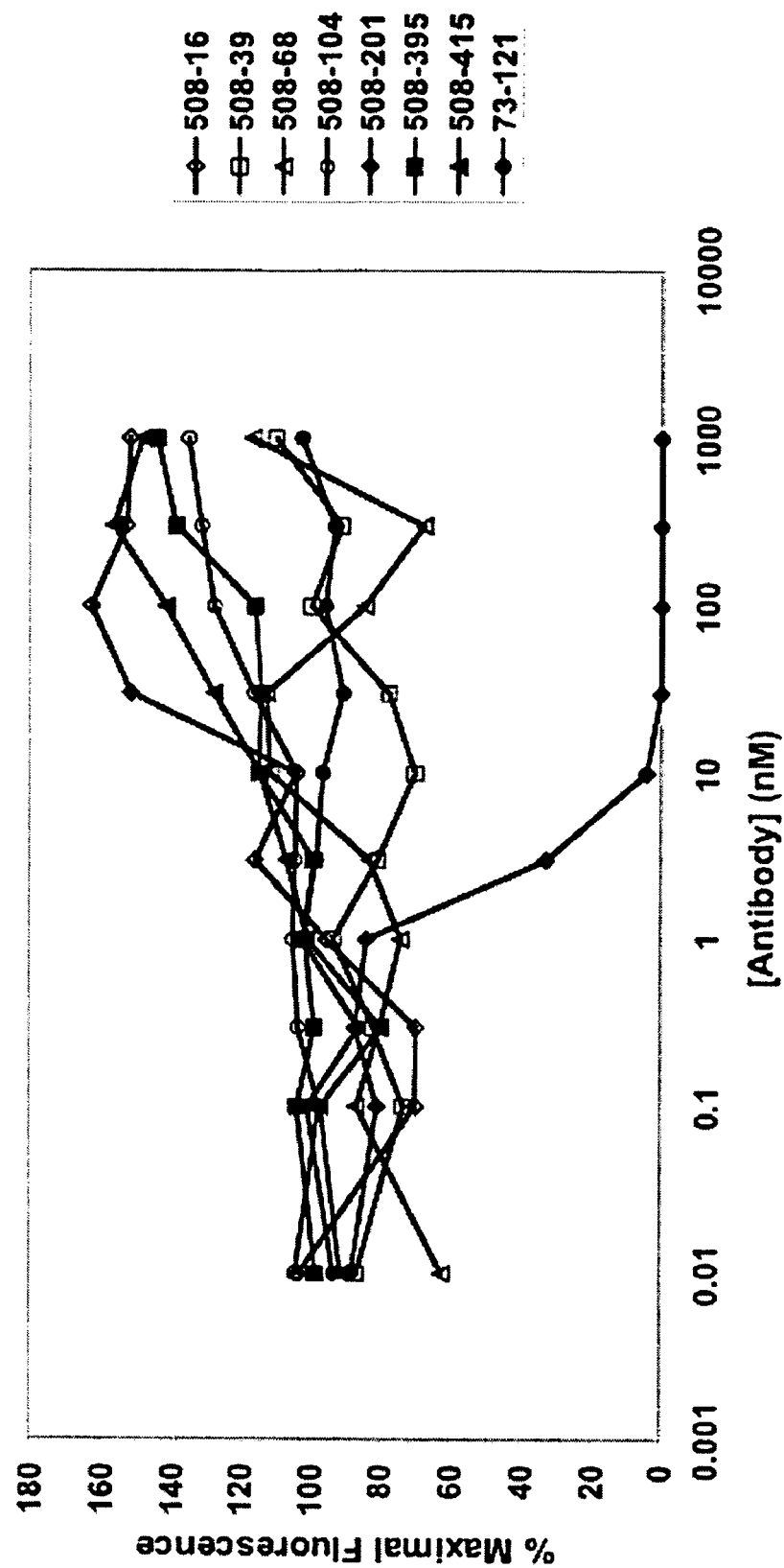
FIG. 33 is a graph depicting the results of FACS experiments to detect antibody blocking of S(590) binding to Vero cells. Monoclonal antibodies were incubated with Vero cells in the presence of myc-tagged S(590). S(590) binding to cells was detected using an anti-myc antibody. The data are plotted as the conc

Human Monoclonal Antibody 508-201 Disrupts the Interaction of S Glycoprotein with Vero E6 Cell Surfaces It has been shown that amino acids 318 to 510 represent the minimal receptor-binding domain of the S glycoprotein. Two of the human monoclonal antibodies described herein bind within this region and six of the human monoclonal antibodies described herein do not. A FACS-based assay was used to determine if the human monoclonal antibodies could specifically disrupt the interaction of SARS CoV S glycoprotein with Vero E6 cells, a cell known to be permissive to viral infection. Briefly, Vero E6 cells were incubated with 30 nM of S(590) containing a carboxy-terminal c-myc tag. Cells and S(590) were incubated either in the presence or absence of varying concentrations of the eight human monoclonal antibodies. S(590)-bound cells were incubated with an anti-c-myc antibody (9E10), and bound 9E10 detected with anti-mouse IgG-PE. Flow cytometry was performed and the data plotted as a percent of the fluorescence observed when no human monoclonal antibody was included (FIG. 33). Antibody 508-201 was the only human monoclonal antibody that specifically blocked binding of S(590) to Vero E6 cells. Although the epitope bound by antibody 73-121 mapped to amino acids 490 to 510 of the S protein, and grouped with antibody 508-201 by epitope mapping, it is clear that antibody 73-121 does not disrupt binding of S(590) with Vero E6 cells. Antibody 73-121 differed from antibody 508-201 with respect to binding to S(1255) and effective neutralizing titers (FIG. 28), suggesting that there may be a difference in binding avidity between the antibodies. Antibodies 508-16, 508-39, 508-68, 508-104, 508-395 and 508-415 also did not block binding of S(590) to Vero E6 cells. This result is not surprising given that the epitopes bound by these antibodies map to regions external to the receptor-binding domain. Interestingly, many of these antibodies enhanced binding of S(590) to Vero E6 cells. Also, binding profiles using this group of antibodies were erratic. These data demonstrate that some antibodies directed against amino acids 490 to 510 of the SARS CoV S glycoprotein can specifically block interaction of the S glycoprotein with the surface of target cells. These data also suggest that antibodies directed against an epitope outside the receptor binding domain of the S protein, amino acids 130-150, do not interfere with S glycoprotein/Vero E6 cell interaction.

Example 15

Various Forms of the S protein as Immunogens in HuMab Mice

HuMab mice were immunized with one of the following forms of the S protein: S(350), S(269), S(270-510), S(510), S(590), or S(1190). Comparable concentrations of serum antibodies that bound to S(1190) were produced in each mouse as measured by ELISA and immunoblot with virus lysate. Thus, each of these forms was immunogenic in these animals. Upon measuring neutralization activities of sera, it was observed that only the S protein fragments that reliably induced high titers of neutralizing antibodies in mice were those that included the ligand binding domain. The results of these assays are shown in Table. 5, below.

TABLE 5

Results of Binding and Neutralization Studies with Sera Generated in HuMab Mice

| S-protein fragment Immunogen | Binds Vero E6 cells specifically | Induces antibodies to S 1190 (ELISA) | Induces neutralizing antibodies |
|---|---|---|---|
| S 350 | No | Yes | Low |
| S 269 | No | Yes | Low |
| S 270-510 | Yes | Yes | High |
| S 510 | Yes | Yes | High |
| S 590 | Yes | Yes | High |
| S 1190 | Yes | Yes | High |

Example 16

Protective Efficacy of Human Monoclonal Antibody 508-68 and Human Monoclonal Antibody 508-201 In Vivo A murine model of SARS-CoV infection was used to test the prophylactic efficacy of two neutralizing human monoclonal antibodies with different epitope specificities, antibodies 508-68 and 508-201. This model has been utilized to demonstrate the effectiveness of humoral immunity in controlling replication of virus in lung tissue. It was developed as a small animal model to test vaccines and antivirals in a manner similar to other respiratory viruses such as Influenza A (Subbarao et al., *J. Virol.*, 78:3572-3577, 2004). Briefly, 4 to 6-week old female BALB/c mice were housed four mice per cage. Mice received 400 μl of diluted or undiluted monoclonal antibodies or post-infection serum by intraperitoneal injection. Antibodies 508-68 and 508-201 were administered in three dilutions: 40, 8, and 1.6 mg/kg. Mice were treated with the antibodies or control sera on day −1. On day 0, mice were bled to allow determination of neutralizing antibody titers in the animals. Next, mice were anesthetized exposed intranasally to $10^5$ TCID$_{50}$ of SARS-CoV, also on day 0. Mice infected in this manner do not exhibit disease, but virus replication can be detected in lungs and in nasal turbinates on day 2. Mice were sacrificed on day 2 and lungs and nasal turbinates were removed. Lung tissue was homogenized in a 10% w/v suspension. Virus titers were determined in Vero cell monolayers in 24- and 96-well plates.

To calculate neutralizing antibody titers from mouse sera, two-fold dilutions of heat-inactivated sera were tested in a microneutralization assay for the presence of antibodies that neutralized the infectivity of 100 TCID$_{50}$ of SARS-CoV in Vero cell monolayers as described in Subbarao et al., *J. Virol.*, 78: 3572-77, 2004. The dilution of serum that completely prevented CPE in 50% of the wells was calculated by the Reed Muench formula.

Figure 34:
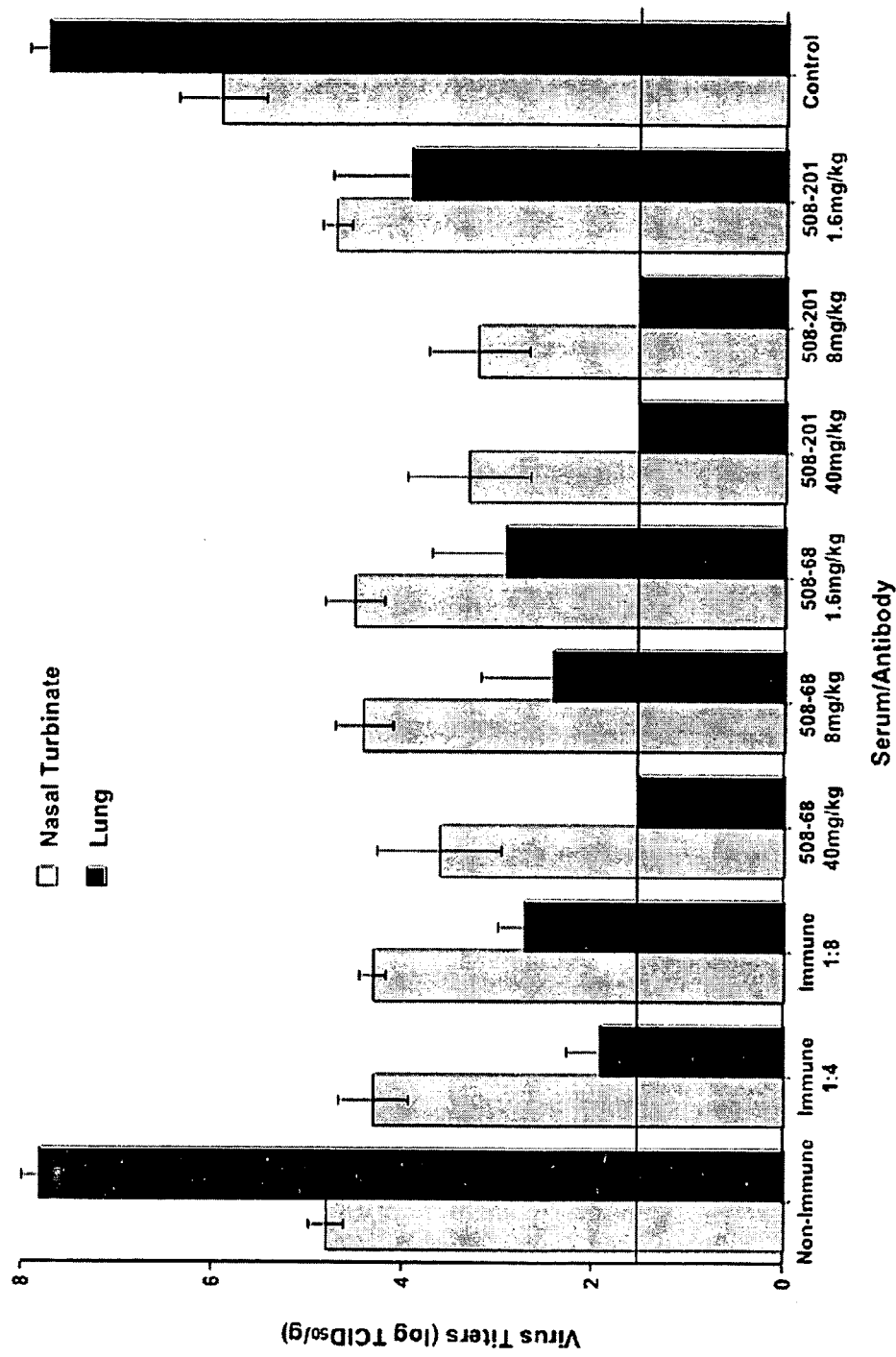
FIG. 34 is a bar graph depicting the results of assays to determine SARS-CoV titers isolated from lung and nasal turbinates of mice treated with non-immune serum, immune serum (from SARS-infected subjects), no serum (neg. control), and various dilutions of 508-68 and 508-201.

The results of these assays are depicted in FIG. 34. Antibodies 508-68 and 508-201 both provided significant levels of protection at all concentrations tested, as judged by virus titers in lung tissues. At the highest concentrations of these antibodies, virus titers in nasal turbinates also had significantly lower concentrations than controls. Animals treated with antibodies of clone 508-201 had generally lower levels of virus in lung and nasal turbinate tissues than observed in animal treated with antibodies of clone 508-68 and control immune serum.

Example 17

Characterization and Mutagenesis of the Human Monoclonal Antibody 508-201 Sequence cDNA encoding the heavy and light chain variable regions of the antibody produced by clone 508-201.2 were obtained from the 508-201.2 primary subclone using standard PCR techniques and sequenced using standard DNA sequencing techniques. The antibody produced by this 508-201.2 is also referred to as 201.2. The nucleotide and amino acid sequences of the variable heavy chain region of 201.2 are shown in FIG. 35 and in SEQ ID NO:15 and 13, respectively. The nucleotide and amino acid sequences of the light chain variable region of 201.2 are shown in FIG. 36 and in SEQ ID NO:16 and 14, respectively.

Comparison of the 201.2 heavy chain immunoglobulin sequence to the known human germline immunoglobulin heavy chain sequences demonstrated that the 201.2 heavy chain utilizes a VH segment from human germline VH DP-44, an undetermined D segment and a JH segment from human germline JH 4b. The alignment of the 201.2 VH sequence to the germline VH DP-44 sequence is shown in FIG. 37. Further analysis of the 201.2 VH sequence using the Kabat system of CDR region determination led to the delineation of the heavy chain CDR1, CDR2 and CD3 regions as shown in FIGS. 35 and 37.

As discussed above, mAb 201.2 utilizes a heavy chain variable region derived from a human DP-44 germline sequence, which is present in the HCo7 transgene (described further in U.S. Pat. Nos. 5,545,806; 5,625,825; and 5,545, 807). Since DP-44 is not a germline sequence that is utilized in the native human immunoglobulin repertoire, it may be advantageous to mutate the VH sequence of 201.2 to reduce potential immunogenicity. One or more framework residues of the 201.2 VH sequence can be mutated to a residue(s) present in the framework of a structurally related VH germline sequence that is more frequently utilized in the native human immunoglobulin repertoire. For example, FIG. 37 shows the alignment of the 201.2 VH sequence with the DP44 germline sequence and also to two structurally related human germline sequences, VH 3-23 and VH 3-7. Given the relatedness of these sequences, one can predict that one can select an anti-SARS human antibody that utilizes a VH region derived from a VH 3-23 or VH 3-7. Moreover, one can mutate one or more residues within the 201.2 VH sequence that differ from the residue(s) at the comparable position in the VH 3-23 or VH 3-7 sequence to the residue(s) that is present in VH 3-23 or VH 3-7, or to a conservative amino acid substitution thereof.

One such mutant was generated. This mutated form of 201.2 provided herein is referred to as 201.2(mut) and has the amino acid sequence shown in FIG. 37 and in SEQ ID NO:17.

In 201.2(mut), the histidine at amino acid position 13 has been mutated to either lysine or glutamine and the methionine at position 90 has been mutated to threonine.

Comparison of the 201.2 light chain immunoglobulin sequence to the known human germline immunoglobulin light chain sequences demonstrated that the 201.2 light chain utilizes a VL segment from human germline VK L6 and a JK segment from human germline JK4. The alignment of the 201.2 VL sequence to the germline VK L6 sequence is shown in FIG. 38. Further analysis of the 201.2 VL sequence using the Kabat system of CDR region determination led to the delineation of the light chain CDR1, CDR2 and CD3 regions as shown in FIGS. 36 and 38.

Example 18

Treatment of SARS-CoV Infected Animals with a Human Monoclonal Antibody

Three groups of hamsters (12 hamsters per group) were challenged intranasally with $10^3$ SARS-CoV virus particles. One group of hamsters was administered human anti-S monoclonal antibody 508-201 intraperitoneally at high (40 mg/kg) doses 24 hours after challenge. A second group was administered 508-201 at low (4 mg/kg) doses. The third group of hamsters was administered an irrelevant antibody (Synagis®, MedImmune, Inc., a monoclonal antibody that binds to a protein produced by Respiratory Syncytial Virus) at a high dose (40 mg/kg) as a negative control. Six animals in each group were sacrificed three days after challenge and another six animals five days after challenge.

Lung tissue was obtained from 3 animals in each group for determining viral titer. Lung and trachea tissues were obtained at both time points from 3 animals in each group for pathology. Serum samples were also obtained at the time of sacrifice to measure serum human IgG concentrations (by an ELISA assay for detection of total human IgG), to measure serum SARS specific protein antibody levels (by an ELISA assay for detection of S270-510-specific IgG), and for a serum SARS neutralization assay. FIG. 39 shows the virus titer from individual animals. FIG. 40 shows the mean virus titer for each treatment group. Animal 3443 in the 40 mg/kg group was omitted from the analysis of mean titer because this animal showed no human serum IgG by serologic tests and had no neutralization (FIG. 41). All other animals had human IgG present in their serum with 508-201 treated animals showing SARS specific human IgG present. The results of the pathology analysis are shown in FIG. 41. Fewer animals treated with 508-201 exhibited pathological effects of virus infection in trachea and lung than animals treated with the negative control antibody. The most severe pathology, lung consolidation, was observed at day 5 in the negative control animals. Animals treated with 508-201 had no lung consolidation at day 5 at either treatment dose.

These data show that hamsters were successfully treated with human monoclonal antibody 508-201 after intranasal challenge with the SARS-CoV virus. This was evident by the observed reduction in viral load and protection from lung consolidation by histopathology.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

SEQUENCE LISTING

<160> NUMBER OF SEQ ID NOS: 148

<210> SEQ ID NO 1
<211> LENGTH: 3570
<212> TYPE: DNA
<213> ORGANISM: SARS-Associated Coronavirus

<400> SEQUENCE: 1
atgttcatct tcctgctgtt cctgaccctg acctccggct ccgacctgga ccgctgcacc 60
accttcgacg acgtgcaggc tcctaactac acccagcaca cctcctccat gcgcggcgtg 120
tactaccctg acgagatctt ccgctccgac accctgtacc tgacccagga cctgttcctg 180
cccttctact ccaacgtgac cggcttccac accatcaacc acaccttcgg caatcccgtg 240
attcccttca aggacggcat ctacttcgcc gccaccgaga agtccaacgt ggtgcgcggc 300
tgggtgttcg gctccaccat gaacaacaag tcccagtccg tgatcatcat caacaactcc 360
accaacgtgg tgatccgcgc ctgcaacttc gagctgtgcg acaatccctt cttcgccgtg 420
tccaagccca tgggcaccca gacccacacc atgatcttcg acaacgcctt caactgcacc 480
ttcgagtaca tctccgacgc cttctccctg gacgtgtccg agaagtccgg caacttcaag 540
cacctgcgcg agttcgtgtt caagaacaag gacggcttcc tgtacgtgta caagggctac 600
cagcccatcg acgtggtgcg cgacctgccc tccggcttca acaccctgaa gcccatcttc 660
aagctgcctc tgggcatcaa cattaccaac ttccgcgcca ttctgaccgc cttctctccc 720
gcccaggaca tctggggcac ctccgccgcc gcctacttcg tgggctacct gaagcccacc 780
accttcatgc tgaagtacga cgagaacggc accattaccg acgccgtgga ctgctcccag 840
aaccctctgg ccgagctgaa gtgctccgtg aagtccttcg agattgacaa gggcatttac 900
cagacctcca acttccgcgt ggtgccctcc ggcgacgtgg tgcgctttcc caacattacc 960
aacctgtgtc ccttcggcga ggtgttcaac gccaccaagt tccctccgt gtacgcctgg 1020 gagcgcaaga agatttccaa ctgcgtggcc gactactccg tgctgtacaa ctccaccttc 1080
ttctccacct tcaagtgcta cggcgtgtcc gccaccaagc tgaacgatct gtgcttctcc 1140
aacgtgtacg ccgactcctt cgtggtgaag ggcgatgatg tgcgccagat tgctcccggc 1200
cagaccggcg tgattgccga ttacaactac aagctgcccg atgatttcat gggctgcgtg 1260
ctggcctgga acacccgcaa cattgatgcc acctccaccg gcaactacaa ctacaagtac 1320
cgctacctgc gccacggcaa gctgcgtccc ttcgagcgcg atatttccaa cgtgcccttc 1380
tctcccgatg gcaagccctg cactcctccc gccctgaact gctactggcc tctgaacgat 1440
tacggcttct acaccaccac cggcattggc taccagccct accgcgtggt ggtgctgtcc 1500
ttcgagctgc tgaacgctcc cgccaccgtg tgcggtccca agctgtccac cgatctgatt 1560
aagaaccagt gcgtgaactt caacttcaac ggcctgaccg gcaccggcgt gctgactccc 1620
tcctccaagc gcttccagcc cttccagcag ttcggccgcg atgtgtccga tttcaccgat 1680
tccgtgcgcg atcccaagac ctccgagatt ctggatattt ctccctgcgc cttcggcggc 1740
gtgtccgtga ttactcccgg caccaacgcc tcctccgagg tggccgtgct gtaccaggat 1800
gtgaactgca ccgatgtgtc caccgccatt cacgccgatc agctgactcc cgcctggcgc 1860
atttactcca ccggcaacaa cgtgttccag acccaggccg gctgcctgat tggcgccgag 1920
cacgtggata cctcctacga gtgcgatatt cccattggcg ccggcatttg cgcctcctac 1980
cacaccgtgt ccctgctgcg ctccacctcc cagaagtcca ttgtggccta caccatgtcc 2040

-continued

```
ctgggcgccg attcctccat tgcctactcc aacaacacca ttgccattcc caccaacttc      2100
tccatttcca ttaccaccga ggtgatgccc gtgtccatgg ccaagacctc cgtggattgc      2160
aacatgtaca tttgcggcga ttccaccgag tgcgccaacc tgctgctgca gtacggctcc      2220
ttctgcaccc agctgaaccg cgccctgtcc ggcattgccg ccgagcagga tcgcaacacc      2280
cgcgaggtgt tcgcccaggt gaagcagatg tacaagactc ccaccctgaa gtacttcggc      2340
ggcttcaact tctcccagat tctgcccgat cctctgaagc ccaccaagcg ctccttcatt      2400
gaggatctgc tgttcaacaa ggtgaccctg gccgatgccg gcttcatgaa gcagtacggc      2460
gagtgcctgg gcgatattaa cgcccgcgat ctgatttgcg cgcagaagtt caacggcctg      2520
accgtgctgc ctcctctgct gaccgatgat atgattgcgg cgtacaccgc ggcgctggtg      2580
tccggcaccg ccaccgcggg ctggaccttc ggcgcgggcg cggcgctgca gattcccttc      2640
gcgatgcaga tggcgtaccg cttcaacggc attggcgtga cccagaacgt gctgtacgag      2700
aaccagaagc agattgcgaa ccagttcaac aaggcgattt cccagattca ggagtccctg      2760
accaccacct ccaccgcgct gggcaagctg caggatgtgg tgaaccagaa cgcgcaggcg      2820
ctgaacaccc tggtgaagca gctgtcctcc aacttcggcg cgatttcctc cgtgctgaac      2880
gatattctgt cccgcctgga taaggtggag gcggaggtgc agattgatcg cctgattacc      2940
ggccgcctgc agtccctgca gacctacgtg acccagcagc tgattcgcgc ggcggagatt      3000
cgcgcgtccg cgaacctggc ggcgaccaag atgtccgagt gcgtgctggg ccagtccaag      3060
cgcgtggatt tctgcggcaa gggctaccac ctgatgtcct ccctcaggc ggcgcctcat       3120 ggcgtggtgt tcctgcacgt gacctacgtg ccctcccagg agcgcaactt caccaccgcg      3180
cccgcgattt gccacgaggg caaggcgtac ttccctcgcg agggcgtgtt cgtgttcaac      3240
ggcacctcct ggttcattac ccagcgcaac ttcttctctc ctcagattat taccaccgat      3300
aacaccttcg tgtccggcaa ctgcgatgtg gtgattggca ttattaacaa caccgtgtac      3360
gatcctctgc agcccgagct ggattccttc aaggaggagc tggataagta cttcaagaac      3420
cacacctctc ccgatgtgga tctgggcgat atttccggca ttaacgcctc cgtggtgaac      3480
attcagaagg agattgatcg cctgaacgag gtggccaaga acctgaacga gtccctgatt      3540
gatctgcagg agctgggcaa gtacgagcag                                      3570
```

<210> SEQ ID NO 2
<211> LENGTH: 1190
<212> TYPE: PRT
<213> ORGANISM: SARS-Associated Coronavirus

<400> SEQUENCE: 2

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95
```

-continued

```
Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
```

```
                515                 520                 525
Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
930                 935                 940
```

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
        980                 985                 990

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp Phe
    1010                1015                1020

Cys Gly Lys Gly Tyr His Leu Met Ser Phe Pro Gln Ala Ala Pro His
1025                1030                1035                1040

Gly Val Val Phe Leu His Val Thr Tyr Val Pro Ser Gln Glu Arg Asn
                1045                1050                1055

Phe Thr Thr Ala Pro Ala Ile Cys His Glu Gly Lys Ala Tyr Phe Pro
            1060                1065                1070

Arg Glu Gly Val Phe Val Phe Asn Gly Thr Ser Trp Phe Ile Thr Gln
        1075                1080                1085

Arg Asn Phe Phe Ser Pro Gln Ile Ile Thr Thr Asp Asn Thr Phe Val
    1090                1095                1100

Ser Gly Asn Cys Asp Val Val Ile Gly Ile Ile Asn Asn Thr Val Tyr
1105                1110                1115                1120

Asp Pro Leu Gln Pro Glu Leu Asp Ser Phe Lys Glu Glu Leu Asp Lys
                1125                1130                1135

Tyr Phe Lys Asn His Thr Ser Pro Asp Val Asp Leu Gly Asp Ile Ser
            1140                1145                1150

Gly Ile Asn Ala Ser Val Val Asn Ile Gln Lys Glu Ile Asp Arg Leu
        1155                1160                1165

Asn Glu Val Ala Lys Asn Leu Asn Glu Ser Leu Ile Asp Leu Gln Glu
    1170                1175                1180

Leu Gly Lys Tyr Glu Gln
1185                1190

<210> SEQ ID NO 3
<211> LENGTH: 1050
<212> TYPE: DNA
<213> ORGANISM: SARS-Associated Coronavirus

<400> SEQUENCE: 3
atgttcatct tcctgctgtt cctgaccctg acctccggct ccgacctgga ccgctgcacc      60
accttcgacg acgtgcaggc tcctaactac acccagcaca cctcctccat gcgcggcgtg     120
tactaccctg acgagatctt ccgctccgac accctgtacc tgacccagga cctgttcctg     180
cccttctact ccaacgtgac cggcttccac catcaacc acaccttcgg caatcccgtg       240
attcccttca aggacggcat ctacttcgcc gccaccgaga gtccaacgt ggtgcgcggc       300 tgggtgttcg gctccaccat gaacaacaag tcccagtccg tgatcatcat caacaactcc     360
accaacgtgg tgatccgcgc ctgcaacttc gagctgtgcg acaatcccct cttcgccgtg     420
tccaagccca tgggcaccca gacccacacc atgatcttcg acaacgcctt caactgcacc     480
ttcgagtaca tctccgacgc cttctccctg acgtgtccg agaagtccgg caacttcaag      540
cacctgcgcg agttcgtgtt caagaacaag gacggcttcc tgtacgtgta caagggctac     600
cagcccatcg acgtggtgcg cgacctgccc tccggcttca acaccctgaa gcccatcttc     660

```
aagctgcctc tgggcatcaa cattaccaac ttccgcgcca ttctgaccgc cttctctccc      720
gcccaggaca tctggggcac ctccgccgcc gcctacttcg tgggctacct gaagcccacc      780
accttcatgc tgaagtacga cgagaacggc accattaccg acgccgtgga ctgctcccag      840
aaccctctgg ccgagctgaa gtgctccgtg aagtccttcg agattgacaa gggcatttac      900
cagacctcca acttccgcgt ggtgccctcc ggcgacgtgg tgcgctttcc caacattacc      960
aacctgtgtc cttcggcga ggtgttcaac gccaccaagt ttccctccgt gtacgcctgg     1020
gagcgcaaga agatttccaa ctgcgtggcc                                       1050
```

<210> SEQ ID NO 4
<211> LENGTH: 350
<212> TYPE: PRT
<213> ORGANISM: SARS-Associated Coronavirus

<400> SEQUENCE: 4

```
Met Phe Ile Phe Leu Leu

```
Phe Arg Val Val Pro Ser Gly Asp Val Arg Phe Pro Asn Ile Thr
305                 310                 315                 320

Asn Leu Cys Pro Phe Gly Glu Val Phe Asn Ala Thr Lys Phe Pro Ser
            325                 330                 335

Val Tyr Ala Trp Glu Arg Lys Lys Ile Ser Asn Cys Val Ala
            340                 345                 350

<210> SEQ ID NO 5
<211> LENGTH: 3570
<212> TYPE: DNA
<213> ORGANISM: SARS-Associated Coronavirus

<400> SEQUENCE: 5
```

| | | | | | |
|---|---|---|---|---|---|
| atgtttattt | tcttattatt | tcttactctc | actagtggta | gtgaccttga | ccggtgcacc | 60 |
| acttttgatg | atgttcaagc | tcctaattac | actcaacata | cttcatctat | gaggggggtt | 120 |
| tactatcctg | atgaaatttt | tagatcagac | actctttatt | taactcagga | tttatttctt | 180 |
| ccatttttatt | ctaatgttac | agggtttcat | actattaatc | atacgtttgg | caaccctgtc | 240 |
| atacctttta | aggatggtat | ttattttgct | gccacagaga | atcaaatgt | tgtccgtggt | 300 |
| tgggtttttg | gttctaccat | gaacaacaag | tcacagtcgg | tgattattat | taacaattct | 360 |
| actaatgttg | ttatacgagc | atgtaacttt | gaattgtgtg | acaaccttt | ctttgctgtt | 420 |
| tctaaaccca | tgggtacaca | gacacatact | atgatattcg | ataatgcatt | taattgcact | 480 |
| ttcgagtaca | tatctgatgc | cttttcgctt | gatgtttcag | aaaagtcagg | taattttaaa | 540 |
| cacttacgag | agtttgtgtt | taaaaataaa | gatgggtttc | tctatgttta | agggctat | 600 |
| caacctatag | atgtagttcg | tgatctacct | tctggttttta | acactttgaa | acctattttt | 660 |
| aagttgcctc | ttggtattaa | cattacaaat | tttagagcca | ttcttacagc | cttttcacct | 720 |
| gctcaagaca | tttggggcac | gtcagctgca | gcctattttg | ttggctattt | aaagccaact | 780 |
| acatttatgc | tcaagtatga | tgaaaatggt | acaatcacag | atgctgttga | ttgttctcaa | 840 |
| aatccacttg | ctgaactcaa | atgctctgtt | aagagctttg | agattgacaa | aggaattac | 900 |
| cagacctcta | atttcagggt | tgttccctca | ggagatgttg | tgagattccc | taatattaca | 960 |
| aacttgtgtc | cttttggaga | ggttttaat | gctactaaat | cccttctgt | ctatgcatgg | 1020 |
| gagagaaaaa | aaatttctaa | ttgtgttgct | gattactctg | tgctctacaa | ctcaacattt | 1080 |
| ttttcaacct | ttaagtgcta | tggcgtttct | gccactaagt | tgaatgatct | ttgcttctcc | 1140 |
| aatgtctatg | cagattcttt | tgtagtcaag | ggagatgatg | taagacaaat | agcgccagga | 1200 |
| caaactggtg | ttattgctga | ttataattat | aaattgccag | atgatttcat | gggttgtgtc | 1260 |
| cttgcttgga | atactaggaa | cattgatgct | acttcaactg | gtaattataa | ttataaaat | 1320 |
| aggtatctta | gacatggcaa | gcttaggccc | tttgagagag | acatatctaa | tgtgcctttc | 1380 |
| tccctgatg | gcaaaccttg | caccccacct | gctcttaatt | gttattggcc | attaaatgat | 1440 |
| tatggttttt | acaccactac | tggcattggc | taccaacctt | acagagttgt | agtactttct | 1500 |
| tttgaacttt | taaatgcacc | ggccacggtt | tgtggaccaa | aattatccac | tgaccttat | 1560 |
| aagaaccagt | gtgtcaattt | taattttaat | ggactcactg | gtactggtgt | gttaactcct | 1620 |
| tcttcaaaga | gatttcaacc | atttcaacaa | tttggccgtg | atgttctga | tttcactgat | 1680 |
| tccgttcgag | atcctaaaac | atctgaaata | ttagacattt | caccttgcgc | ttttggggt | 1740 |
| gtaagtgtaa | ttcacctgg | aacaaatgct | tcatctgaag | ttgctgttct | atatcaagat | 1800 |
| gttaactgca | ctgatgtttc | tacagcaatt | catgcagatc | aactcacacc | agcttggcgc | 1860 |

```
atatattcta ctggaaacaa tgtattccag actcaagcag gctgtcttat aggagctgag    1920
catgtcgaca cttcttatga gtgcgacatt cctattggag ctggcatttg tgctagttac    1980
catacagttt ctttattacg tagtactagc caaaaatcta ttgtggctta tactatgtct    2040
ttaggtgctg atagttcaat tgcttactct aataacacca ttgctatacc tactaacttt    2100
tcaattagca ttactacaga agtaatgcct gtttctatgg ctaaaacctc cgtagattgt    2160
aatatgtaca tctgcggaga ttctactgaa tgtgctaatt tgcttctcca atatggtagc    2220
ttttgcacac aactaaatcg tgcactctca ggtattgctg ctgaacagga tcgcaacaca    2280
cgtgaagtgt tcgctcaagt caaacaaatg tacaaaaccc caactttgaa atattttggt    2340
ggttttaatt tttcacaaat attacctgac cctctaaagc caactaagag gtcttttatt    2400
gaggacttgc tctttaataa ggtgacactc gctgatgctg gcttcatgaa gcaatatggc    2460
gaatgcctag gtgatattaa tgctagagat ctcatttgtg cgcagaagtt caatggactt    2520
acagtgttgc cacctctgct cactgatgat atgattgctg cctacactgc tgctctagtt    2580
agtggtactg ccactgctgg atggacattt ggtgctggcg ctgctcttca aataccttt     2640
gctatgcaaa tggcatatag gttcaatggc attggagtta cccaaaatgt ctctatgag     2700
aaccaaaaac aaatcgccaa ccaatttaac aaggcgatta gtcaaattca gaatcactt     2760
acaacaacat caactgcatt gggcaagctg caagacgttg ttaaccagaa tgctcaagca    2820
ttaaacacac ttgttaaaca acttagctct aattttggtg caatttcaag tgtgctaaat    2880
gatatccttt cgcgacttga taaagtcgag gcggaggtac aaattgacag gttaattaca    2940
ggcagacttc aaagccttca aacctatgta acacaacaac taatcagggc tgctgaaatc    3000
agggcttctg ctaatcttgc tgctactaaa atgtctgagt gtgttcttgg acaatcaaaa    3060
agagttgact tttgtggaaa gggctaccac cttatgtcct tcccacaagc agccccgcat    3120
ggtgttgtct tcctacatgt cacgtatgtg ccatcccagg agaggaactt caccacagcg    3180
ccagcaattt gtcatgaagg caaagcatac ttccctcgtg aaggtgtttt tgtgtttaat    3240
ggcacttctt ggtttattac acagaggaac ttctttttctc cacaaataat tactacagac    3300
aatacatttg tctcaggaaa ttgtgatgtc gttattggca tcattaacaa cacagtttat    3360
gatcctctgc aacctgagct tgactcattc aaagaagagc tggacaagta cttcaaaaat    3420
catacatcac cagatgttga tcttggcgac atttcaggca ttaacgcttc tgtcgtcaac    3480
attcaaaaag aaattgaccg cctcaatgag gtcgctaaaa atttaaatga atcactcatt    3540
gaccttcaag aattgggaaa atatgagcaa                                     3570

<210> SEQ ID NO 6
<211> LENGTH: 3570
<212> TYPE: DNA
<213> ORGANISM: SARS-Associated Coronavirus

<400> SEQUENCE: 6
atgttcatct tcctgctgtt cctgacccty acctccggct ccgacctgga ccgctgcacc      60
accttcgacg acgtgcaggc tcctaactac acccagcaca cctcctccat gcgcggcgtg     120
tactaccctg acgagatctt ccgctccgac accctgtacc tgacccagga cctgttcctg     180
cccttctact ccaacgtgac cggcttccac accatcaacc acaccttcgg caatcccgtg     240
attcccttca aggacggcat ctacttcgcc gccaccgaga agtccaacgt ggtgcgcggc     300
tgggtgttcg gctccaccat gaacaacaag tcccagtccg tgatcatcat caacaactcc     360
accaacgtgg tgatccgcgc ctgcaacttc gagctgtgcg acaatcccct cttcgccgtg     420
```

-continued

```
tccaagccca tgggcaccca gacccacacc atgatcttcg acaacgcctt caactgcacc      480
ttcgagtaca tctccgacgc cttctccctg gacgtgtccg agaagtccgg caacttcaag      540
cacctgcgcg agttcgtgtt caagaacaag gacggcttcc tgtacgtgta caagggctac      600
cagcccatcg acgtggtgcg cgacctgccc tccggcttca cacccctgaa gcccatcttc      660
aagctgcctc tgggcatcaa cattaccaac ttccgcgcca ttctgaccgc cttctctccc      720
gcccaggaca tctggggcac ctccgccgcc gcctacttcg tgggctacct gaagcccacc      780
accttcatgc tgaagtacga cgagaacggc accattaccg acgccgtgga ctgctcccag      840
aaccctctgg ccgagctgaa gtgctccgtg aagtccttcg agattgacaa gggcatttac      900
cagacctcca acttccgcgt ggtgccctcc ggcgacgtgg tgcgcttccc caacattacc      960
aacctgtgtc ccttcggcga ggtgttcaac gccaccaagt tccctccgt gtacgcctgg     1020 gagcgcaaga agatttccaa ctgcgtggcc gactactccg tgctgtacaa ctccaccttc     1080
ttctccacct tcaagtgcta cggcgtgtcc gccaccaagc tgaacgatct gtgcttctcc     1140
aacgtgtacg ccgactcctt cgtggtgaag ggcgatgatg tgcgccagat tgctcccggc     1200
cagaccggcg tgattgccga ttacaactac aagctgcccg atgatttcat gggctgcgtg     1260
ctggcctgga cacccgcaa cattgatgcc acctccaccg caactacaa ctacaagtac     1320 cgctacctgc gccacggcaa gctgcgtccc ttcgagcgcg atatttccaa cgtgcccttc     1380
tctcccgatg caagccctg cactcctccc gccctgaact gctactggcc tctgaacgat     1440
tacggcttct acaccaccac cggcattggc taccagccct accgcgtggt ggtgctgtcc     1500
ttcgagctgc tgaacgctcc cgccaccgtg tgcggtccca agctgtccac cgatctgatt     1560
aagaaccagt gcgtgaactt caacttcaac ggcctgaccg caccggcgt gctgactccc     1620 tcctccaagc gcttccagcc cttccagcag ttcggccgcg atgtgtccga tttcaccgat     1680
tccgtgcgcg atcccaagac ctccgagatt ctggatattt ctccctgcgc cttcggcggc     1740
gtgtccgtga ttactcccgg caccaacgcc tcctccgagg tggccgtgct gtaccaggat     1800
gtgaactgca ccgatgtgtc caccgccatt cacgccgatc agctgactcc cgcctggcgc     1860
atttactcca ccggcaacaa cgtgttccag acccaggccg gctgcctgat ggcgccgag     1920 cacgtggata cctcctacga gtgcgatatt cccattggcg ccggcatttg cgcctcctac     1980
cacaccgtgt ccctgctgcg ctccaccctcc cagaagtcca ttgtggccta ccatgtgcc     2040 ctgggcgccg attcctccat tgcctactcc aacaacacca ttgccattcc caccaacttc     2100
tccatttcca ttaccaccga ggtgatgccc gtgtccatgg ccaagacctc cgtggattgc     2160
aacatgtaca tttgcggcga ttccaccgag tgcgccaacc tgctgctgca gtacggctcc     2220
ttctgcaccc agctgaaccg cgccctgtcc ggcattgccg ccgagcagga tcgcaacacc     2280
cgcgaggtgt tcgcccaggt gaagcagatg tacaagactc ccaccctgaa gtacttcggc     2340
ggcttcaact tctcccagat tctgcccgat cctctgaagc ccaccaagcg ctccttcatt     2400
gaggatctgc tgttcaacaa ggtgaccctg gccgatgccg gcttcatgaa gcagtacggc     2460
gagtgcctgg gcgatattaa cgcccgcgat ctgatttgcg cgcagaagtt caacggcctg     2520
accgtgctgc ctcctctgct gaccgatgat atgattgcgg cgtacaccgc ggcgctggtg     2580
tccggcaccg ccaccgcggg ctggaccttc ggcgcgggcg cggcgctgca gattcccttc     2640
gcgatgcaga tggcgtaccg cttcaacggc attggcgtga cccagaacgt gctgtacgag     2700
aaccagaagc agattgcgaa ccagttcaac aaggcgattt cccagattca ggagtccctg     2760
```

-continued

```
accaccacct ccaccgcgct gggcaagctg caggatgtgg tgaaccagaa cgcgcaggcg    2820
ctgaacaccc tggtgaagca gctgtcctcc aacttcggcg cgatttcctc cgtgctgaac    2880
gatattctgt cccgcctgga taaggtggag gcggaggtgc agattgatcg cctgattacc    2940
ggccgcctgc agtccctgca gacctacgtg acccagcagc tgattcgcgc ggcggagatt    3000
cgcgcgtccg cgaacctggc ggcgaccaag atgtccgagt gcgtgctggg ccagtccaag    3060
cgcgtggatt tctgcggcaa gggctaccac ctgatgtcct ccctcaggc ggcgcctcat    3120 ggcgtggtgt cctgcacgt gacctacgtg ccctcccagg agcgcaactt caccaccgcg    3180
cccgcgattt gccacgaggg caaggcgtac ttccctcgcg agggcgtgtt cgtgttcaac    3240
ggcacctcct ggttcattac ccagcgcaac ttcttctctc ctcagattat taccaccgat    3300
aacaccttcg tgtccggcaa ctgcgatgtg gtgattggca ttattaacaa caccgtgtac    3360
gatcctctgc agcccgagct ggattccttc aaggaggagc tggataagta cttcaagaac    3420
cacacctctc ccgatgtgga tctgggcgat atttccggca ttaacgcctc cgtggtgaac    3480
attcagaagg agattgatcg cctgaacgag gtggccaaga acctgaacga gtccctgatt    3540
gatctgcagg agctgggcaa gtacgagcag                                     3570
```

```
<210> SEQ ID NO 7
<211> LENGTH: 4
<212> TYPE: PRT
<213> ORGANISM: SARS-Associated Coronavirus

<400> SEQUENCE: 7

Ser Tyr Asp Met
 1

<210> SEQ ID NO 8
<211> LENGTH: 15
<212> TYPE: PRT
<213> ORGANISM: SARS-Associated Coronavirus

<400> SEQUENCE: 8

Val Val Gly Thr Gly Asp Gly Thr Tyr Tyr Ala Asp Ser Val Lys
 1               5                  10                  15

<210> SEQ ID NO 9
<211> LENGTH: 8
<212> TYPE: PRT
<213> ORGANISM: SARS-Associated Coronavirus

<400> SEQUENCE: 9

Asp Gln Trp Trp Gly Ser Asp Tyr
 1               5

<210> SEQ ID NO 10
<211> LENGTH: 11
<212> TYPE: PRT
<213> ORGANISM: SARS-Associated Coronavirus

<400> SEQUENCE: 10

Arg Ala Ser Gln Ser Val Ser Ser Tyr Leu Ala
 1               5                  10

<210> SEQ ID NO 11
<211> LENGTH: 7
<212> TYPE: PRT
<213> ORGANISM: SARS-Associated Coronavirus

<400> SEQUENCE: 11
```

Asp Ala Ser Asn Arg Ala Thr
 1               5

<210> SEQ ID NO 12
<211> LENGTH: 9
<212> TYPE: PRT
<213> ORGANISM: SARS-Associated Coronavirus

<400> SEQUENCE: 12

Gln Gln Arg Ser Asn Trp Pro Leu Thr
 1               5

<210> SEQ ID NO 13
<211> LENGTH: 116
<212> TYPE: PRT
<213> ORGANISM: SARS-Associated Coronavirus

<400> SEQUENCE: 13

Glu Val Gln Leu Val Gln Ser Gly Gly Gly Leu Val His Pro Gly Gly
 1               5                  10                  15

Ser Leu Arg Leu Ser Cys Ala Gly Ser Gly Phe Thr Phe Ser Ser Tyr
             20                  25                  30

Asp Met His Trp Val Arg Gln Ala Pro Gly Lys Gly Leu Glu Trp Val
         35                  40                  45

Ser Val Val Gly Thr Gly Asp Gly Thr Tyr Tyr Ala Asp Ser Val Lys
     50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                 85                  90                  95

Arg Asp Gln Trp Trp Gly Ser Asp Tyr Trp Gly Gln Gly Thr Leu Val
            100                 105                 110

Thr Val Ser Ser
        115

<210> SEQ ID NO 14
<211> LENGTH: 107
<212> TYPE: PRT
<213> ORGANISM: SARS-Associated Coronavirus

<400> SEQUENCE: 14

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 15
<211> LENGTH: 348

```
<212> TYPE: DNA
<213> ORGANISM: SARS-Associated Coronavirus

<400> SEQUENCE: 15
gaggttcagc tggtgcagtc tgggggaggc ttggtacatc ctgggggtc cctgagactc      60 tcctgtgcag gctctggatt caccttcagt agctatgata tgcactgggt tcgccaggct     120
ccaggaaaag gtctggagtg gtatcagtt gttggtactg gtgatggcac atactatgca     180
gactccgtga agggccgatt caccatctcc agagacaatg ccaagaactc cttgtatctt     240
caaatgaaca gcctgagagc cgaggacatg gctgtgtatt actgtgcaag agatcaatgg     300
tggggatccg actactgggg ccagggaacc ctggtcaccg tctcctca                  348

<210> SEQ ID NO 16
<211> LENGTH: 321
<212> TYPE: DNA
<213> ORGANISM: SARS-Associated Coronavirus

<400> SEQUENCE: 16
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa a                                                321

<210> SEQ ID NO 17
<211> LENGTH: 105
<212> TYPE: PRT
<213> ORGANISM: SARS-Associated Coronavirus
<220> FEATURE:
<221> NAME/KEY: VARIANT
<222> LOCATION: 13
<223> OTHER INFORMATION: Xaa = Lys or Gln

<400> SEQUENCE: 17

Glu Val Gln Leu Val Gln Ser Gly Gly Gly Leu Val Xaa Pro Gly Gly
 1               5                  10                  15

Ser Leu Arg Leu Ser Cys Ala Gly Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ser Val Val Gly Thr Gly Asp Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Gln Trp Trp Gly Ser Asp Tyr
            100                 105

<210> SEQ ID NO 18
<211> LENGTH: 97
<212> TYPE: PRT
<213> ORGANISM: SARS-Associated Coronavirus

<400> SEQUENCE: 18

Glu Val Gln Leu Val Gln Ser Gly Gly Gly Leu Val His Pro Gly Gly
```

```
                1               5                   10                  15
Ser Leu Arg Leu Ser Cys Ala Gly Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ser Ala Ile Gly Thr Gly Gly Thr Tyr Tyr Ala Asp Ser Val Lys
        50                  55                  60

Gly Arg Phe Thr Ile Ser Arg Asp Asn Ala Lys Asn Ser Leu Tyr Leu
65                      70                  75                  80

Gln Met Asn Ser Leu Arg Ala Glu Asp Met Ala Val Tyr Tyr Cys Ala
                85                  90                  95

Arg

<210> SEQ ID NO 19
<211> LENGTH: 98
<212> TYPE: PRT
<213> ORGANISM: SARS-Associated Coronavirus

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                85                  90                  95

Ala Arg

<210> SEQ ID NO 20
<211> LENGTH: 98
<212> TYPE: PRT
<213> ORGANISM: SARS-Associated Coronavirus

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Lys

<210> SEQ ID NO 21
<211> LENGTH: 107
<212> TYPE: PRT
```

<213> ORGANISM: SARS-Associated Coronavirus

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 22
<211> LENGTH: 198
<212> TYPE: DNA
<213> ORGANISM: SARS-Associated Coronavirus

<400> SEQUENCE: 22
tacattaagt ggccctggta cgtgtggctg ggcttcattg ccggcctgat tgccattgtg      60
atggtgacca ttctgctgtg ctgcatgacc tcctgctgct cctgcctgaa gggcgcctgc    120
tcctgcggct cctgctgcaa gttcgatgag gatgattccg agcccgtgct gaagggcgtg    180
aagctgcact acacctaa                                                  198

<210> SEQ ID NO 23
<211> LENGTH: 65
<212> TYPE: PRT
<213> ORGANISM: SARS-Associated Coronavirus

<400> SEQUENCE: 23

Tyr Ile Lys Trp Pro Trp Tyr Val Trp Leu Gly Phe Ile Ala Gly Leu
1               5                   10                  15

Ile Ala Ile Val Met Val Thr Ile Leu Leu Cys Cys Met Thr Ser Cys
            20                  25                  30

Cys Ser Cys Leu Lys Gly Ala Cys Ser Cys Gly Ser Cys Cys Lys Phe
        35                  40                  45

Asp Glu Asp Asp Ser Glu Pro Val Leu Lys Gly Val Lys Leu His Tyr
    50                  55                  60

Thr
65

<210> SEQ ID NO 24
<211> LENGTH: 35
<212> TYPE: DNA
<213> ORGANISM: SARS-Associated Coronavirus

<400> SEQUENCE: 24
gcgctgcaag cttgccgcca ccatgttcat cttcc                                35

<210> SEQ ID NO 25
<211> LENGTH: 70
<212> TYPE: DNA
<213> ORGANISM: SARS-Associated Coronavirus

```
<400> SEQUENCE: 25
tgctgttcct gaccctgacc tccggctccg acctggaccg ctgcaccacc ttcgacgacg    60
tgcaggctcc                                                          70

<210> SEQ ID NO 26
<211> LENGTH: 70
<212> TYPE: DNA
<213> ORGANISM: SARS-Associated Coronavirus

<400> SEQUENCE: 26
taactacacc cagcacacct cctccatgcg cggcgtgtac taccctgacg agatcttccg    60
ctccgacacc                                                          70

<210> SEQ ID NO 27
<211> LENGTH: 70
<212> TYPE: DNA
<213> ORGANISM: SARS-Associated Coronavirus

<400> SEQUENCE: 27
ctgtacctga cccaggacct gttcctgccc ttctactcca acgtgaccgg cttccacacc    60
atcaaccaca                                                          70

<210> SEQ ID NO 28
<211> LENGTH: 70
<212> TYPE: DNA
<213> ORGANISM: SARS-Associated Coronavirus

<400> SEQUENCE: 28
ccttcggcaa tcccgtgatt cccttcaagg acggcatcta cttcgccgcc accgagaagt    60
ccaacgtggt                                                          70

<210> SEQ ID NO 29
<211> LENGTH: 70
<212> TYPE: DNA
<213> ORGANISM: SARS-Associated Coronavirus

<400> SEQUENCE: 29
gcgcggctgg gtgttcggct ccaccatgaa caacaagtcc cagtccgtga tcatcatcaa    60
caactccacc                                                          70

<210> SEQ ID NO 30
<211> LENGTH: 70
<212> TYPE: DNA
<213> ORGANISM: SARS-Associated Coronavirus

<400> SEQUENCE: 30
aacgtggtga tccgcgcctg caacttcgag ctgtgcgaca tcccttctt cgccgtgtcc     60 aagcccatgg                                                          70

<210> SEQ ID NO 31
<211> LENGTH: 70
<212> TYPE: DNA
<213> ORGANISM: SARS-Associated Coronavirus

<400> SEQUENCE: 31
gcacccagac ccacaccatg atcttcgaca acgccttcaa ctgcaccttc gagtacatct    60
ccgacgcctt                                                          70
```

```
<210> SEQ ID NO 32
<211> LENGTH: 70
<212> TYPE: DNA
<213> ORGANISM: SARS-Associated Coronavirus

<400> SEQUENCE: 32
ctccctggac gtgtccgaga agtccggcaa cttcaagcac ctgcgcgagt tcgtgttcaa      60
gaacaaggac                                                            70

<210> SEQ ID NO 33
<211> LENGTH: 70
<212> TYPE: DNA
<213> ORGANISM: SARS-Associated Coronavirus

<400> SEQUENCE: 33
ggcttcctgt acgtgtacaa gggctaccag cccatcgacg tggtgcgcga cctgcccttcc     60 ggcttcaaca                                                            70

<210> SEQ ID NO 34
<211> LENGTH: 70
<212> TYPE: DNA
<213> ORGANISM: SARS-Associated Coronavirus

<400> SEQUENCE: 34
ccctgaagcc catcttcaag ctgcctctgg gcatcaacat taccaacttc cgcgccattc      60
tgaccgcctt                                                            70

<210> SEQ ID NO 35
<211> LENGTH: 70
<212> TYPE: DNA
<213> ORGANISM: SARS-Associated Coronavirus

<400> SEQUENCE: 35
ctctcccgcc caggacatct ggggcacctc cgccgccgcc tacttcgtgg gctacctgaa      60
gcccaccacc                                                            70

<210> SEQ ID NO 36
<211> LENGTH: 70
<212> TYPE: DNA
<213> ORGANISM: SARS-Associated Coronavirus

<400> SEQUENCE: 36
ttcatgctga agtacgacga gaacggcacc attaccgacg ccgtggactg ctcccagaac      60
cctctggccg                                                            70

<210> SEQ ID NO 37
<211> LENGTH: 70
<212> TYPE: DNA
<213> ORGANISM: SARS-Associated Coronavirus

<400> SEQUENCE: 37
agctgaagtg ctccgtgaag tccttcgaga ttgacaaggg catttaccag acctccaact      60
ccgcgtggt                                                             70

<210> SEQ ID NO 38
<211> LENGTH: 70
<212> TYPE: DNA
<213> ORGANISM: SARS-Associated Coronavirus

<400> SEQUENCE: 38
```

```
gccctccggc gacgtggtgc gctttcccaa cattaccaac ctgtgtccct tcggcgaggt    60
gttcaacgcc                                                          70

<210> SEQ ID NO 39
<211> LENGTH: 70
<212> TYPE: DNA
<213> ORGANISM: SARS-Associated Coronavirus

<400> SEQUENCE: 39
accaagtttc cctccgtgta cgcctgggag cgcaagaaga tttccaactg cgtggccgac    60
tactccgtgc                                                          70

<210> SEQ ID NO 40
<211> LENGTH: 70
<212> TYPE: DNA
<213> ORGANISM: SARS-Associated Coronavirus

<400> SEQUENCE: 40
tgtacaactc caccttcttc tccaccttca agtgctatgg cgtatctgcc accaagctga    60
acgatctttg                                                          70

<210> SEQ ID NO 41
<211> LENGTH: 70
<212> TYPE: DNA
<213> ORGANISM: SARS-Associated Coronavirus

<400> SEQUENCE: 41
cttctccaac gtgtacgctg actccttcgt ggtgaaaggt gatgatgttc gtcagattgc    60
tcctggtcag                                                          70

<210> SEQ ID NO 42
<211> LENGTH: 70
<212> TYPE: DNA
<213> ORGANISM: SARS-Associated Coronavirus

<400> SEQUENCE: 42
actggtgtga ttgctgatta caactacaag ctgcctgatg atttcatggg ttgcgtgctg    60
gcttggaaca                                                          70

<210> SEQ ID NO 43
<211> LENGTH: 70
<212> TYPE: DNA
<213> ORGANISM: SARS-Associated Coronavirus

<400> SEQUENCE: 43
ctcgtaacat tgatgctacc tccactggta actacaacta caagtatcgt tacctgcgtc    60
atggtaagct                                                          70

<210> SEQ ID NO 44
<211> LENGTH: 70
<212> TYPE: DNA
<213> ORGANISM: SARS-Associated Coronavirus

<400> SEQUENCE: 44
gcgtcctttc gagcgtgata tttccaacgt gcctttctct cctgatggca agccttgcac    60
tcctccagct                                                          70

<210> SEQ ID NO 45
```

-continued

<211> LENGTH: 70
<212> TYPE: DNA
<213> ORGANISM: SARS-Associated Coronavirus

<400> SEQUENCE: 45
ctgaactgct actggcctct gaacgattac ggtttctaca ccactaccgg cattggctac 60
cagccttatc 70

<210> SEQ ID NO 46
<211> LENGTH: 70
<212> TYPE: DNA
<213> ORGANISM: SARS-Associated Coronavirus

<400> SEQUENCE: 46
gtgtggttgt gctgtctttc gagctgctga acgctcctgc taccgtgtgc ggtcctaagc 60
tgtctaccga 70

<210> SEQ ID NO 47
<211> LENGTH: 70
<212> TYPE: DNA
<213> ORGANISM: SARS-Associated Coronavirus

<400> SEQUENCE: 47
tctgattaag aaccagtgcg tgaacttcaa cttcaacggc ctgaccggca ccggcgtgct 60
gactccctcc 70

<210> SEQ ID NO 48
<211> LENGTH: 70
<212> TYPE: DNA
<213> ORGANISM: SARS-Associated Coronavirus

<400> SEQUENCE: 48
tccaagcgct tccagccctt ccagcagttc ggccgcgatg tgtccgattt caccgattcc 60
gtgcgcgatc 70

<210> SEQ ID NO 49
<211> LENGTH: 70
<212> TYPE: DNA
<213> ORGANISM: SARS-Associated Coronavirus

<400> SEQUENCE: 49
ccaagacctc cgagattctg gatatttctc cctgcgcctt cggcggcgtg tccgtgatta 60
ctcccggcac 70

<210> SEQ ID NO 50
<211> LENGTH: 70
<212> TYPE: DNA
<213> ORGANISM: SARS-Associated Coronavirus

<400> SEQUENCE: 50
caacgcctcc tccgaggtgg ccgtgctgta ccaggatgtg aactgcaccg atgtgtccac 60
cgccattcac 70

<210> SEQ ID NO 51
<211> LENGTH: 70
<212> TYPE: DNA
<213> ORGANISM: SARS-Associated Coronavirus

<400> SEQUENCE: 51
gccgatcagc tgactcccgc ctggcgcatt tactccaccg gcaacaacgt gttccagacc 60
caggccggct 70

<210> SEQ ID NO 52
<211> LENGTH: 70
<212> TYPE: DNA
<213> ORGANISM: SARS-Associated Coronavirus

<400> SEQUENCE: 52
gcctgattgg cgccgagcac gtggatacct cctacgagtg cgatattccc attggcgccg    60
gcatttgcgc    70

<210> SEQ ID NO 53
<211> LENGTH: 70
<212> TYPE: DNA
<213> ORGANISM: SARS-Associated Coronavirus

<400> SEQUENCE: 53
ctcctaccac accgtgtccc tgctgcgctc cacctcccag aagtccattg tggcctacac    60
catgtccctg    70

<210> SEQ ID NO 54
<211> LENGTH: 70
<212> TYPE: DNA
<213> ORGANISM: SARS-Associated Coronavirus

<400> SEQUENCE: 54
ggcgccgatt cctccattgc ctactccaac aacaccattg ccattcccac caacttctcc    60
atttccatta    70

<210> SEQ ID NO 55
<211> LENGTH: 70
<212> TYPE: DNA
<213> ORGANISM: SARS-Associated Coronavirus

<400> SEQUENCE: 55
ccaccgaggt gatgcccgtg tccatggcca agacctccgt ggattgcaac atgtacattt    60
gcggcgattc    70

<210> SEQ ID NO 56
<211> LENGTH: 70
<212> TYPE: DNA
<213> ORGANISM: SARS-Associated Coronavirus

<400> SEQUENCE: 56
caccgagtgc gccaacctgc tgctgcagta cggctccttc tgcacccagc tgaaccgcgc 60
cctgtccggc 70

<210> SEQ ID NO 57
<211> LENGTH: 70
<212> TYPE: DNA
<213> ORGANISM: SARS-Associated Coronavirus

<400> SEQUENCE: 57
attgccgccg agcaggatcg caacacccgc gaggtgttcg cccaggtgaa gcagatgtac 60
aagactccca 70

<210> SEQ ID NO 58
<211> LENGTH: 70
<212> TYPE: DNA

<213> ORGANISM: SARS-Associated Coronavirus

<400> SEQUENCE: 58

```
ccctgaagta cttcggcggc ttcaacttct cccagattct gcccgatcct ctgaagccca      60
ccaagcgctc                                                             70
```

<210> SEQ ID NO 59
<211> LENGTH: 70
<212> TYPE: DNA
<213> ORGANISM: SARS-Associated Coronavirus

<400> SEQUENCE: 59

```
cttcattgag atctgctgt tcaacaaggt gaccctggcc gatgccggct tcatgaagca       60
gtacggcgag                                                             70
```

<210> SEQ ID NO 60
<211> LENGTH: 70
<212> TYPE: DNA
<213> ORGANISM: SARS-Associated Coronavirus

<400> SEQUENCE: 60

```
tgcctgggcg atattaacgc ccgcgatctg atttgcgcgc agaagttcaa cggcctgacc      60
gtgctgcctc                                                             70
```

<210> SEQ ID NO 61
<211> LENGTH: 70
<212> TYPE: DNA
<213> ORGANISM: SARS-Associated Coronavirus

<400> SEQUENCE: 61

```
ctctgctgac cgatgatatg attgcggcgt acaccgcggc gctggtgtcc ggcaccgcca      60
ccgcgggctg                                                             70
```

<210> SEQ ID NO 62
<211> LENGTH: 70
<212> TYPE: DNA
<213> ORGANISM: SARS-Associated Coronavirus

<400> SEQUENCE: 62

```
gaccttcggc gcgggcgcgg cgctgcagat tcccttcgcg atgcagatgg cgtaccgctt      60
caacggcatt                                                             70
```

<210> SEQ ID NO 63
<211> LENGTH: 70
<212> TYPE: DNA
<213> ORGANISM: SARS-Associated Coronavirus

<400> SEQUENCE: 63

```
ggcgtgaccc agaacgtgct gtacgagaac cagaagcaga ttgcgaacca gttcaacaag      60
gcgatttccc                                                             70
```

<210> SEQ ID NO 64
<211> LENGTH: 70
<212> TYPE: DNA
<213> ORGANISM: SARS-Associated Coronavirus

<400> SEQUENCE: 64

```
agattcagga gtccctgacc accacctcca ccgcgctggg caagctgcag gatgtggtga      60
accagaacgc                                                             70
```

<210> SEQ ID NO 65
<211> LENGTH: 70
<212> TYPE: DNA
<213> ORGANISM: SARS-Associated Coronavirus

<400> SEQUENCE: 65
gcaggcgctg aacaccctgg tgaagcagct gtcctccaac ttcggcgcga tttcctccgt    60
gctgaacgat                                                          70

<210> SEQ ID NO 66
<211> LENGTH: 70
<212> TYPE: DNA
<213> ORGANISM: SARS-Associated Coronavirus

<400> SEQUENCE: 66
attctgtccc gcctggataa ggtggaggcg gaggtgcaga ttgatcgcct gattaccggc    60
cgcctgcagt                                                          70

<210> SEQ ID NO 67
<211> LENGTH: 70
<212> TYPE: DNA
<213> ORGANISM: SARS-Associated Coronavirus

<400> SEQUENCE: 67
ccctgcagac ctacgtgacc cagcagctga ttcgcgcggc ggagattcgc gcgtccgcga    60
acctggcggc                                                          70

<210> SEQ ID NO 68
<211> LENGTH: 70
<212> TYPE: DNA
<213> ORGANISM: SARS-Associated Coronavirus

<400> SEQUENCE: 68
gaccaagatg tccgagtgcg tgctgggcca gtccaagcgc gtggatttct cggcaaggg    60 ctaccacctg                                                          70

<210> SEQ ID NO 69
<211> LENGTH: 70
<212> TYPE: DNA
<213> ORGANISM: SARS-Associated Coronavirus

<400> SEQUENCE: 69
atgtccttcc ctcaggcggc gcctcatggc gtggtgttcc tgcacgtgac ctacgtgccc    60
tcccaggagc                                                          70

<210> SEQ ID NO 70
<211> LENGTH: 70
<212> TYPE: DNA
<213> ORGANISM: SARS-Associated Coronavirus

<400> SEQUENCE: 70
gcaacttcac caccgcgccc gcgatttgcc acgagggcaa ggcgtacttc cctcgcgagg    60
gcgtgttcgt                                                          70

<210> SEQ ID NO 71
<211> LENGTH: 70
<212> TYPE: DNA
<213> ORGANISM: SARS-Associated Coronavirus -continued

```
<400> SEQUENCE: 71
gttcaacggc acctcctggt tcattaccca gcgcaacttc ttctctcctc agattattac      60
caccgataac                                                            70

<210> SEQ ID NO 72
<211> LENGTH: 70
<212> TYPE: DNA
<213> ORGANISM: SARS-Associated Coronavirus

<400> SEQUENCE: 72
accttcgtgt ccggcaactg cgatgtggtg attggcatta ttaacaacac cgtgtacgat      60
cctctgcagc                                                            70

<210> SEQ ID NO 73
<211> LENGTH: 70
<212> TYPE: DNA
<213> ORGANISM: SARS-Associated Coronavirus

<400> SEQUENCE: 73
ccgagctgga ttccttcaag gaggagctgg ataagtactt caagaaccac acctctcccg      60
atgtggatct                                                            70

<210> SEQ ID NO 74
<211> LENGTH: 70
<212> TYPE: DNA
<213> ORGANISM: SARS-Associated Coronavirus

<400> SEQUENCE: 74
gggcgatatt tccggcatta acgcctccgt ggtgaacatt cagaaggaga ttgatcgcct      60
gaacgaggtg                                                            70

<210> SEQ ID NO 75
<211> LENGTH: 70
<212> TYPE: DNA
<213> ORGANISM: SARS-Associated Coronavirus

<400> SEQUENCE: 75
gccaagaacc tgaacgagtc cctgattgat ctgcaggagc tgggcaagta cgagcagtct      60
agaggttgcg                                                            70

<210> SEQ ID NO 76
<211> LENGTH: 35
<212> TYPE: DNA
<213> ORGANISM: SARS-Associated Coronavirus

<400> SEQUENCE: 76
cgcaacctct agactgctcg tacttgccca gctcc                                35

<210> SEQ ID NO 77
<211> LENGTH: 70
<212> TYPE: DNA
<213> ORGANISM: SARS-Associated Coronavirus

<400> SEQUENCE: 77
tgcagatcaa tcagggactc gttcaggttc ttggccacct cgttcaggcg atcaatctcc      60
ttctgaatgt                                                            70

<210> SEQ ID NO 78
<211> LENGTH: 70
```

-continued

<212> TYPE: DNA
<213> ORGANISM: SARS-Associated Coronavirus

<400> SEQUENCE: 78
tcaccacgga ggcgttaatg ccggaaatat cgcccagatc cacatcggga gaggtgtggt 60
tcttgaagta 70

<210> SEQ ID NO 79
<211> LENGTH: 70
<212> TYPE: DNA
<213> ORGANISM: SARS-Associated Coronavirus

<400> SEQUENCE: 79
cttatccagc tcctccttga aggaatccag ctcgggctgc agaggatcgt acacggtgtt 60
gttaataatg 70

<210> SEQ ID NO 80
<211> LENGTH: 70
<212> TYPE: DNA
<213> ORGANISM: SARS-Associated Coronavirus

<400> SEQUENCE: 80
ccaatcacca catcgcagtt gccggacacg aaggtgttat cggtggtaat aatctgagga 60
gagaagaagt 70

<210> SEQ ID NO 81
<211> LENGTH: 70
<212> TYPE: DNA
<213> ORGANISM: SARS-Associated Coronavirus

<400> SEQUENCE: 81
tgcgctgggt aatgaaccag gaggtgccgt tgaacacgaa cacgccctcg cgagggaagt 60
acgccttgcc 70

<210> SEQ ID NO 82
<211> LENGTH: 70
<212> TYPE: DNA
<213> ORGANISM: SARS-Associated Coronavirus

<400> SEQUENCE: 82
ctcgtggcaa atcgcgggcg cggtggtgaa gttgcgctcc tgggagggca cgtaggtcac 60
gtgcaggaac 70

<210> SEQ ID NO 83
<211> LENGTH: 70
<212> TYPE: DNA
<213> ORGANISM: SARS-Associated Coronavirus

<400> SEQUENCE: 83
accacgccat gaggcgccgc ctgagggaag gacatcaggt ggtagccctt gccgcagaaa 60
tccacgcgct 70

<210> SEQ ID NO 84
<211> LENGTH: 70
<212> TYPE: DNA
<213> ORGANISM: SARS-Associated Coronavirus

<400> SEQUENCE: 84
tggactggcc cagcacgcac tcggacatct tggtcgccgc caggttcgcg gacgcgcgaa 60
tctccgccgc                                                            70

<210> SEQ ID NO 85
<211> LENGTH: 70
<212> TYPE: DNA
<213> ORGANISM: SARS-Associated Coronavirus

<400> SEQUENCE: 85
gcgaatcagc tgctgggtca cgtaggtctg cagggactgc aggcggccgg taatcaggcg    60
atcaatctgc                                                            70

<210> SEQ ID NO 86
<211> LENGTH: 70
<212> TYPE: DNA
<213> ORGANISM: SARS-Associated Coronavirus

<400> SEQUENCE: 86
acctccgcct ccaccttatc caggcgggac agaatatcgt tcagcacgga ggaaatcgcg    60
ccgaagttgg                                                            70

<210> SEQ ID NO 87
<211> LENGTH: 70
<212> TYPE: DNA
<213> ORGANISM: SARS-Associated Coronavirus

<400> SEQUENCE: 87
aggacagctg cttccaccagg gtgttcagcg cctgcgcgtt ctggttcacc acatcctgca    60
gcttgcccag                                                            70

<210> SEQ ID NO 88
<211> LENGTH: 70
<212> TYPE: DNA
<213> ORGANISM: SARS-Associated Coronavirus

<400> SEQUENCE: 88
cgcggtggag gtggtggtca gggactcctg aatctgggaa atcgccttgt tgaactggtt    60
cgcaatctgc                                                            70

<210> SEQ ID NO 89
<211> LENGTH: 70
<212> TYPE: DNA
<213> ORGANISM: SARS-Associated Coronavirus

<400> SEQUENCE: 89
ttctggttct cgtacagcac gttctgggtc acgccaatgc cgttgaagcg gtacgccatc    60
tgcatcgcga                                                            70

<210> SEQ ID NO 90
<211> LENGTH: 70
<212> TYPE: DNA
<213> ORGANISM: SARS-Associated Coronavirus

<400> SEQUENCE: 90
agggaatctg cagcgccgcg cccgcgccga aggtccagcc cgcggtggcg gtgccggaca    60
ccagcgccgc                                                            70

<210> SEQ ID NO 91
<211> LENGTH: 70
<212> TYPE: DNA
<213> ORGANISM: SARS-Associated Coronavirus

```
<400> SEQUENCE: 91
ggtgtacgcc gcaatcatat catcggtcag cagaggaggc agcacggtca ggccgttgaa      60
cttctgcgcg                                                             70

<210> SEQ ID NO 92
<211> LENGTH: 70
<212> TYPE: DNA
<213> ORGANISM: SARS-Associated Coronavirus

<400> SEQUENCE: 92
caaatcagat cgcgggcgtt aatatcgccc aggcactcgc cgtactgctt catgaagccg      60
gcatcggcca                                                             70

<210> SEQ ID NO 93
<211> LENGTH: 70
<212> TYPE: DNA
<213> ORGANISM: SARS-Associated Coronavirus

<400> SEQUENCE: 93
gggtcacctt gttgaacagc agatcctcaa tgaaggagcg cttggtgggc ttcagaggat      60
cgggcagaat                                                             70

<210> SEQ ID NO 94
<211> LENGTH: 70
<212> TYPE: DNA
<213> ORGANISM: SARS-Associated Coronavirus

<400> SEQUENCE: 94
ctgggagaag ttgaagccgc cgaagtactt cagggtggga gtcttgtaca tctgcttcac      60
ctgggcgaac                                                             70

<210> SEQ ID NO 95
<211> LENGTH: 70
<212> TYPE: DNA
<213> ORGANISM: SARS-Associated Coronavirus

<400> SEQUENCE: 95
acctcgcggg tgttgcgatc ctgctcggcg gcaatgccgg acagggcgcg gttcagctgg      60
gtgcagaagg                                                             70

<210> SEQ ID NO 96
<211> LENGTH: 70
<212> TYPE: DNA
<213> ORGANISM: SARS-Associated Coronavirus

<400> SEQUENCE: 96
agccgtactg cagcagcagg ttggcgcact cggtggaatc gccgcaaatg tacatgttgc      60
aatccacgga                                                             70

<210> SEQ ID NO 97
<211> LENGTH: 70
<212> TYPE: DNA
<213> ORGANISM: SARS-Associated Coronavirus

<400> SEQUENCE: 97
ggtcttggcc atggacacgg gcatcacctc ggtggtaatg gaaatggaga agttggtggg      60
aatggcaatg                                                             70
```

<210> SEQ ID NO 98
<211> LENGTH: 70
<212> TYPE: DNA
<213> ORGANISM: SARS-Associated Coronavirus

<400> SEQUENCE: 98
gtgttgttgg agtaggcaat ggaggaatcg gcgcccaggg acatggtgta ggccacaatg    60
gacttctggg                                                          70

<210> SEQ ID NO 99
<211> LENGTH: 70
<212> TYPE: DNA
<213> ORGANISM: SARS-Associated Coronavirus

<400> SEQUENCE: 99
aggtggagcg cagcagggac acggtgtggt aggaggcgca aatgccggcg ccaatgggaa    60
tatcgcactc                                                          70

<210> SEQ ID NO 100
<211> LENGTH: 70
<212> TYPE: DNA
<213> ORGANISM: SARS-Associated Coronavirus

<400> SEQUENCE: 100
gtaggaggta tccacgtgct cggcgccaat caggcagccg gcctgggtct ggaacacgtt    60
gttgccggtg                                                          70

<210> SEQ ID NO 101
<211> LENGTH: 70
<212> TYPE: DNA
<213> ORGANISM: SARS-Associated Coronavirus

<400> SEQUENCE: 101
gagtaaatgc gccaggcggg agtcagctga tcggcgtgaa tggcggtgga cacatcggtg    60
cagttcacat                                                          70

<210> SEQ ID NO 102
<211> LENGTH: 70
<212> TYPE: DNA
<213> ORGANISM: SARS-Associated Coronavirus

<400> SEQUENCE: 102
cctggtacag cacggccacc tcggaggagg cgttggtgcc gggagtaatc acggacacgc    60
cgccgaaggc                                                          70

<210> SEQ ID NO 103
<211> LENGTH: 70
<212> TYPE: DNA
<213> ORGANISM: SARS-Associated Coronavirus

<400> SEQUENCE: 103
gcagggagaa atatccagaa tctcggaggt cttgggatcg cgcacggaat cggtgaaatc    60
ggacacatcg                                                          70

<210> SEQ ID NO 104
<211> LENGTH: 70
<212> TYPE: DNA
<213> ORGANISM: SARS-Associated Coronavirus

<400> SEQUENCE: 104

-continued cggccgaact gctggaaggg ctggaagcgc ttggaggagg gagtcagcac gccggtgccg     60
gtcaggccgt                                                            70

<210> SEQ ID NO 105
<211> LENGTH: 70
<212> TYPE: DNA
<213> ORGANISM: SARS-Associated Coronavirus

<400> SEQUENCE: 105
tgaagttgaa gttcacgcac tggttcttaa tcagatcggt agacagctta ggaccgcaca     60
cggtagcagg                                                            70

<210> SEQ ID NO 106
<211> LENGTH: 70
<212> TYPE: DNA
<213> ORGANISM: SARS-Associated Coronavirus

<400> SEQUENCE: 106
agcgttcagc agctcgaaag acagcacaac cacacgataa ggctggtagc caatgccggt     60
agtggtgtag                                                            70

<210> SEQ ID NO 107
<211> LENGTH: 70
<212> TYPE: DNA
<213> ORGANISM: SARS-Associated Coronavirus

<400> SEQUENCE: 107
aaaccgtaat cgttcagagg ccagtagcag ttcagagctg gaggagtgca aggcttgcca     60
tcaggagaga                                                            70

<210> SEQ ID NO 108
<211> LENGTH: 70
<212> TYPE: DNA
<213> ORGANISM: SARS-Associated Coronavirus

<400> SEQUENCE: 108
aaggcacgtt ggaaatatca cgctcgaaag gacgcagctt accatgacgc aggtaacgat     60
acttgtagtt                                                            70

<210> SEQ ID NO 109
<211> LENGTH: 70
<212> TYPE: DNA
<213> ORGANISM: SARS-Associated Coronavirus

<400> SEQUENCE: 109
gtagttacca gtggaggtag catcaatgtt acgagtgttc caagccagca cgcaacccat     60
gaaatcatca                                                            70

<210> SEQ ID NO 110
<211> LENGTH: 70
<212> TYPE: DNA
<213> ORGANISM: SARS-Associated Coronavirus

<400> SEQUENCE: 110
ggcagcttgt agttgtaatc agcaatcaca ccagtctgac caggagcaat ctgacgaaca     60
tcatcacctt                                                            70

<210> SEQ ID NO 111

-continued

<211> LENGTH: 70
<212> TYPE: DNA
<213> ORGANISM: SARS-Associated Coronavirus

<400> SEQUENCE: 111
tcaccacgaa ggagtcagcg tacacgttgg agaagcaaag atcgttcagc ttggtggcag 60
atacgccata 70

<210> SEQ ID NO 112
<211> LENGTH: 70
<212> TYPE: DNA
<213> ORGANISM: SARS-Associated Coronavirus

<400> SEQUENCE: 112
gcacttgaag gtggagaaga aggtggagtt gtacagcacg gagtagtcgg ccacgcagtt 60
ggaaatcttc 70

<210> SEQ ID NO 113
<211> LENGTH: 70
<212> TYPE: DNA
<213> ORGANISM: SARS-Associated Coronavirus

<400> SEQUENCE: 113
ttgcgctccc aggcgtacac ggagggaaac ttggtggcgt tgaacacctc gccgaaggga 60
cacaggttgg 70

<210> SEQ ID NO 114
<211> LENGTH: 70
<212> TYPE: DNA
<213> ORGANISM: SARS-Associated Coronavirus

<400> SEQUENCE: 114
taatgttggg aaagcgcacc acgtcgccgg agggcaccac gcggaagttg gaggtctggt 60
aaatgccctt 70

<210> SEQ ID NO 115
<211> LENGTH: 70
<212> TYPE: DNA
<213> ORGANISM: SARS-Associated Coronavirus

<400> SEQUENCE: 115
gtcaatctcg aaggacttca cggagcactt cagctcggcc agagggttct gggagcagtc 60
cacggcgtcg 70

<210> SEQ ID NO 116
<211> LENGTH: 70
<212> TYPE: DNA
<213> ORGANISM: SARS-Associated Coronavirus

<400> SEQUENCE: 116
gtaatggtgc cgttctcgtc gtacttcagc atgaaggtgg tgggcttcag gtagcccacg 60
aagtaggcgg 70

<210> SEQ ID NO 117
<211> LENGTH: 70
<212> TYPE: DNA
<213> ORGANISM: SARS-Associated Coronavirus

<400> SEQUENCE: 117
cggcggaggt gccccagatg tcctgggcgg gagagaaggc ggtcagaatg gcgcggaagt 60
tggtaatgtt 70

<210> SEQ ID NO 118
<211> LENGTH: 70
<212> TYPE: DNA
<213> ORGANISM: SARS-Associated Coronavirus

<400> SEQUENCE: 118
gatgcccaga ggcagcttga agatgggctt cagggtgttg aagccggagg gcaggtcgcg    60
caccacgtcg                                                           70

<210> SEQ ID NO 119
<211> LENGTH: 70
<212> TYPE: DNA
<213> ORGANISM: SARS-Associated Coronavirus

<400> SEQUENCE: 119
atgggctggt agcccttgta cacgtacagg aagccgtcct tgttcttgaa cacgaactcg    60
cgcaggtgct                                                           70

<210> SEQ ID NO 120
<211> LENGTH: 70
<212> TYPE: DNA
<213> ORGANISM: SARS-Associated Coronavirus

<400> SEQUENCE: 120
tgaagttgcc ggacttctcg gacacgtcca gggagaaggc gtcggagatg tactcgaagg    60
tgcagttgaa                                                           70

<210> SEQ ID NO 121
<211> LENGTH: 70
<212> TYPE: DNA
<213> ORGANISM: SARS-Associated Coronavirus

<400> SEQUENCE: 121
ggcgttgtcg aagatcatgg tgtgggtctg ggtgcccatg ggcttggaca cggcgaagaa    60
gggattgtcg                                                           70

<210> SEQ ID NO 122
<211> LENGTH: 70
<212> TYPE: DNA
<213> ORGANISM: SARS-Associated Coronavirus

<400> SEQUENCE: 122
cacagctcga agttgcaggc gcggatcacc acgttggtgg agttgttgat gatgatcacg    60
gactgggact                                                           70

<210> SEQ ID NO 123
<211> LENGTH: 70
<212> TYPE: DNA
<213> ORGANISM: SARS-Associated Coronavirus

<400> SEQUENCE: 123
tgttgttcat ggtggagccg aacacccagc cgcgcaccac gttggacttc tcggtggcgg    60
cgaagtagat                                                           70

<210> SEQ ID NO 124
<211> LENGTH: 70
<212> TYPE: DNA

-continued

<213> ORGANISM: SARS-Associated Coronavirus

<400> SEQUENCE: 124
gccgtccttg aagggaatca cgggattgcc gaaggtgtgg ttgatggtgt ggaagccggt 60
cacgttggag 70

<210> SEQ ID NO 125
<211> LENGTH: 70
<212> TYPE: DNA
<213> ORGANISM: SARS-Associated Coronavirus

<400> SEQUENCE: 125
tagaagggca ggaacaggtc ctgggtcagg tacagggtgt cggagcggaa gatctcgtca 60
gggtagtaca 70

<210> SEQ ID NO 126
<211> LENGTH: 70
<212> TYPE: DNA
<213> ORGANISM: SARS-Associated Coronavirus

<400> SEQUENCE: 126
cgccgcgcat ggaggaggtg tgctgggtgt agttaggagc ctgcacgtcg tcgaaggtgg 60
tgcagcggtc 70

<210> SEQ ID NO 127
<211> LENGTH: 70
<212> TYPE: DNA
<213> ORGANISM: SARS-Associated Coronavirus

<400> SEQUENCE: 127
caggtcggag ccggaggtca gggtcaggaa cagcaggaag atgaacatgg tggcggcaag 60
cttgcagcgc 70

<210> SEQ ID NO 128
<211> LENGTH: 70
<212> TYPE: DNA
<213> ORGANISM: SARS-Associated Coronavirus

<400> SEQUENCE: 128
accaagtttc cctccgtgta cgcctgggag cgcaagaaga tttccaactg cgtggcctct 60
agaggttgcg 70

<210> SEQ ID NO 129
<211> LENGTH: 35
<212> TYPE: DNA
<213> ORGANISM: SARS-Associated Coronavirus

<400> SEQUENCE: 129
cgcaacctct agaggccacg cagttggaaa tcttc 35

<210> SEQ ID NO 130
<211> LENGTH: 92
<212> TYPE: DNA
<213> ORGANISM: SARS-Associated Coronavirus

<400> SEQUENCE: 130
gcacttgaag gtggagaaga aggtggagtt gtacagcacg gagtagtcgg ccacgcagtt 60
ggaaatcttc ttgcgctccc aggcgtacac gg 92

```
<210> SEQ ID NO 131
<211> LENGTH: 48
<212> TYPE: DNA
<213> ORGANISM: SARS-Associated Coronavirus

<400> SEQUENCE: 131
gagtgcctct agagcacttg aaggtggaga agaaggtgga gttgtaca            48

<210> SEQ ID NO 132
<211> LENGTH: 48
<212> TYPE: DNA
<213> ORGANISM: SARS-Associated Coronavirus

<400> SEQUENCE: 132
gactgccaag ctttgtacaa ctccaccttc ttctccacct tcaagtgc            48

<210> SEQ ID NO 133
<211> LENGTH: 48
<212> TYPE: DNA
<213> ORGANISM: SARS-Associated Coronavirus

<400> SEQUENCE: 133
gattgcctct agagtaggag gtatccacgt gctcggcgcc aatcaggc            48

<210> SEQ ID NO 134
<211> LENGTH: 48
<212> TYPE: DNA
<213> ORGANISM: SARS-Associated Coronavirus

<400> SEQUENCE: 134
gaccgcaaag cttgcctgat tggcgccgag cacgtggata cctcctac            48

<210> SEQ ID NO 135
<211> LENGTH: 48
<212> TYPE: DNA
<213> ORGANISM: SARS-Associated Coronavirus

<400> SEQUENCE: 135
ggactgctct agacgcggtg gaggtggtgg tcagggactc ctgaatct            48

<210> SEQ ID NO 136
<211> LENGTH: 48
<212> TYPE: DNA
<213> ORGANISM: SARS-Associated Coronavirus

<400> SEQUENCE: 136
cgagtacaag cttagattca ggagtccctg accaccacct ccaccgcg            48

<210> SEQ ID NO 137
<211> LENGTH: 50
<212> TYPE: DNA
<213> ORGANISM: SARS-Associated Coronavirus

<400> SEQUENCE: 137
gcgctgcaag cttgccgcca ccatgttcat cttcctgctg ttcctgaccc          50

<210> SEQ ID NO 138
<211> LENGTH: 70
<212> TYPE: DNA
<213> ORGANISM: SARS-Associated Coronavirus

<400> SEQUENCE: 138
caaagatcgt tcagcttggt ggcagatacg ccatagcact tgaaggtgga gaagaaggtg    60
```

-continued

```
gagttgtaca                                                              70

<210> SEQ ID NO 139
<211> LENGTH: 70
<212> TYPE: DNA
<213> ORGANISM: SARS-Associated Coronavirus

<400> SEQUENCE: 139
gaagatttcc aactgcgtgg ccgactactc cgtgctgtac aactccacct tcttctccac        60
cttcaagtgc                                                              70

<210> SEQ ID NO 140
<211> LENGTH: 70
<212> TYPE: DNA
<213> ORGANISM: SARS-Associated Coronavirus

<400> SEQUENCE: 140
gcgcaaatgc cggcgccaat gggaatatcg cactcgtagg aggtatccac gtgctcggcg        60
ccaatcaggc                                                              70

<210> SEQ ID NO 141
<211> LENGTH: 70
<212> TYPE: DNA
<213> ORGANISM: SARS-Associated Coronavirus

<400> SEQUENCE: 141
caccggcaac aacgtgttcc agacccaggc cggctgcctg attggcgccg agcacgtgga        60
tacctcctac                                                              70

<210> SEQ ID NO 142
<211> LENGTH: 70
<212> TYPE: DNA
<213> ORGANISM: SARS-Associated Coronavirus

<400> SEQUENCE: 142
gcgttctggt tcaccacatc ctgcagcttg cccagcgcgg tggaggtggt ggtcagggac        60
tcctgaatct                                                              70

<210> SEQ ID NO 143
<211> LENGTH: 70
<212> TYPE: DNA
<213> ORGANISM: SARS-Associated Coronavirus

<400> SEQUENCE: 143
gcagattgcg aaccagttca acaaggcgat ttcccagatt caggagtccc tgaccaccac        60
ctccaccgcg                                                              70

<210> SEQ ID NO 144
<211> LENGTH: 50
<212> TYPE: DNA
<213> ORGANISM: SARS-Associated Coronavirus

<400> SEQUENCE: 144
cgcaacctct agactgctcg tacttgccca gctcctgcag atcaatcagg                   50

<210> SEQ ID NO 145
<211> LENGTH: 49
<212> TYPE: DNA
<213> ORGANISM: SARS-Associated Coronavirus

<400> SEQUENCE: 145
```

-continued

```
gcgtagtgga tccggctccg acctggaccg ctgcaccacc ttcgacgac              49

<210> SEQ ID NO 146
<211> LENGTH: 51
<212> TYPE: DNA
<213> ORGANISM: SARS-Associated Coronavirus

<400> SEQUENCE: 146
cgcaaccaag cttctaggcc acgcagttgg aaatcttctt gcgctcccag g           51

<210> SEQ ID NO 147
<211> LENGTH: 49
<212> TYPE: DNA
<213> ORGANISM: SARS-Associated Coronavirus

<400> SEQUENCE: 147
gcgtagtgga tccggctccg acctggaccg ctgcaccacc ttcgacgac              49

<210> SEQ ID NO 148
<211> LENGTH: 50
<212> TYPE: DNA
<213> ORGANISM: SARS-Associated Coronavirus

<400> SEQUENCE: 148
ccatgctgag ctcgcggcca cgcagttgga aatcttcttg cgctcccagg             50
```

What is claimed is:

1. An isolated monoclonal antibody, or antigen binding portion thereof, that specifically binds to a SARS-CoV spike glycoprotein polypeptide (an S polypeptide), or fragment thereof, wherein the antibody, or antigen binding portion thereof, cross-competes for binding to the S polypeptide with a reference antibody, or antigen binding fragment thereof, that comprises:

(a) a heavy chain variable region comprising the amino acid sequence shown in SEQ ID NO:13 or SEQ ID NO:149; and (b) a light chain variable region comprising the amino acid sequence shown in SEQ ID NO:14.

2. A monoclonal antibody, or antigen binding portion thereof, that binds to a SARS-CoV spike glycoprotein polypeptide (an S polypeptide), or fragment thereof, comprising:

(a) a heavy chain variable region CDR1 comprising the amino acid sequence shown in SEQ ID NO:7;

(b) a heavy chain variable region CDR2 comprising the amino acid sequence shown in SEQ ID NO:8;

(c) a heavy chain variable region CDR3 comprising the amino acid sequence shown in SEQ ID NO:9;

(d) a light chain variable region CDR1 comprising the amino acid sequence shown in SEQ ID NO:10;

(e) a light chain variable region CDR2 comprising the amino acid sequence shown in SEQ ID NO:11; and (f) a light chain variable region CDR3 comprising the amino acid sequence shown in SEQ ID NO:12.

3. A monoclonal antibody, or antigen binding portion thereof, that binds to a SARS-CoV spike glycoprotein polypeptide (an S polypeptide), or fragment thereof, comprising:

(a) a heavy chain variable region comprising the amino acid sequence shown in SEQ ID NO:13, SEQ ID NO:17 or SEQ ID NO:149; and (b) a light chain variable region comprising the amino acid sequence shown in SEQ ID NO:14.

4. The antibody, or antigen binding fragment thereof, of claim 1, 2 or 3, which is a human antibody, or antigen binding fragment thereof.

5. The antibody, or antigen binding fragment thereof, of claim 1, 2 or 3, which is a humanized or chimeric antibody, or antigen binding fragment thereof.

6. A composition comprising an antibody, or antigen binding fragment thereof, of claim 1, 2 or 3, and a pharmaceutically acceptable carrier.

7. An immunoconjugate comprising the antibody, or antigen-binding portion thereof, of claim 1, 2 or 3, linked to a therapeutic agent.

8. An isolated antibody, or antigen binding portion thereof, that binds to an S polypeptide of SARS-CoV, wherein the heavy chain variable region comprises the amino acid sequence set forth in SEQ ID NO:13 or SEQ ID NO:149.

9. An isolated antibody, or antigen binding portion thereof, that binds to an S polypeptide of SARS-CoV, wherein the light chain variable region comprises the amino acid sequence set forth in SEQ ID NO:14.

10. The antibody, or antigen binding fragment thereof, of claim 2, 8 or 9 which is a human, humanized or chimeric antibody, or antigen binding fragment thereof.

11. An isolated monoclonal antibody, or an antigen binding portion thereof, which binds to an epitope on the S polypeptide of SARS-CoV recognized by the antibody of claim 2 or 3.

12. The isolated monoclonal antibody, or an antigen binding portion thereof, of claim 11 wherein the antibody, or an antigen binding portion thereof, binds to an epitope on the S polypeptide of SARS-CoV between amino acids 490 and 510.

* * * * *